(12) United States Patent
Damaj et al.

(10) Patent No.: US 8,900,625 B2
(45) Date of Patent: Dec. 2, 2014

(54) ANTIMICROBIAL COMPOUNDS AND METHODS OF USE

(71) Applicant: Nexmed Holdings, Inc., San Diego, CA (US)

(72) Inventors: Bassam B. Damaj, San Diego, CA (US); Richard M. Martin, San Diego, CA (US)

(73) Assignee: Nexmed Holdings, Inc., San Diego, CA (US)

(*) Notice: Subject to any disclaimer, the term of this patent is extended or adjusted under 35 U.S.C. 154(b) by 4 days.

(21) Appl. No.: 13/835,619

(22) Filed: Mar. 15, 2013

(65) Prior Publication Data
US 2014/0170207 A1    Jun. 19, 2014

Related U.S. Application Data

(60) Provisional application No. 61/737,761, filed on Dec. 15, 2012.

(51) Int. Cl.
| | |
|---|---|
| *C07C 229/12* | (2006.01) |
| *C07C 309/30* | (2006.01) |
| *A01N 37/44* | (2006.01) |
| *A61K 9/00* | (2006.01) |
| *A61K 31/7008* | (2006.01) |

(52) U.S. Cl.
CPC ............. *C07C 229/12* (2013.01); *A01N 37/44* (2013.01); *C07C 309/30* (2013.01); *A61K 9/00* (2013.01); *A61K 31/7008* (2013.01)
USPC ........... 424/447; 424/443; 560/155; 560/170; 560/38; 514/551; 514/538

(58) Field of Classification Search
CPC ...... C07C 229/12; C07C 309/30; A01N 37/44
See application file for complete search history.

(56) References Cited

U.S. PATENT DOCUMENTS

| | | | |
|---|---|---|---|
| 4,980,378 A | 12/1990 | Wong et al. | |
| 6,118,020 A | 9/2000 | Buyuktimkin et al. | |
| 6,841,574 B2 | 1/2005 | Frank et al. | |
| 2009/0099266 A1* | 4/2009 | Kepka et al. | 514/655 |

FOREIGN PATENT DOCUMENTS

| | | |
|---|---|---|
| WO | WO 2011139370 A1 * | 11/2011 |
| WO | WO 2012/075107 A2 | 6/2012 |

OTHER PUBLICATIONS

International Search Report from PCT/US2013/073937 dated Mar. 14, 2014.

* cited by examiner

Primary Examiner — David J Blanchard
Assistant Examiner — Nicole Babson
(74) Attorney, Agent, or Firm — Foley & Lardner LLP

(57) ABSTRACT

The present disclosure provides antimicrobial compounds, compositions comprising such antimicrobial compounds, and methods of their use, in particular, antibacterial compounds and antifungal compounds. In certain aspects, the antimicrobial compounds are effective against pathogens of hospital-acquired infections. In certain aspects, the antimicrobial compounds are effective against pathogens that are resistant to antibiotics. The antimicrobial compounds can be used in antibacterial compositions, antifungal compositions, antiseptic compositions and disinfectant compositions. The antimicrobial compounds can be used as adjuncts in antibacterial compositions and antifungal compositions.

35 Claims, 60 Drawing Sheets

ANTIMICROBIAL COMPOUNDS AND METHODS OF USE

CROSS-REFERENCE TO RELATED APPLICATIONS

This application claims benefit under 35 U.S.C. §119 of U.S. Provisional Application Ser. No. 61/737,761, filed Dec. 15, 2012, the contents of which are hereby incorporated by reference.

BACKGROUND OF THE INVENTION

1. Field of the Invention

The present disclosure relates to antimicrobial compounds, in particular to antibacterial compounds and antifungal compounds. In certain embodiments, the antimicrobial compounds are effective against pathogens of hospital-acquired infections. In certain embodiments, the antimicrobial compounds are effective against pathogens that are resistant to antibiotics.

2. Description of the Background

Widespread use of antibiotics in recent decades has led to proliferation of pathogens having multiple drug resistance, often encoded by transmissible plasmids, and therefore capable of spreading rapidly between species. Many previously useful antibiotics are no longer effective against infectious organisms isolated from human and animal subjects. The specter of epidemic forms of bacterial diseases such as tuberculosis and fungal diseases, which are refractory to known antibiotic agents, may be realized in the near future. Development of novel antimicrobial compounds is a continuing urgent public health need.

Antibiotic-resistant strains of pathogenic microbes are a particular concern in cases of nosocomial infections. A nosocomial infection, also known as a hospital-acquired infection or HAI, is an infection whose development is favored by a hospital environment, such as one acquired by a patient during a hospital visit or one developing among hospital staff. Such infections include fungal and bacterial infections and are aggravated by the reduced resistance of individual patients, in particular, immune-compromised patients. The 10 most common pathogens (accounting for 84% of any reported HAIs in the U.S. in 2006-2007) were coagulase-negative staphylococci (15%), *Staphylococcus aureus* (15%), *Enterococcus* species (12%), *Candida* species (11%), *Escherichia coli* (10%), *Pseudomonas aeruginosa* (8%), *Klebsiella pneumoniae* (6%), *Enterobacter* species (5%), *Acinetobacter baumannii* (3%), and *Klebsiella oxytoca* (2%). The pooled mean proportion of pathogenic isolates resistant to antimicrobial agents varied significantly across types of HAI for some pathogen-antimicrobial combinations. As many as 16% of all HAIs were associated with the following multidrug-resistant pathogens: methicillin-resistant *S. aureus* (MRSA) (8% of HAIs), vancomycin-resistant *Enterococcus faecium* (4%), carbapenem-resistant *P. aeruginosa* (2%), extended-spectrum cephalosporin-resistant *K. pneumoniae* (1%), extended-spectrum cephalosporin-resistant *E. coli* (0.5%), and carbapenem-resistant *A. baumannii, K. pneumonlae, K. oxytoca*, and *E. coli* (0.5%). Hidron, A., et al., Antimicrobial-Resistant Pathogens Associated With Health-care-Associated Infections: Annual Summary of Data Reported to the National Healthcare Safety Network at the Centers for Disease Control and Prevention, 2006-2007, Infect. Control Hosp. Epidemiol. 2008; 29:996-1011, abstract.

SUMMARY OF THE INVENTION

The present disclosure provides antimicrobial compounds, compositions comprising such antimicrobial compounds, and methods of their use, in particular, antibacterial compounds and antifungal compounds. In certain aspects, the antimicrobial compounds are effective against pathogens of hospital-acquired infections. In certain aspects, the antimicrobial compounds are effective against pathogens that are resistant to antibiotics. The antimicrobial compounds can be used in antibacterial compositions, antifungal compositions, antiseptic compositions and disinfectant compositions. The antimicrobial compounds can be used as adjuncts in antibacterial compositions and antifungal compositions.

In certain embodiments, the antimicrobial compound inhibits growth of a bacteria (e.g., cutaneous, mucosal, or enteric bacteria), fungus, or virus. In preferred embodiments, with respect to bacteria, the antimicrobial compound inhibits growth of a cell selected from the genera consisting of *Acinetobacter, Bacillus, Enterobacter, Enterococcus, Escherichia, Klebsiella, Corynebacterium, Haemophilus, Proteus, Pseudomonas, Serratia, Staphylococcus*, and *Streptococcus*. In preferred embodiments, with respect to fungi, the antimicrobial compound inhibits growth of a cell selected from the genera consisting of *Aspergillus*, and *Candida*.

The compound of Formula I is provided

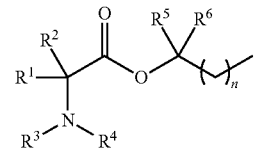

where n is an integer from 6-12 inclusive; $R^1$, and $R^2$, are the same or different and are selected independently from the group consisting of H, substituted or unsubstituted, straight or branched chain $C_1$-$C_{10}$ alkyl, $CH_3$, $CHOHCH_3$, $CH(CH_3)_2$, $CH_2C_6H_6$, and $CH_2CH(CH_3)_2$; $R^3$, and $R^4$, are the same or different and are selected independently from the group consisting of H, substituted or unsubstituted, straight or branched chain $C_1$-$C_{10}$ alkyl, $C_6$-$C_{10}$ aryl or $C_6$-$C_{10}$ heteroaryl, $CH_3$, $CH(CH_3)_2$, $CH_2CHOH$, $CH_2CH(CH_3)_2$, and $(CH_2)_2N(CH_2CH_3)_2$; $R^5$, and $R^6$, are the same or different and are selected independently from the group consisting of H and $CH_3$, and pharmaceutically acceptable salts thereof. In certain embodiments, the compound of Formula I is configured wherein $R^1$ is H and $R^2$ is selected from the group consisting of $CHOHCH_3$, $CH(CH_3)$, $CH_2C_6H_6$, and $CH_2CH(CH_3)_2$. In certain embodiments, the compound of Formula I is configured wherein $R^1$ is $CH_3$ and $R^2$ is $CH_3$. In other embodiments, the compound Formula I is configured wherein $R^3$ is H and $R^4$ is selected from the group consisting of $CH(CH_3)_2$, $CH_2CHOH$, $CH_2CH(CH_3)_2$, and $(CH_2)_2N(CH_2CH_3)_2$. Typically, the salt of the compound is selected from the group consisting of hydrochloride, phosphate, maleate, 2-hydroxypropane-1,2,3-tricarboxylate, sulfonate, methane sulfonate, ethane sulfonate, 2-hydroxyethane sulfonate, benzene sulfonate, 4-methyl-benzene sulfonate, and heminaphthalene-1,5-disulfonate.

In preferred embodiments, the compound of Formula I is provided

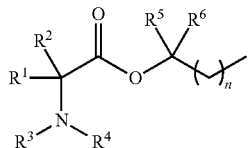

where n is an integer from 6-12 inclusive; $R^1$, and $R^2$, are the same or different and are selected independently from the group consisting of H, $CH_3$, $CHOHCH_3$, $CH(CH_3)_2$, $CH_2C_6H_6$, and $CH_2CH(CH_3)_2$; $R^3$, and $R^4$, are the same or different and are selected independently from the group consisting of H, $CH_3$, $CH(CH_3)_2$, $CH_2CHOH$, $CH_2CH(CH_3)$, and $(CH_2)_2N(CH_2CH_3)_2$; $R^5$, and $R^6$, are the same or different and are selected independently from the group consisting of H and $CH_3$, and pharmaceutically acceptable salts thereof. In certain embodiments, the compound of Formula I is configured wherein $R^1$ is H and $R^2$ is selected from the group consisting of $CHOHCH_3$, $CH(CH_3)_2$, $CH_2C_6H_6$, and $CH_2CH(CH_3)_2$. In certain embodiments, the compound of Formula I is configured wherein $R^1$ is $CH_3$ and $R^2$ is $CH_3$. In other embodiments, the compound Formula I is configured wherein $R^3$ is H and $R^4$ is selected from the group consisting of $CH(CH_3)_2$, $CH_2CHOH$, $CH_2CH(CH_3)_2$, and $(CH_2)_2N(CH_2CH_3)_2$. Typically, the salt of the compound is selected from the group consisting of hydrochloride, phosphate, maleate, 2-hydroxypropane-1,2,3-tricarboxylate, sulfonate, methane sulfonate, ethane sulfonate, 2-hydroxyethane sulfonate, benzene sulfonate, 4-methyl-benzene sulfonate, and heminaphthalene-1,5-disulfonate.

Exemplary compounds include dodecyl 2-(dimethylamino)propanoate 4-methylbenzenesulfonate, dodecyl 2-(dimethylamino)propanoate sulfate, dodecyl 2-(dimethylamino)propanoate 2-hydroxypropane-1,2,3-tricarboxylate, dodecyl 2-(dimethylamino)propanoate phosphate, dodecyl 2-(dimethylamino)propanoate benzenesulfonate, dodecyl 2-(dimethylamino)propanoate maleate, dodecyl 2-(dimethylamino)propanoate methanesulfonate, dodecyl 2-(dimethylamino)propanoate ethanesulfonate, dodecyl 2-(dimethylamino)propanoate heminaphthalene-1,5-disulfonate, dodecyl 2-(dimethylamino)propanoate 2-hydroxyethanesulfonate, dodecyl 2-(dimethylamino)-3-hydroxybutanoate hydrochloride, dodecyl 2-(dimethylamino)acetate hydrochloride, dodecyl 2-(dimethylamino)-3-methylbutanoate hydrochloride, dodecyl 2-(dimethylamino)-3-phenylpropanoate hydrochloride, dodecyl 2-(dimethylamino)-4-methylpentanoate hydrochloride, D-dodecyl 2-(dimethylamino)propanoate hydrochloride, L-dodecyl 2-(dimethylamino)propanoate hydrochloride, dodecyl 2-(dimethylamino)-2-methylpropanoate hydrochloride, dodecyl 2-(methylamino)propanoate hydrochloride, dodecyl 2-(isopropylamino)propanoate hydrochloride, dodecyl 2-((2-hydroxyethyl)amino)propanoate hydrochloride, dodecyl 2-((2-(diethylamino)ethyl)amino)propanoate dihydrochloride, tridecan-2-yl 2-(dimethylamino)propanoate hydrochloride, 2-methyltridecan-2-yl 2-(dimethylamino)propanoate hydrochloride, tetradecyl 2-(dimethylamino)propanoate hydrochloride, undecyl 2-(dimethylamino)propanoate hydrochloride, decyl 2-(dimethylamino)propanoate hydrochloride, tridecyl 2-(dimethylamino)propanoate hydrochloride, octyl 2-(dimethylamino)propanoate hydrochloride, and tridecan-2-yl 2-(dimethylamino)-2-methylpropanoate.

In certain embodiments, the compound is selected from the group consisting of dodecyl 2-(methylamino)propanoate hydrochloride, dodecyl 2-(isopropylamino)propanoate hydrochloride, dodecyl 2-((2-hydroxyethyl)amino)propanoate hydrochloride, and dodecyl 2-((2-(diethylamino)ethyl)amino)propanoate dihydrochloride.

In certain embodiments, the compound is selected from the group consisting of

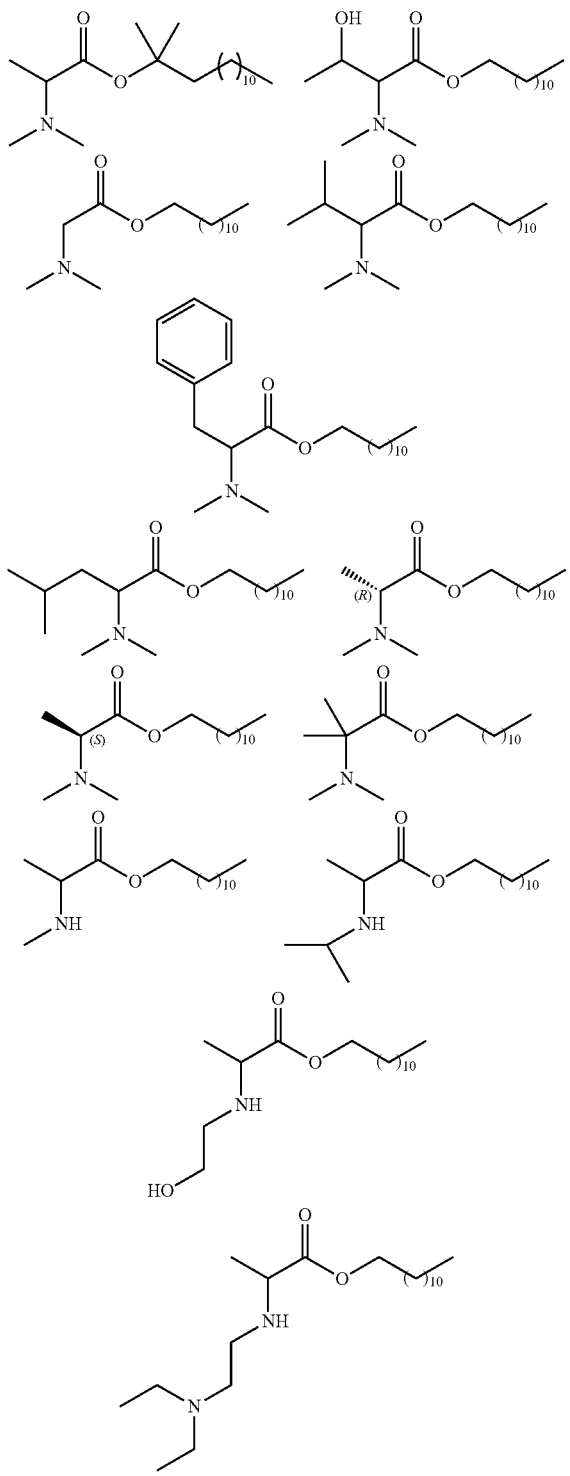

-continued

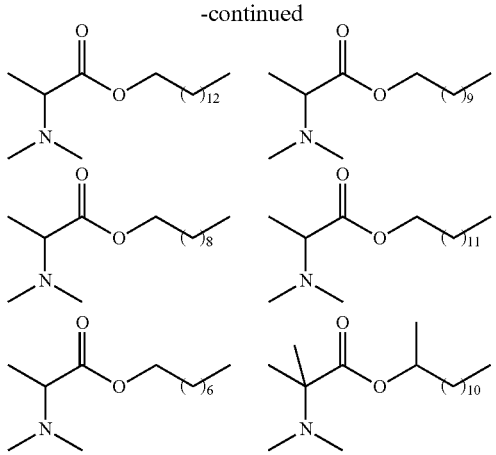

and pharmaceutically acceptable salts thereof.

In other aspects, a method of inhibiting the growth of a microorganism is provided, comprising the steps of providing an effective amount of the compound of formula I

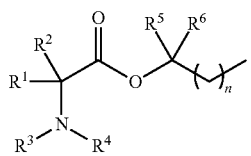

I where n is an integer from 6-12 inclusive; $R^1$, and $R^2$, are the same or different and are selected independently from the group consisting of H, substituted or unsubstituted, straight or branched chain $C_1$-$C_{10}$ alkyl, $CH_3$, $CHOHCH_3$, $CH(CH_3)_2$, $CH_2C_6H_6$, and $CH_2CH(CH_3)_2$; $R^3$, and $R^4$, are the same or different and are selected independently from the group consisting of H, substituted or unsubstituted, straight or branched chain $C_1$-$C_{10}$ alkyl, $C_6$-$C_{10}$ aryl or $C_6$-$C_{10}$ heteroaryl, $CH_3$, $CH(CH_3)_2$, $CH_2CHOH$, $CH_2CH(CH_3)_2$, and $(CH_2)_2N(CH_2CH_3)_2$; $R^5$, and $R^6$, are the same or different and are selected independently from the group consisting of H and $CH_3$ and pharmaceutically acceptable salts thereof. In certain embodiments, the compound of Formula I is configured wherein $R^1$ is H and $R^2$ is selected from the group consisting of $CHOHCH_3$, $CH(CH_3)_2$, $CH_2C_6H_6$, and $CH_2CH(CH_3)_2$. Typically, the microorganism is a member of a genus selected from the group consisting of *Acinetobacter, Bacillus, Enterobacter, Enterococcus, Escherichia, Klebsiella, Corynebacterium, Haemophilus, Proteus, Pseudomonas, Serratia, Staphylococcus, Streptococcus, Aspergillus*, and *Candida*.

In other aspects, a disinfectant composition is provided, comprising an effective amount of the compound of formula I

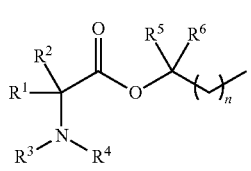

I where n is an integer from 6-12 inclusive; $R^1$, and $R^2$, are the same or different and are selected independently from the group consisting of H, substituted or unsubstituted, straight or branched chain $C_1$-$C_{10}$ alkyl, $CH_3$, $CHOHCH_3$, $CH(CH_3)_2$, $CH_2CH_6$, and $CH_2CH(CH_3)_2$; $R^3$, and $R^4$, are the same or different and are selected independently from the group consisting of H, substituted or unsubstituted, straight or branched chain $C_1$-$C_{10}$ alkyl, $C_6$-$C_{10}$ aryl or $C_6$-$C_{10}$ heteroaryl, $CH_3$, $CH(CH_3)_2$, $CH_2CHOH$, $CH_2CH(CH_3)_2$, and $(CH_2)_2N(CH_2CH_3)_2$; $R^5$, and $R^6$, are the same or different and are selected independently from the group consisting of H and $CH_3$, and pharmaceutically acceptable salts thereof. In certain embodiments, the compound of Formula I is configured wherein $R^1$ is H and $R^2$ is selected from the group consisting of $CHOHCH3$, $CH(CH_3)_2$, $CH_2C_6H_6$, and $CH_2CH(CH_3)_2$, and contacting the microorganism with the compound. Also provided is a method of sanitizing a surface comprising treating the surface with such a disinfectant composition.

In other aspects, a surface having a coating of an antimicrobially effective amount of the compound of formula I

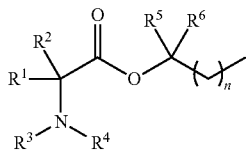

I where n is an integer from 6-12 inclusive; $R^1$, and $R^2$, are the same or different and are selected independently from the group consisting of 1H, substituted or unsubstituted, straight or branched chain $C_1$-$C_{10}$ alkyl, $CH_3$, $CHOHCH_3$, $CH(CH_3)_2$, $CH_2C_6H_6$, and $CH_2CH(CH_3)_2$; $R^3$, and $R^4$, are the same or different and are selected independently from the group consisting of H, substituted or unsubstituted, straight or branched chain $C_1$-$C_{10}$ alkyl, $C_6$-$C_{10}$ aryl or $C_6$-$C_{10}$ heteroaryl, $CH_3$, $CH(CH_3)_2$, $CH_2CHOH$, $CH_2CH(CH_3)_2$, and $(CH_2)_2N(CH_2CH_3)_2$; $R^5$, and $R^6$, are the same or different and are selected independently from the group consisting of H and $CH_3$, and pharmaceutically acceptable salts thereof. In certain embodiments, the compound of Formula I is configured wherein $R^1$ is H and $R^2$ is selected from the group consisting of $CHOHCH_3$, $CH(CH_3)_2$, $CH_2C_6H_6$, and $CH_2CH(CH_3)_2$. The surface can be that of a bandage or a surgical instrument.

The above described and other features are exemplified by the following figures and detailed description.

BRIEF DESCRIPTION OF THE DRAWINGS

The foregoing and other features and advantages will be apparent from the following more particular description of exemplary embodiments of the disclosure, as illustrated in the accompanying drawings, in which like reference characters refer to the same parts throughout the different views. The drawings are not necessarily to scale, emphasis instead being placed upon illustrating the principles of the disclosure.

DETAILED DESCRIPTION OF PREFERRED EMBODIMENTS

Figure 1A:
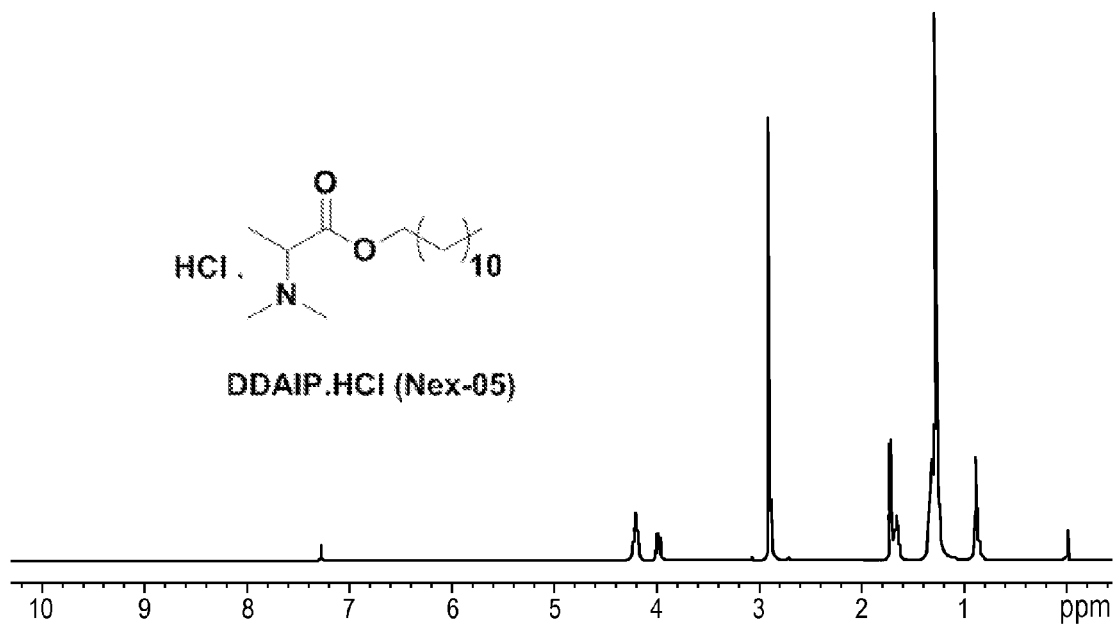
FIG. 1A is a $^1$H-NMR spectrum (400 MHz, $CDCl_3$) of dodecyl 2-(dimethylamino)propanoate hydrochloride (Nex-05).

As used herein and in the appended claims, the singular forms a, an, and the include plural referents unless the context clearly dictates otherwise. Thus, for example, reference to bacteria includes a plurality of bacteria species. Unless defined otherwise, all technical and scientific terms used herein have the same meaning as commonly understood to one of ordinary skill in the art to which this disclosure belongs. Although any methods, devices and materials similar or equivalent to those described herein can be used in the practice or testing of the invention, the preferred methods, devices and materials are now described.

Where the compounds according to the invention have at least one asymmetric center, they may accordingly exist as enantiomers. Where the compounds according to the invention possess two or more asymmetric centers, they may additionally exist as diastereoisomers. It is to be understood that all such isomers and mixtures thereof in any proportion are encompassed within the scope of the present invention. The examples of the use of stereroisomeric compounds in the practice of the present invention disclosed herein are illustrative examples, and are not limiting.

Practice of the embodiments of the invention also involves pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. It is also envisioned that the compounds of the present invention may be incorporated into transdermal patches designed to deliver the appropriate amount of the drug in a continuous fashion. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium caboxymethylcellulose, methylcellulose, polyvinylpyrrolidone or gelatin.

Additional ingredients such as coloring agents, anti-microbial preservatives, emulsifiers, perfumes, active ingredient stabilizers, and the like may be included in the compositions as long as the resulting composition retains desirable properties, as described above. When present, preservatives are usually added in amounts of about 0.05 to about 0.30%. Suitable preservatives include methylparabens (methyl PABA), propylparabens (propyl PABA) and butylhydroxy toluene (BHT). Suitable perfumes and fragrances are known in the art; a suitable fragrance is up to about 5 percent myrtenol, preferably about 2 percent myrtenol, based on the total weight of the composition.

The term "antimicrobial" refers to an ability to prevent, resist, kill, or inhibit the growth of microorganisms (including, without limitation, viruses, bacteria, yeast, fungi, protozoa, etc.), or to attenuate the severity of a microbial infection. The antimicrobial compounds of the present invention are compounds that may be used in the treatment of disease and infection or preservation of an uninfected surface.

The term "active antimicrobial agent" as used herein, refers to compounds with known activity for the treatment of disease caused by microbes, and in particular agents that are effective in sublingual, intraocular, intraaural, and particularly topical, application.

The term "active pharmaceutical ingredient" means any substance or mixture of substances intended to be used in the manufacture of a drug (medicinal) product and that when used in the production of a drug becomes an active ingredient of the drug product. Such substances are intended to furnish pharmacological activity or other direct effect in the diagnosis, cure, mitigation, treatment or prevention of disease or to effect the structure and function of the body.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease (or infection) and/or adverse effect attributable to the disease (or infection). The terms "treatment", "treating" and the like as used herein includes:

(a) preventing a microbial disease and/or infection from occurring in a subject who may be predisposed to but has not yet been diagnosed as having it;

(b) inhibiting the progress or transmission of a microbial disease and/or infection, i.e., arresting its development or maintenance; or (c) relieving a bacterial disease (i.e., causing regression and/or amelioration of the disease) and/or infection.

Bactericidal and/or bacteriostatic activity of the disclosed compositions including compounds of the invention may be measured using any number of methods available to those skilled in the art. One example of such a method is measurement of antibacterial activity through use of a MIC (minimal inhibitory concentration) test that is recognized to be predictive of in vivo efficacy for the treatment of a bacterial infection with antibiotics. In preferred embodiments, the disclosed compositions display antibacterial activity in this test, even without pretreatment of the bacteria to permeabilize the membrane.

In preferred embodiments, the present invention provides methods of inhibiting the growth of microorganisms by contacting the microorganisms with compositions of the invention in which the active agent is disclosed antimicrobial compound. These methods are effective against infections in vivo, and particularly topical infections. This is demonstrated by test data showing the minimum inhibitory concentrations (MIC) and time kill studies of compositions against various pathogenic organisms cultured in vitro under standard conditions. These in vitro tests strongly correlate with in vivo activity, as is evidenced by the widespread use of the MIC determinations to predict utility of antimicrobial compositions in treatment of infection in animals, including humans.

Compositions of the invention may be provided as topical disinfectants for sterilization of surfaces such as countertops, surgical instruments, bandages, patches, medical devices, and skin; as pharmaceutical compositions, including by way of example creams, lotions, ointments, gels, sprays, or solutions for external application to skin and mucosal surfaces, including the cornea, dermal cuts and abrasions, burns, and sites of bacterial or fungal infection; as pharmaceutical compositions, including by way of example creams, lotions, ointments, emulsions, liposome dispersions, gaseous suspension of fine solid or liquid particles, or formulations, suppositories, or solutions, for administration to internal mucosal surfaces such as the oral cavity or vagina to inhibit the growth of bacteria or fungi, including yeasts; and as pharmaceutical compositions such as creams, gels, or ointments for coating indwelling catheters and similar implants which are susceptible to harboring bacterial or fungal infection.

Particular formulations may be manufactured according to methods well known in the art. Formulations are given in, for example, Remington's The Science and Practice of Pharmacy and similar reference works.

In certain embodiments, the disclosed antimicrobial compounds are useful as stabilizing and/or preservative compounds in topical antibiotic compositions, both prescription (e.g., benzomycin creams) and over-the-counter (e.g., anti-acne medications containing salicylic acid, benzoyl peroxide and the like.) When used in the therapeutic treatment of disease, an appropriate dosage of a composition containing the disclosed antimicrobial compounds of the invention and an active ingredient may be determined by any of several well established methodologies. For instance, animal studies are commonly used to determine the maximal tolerable dose, or MTD, of bioactive agent per kilogram weight. In general, at least one of the animal species tested is mammalian. Those skilled in the art regularly extrapolate doses for efficacy and avoiding toxicity to other species, including human. Additionally, therapeutic dosages may also be altered depending upon factors such as the severity of infection, and the size or species of the host.

Where the therapeutic use of the presently described antimicrobial compositions is contemplated, the compositions are preferably administered in a pharmaceutically acceptable topical carrier. Besides the pharmaceutically acceptable topical carrier, the composition of the invention can also comprise additives, such as stabilizers, excipients, buffers and preservatives, Typically, but not necessarily, the preferred formulation for a given antimicrobial composition is dependant on the location in a host where a given infectious organism would be expected to initially invade, or where a given infectious organism would be expected to colonize or concentrate. For example, topical infections are preferably treated or prevented by formulations designed for application to specific body surfaces, e.g., skin, mucous membranes, etc. In such an embodiment, the composition containing the antimicrobial compound is formulated in a water, ethanol, and propylene glycol base for topical administration. Alternatively, where the targeted pathogen colonizes nasal passages, compositions suitable for intranasal administration can be formulated. For such a targeted pathogen colony, a buccal spray may be a preferred method of delivery.

Preferably, animal subjects that may be treated using the compositions of the present invention include, but are not limited to, invertebrates, vertebrates, birds, mammals such as pigs, goats, sheep, cows, dogs, cats, and particularly humans. The presently described compositions are also contemplated to be effective in combating bacterial contamination of laboratory cultures, consumables (food or beverage preparations), medical devices, hospital apparatus, or industrial processes.

Given that bacterial and fungal infections are particularly problematic in immuno-compromised individuals, such as patients suffering from acquired immunodeficiency disease syndrome (AIDS), HIV-infected individuals, patients undergoing chemotherapy or radiation therapy, or bone marrow transplantation, etc., an additional embodiment of the presently described invention is the use of the presently described antimicrobial compounds as prophylactic agents to prevent and/or treat infection in immuno-compromised patients.

Examples of bacterial organisms against which the methods and compositions of the invention are effective include gram positive bacteria, gram negative bacteria, and acid fast bacteria, and particularly, *Staphylococcus aureus, Streptococcus pyogenes, Streptococcus pneumoniae* and *Escherichia coli*.

A range of fungi or moulds, called dermatophytes, cause fungal infections of the skin. These fungi are parasites on the skin and cause different symptoms in different parts of the body. They are very infectious and are passed from person to person. Although typically these infections are topical, in certain patients (e.g., immunosuppressed patients) they may occur systemically or internally. Vaginal yeast infections are generally caused by *Candida albicans*, which, along with a few types of bacteria, are normally present in relatively small numbers in the vaginal area. Sometimes the yeast multiply rapidly and take over, causing candidiasis or monilia. This is often due to a change in the vaginal environment, injury, sexual transmission, HIV infection, etc. Common environmental disruptions that favor yeast include increased pH, increased heat and moisture, allergic reactions, elevated sugar levels, hormonal fluxes, and reductions in the populations of bacteria that are normally present.

In further embodiments, the disclosed antimicrobial compounds can also be used as adjuncts in conjunction with conventional antimicrobial agents in compositions of the present invention. The added activity of the active ingredients may provide for a more efficacious composition, and can provide multiple mechanisms by which the microbes are targeted.

The structural formulas and characteristics of the antimicrobial compounds are summarized in Table 1, below. Further details of the methods of making and methods of use of these antimicrobial compounds are provided in working Examples 1-35, below.

TABLE 1

| | Code | Name | Structure | Base MW | Salt MW | g | Appear. | Sol. | pH |
|---|---|---|---|---|---|---|---|---|---|
| 1 | Nex-01 | Dodecyl 2-(dimethylamino)propanoate 4-methyl-benzenesulfonate | 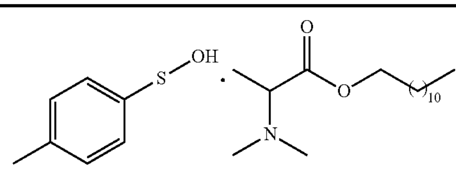 | 285 | 457 | 100 | White powder | 35% | 4.25 |
| 2 | Nex-03 | Dodecyl 2-(dimethylamino)propanoate sulfate | 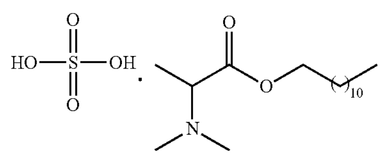 | 285 | 383 | 100 | White powder | 37% | 1.60 |
| 3 | Nex-05 | Dodecyl 2-(dimethylamino)propanoate hydrochloride | 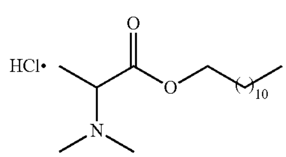 | 285 | 321 | 100 | White powder | 31% | 2.87 |
| 4 | Nex-07 | Dodecyl 2-(dimethylamino)propanoate 2-hydroxypropane-1,2,3-tricarboxylate | 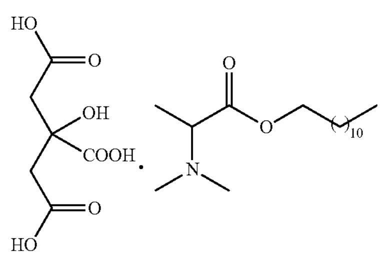 | 285 | 477 | 100 | White powder | 36% | 3.24 |
| 5 | Nex-15 | Dodecyl 2-(dimethylamino)propanoate phosphate | 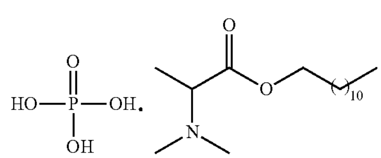 | 285 | 383 | 100 | White paste | 33% | 2.01 |
| 6 | Nex-16 | Dodecyl 2-(dimethylamino)propanoate benzenesulfonate | 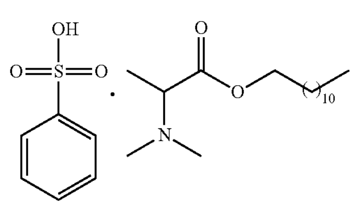 | 285 | 443 | 100 | White powder | 33% | 3.40 |

TABLE 1-continued

| | Code | Name | Structure | Base MW | Salt MW | g | Appear. | Sol. | pH |
|---|---|---|---|---|---|---|---|---|---|
| 7 | Nex-20 | Dodecyl 2-(dimethylamino) propanoate maleate | 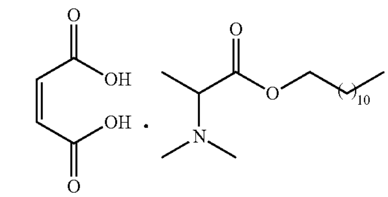 | 285 | 401 | 100 | White powder | 31% | 3.39 |
| 8 | Nex-22 | Dodecyl 2-(dimethylamino) propanoate methanesulfonate | 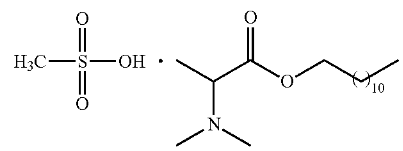 | 285 | 381 | 100 | White powder | 35% | 3.25 |
| 9 | Nex-30 | Dodecyl 2-(dimethylamino) propanoate ethanesulfonate | 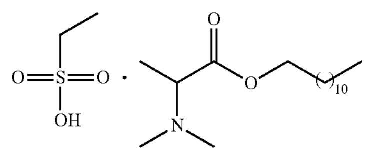 | 285 | 395 | 100 | White powder | 33% | 3.79 |
| 10 | Nex-32 | Dodecyl 2-(dimethylamino) propanoate heminaphthalene-1,5-disulfonate | 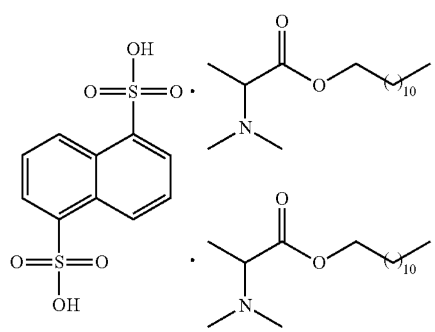 | 285 | 859 | 100 | White powder | 34% | 3.87 |
| 11 | Nex-46 | Dodecyl 2-(dimethylamino) propanoate 2-hydroxyethanesulfonate | 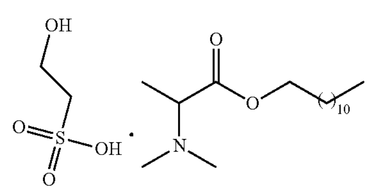 | 285 | 411 | 100 | Waxy solid | 33% | 2.95 |
| 12 | Nex-51 | Dodecyl 2-(dimethylamino)-3-hydroxybutanoate hydrochloride | 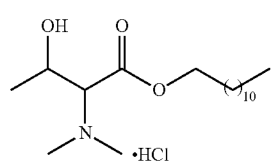 | 315 | 352 | 22 | White jelly thick liquid | 98% | 0.56 |
| 13 | Nex-52 | Dodecyl 2-(dimethylamino) acetate hydrochloride | 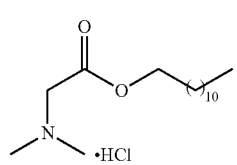 | 271 | 308 | 26 | White solid | 49% | 3.30 |
| 14 | Nex-53 | Dodecyl 2-(dimethylamino)-3-methylbutanoate hydrochloride | 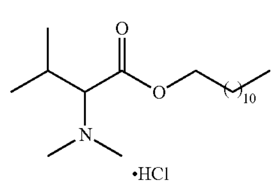 | 314 | 350 | 25 | White solid | 44% | 1.69 |

TABLE 1-continued

| | Code | Name | Structure | Base MW | Salt MW | g | Appear. | Sol. | pH |
|---|---|---|---|---|---|---|---|---|---|
| 15 | Nex-54 | Dodecyl 2-(dimethylamino)-3-phenylpropanoate hydrochloride | 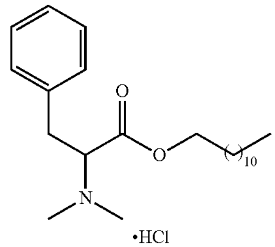 [SMILES: CCCOC(=O)C(Cc1ccccc1)N(C)C ; Cl] | 362 | 398 | 36 | White powder | 58% | 2.16 |
| 16 | Nex-55 | Dodecyl 2-(dimethylamino)-4-methylpentanoate hydrochloride | 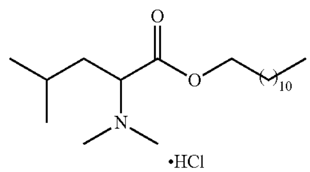 | 328 | 364 | 25 | White solid | 50% | 1.84 |
| 17 | Nex-56 | D-Dodecyl 2-(dimethylamino) propanoate hydrochloride | 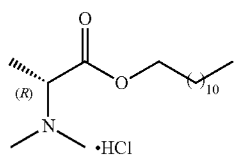 | 285 | 321 | 25 | White powder | 50% | 1.70 |
| 18 | Nex-57 | L-Dodecyl 2-(dimethylamino) propanoate hydrochloride | 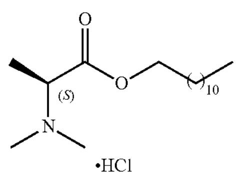 | 285 | 321 | 25 | White solid | 53% | 1.57 |
| 19 | Nex-58 | Dodecyl 2-(dimethylamino)-2-methylpropanoate hydrochloride | 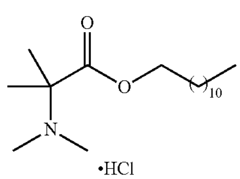 | 299 | 336 | 31 | White solid | 51% | 2.27 |
| 20 | Nex-59 | Dodecyl 2-(methylamino) propanoate hydrochloride | 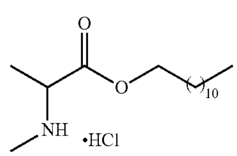 | 271 | 308 | 18 | White powder | 33% | 2.17 |
| 21 | Nex-60 | Dodecyl 2-(isopropylamino) propanoate hydrochloride | 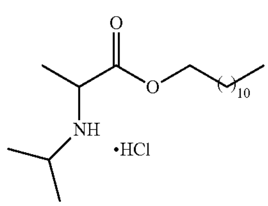 | 299 | 336 | 20 | White solid | 46% | 2.04 |
| 22 | Nex-61 | Dodecyl 2-((2-hydroxyethyl)amino) propanoate hydrochloride | 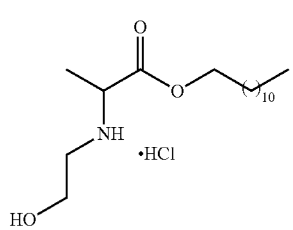 | 301 | 338 | 21 | White solid | 40% | 1.50 |

TABLE 1-continued

| | Code | Name | Structure | Base MW | Salt MW | g | Appear. | Sol. | pH |
|---|---|---|---|---|---|---|---|---|---|
| 23 | Nex-62 | Dodecyl 2-((2-(diethylamino)ethyl) amino) propanoate dihydrochloride | 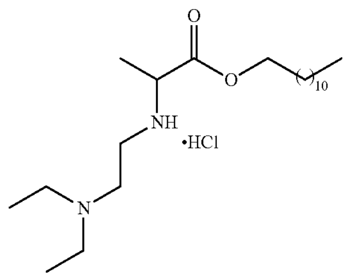 [SMILES: CCCOC(=O)C(C)NCCN(CC)CC ; Cl] | 357 | 430 | 25 | White solid | 48% | 0.73 |
| 24 | Nex-64 | Tridecan-2-yl 2-(dimethylamino) propanoate hydrochloride | 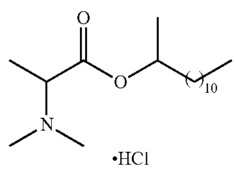 | 299 | 336 | 25 | White powder | 44% | 1.95 |
| 25 | Nex-65 | 2-Methyltridecan-2-yl 2-(dimethylamino) propanoate hydrochloride | 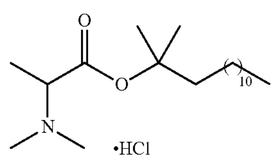 | 314 | 350 | 17 | White powder | 51% | 1.66 |
| 26 | Nex-66 | Tetradecyl 2-(dimethylamino) propanoate hydrochloride | 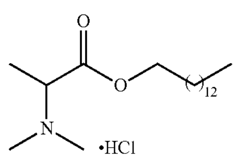 | 314 | 350 | 11 | White powder | 48% | 2.35 |
| 27 | Nex-67 | Undecyl 2-(dimethylamino) propanoate hydrochloride | 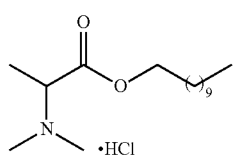 | 271 | 308 | 15 | Waxy solid | 81% | 3.77 |
| 28 | Nex-68 | Decyl 2-(dimethylamino) propanoate hydrochloride | 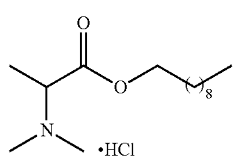 | 257 | 294 | 14 | White powder | 97% | 0.87 |
| 29 | Nex-69 | Tridecyl 2-(dimethylamino) propanoate hydrochloride | 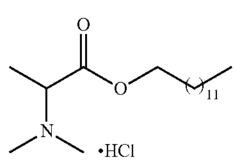 | 299 | 336 | 10 | White powder | 51% | 1.64 |
| 30 | Nex-70 | Octyl 2-(dimethylamino) propanoate hydrochloride | 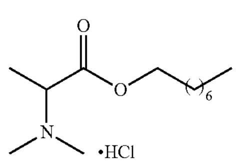 | 229 | 266 | 18 | Waxy solid | 134% | 0.88 |

TABLE 1-continued

| Code | Name | Structure | Base MW | Salt MW | g | Appear. | Sol. | pH |
|---|---|---|---|---|---|---|---|---|
| 31 | Nex-71 | Tridecan-2-yl 2-(dimethylamino)-2-methylpropanoate | | 314 | N/A | 13 | Waxy solid | N/A | N/A |

WORKING EXAMPLES

The following non-limiting examples further illustrate the various embodiments described herein. Example 1 provides a method of synthesizing dodecyl 2-(dimethylamino)propanoate (DDAIP) and dodecyl 2-(dimethylamino)propanoate hydrochloride salt. Examples 2-12 disclose methods of synthesizing other salts of DDAIP. The salts of DDAIP that were prepared include the sulfate, the phosphate, and organic salts including the 4-methylbenzenesulfonate, the 2-hydroxypropane-1,2,3-tricarboxylate, benzenesulfonate, the maleate, the methanesulfonate, the ethanesulfonate, the heminaphtalene-1,5-disulfonate, and the 2-hydroxyethanesulfonate. Examples 13-32 describe the methods of making and the characterization of related compounds and their hydrochloride salts. In view of the teachings of Examples 2-12 and the knowledge of the skilled artisan, the production of salts disclosed herein, as well as other salts, of the antimicrobial compounds is routine.

Example 1

Synthesis of Dodecyl 2-(dimethylamino)propanoate and Dodecyl 2-(dimethylamino)propanoate Hydrochloride salt

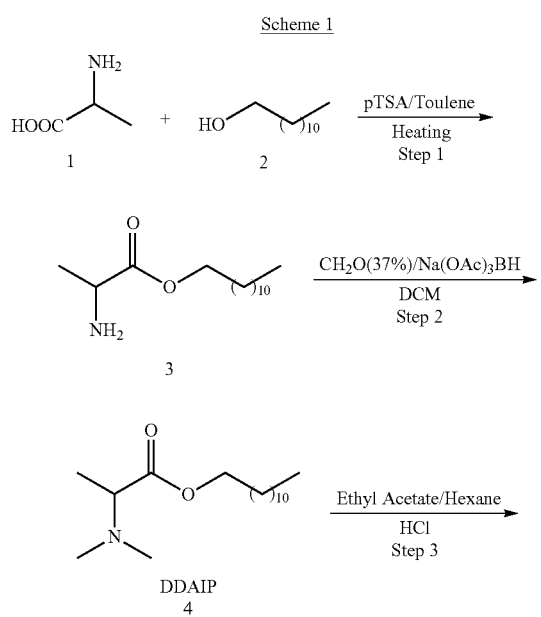

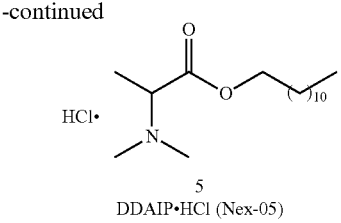

DDAIP·HCl (Nex-05)

Synthesis of Dodecyl 2-aminopropanoate (3)

To a stirred solution of DL-alanine 1 (5 g, 56.1 mmol) in toluene (100 mL) was added dodecanol 2 (9.42 g, 50.5 mmol) in one lot, followed by pTSA (11.75 g, 61.7 mmol). After addition, the temperature of the reaction mixture was slowly raised to reflux temperature, the water was separated azeotropically, and the reaction mixture was monitored by TLC. The reaction mixture was concentrated under vacuum, the obtained residue was taken in ethyl acetate (200 mL) and washed with aqueous 5% $Na_2CO_3$ (3×50 mL) followed by brine solution. The organic layer was dried over $Na_2SO_4$ and concentrated under vacuum to afford crude dodecyl 2-aminopropanoate 3 (14.4 g, yield: 100%) as a liquid.

Synthesis of Dodecyl 2-(dimethylamino) Propanoate (DDAIP) (4)

To a stirred solution of dodecyl 2-aminopropanoate 3 (5 g, 19.4 mmol) in DCM (100 mL) was added aqueous formaldehyde solution (37% w/v) (2.03 g, 67.9 mmol) in one lot at 0° C. and slowly added $Na(OAc)_3BH$ (10.29 g, 48.5 mmol) over a period of ½ h. After addition, the temperature of the reaction mixture was slowly raised to room temperature (RT), stirred at RT for 24 h; the reaction mixture was monitored by TLC. The reaction mixture was quenched with ice-cold water, the organic layer was separated and the aqueous layer was extracted with DCM (2×40 mL). The combined organic layers were washed with brine solution. The organic layer was dried over $Na_2SO_4$ and concentrated under vacuum to afford dodecyl 2-(dimethylamino)propanoate (DDAIP) 4 (4.2 g, yield: 75.9%) as a liquid.

Synthesis of Dodecyl 2-(dimethylamino)propanoate Hydrochloride (5, Nex-05)

A stirred solution of dodecyl 2-(dimethylamino)propanoate 4 (5 g, 17.54 mmol) in ethyl acetate/hexane/MeOH (10:10:1 mL) was cooled to 0° C. The reaction mixture was purged with dry HCl gas for 30 minutes, and the reaction mixture was monitored by TLC. The reaction mixture was concentrated under vacuum, and the obtained residue was flushed with ethyl acetate (3×52 mL) followed by hexane (5×50 mL) to afford wet dodecyl 2-(dimethylamino)propanoate hydrochloride 5 (5.5 g) as a semi solid. The semi solid was taken in ethyl acetate/hexane (10:10 mL) and heated to reflux, and stirred at reflux for 30 minutes. The reaction mixture was slowly cooled to RT and then to 0° C. The obtained solid was filtered under nitrogen and dried under vacuum to afford dodecyl 2-(dimethylamino)propanoate.HCl salt 5 (3 g, yield: 53.5%) as a white hygroscopic solid, mp: 86-92° C.

FIG. 1A is a $^1$H-NMR spectrum (400 MHz, CDCl$_3$) of dodecyl 2-(dimethylamino)propanoate hydrochloride (Nex-05).

Figure 1B:
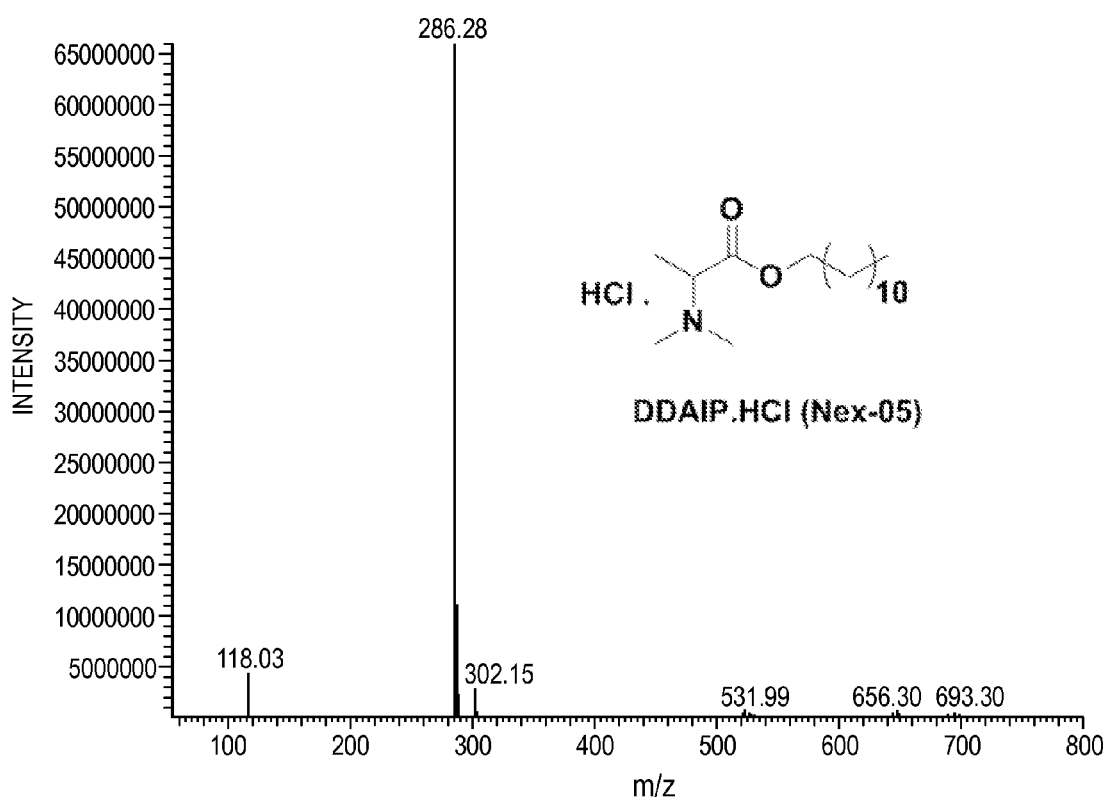
FIG. 1B is a LCMS spectrum: 286 ($M^+$+1) of dodecyl 2-(dimethylamino)propanoate hydrochloride.

FIG. 1B is a LCMS spectrum: 286 (M$^+$+1) of dodecyl 2-(dimethylamino)propanoate hydrochloride.

Figure 1C:
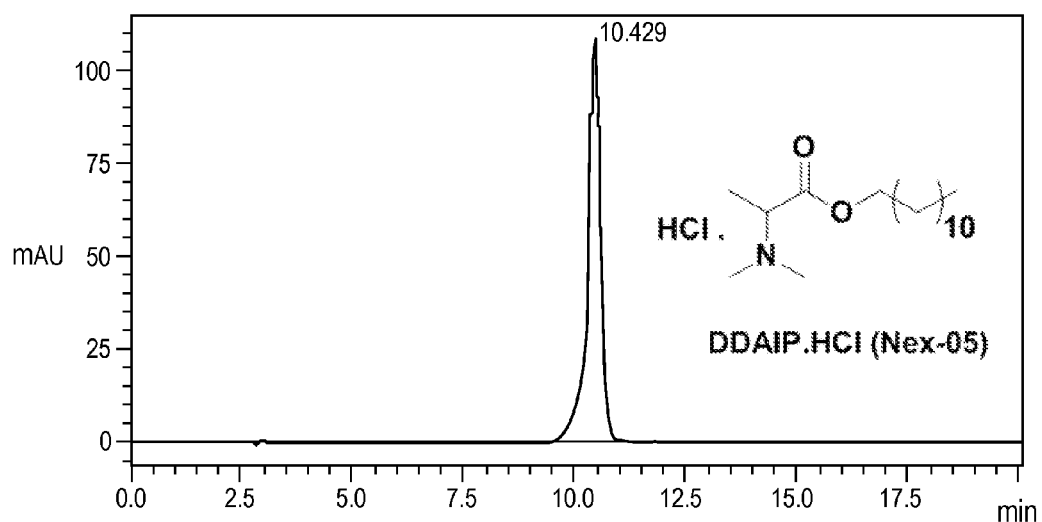
FIG. 1C is a HPLC chromatogram of dodecyl 2-(dimethylamino)propanoate hydrochloride showing a peak area of 100%. Methods: column: Dionex, Acclaim Surfactant (4.6× 250 mm, 5 um); mobile phase: A: 50 mM ammonium bicarbonate (pH-7.0)/B: acetonitrile; injection volume 10 µL, column temperature, 25° C., flow rate 1.0 mL/min, isocratic A:B (30:70).

FIG. 1C is a HPLC chromatogram of dodecyl 2-(dimethylamino)propanoate hydrochloride showing a peak area of 100%. Methods: column: Dionex, Acclaim Surfactant (4.6× 250 mm, 5 um); mobile phase: A: 50 mM ammonium bicarbonate (pH-7.0)/B: acetonitrile; injection volume 10 μL, column temperature, 25° C., flow rate 1.0 mL/min, isocratic A:B (30:70).

Example 2

Synthesis of Dodecyl 2-(dimethylamino)propanoate p-toluene sulfonate salt (Nex-01)

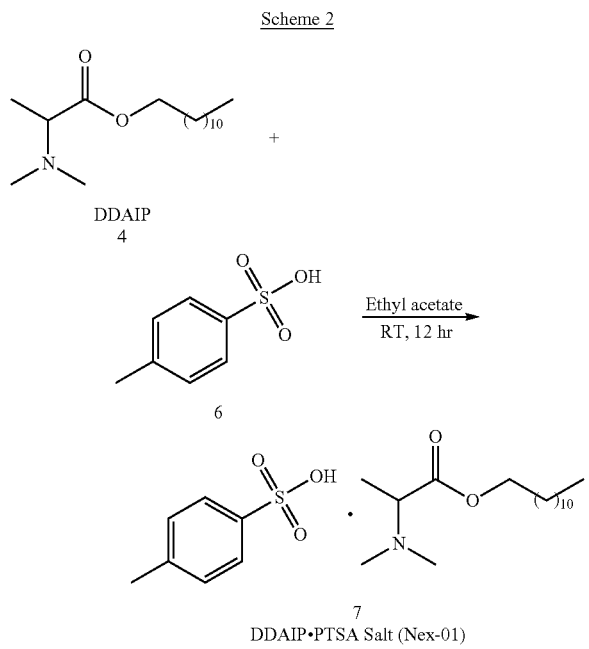

Synthesis of Dodecyl 2-(dimethylamino)propanoate p-toluene sulfonate salt (7, Nex-01)

A stirred solution of DDAIP base 4 (80 g, 280 mmol) in ethyl acetate (500 mL) was cooled to 0° C. then p-toluene sulfonic acid H$_2$O 6 (53.4 g, 280 mmol) was added in one lot. After addition, the temperature of the reaction mixture was slowly raised to RT and stirred at RT for 12 h; the reaction mixture was monitored by TLC. The reaction mixture was concentrated under vacuum and flushed with hexane. The obtained residue was taken in n-hexane (20 mL) and stirred at RT for 2 h (No solid). The obtained sticky solid kept in a deep freezer for 12 h to afford dodecyl 2-(dimethylamino)propanoate PTSA salt (7, Nex-01) (130 g, yield: 97.4%) as a hygroscopic solid, Mp: 60-65° C. $^1$H-NMR (400 MHz, CDCl$_3$): δ 0.9 (t, 3H), 1.3 (m, 18H), 1.6 (d, 3H), 1.6 (q, 2H), 2.35 (s, 3H), 3 (m, 6H), 4.1 (t, 2H), 4.25 (q, 1H), 7.18 (d, 2H), 7.78 (d, 2H); LCMS: 286 (M$^+$+1); HPLC: 80.48%.

Figure 2A:
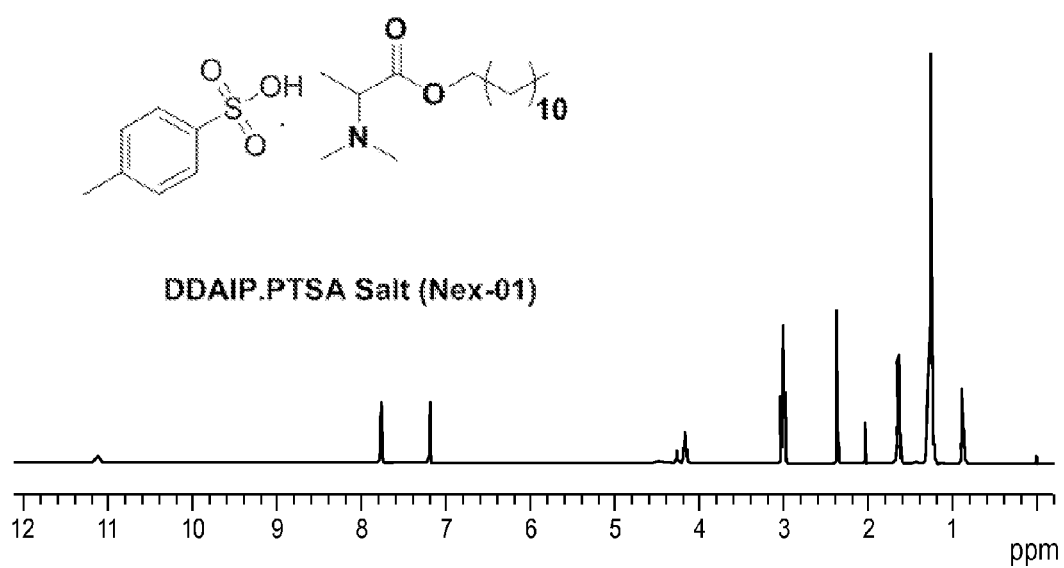
FIG. 2A is a $^1$H-NMR spectrum (400 MHz, CDCl$_3$) of dodecyl 2-(dimethylamino)propanoate p-toluene sulfonate salt (Nex-01).

FIG. 2A is a $^1$H-NMR spectrum (400 MHz, CDCl$_3$) of dodecyl 2-(dimethylamino)propanoate p-toluene sulfonate salt (Nex-01).

Figure 2B:
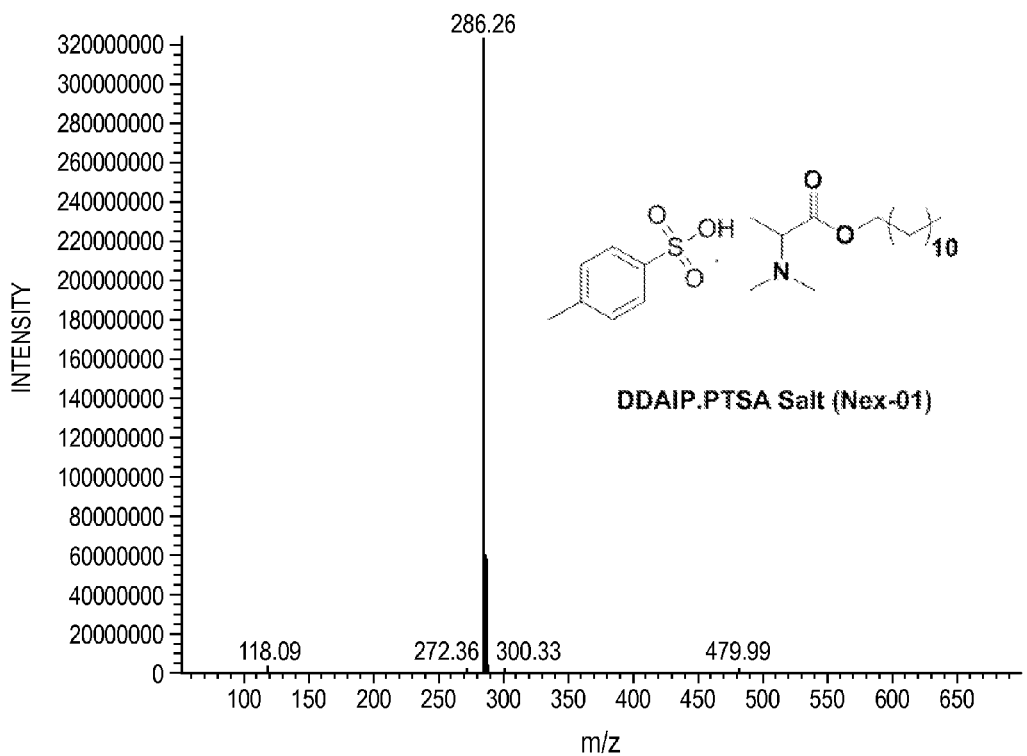
FIG. 2B is a LCMS spectrum: 286 (M$^+$+1) of d dodecyl 2-(dimethylamino)propanoate p-toluene sulfonate salt.

FIG. 2B is a LCMS spectrum: 286 (M$^+$+1) of d dodecyl 2-(dimethylamino)propanoate p-toluene sulfonate salt.

Figure 2C:
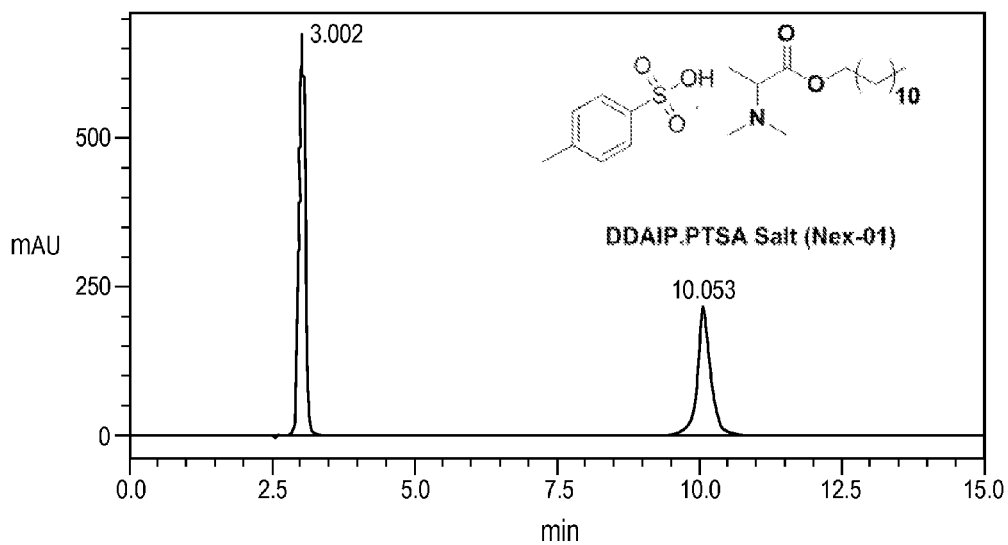
FIG. 2C is a HPLC chromatogram of dodecyl 2-(dimethylamino)propanoate p-toluene sulfonate salt showing a peak area of 80.48%. Methods as in FIG. 1C.

FIG. 2C is a HPLC chromatogram of dodecyl 2-(dimethylamino)propanoate p-toluene sulfonate salt showing a peak area of 80.48%. Methods as in FIG. 1C.

Example 3

Synthesis of Dodecyl 2-(dimethylamino)propanoate sulfonate salt (Nex-03)

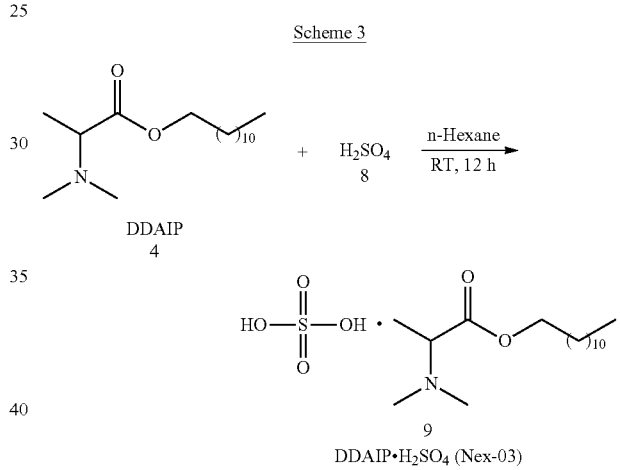

Synthesis of Dodecyl 2-(dimethylamino)propanoate sulfonate salt (9, Nex-03)

A stirred solution of DDAIP base 4 (85 g, 298 mmol) in n-hexane (500 mL) was cooled to 0° C., and then concentrated H$_2$SO$_4$ 7 (29.22 g, 298 mmol) was added drop wise. After addition, the temperature of the reaction mixture was slowly raised to RT and stirred at RT for 12 h; the reaction mixture was monitored by TLC. The reaction mixture was concentrated under vacuum to obtain a sticky solid. The obtained sticky solid kept in deep freezer for 12 h to afford dodecyl 2-(dimethylamino)propanoate sulfonic salt (9, Nex-03) (110 g, yield: 96.4%) as a hygroscopic solid, Mp: 58-63° C. $^1$H-NMR (400 MHz, CDCl$_3$): δ 0.9 (t, 3H), 1.25 (m, 18H), 1.6 (d, 3H), 1.62 (q, 2H), 3.1 (s, 6H), 4.1 (q, 1H), 4.2 (t, 2H); LCMS: 286 (M$^+$+1); HPLC: 98.98%.

Figure 3A:
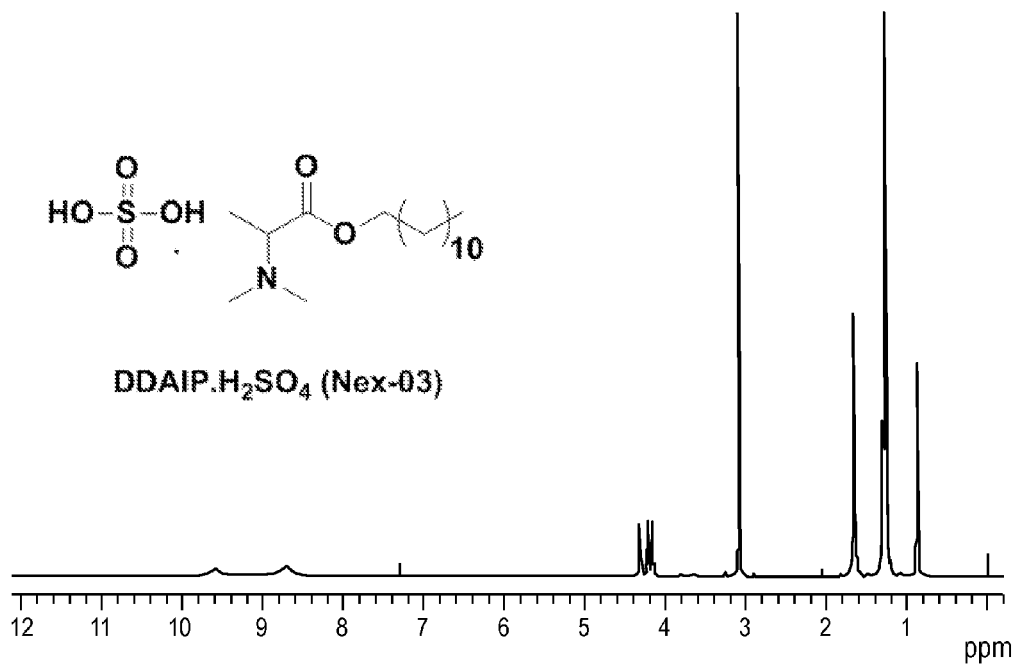
FIG. 3A is a $^1$H-NMR spectrum (400 MHz, CDCl$_3$) of dodecyl 2-(dimethylamino)propanoate sulfonic salt (Nex-03).

FIG. 3A is a $^1$H-NMR spectrum (400 MHz, CDCl$_3$) of dodecyl 2-(dimethylamino)propanoate sulfonic salt (Nex-03).

Figure 3B:
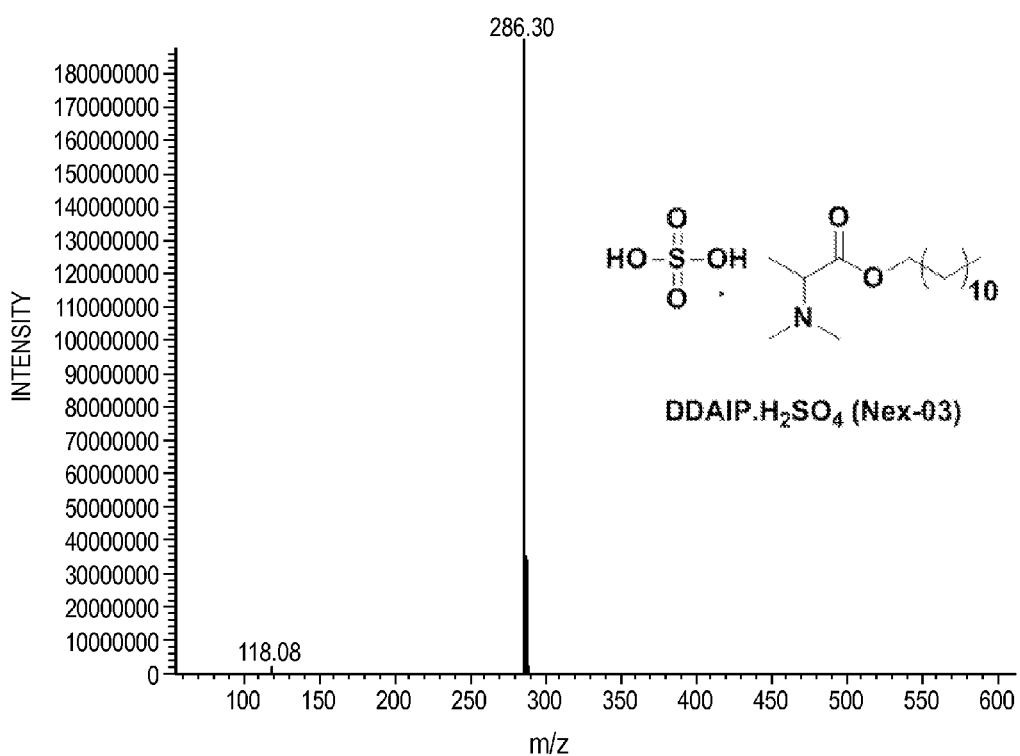
FIG. 3B is a LCMS spectrum: 286 (M$^+$+1) of dodecyl 2-(dimethylamino)propanoate sulfonic salt.

FIG. 3B is a LCMS spectrum: 286 (M$^+$+1) of dodecyl 2-(dimethylamino)propanoate sulfonic salt.

Figure 3C:
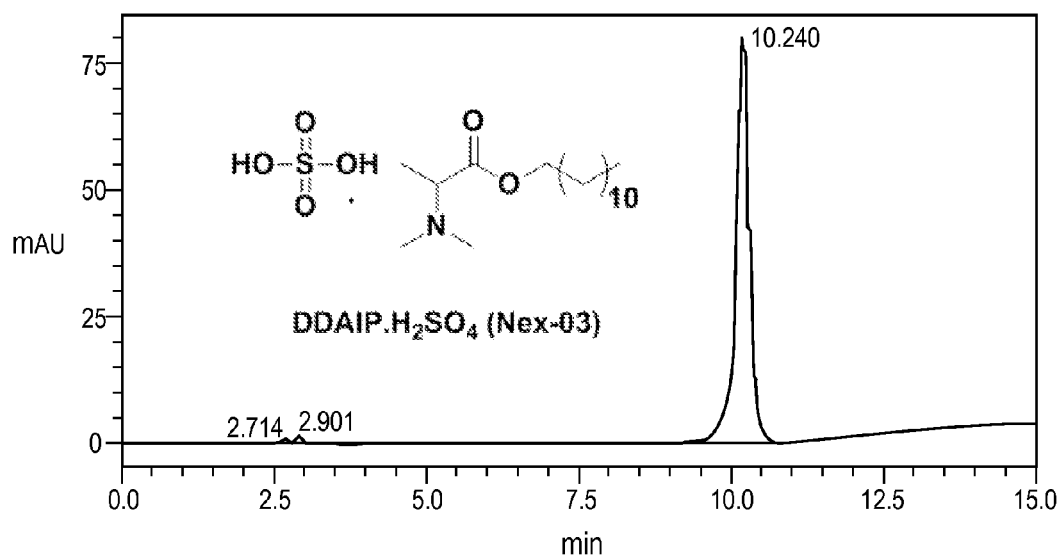
FIG. 3C is a HPLC chromatogram of dodecyl 2-(dimethylamino)propanoate sulfonic salt showing a peak area of 98.98%. Methods as in FIG. 1C.

FIG. 3C is a HPLC chromatogram of dodecyl 2-(dimethylamino)propanoate sulfonic salt showing a peak area of 98.98%. Methods as in FIG. 1C.

Example 4

Synthesis of Dodecyl 2-(dimethylamino)propanoate hydrochloride Salt (Nex-05)

Scheme 4

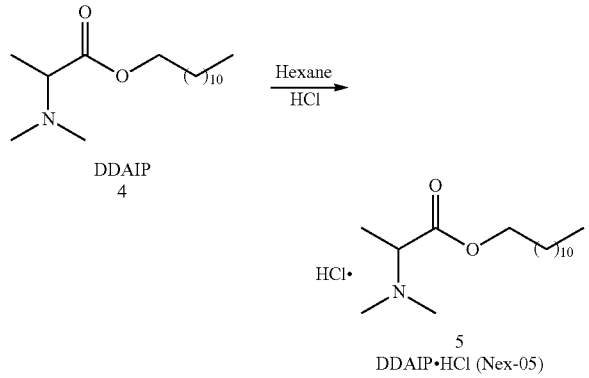

Synthesis of Dodecyl 2-(dimethylamino)propanoate HCl Salt (5, Nex-05)

A stirred solution of DDAIP base 4 (100 g, 350 mmol) in hexane (500 mL) was cooled to 0° C. The reaction mixture was purged with dry HCl gas for 2 h, and the reaction mixture was monitored by TLC. The obtained solid was filtered under vacuum, the obtained semi solid was taken in ethyl acetate/hexane (250/250 mL), heated to reflux, and stirred at reflux for 30 minutes. The reaction mixture was slowly cooled to RT and then to 0° C. The obtained solid was filtered under nitrogen and dried under vacuum to afford dodecyl 2-(dimethylamino)propanoate HCl salt (5, Nex-05) (92 g, yield: 81.56%) as a white hygroscopic solid, mp: 86-92° C. $^1$H-NMR (400 MHz, CDCl$_3$): δ 0.85 (t, 31H), 1.2-1.4 (m, 18H), 1.65 (q, 2H), 1.75 (d, 3H), 2.9 (s, 6H), 3.95 (q, 18), 4.2 (t, 2H); LCMS: 286 (M$^+$+1); HPLC: 100%.

Example 5

Synthesis of Dodecyl 2-(dimethylamino)propanoate citrate Salt (Nex-07)

Scheme 5

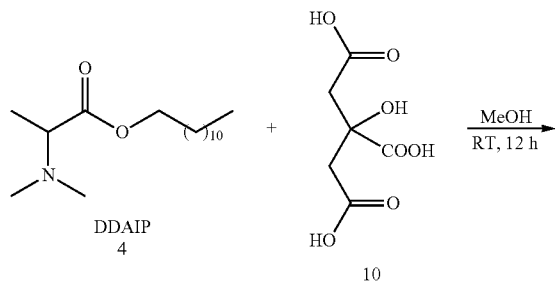

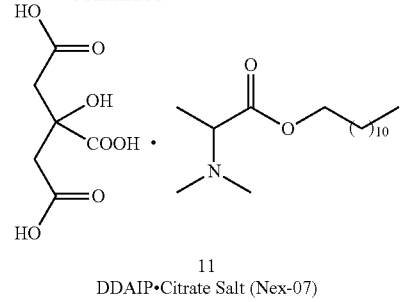

11
DDAIP•Citrate Salt (Nex-07)

Synthesis of Dodecyl 2-(dimethylamino)propanoate citrate salt (11, Nex-07)

A stirred solution of DDAIP base 4 (75 g, 263 mmol) in methanol (600 mL) was cooled to 0° C. then citric acid 8 (50.4 g, 0.263) was added in one lot. After addition, the temperature of the reaction mixture was slowly raised to RT, stirred at RT for 12 h, and the reaction mixture was monitored by TLC. The solvent was concentrated under vacuum. The residue was diluted with n-hexane (100 mL) which was not miscible with the product. Some seeding material was prepared (scratching the crude in a glass vial), and seeded to the crude to afford dodecyl 2-(dimethylamino)propanoate citrate salt (11, Nex-07) (120 g, yield: 95.6%) as a white solid, mp: 62-67° C. $^1$H-NMR (400 MHz, CDCl$_3$): δ 0.85 (t, 3H), 1.3 (m, 18H), 1.5 (d, 3H), 1.7 (q, 2H), 2.7 (m, 2H), 2.9 (s, 6H), 4.1 (q, 1H), 4.2 (t, 2H); LCMS: 286 (M$^+$+1); HPLC: 88%.

Figure 4A:
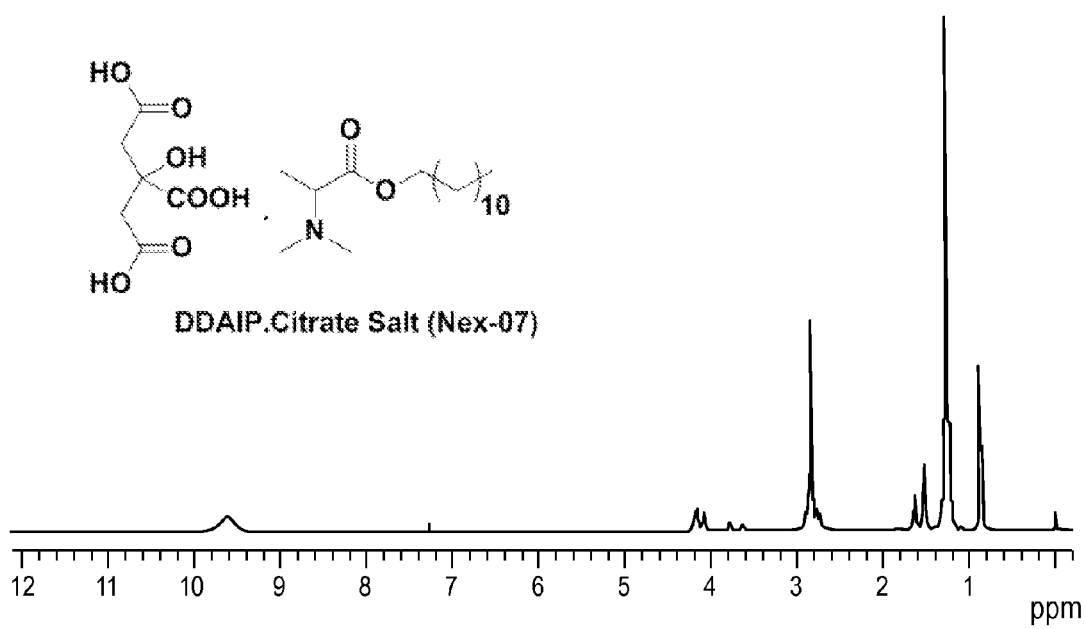
FIG. 4A is a $^1$H-NMR spectrum (400 MHz, CDCl$_3$) of dodecyl 2-(dimethylamino)propanoate citrate salt (Nex-07).

FIG. 4A is a $^1$H-NMR spectrum (400 MHz, CDCl$_3$) of dodecyl 2-(dimethylamino)propanoate citrate salt (Nex-07).

Figure 4B:
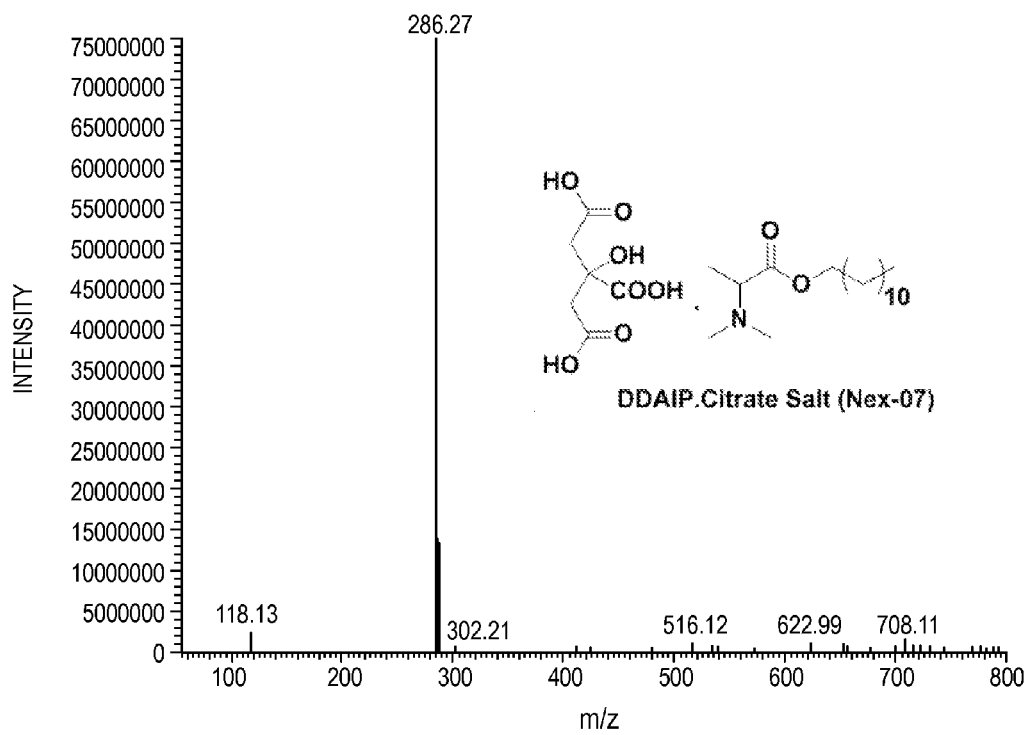
FIG. 4B is a LCMS spectrum: 286 (M$^+$+1) of dodecyl 2-(dimethylamino)propanoate citrate salt.

FIG. 4B is a LCMS spectrum: 286 (M*+1) of dodecyl 2-(dimethylamino)propanoate citrate salt.

Figure 4C:
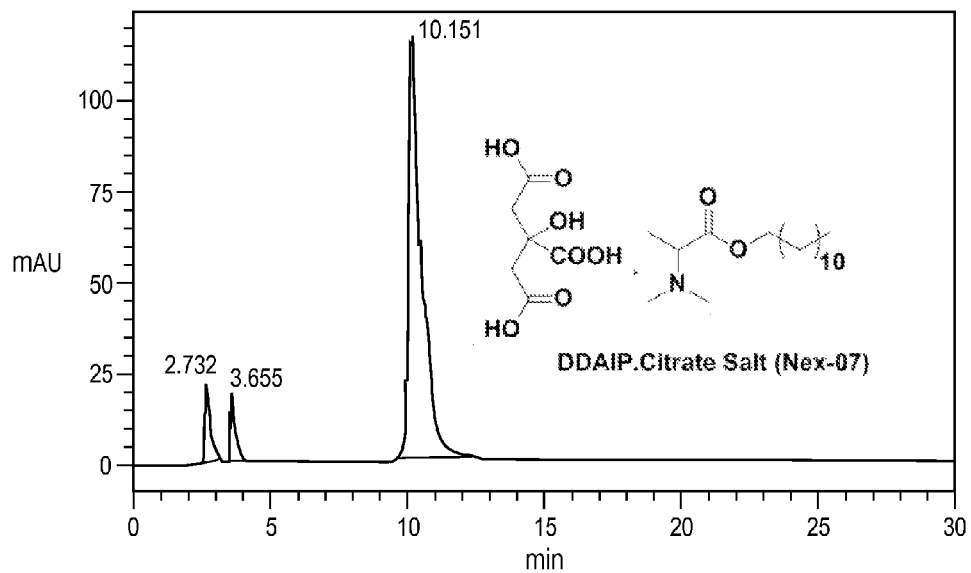
FIG. 4C is a HPLC chromatogram of dodecyl 2-(dimethylamino)propanoate citrate salt showing a peak area of 88%. Methods as in FIG. 1C.

FIG. 4C is a HPLC chromatogram of dodecyl 2-(dimethylamino)propanoate citrate salt showing a peak area of 88%. Methods as in FIG. 1C.

Figure 4D:
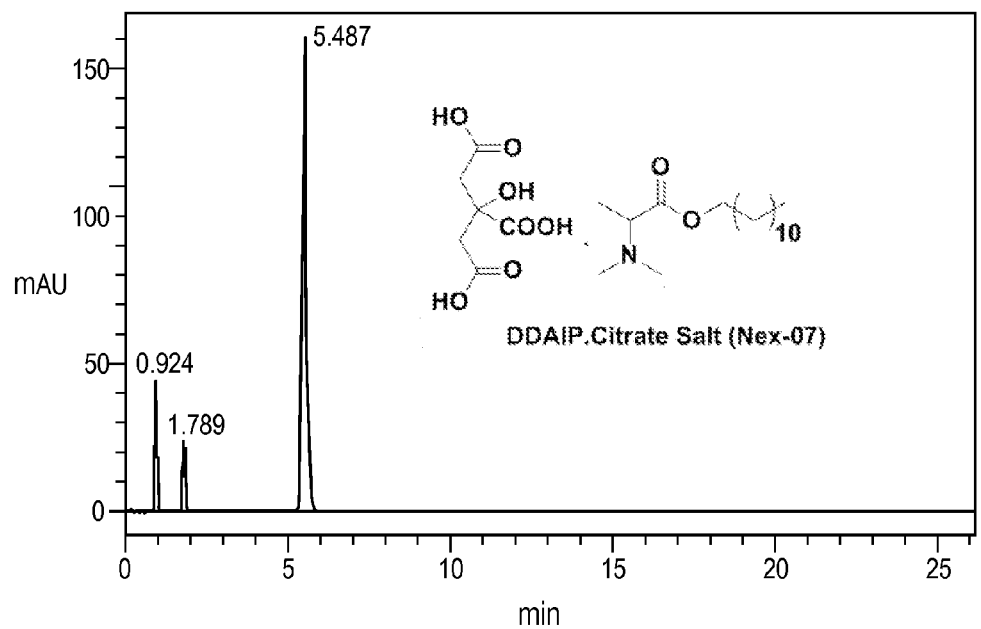
FIG. 4D is a HPLC chromatogram of dodecyl 2-(dimethylamino)propanoate citrate salt showing a peak area of 88%. Methods: column; Zorbax SB Phenyl (150×4.6 mm, 3.5 µm); mobile phase: A: 50 mM ammonium bicarbonate (pH-7.0)/B: acetonitrile; injection volume 10 µL, column temperature, 25° C., flow rate 1.4 ml/min, isocratic A:B (30:70).

FIG. 4D is a HPLC chromatogram of dodecyl 2-(dimethylamino)propanoate citrate salt showing a peak area of 88%. Methods: column: Zorbax SB Phenyl (150×4.6 mm, 3.5 µm); mobile phase: A: 50 mM ammonium bicarbonate (pH-7.0)/B: acetonitrile; injection volume 10 µL, column temperature, 25° C., flow rate 1.4 mL/min, isocratic A:B (30:70).

Example 6

Synthesis of Dodecyl 2-(dimethylamino)propanoate phosphorate Salt (Nex-15)

Scheme 6

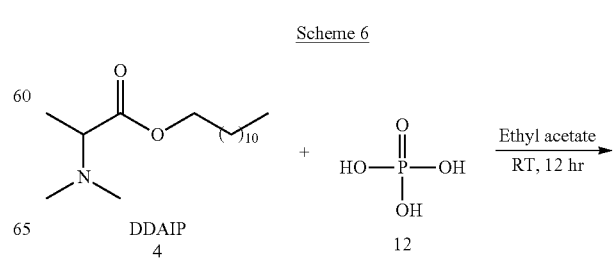

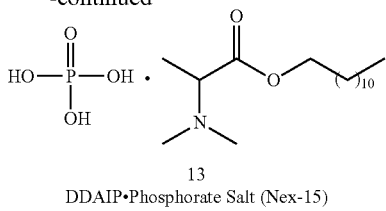

13
DDAIP•Phosphorate Salt (Nex-15)

Synthesis of Dodecyl 2-(dimethylamino)propanoate phosphorate Salt (Nex-15)

A stirred solution of DDAIP base 4 (100 g, 350 mmol) in ethyl acetate (500 mL) was cooled to 0° C. and then phosphoric acid 12 (34.38 g, 350 mmol) was added in one lot. After addition, the temperature of the reaction mixture was slowly raised to RT and stirred at RT for 12 h; the reaction mixture was monitored by TLC. The reaction mixture was concentrated under vacuum. The obtained sticky solid was taken in n-hexane (200 mL) and stirred at RT for 2 h to afford dodecyl 2-(dimethylamino)propanoate phosphorate salt (13, Nex-15) (125 g, 93%) as a sticky solid. $^1$H-NMR (400 MHz, CDCl$_3$): δ 0.85 (t, 3H), 1.2-1.4 (m, 18H), 1.55 (d, 3H), 1.7 (q, 2H), 2.85 (s, 6H), 4.1 (q, 1H), 4.2 (t, 2H); LCMS: 286 (M$^+$+1); HPLC: 95.8%.

Figure 5A:
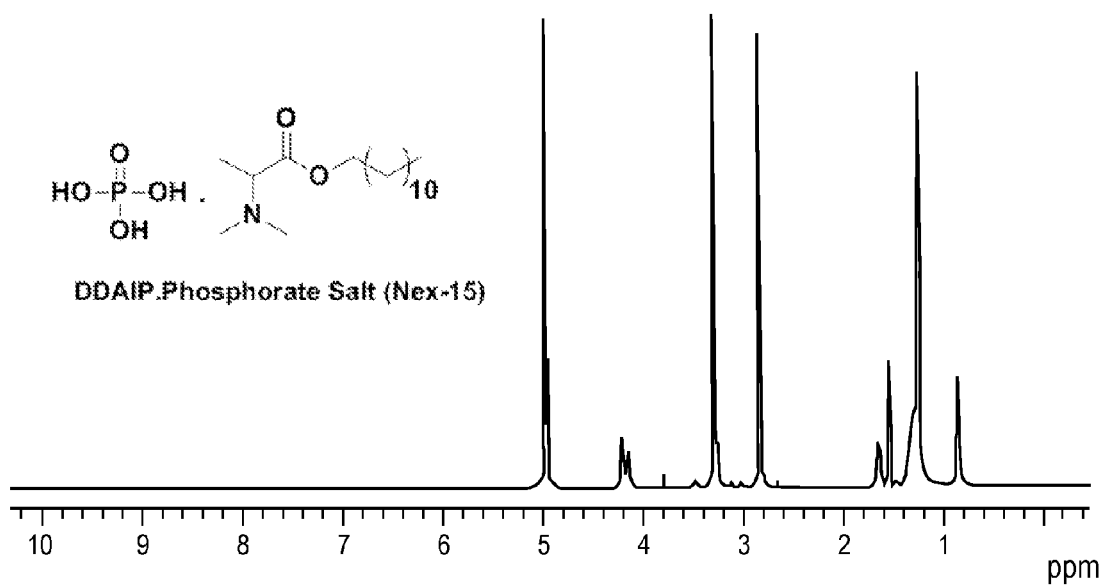
FIG. 5A is a $^1$H-NMR spectrum (400 MHz, CDCl$_3$) of dodecyl 2-(dimethylamino)propanoate phosphorate salt (Nex-15).

FIG. 5A is a $^1$H-NMR spectrum (400 MHz, CDCl$_3$) of dodecyl 2-(dimethylamino)propanoate phosphorate salt (Nex-15).

Figure 5B:
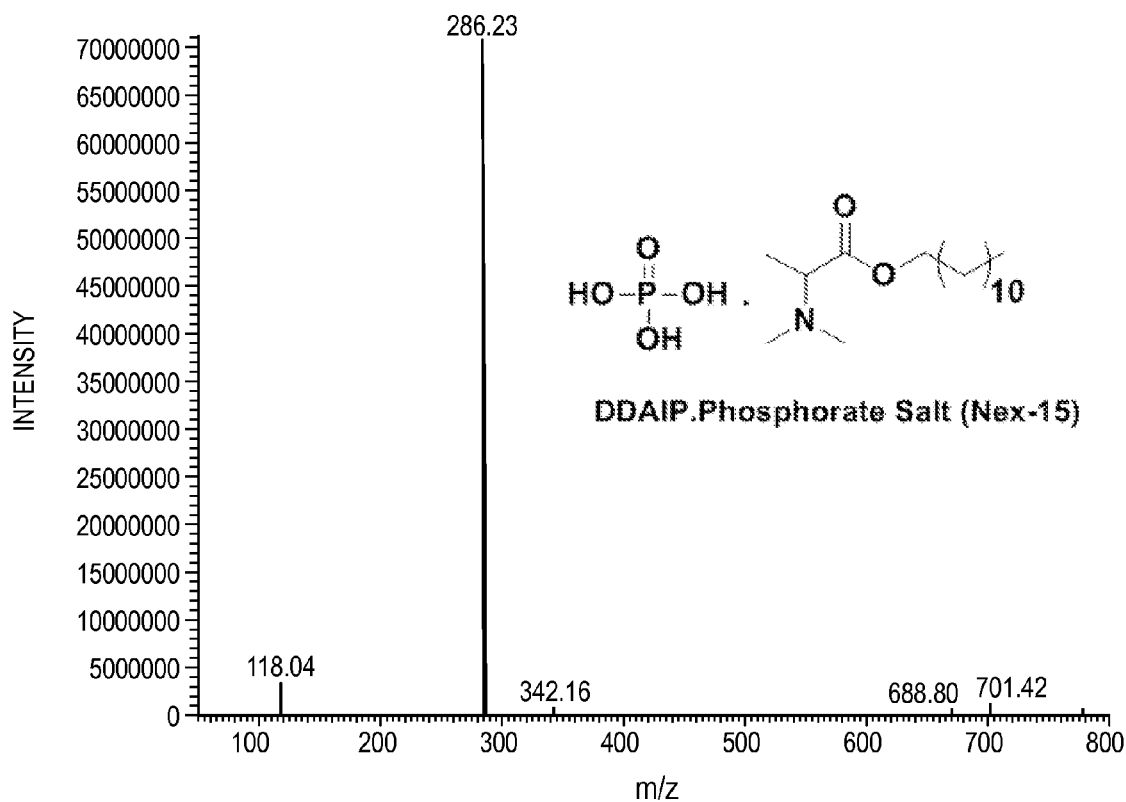
FIG. 5B is a LCMS spectrum: 286 (M$^+$+1) of dodecyl 2-(dimethylamino)propanoate phosphorate salt.

FIG. 5B is a LCMS spectrum: 286 (M$^+$+1) of dodecyl 2-(dimethylamino)propanoate phosphorate salt.

Figure 5C:
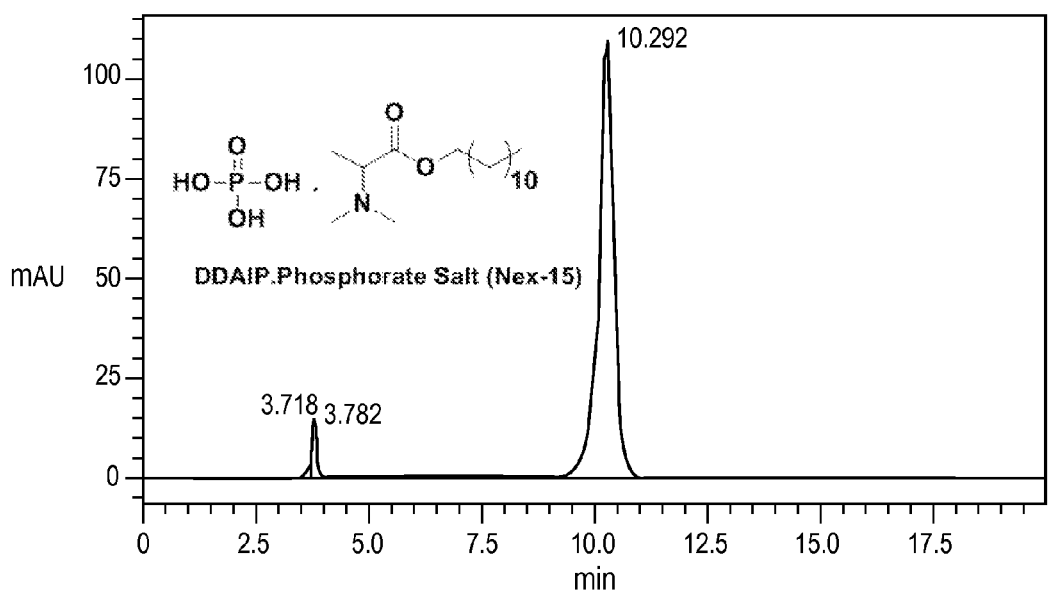
FIG. 5C is a HPLC chromatogram of dodecyl 2-(dimethylamino)propanoate phosphorate salt showing a peak area of 95.8%. Methods as in FIG. 1C.

FIG. 5C is a HPLC chromatogram of dodecyl 2-(dimethylamino)propanoate phosphorate salt showing a peak area of 95.8%. Methods as in FIG. 1C.

Example 7

Synthesis of Dodecyl 2-(dimethylamino)propanoate benzene sulfonate Salt (Nex-16)

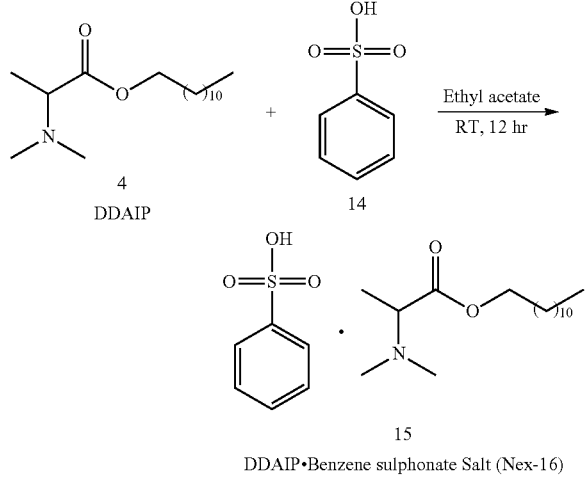

Scheme 7

4
DDAIP

14

15
DDAIP•Benzene sulphonate Salt (Nex-16)

Synthesis of Dodecyl 2-(dimethylamino)propanoate Benzene sulfonate salt (15, Nex-16)

A stirred solution of DDAIP base 4 (75 g, 263 mmol) in ethyl acetate (500 mL) was cooled to 0° C., then benzene sulfonic acid 14 (41.55 g, 263 mmol) was added in one lot. After addition, the temperature of the reaction mixture was slowly raised to RT and stirred at RT for 24 h; the reaction mixture was monitored by TLC. The reaction mixture was concentrated under vacuum. The residue washed with hexane (2×30 mL); after workup a sticky solid was observed. The obtained sticky solid was kept in deep freezer for 12 h to afford dodecyl 2-(dimethylamino)propanoate benzene sulfonate salt (15, Nex-16) (116 g, yield: 99.5%) as a solid, mp: 55-62° C. $^1$H-NMR (400 MHz, CDCl$_3$): δ 0.9 (t, 3H), 1.3 (m, 18H), 1.65 (d, 3H), 1.65 (q, 2H), 3 (s, 6H), 4.2 (q, 1H), 4.2 (t, 2H), 7.4 (m, 3H), 7.9 (d, 2H); LCMS: 286 (M$^+$+1); HPLC: 80.48%.

Figure 6A:
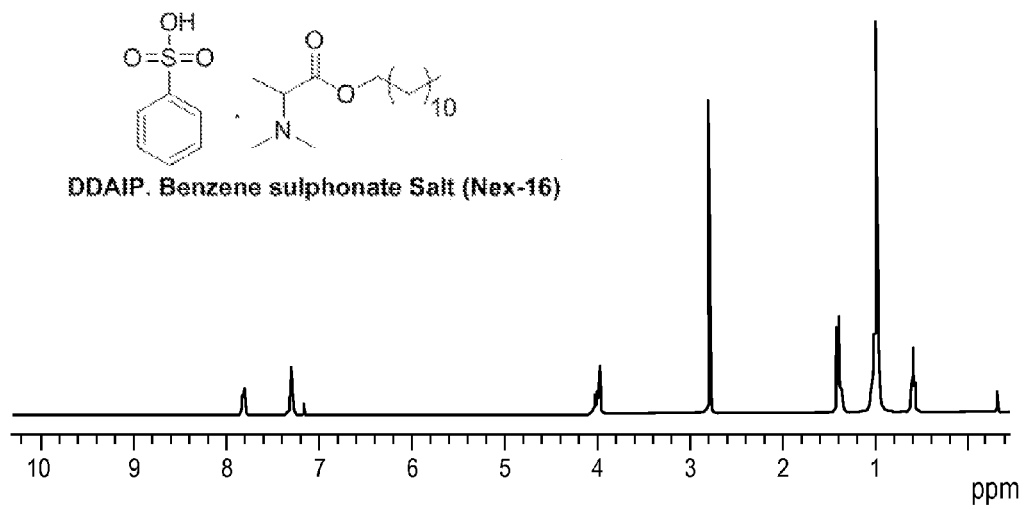
FIG. 6A is a $^1$H-NMR spectrum (400 MHz, CDCl$_3$) of dodecyl 2-(dimethylamino)propanoate benzene sulfonate salt (Nex-16).

FIG. 6A is a $^1$H-NMR spectrum (400 MHz, CDCl$_3$) of dodecyl 2-(dimethylamino)propanoate benzene sulfonate salt (Nex-16).

Figure 6B:
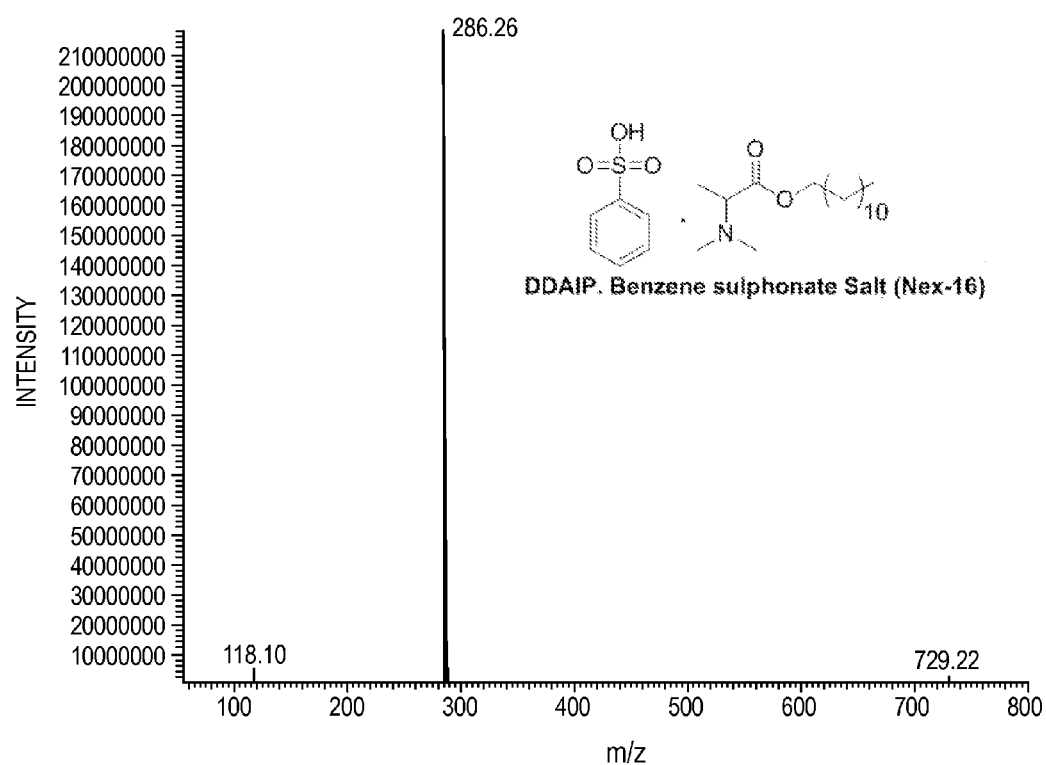
FIG. 6B is a LCMS spectrum: 286 (M$^+$+1) of dodecyl 2-(dimethylamino)propanoate benzene sulfonate salt.

FIG. 6B is a LCMS spectrum: 286 (M$^+$+1) of dodecyl 2-(dimethylamino)propanoate benzene sulfonate salt.

Figure 6C:
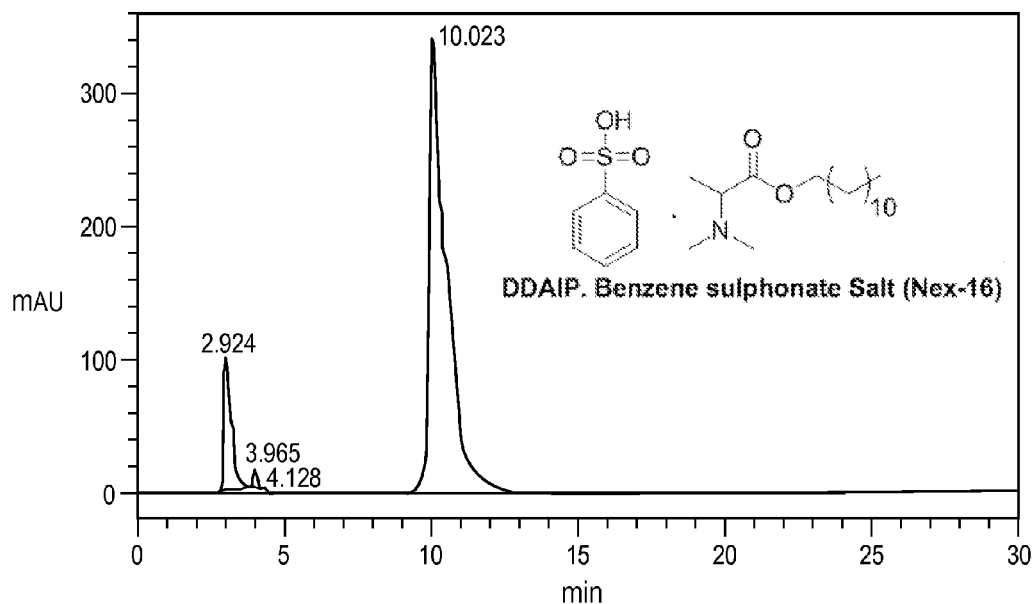
FIG. 6C is a HPLC chromatogram of dodecyl 2-(dimethylamino)propanoate benzene sulfonate salt showing a peak area of 87.5%. Methods as in FIG. 1C.

FIG. 6C is a HPLC chromatogram of dodecyl 2-(dimethylamino)propanoate benzene sulfonate salt showing a peak area of 87.5%. Methods as in FIG. 1C.

Figure 6D:
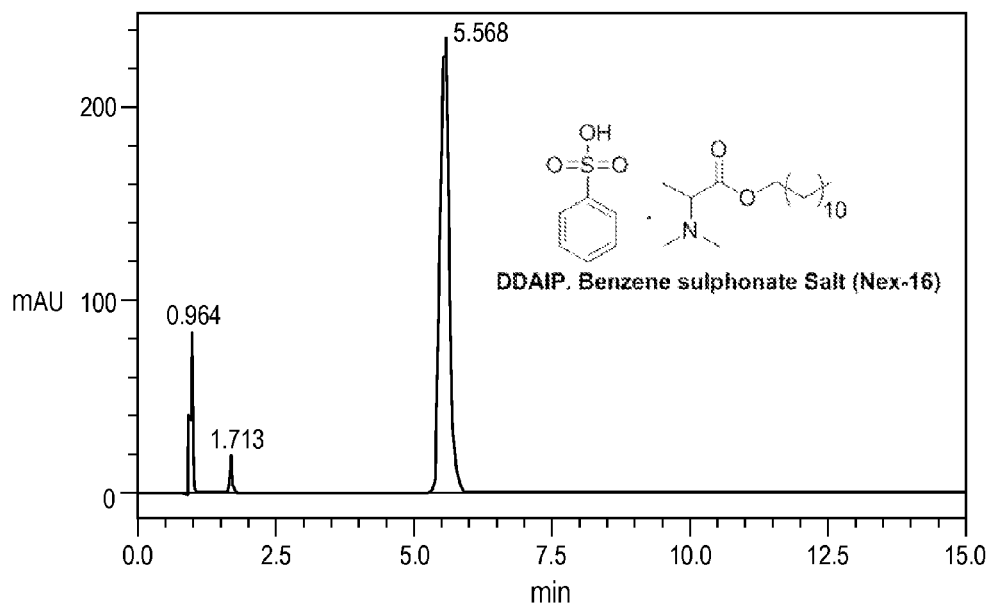
FIG. 6D is a HPLC chromatogram of dodecyl 2-(dimethylamino)propanoate benzene sulfonate salt showing a peak area of 87.3%. Methods as in FIG. 4D.

FIG. 6D is a HPLC chromatogram of dodecyl 2-(dimethylamino)propanoate benzene sulfonate salt showing a peak area of 87.3%. Methods as in FIG. 4D.

Example 8

Synthesis of Dodecyl 2-(dimethylamino)propanoate maleate Salt (Nex-20)

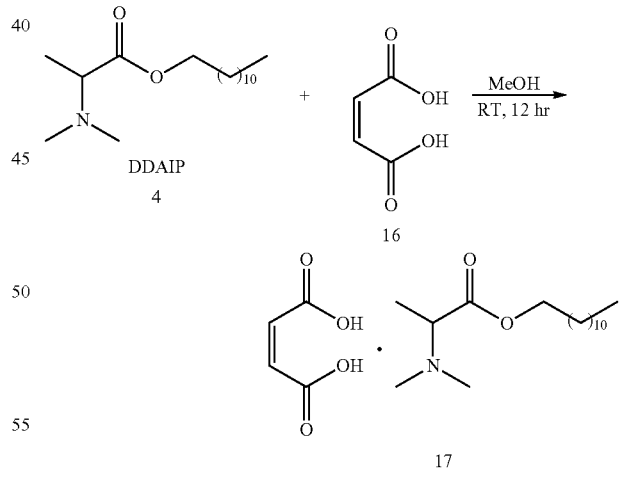

Scheme 8

DDAIP
4

16

17
DDAIP•Maleate Salt (Nex-20)

Synthesis of Dodecyl 2-(dimethylamino)propanoate maleate salt (17, Nex-20)

A stirred solution of DDAIP base 4 (80 g, 280 mmol) in methanol (600 mL) was cooled to 0° C., then maleic acid 16 (32.48 g, 280 mmol) was added in one lot. After addition, the temperature of the reaction mixture was slowly raised to RT and stirred at RT for 12 h; the reaction mixture was monitored by TLC. The reaction mixture was concentrated under vacuum and flushed with ethyl acetate (2×100 mL). The obtained residue was taken in n-hexane (200 mL) and stirred at RT for ½ h (No solid). The reaction mixture was concentrated under vacuum. The obtained sticky solid was kept in deep freezer for 2 h to afford dodecyl 2-(dimethylamino) propanoate maleate salt (17, Nex-20) (111 g, yield: 98.6%) as a solid, mp: 65-70° C. $^1$H-NMR (400 MHz, CDCl$_3$): δ 0.9 (t, 3H), 1.25 (m, 18H), 1.6 (d, 3H), 1.65 (q, 2H), 2.9 (s, 6H), 4.1 (q, 1H), 4.2 (t, 2H), 6.3 (d, 2H); LCMS: 286 (M$^+$+1); HPLC: 80.48%.

Figure 7A:
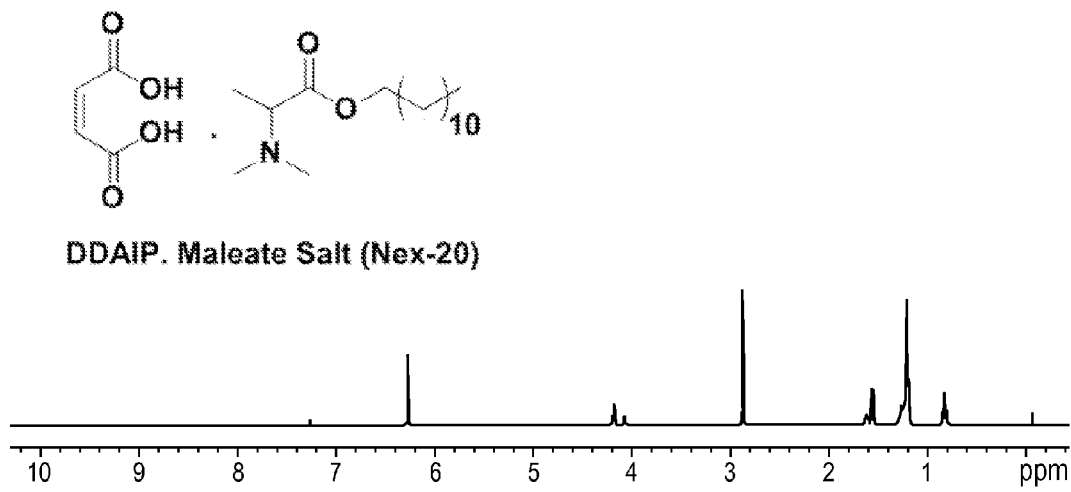
FIG. 7A is a $^1$H-NMR spectrum (400 MHz, CDCl$_3$) of dodecyl 2-(dimethylamino)propanoate maleate salt (Nex-20).

FIG. 7A is a $^1$H-NMR spectrum (400 MHz, CDCl$_3$) of dodecyl 2-(dimethylamino)propanoate maleate salt (Nex-20).

Figure 7B:
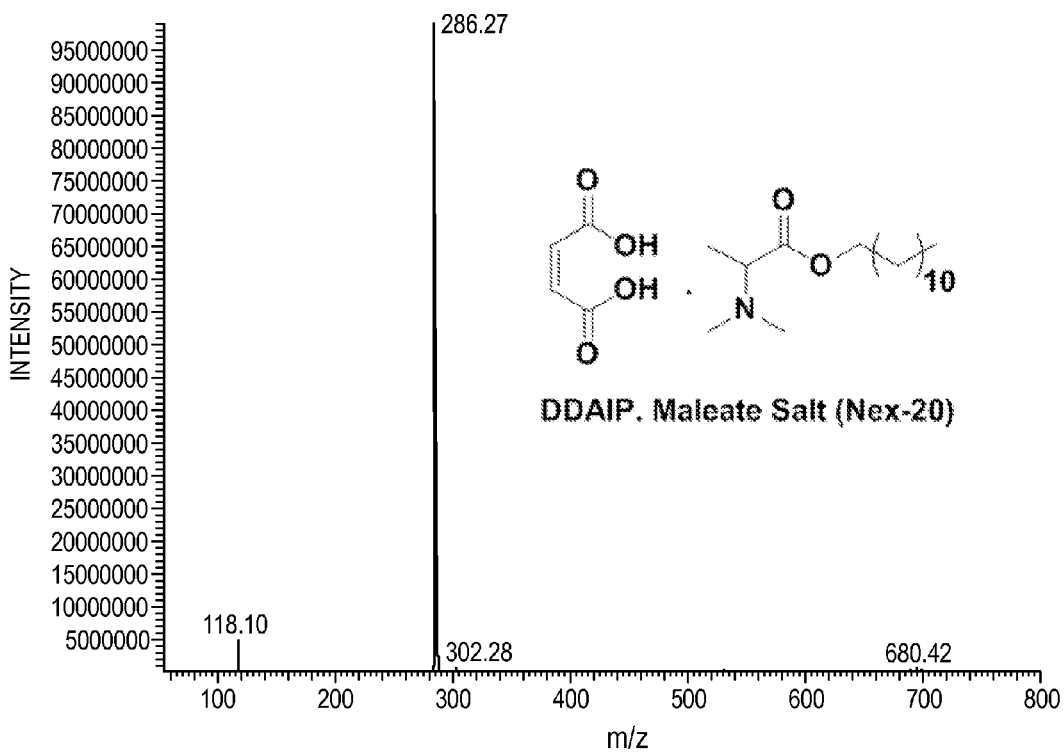
FIG. 7B is a LCMS spectrum: 286 (M$^+$+1) of dodecyl 2-(dimethylamino)propanoate maleate salt.

FIG. 7B is a LCMS spectrum: 286 (M$^+$+1) of dodecyl 2-(dimethylamino)propanoate maleate salt.

Figure 7C:
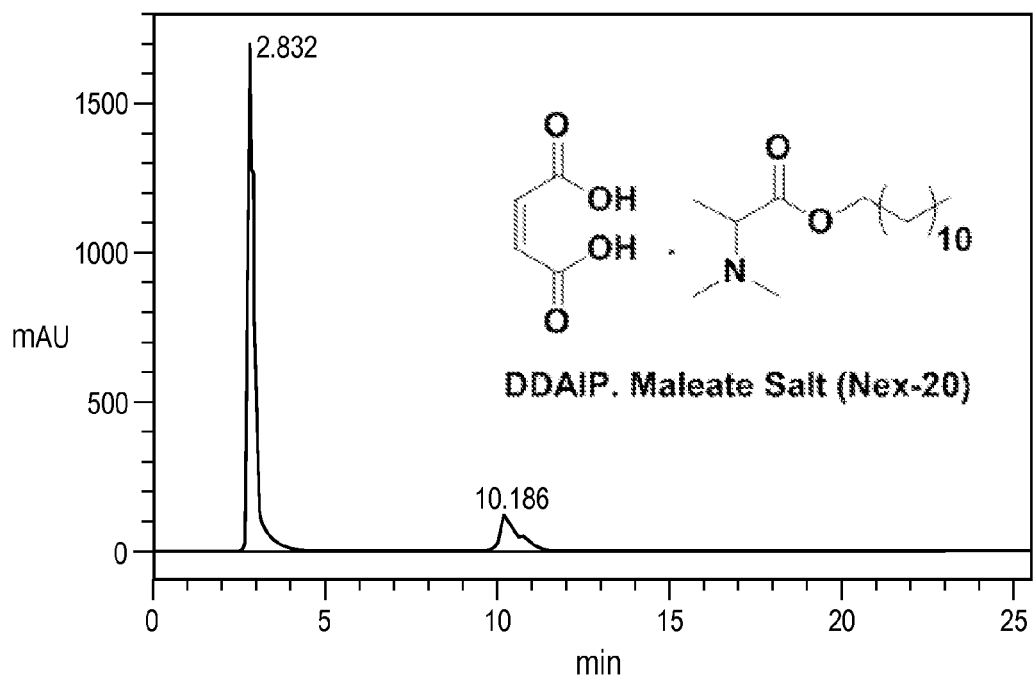
FIG. 7C is a HPLC chromatogram of dodecyl 2-(dimethylamino)propanoate maleate salt showing a peak area of 87.8%. Methods as in FIG. 1C.

FIG. 7C is a HPLC chromatogram of dodecyl 2-(dimethylamino)propanoate maleate salt showing a peak area of 87.8%. Methods as in FIG. 1C.

Figure 7D:
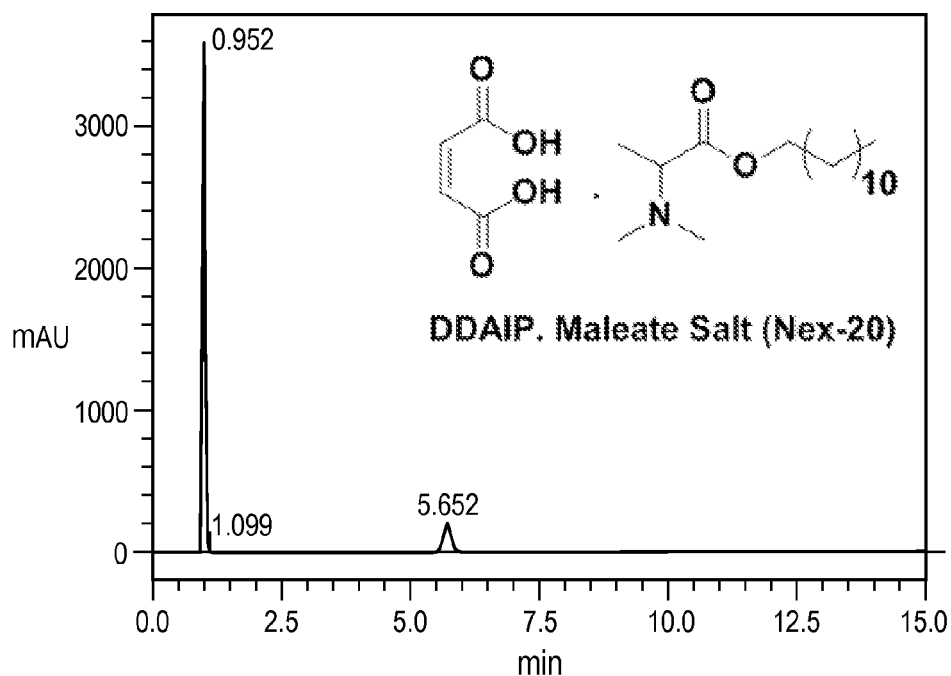
FIG. 7D is a HPLC chromatogram of dodecyl 2-(dimethylamino)propanoate maleate salt showing a peak area of 85.9%. Methods as in FIG. 4D.

FIG. 7D is a HPLC chromatogram of dodecyl 2-(dimethylamino)propanoate maleate salt showing a peak area of 85.9%. Methods as in FIG. 4D.

Example 9

Synthesis of Dodecyl 2-(dimethylamino)propanoate methane sulfonate Salt (Nex-22)

CDCl$_3$): δ 0.9 (t, 3H), 1.35 (m, 18H), 1.65 (q, 2H), 1.7 (d, 3H), 2.8 (s, 3H), 3 (s, 6H), 4.15 (q, 1H), 4.2 (t, 2H); LCMS: 286 (M+); HPLC: 100%.

Figure 8A:
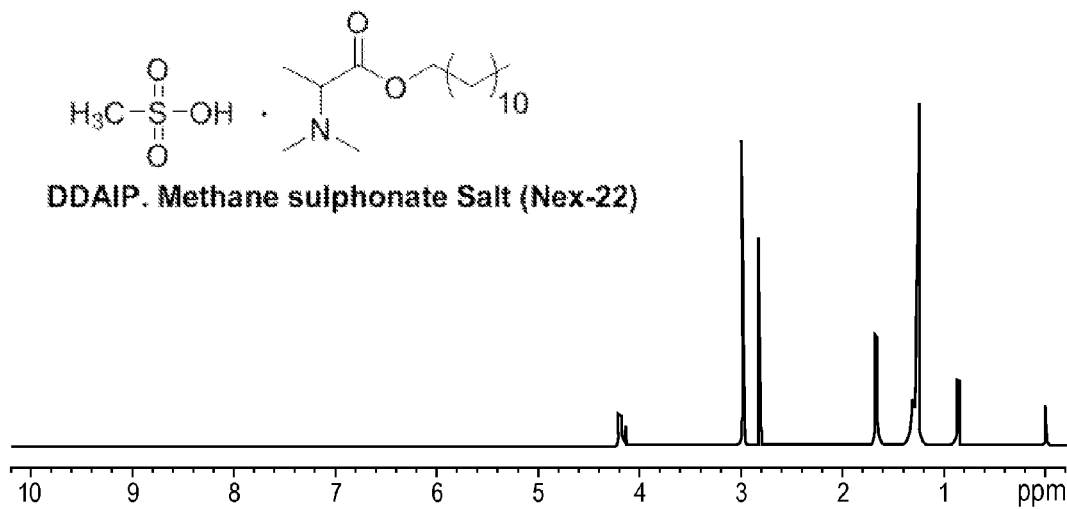
FIG. 8A is a $^1$H-NMR spectrum (400 MHz, CDCl$_3$) of dodecyl 2-(dimethylamino)propanoate methane sulfonate salt (Nex-22).

FIG. 8A is a $^1$H-NMR spectrum (400 MHz, CDCl$_3$) of dodecyl 2-(dimethylamino)propanoate methane sulfonate salt (Nex-22).

Figure 8B:
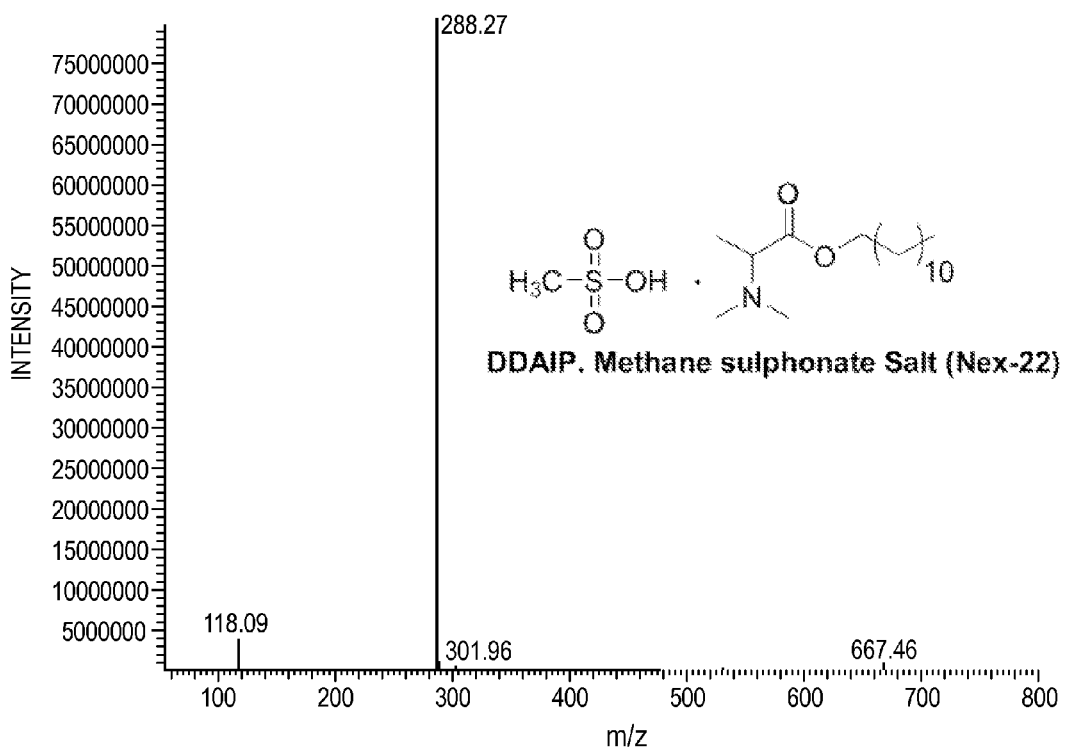
FIG. 8B is a LCMS spectrum: 286 (M$^+$+1) of dodecyl 2-(dimethylamino)propanoate methane sulfonate salt.

FIG. 8B is a LCMS spectrum: 286 (M$^+$+1) of dodecyl 2-(dimethylamino)propanoate methane sulfonate salt.

Figure 8C:
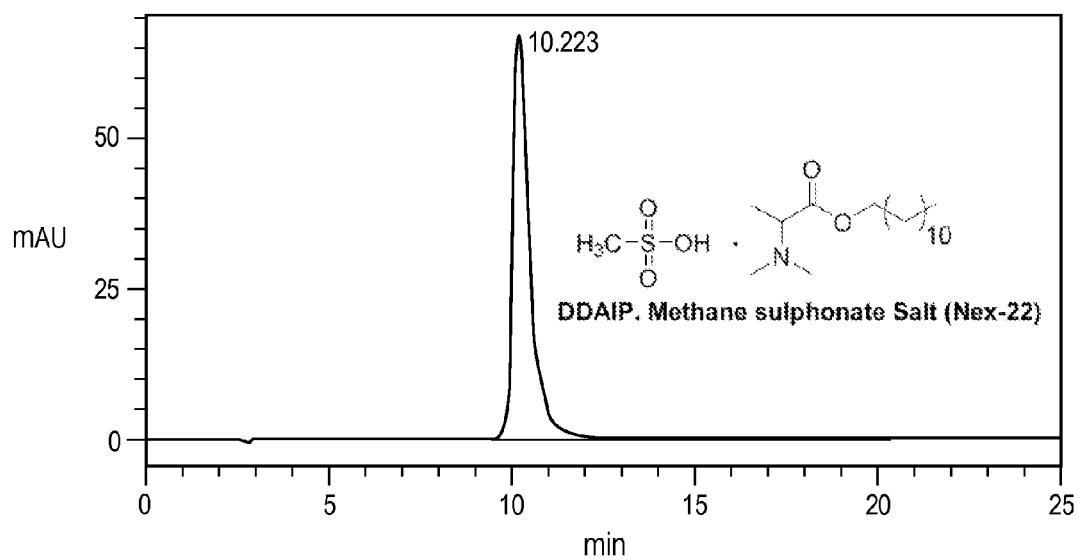
FIG. 8C is a HPLC chromatogram of dodecyl 2-(dimethylamino)propanoate methane sulfonate salt showing a peak area of 100.0%. Methods as in FIG. 1C.

FIG. 8C is a HPLC chromatogram of dodecyl 2-(dimethylamino)propanoate methane sulfonate salt showing a peak area of 100.0%. Methods as in FIG. 1C.

Figure 8D:
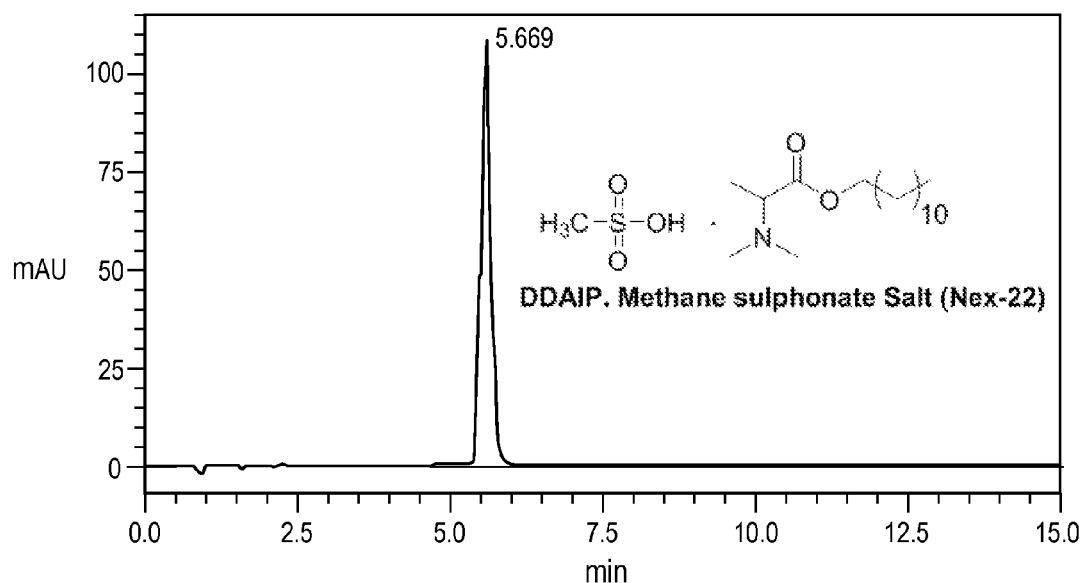
FIG. 8D is a HPLC chromatogram of dodecyl 2-(dimethylamino)propanoate methane sulfonate salt showing a peak area of 100.0%. Methods as in FIG. 4D.

FIG. 8D is a HPLC chromatogram of dodecyl 2-(dimethylamino)propanoate methane sulfonate salt showing a peak area of 100.0%. Methods as in FIG. 4D.

Example 10

Synthesis of Dodecyl 2-(dimethylamino)propanoate ethane sulfonate Salt (Nex-30)

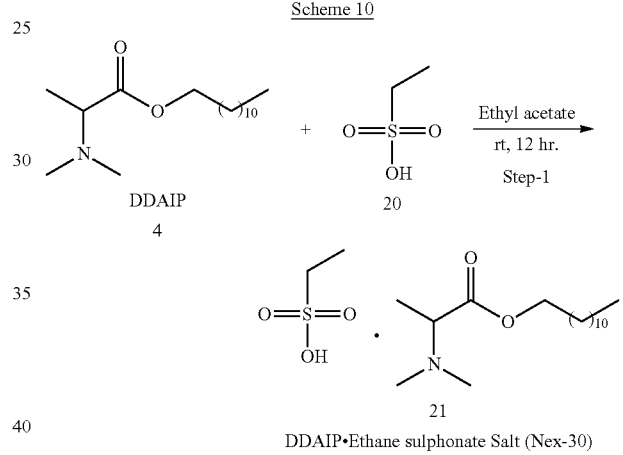

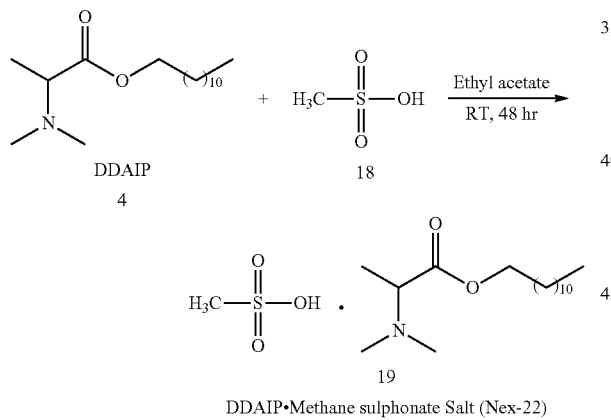

Synthesis of Dodecyl 2-(dimethylamino)propanoate Methane sulfonate salt (19, Nex-22)

A stirred solution of DDAIP base 4 (85 g, 298 mmol) in ethyl acetate (500 mL) was cooled to 0° C., then methane sulfonic acid 18 (28.6 g, 298 mmol) was added in one lot. After addition, the temperature of the reaction mixture was slowly raised to RT and stirred at RT for 48 h; the reaction mixture was monitored by TLC. The reaction mixture was concentrated under vacuum. The obtained residue was taken in n-hexane (30 mL) and stirred at RT for ½ h (No solid). The reaction mixture was concentrated under vacuum and flushed with hexane (3×30 mL) to afford dodecyl 2-(dimethylamino) propanoate methane sulfonate salt (19, Nex-22) (110 g, yield: 97.34%) as a solid, mp: 66-72° C. $^1$H-NMR (400 MHz, Synthesis of Dodecyl 2-(dimethylamino)propanoate ethane sulfonate Salt (21, Nex-30)

A stirred solution of DDAIP base 4 (85 g, 298 mmol) in ethyl acetate (600 mL) was cooled to 0° C., then ethane sulfonic acid 20 (32.79 g, 298 mmol) was added in one lot. After addition, the temperature of the reaction mixture was slowly raised to RT, stirred at RT for 12 h and the reaction mixture was monitored by TLC. The reaction mixture was concentrated under vacuum and flushed with hexane. The obtained residue was taken in n-hexane (200 mL) and stirred at RT for 2 h (No solid). The obtained sticky solid kept in deep freezer for 12 h to afford dodecyl 2-(dimethylamino)propanoate ethane sulfonate salt (21, Nex-30) (116 g, yield: 98.4%) as a hygroscopic solid, Mp: 45-50° C. $^1$H-NMR (400 MHz, CDCl$_3$): δ 0.9 (t, 31H), 1.3 (m, 18H), 1.35 (t, 3H), 1.7 (d, 31H), 1.8 (q, 21H), 2.9 (q, 2H), 3 (m, 6H), 4.2 (m, 2H), 4.2 (m, 1H); LCMS: 286 (M$^+$+1); HPLC: 99.47%.

Figure 9A:
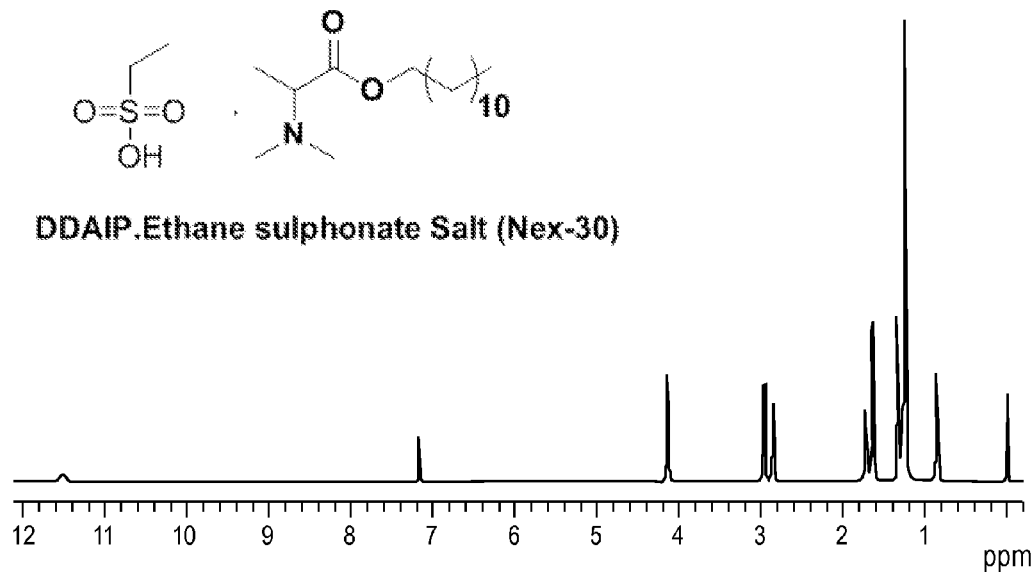
FIG. 9A is a $^1$H-NMR spectrum (400 MHz, CDCl$_3$) of dodecyl 2-(dimethylamino)propanoate ethane sulfonate salt (Nex-30).

FIG. 9A is a $^1$H-NMR spectrum (400 MHz, CDCl$_3$) of dodecyl 2-(dimethylamino)propanoate ethane sulfonate salt (Nex-30).

Figure 9B:
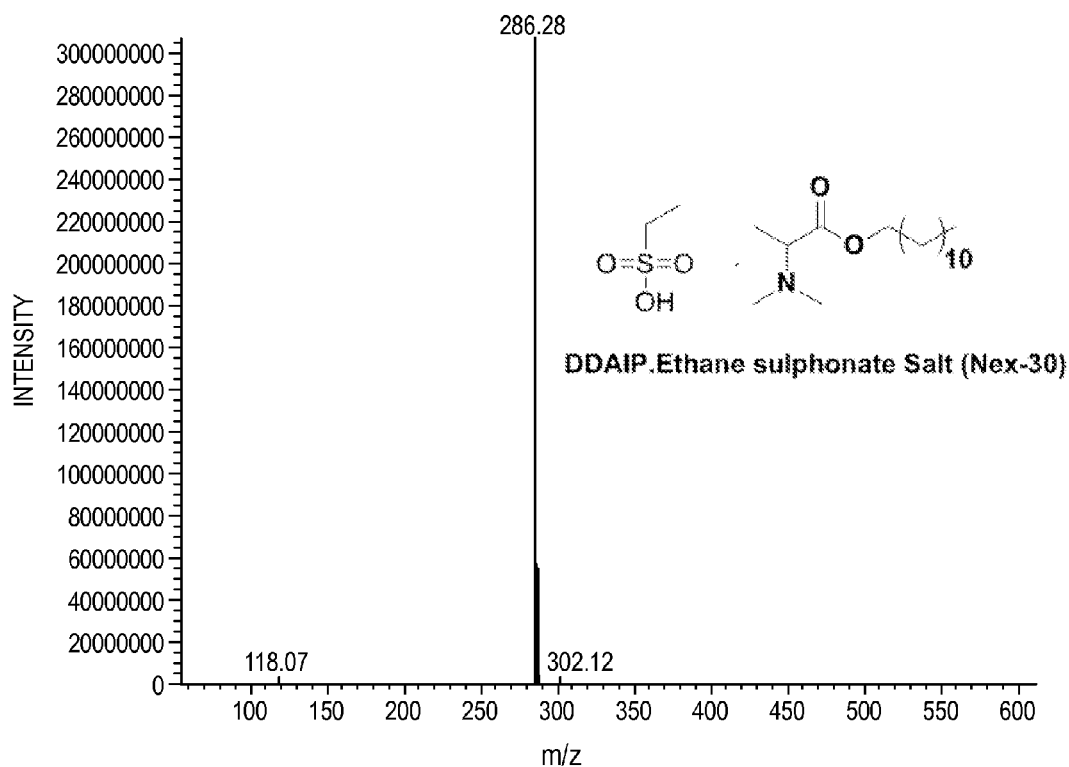
FIG. 9B is a LCMS spectrum: 286 (M$^+$+1) of dodecyl 2-(dimethylamino)propanoate ethane sulfonate salt.

FIG. 9B is a LCMS spectrum: 286 (M$^+$+1) of dodecyl 2-(dimethylamino)propanoate ethane sulfonate salt.

Figure 9C:
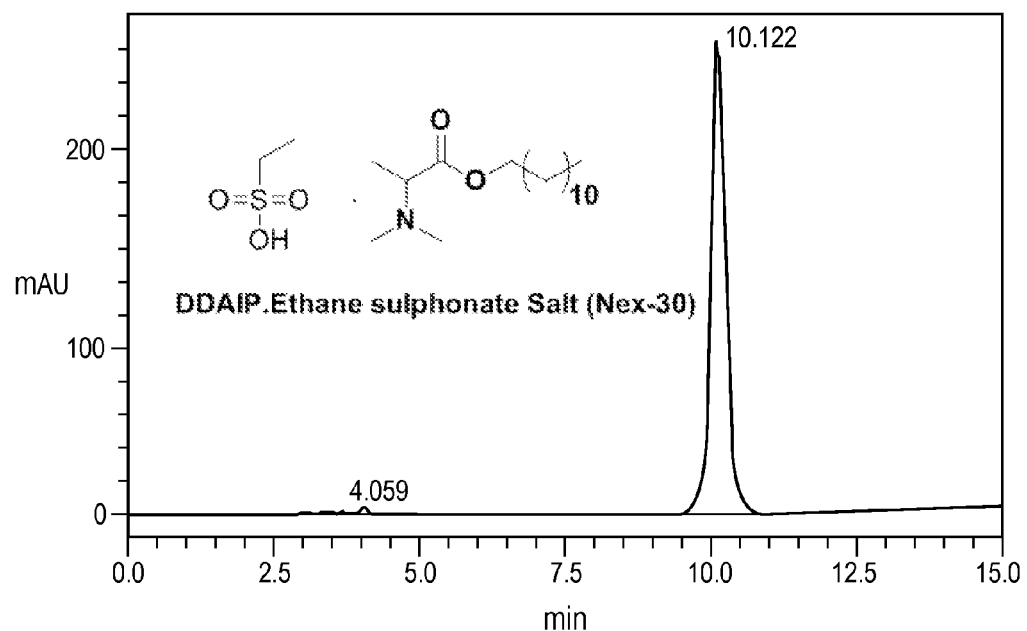
FIG. 9C is a HPLC chromatogram of dodecyl 2-(dimethylamino)propanoate ethane sulfonate salt showing a peak area of 99.5%. Methods as in FIG. 1C.

FIG. 9C is a HPLC chromatogram of dodecyl 2-(dimethylamino)propanoate ethane sulfonate salt showing a peak area of 99.5%. Methods as in FIG. 1C.

Example 11

Synthesis of Dodecyl 2-(dimethylamino)propanoate 1,5-napthalene disulfonate Salt (Nex-32)

Scheme 11

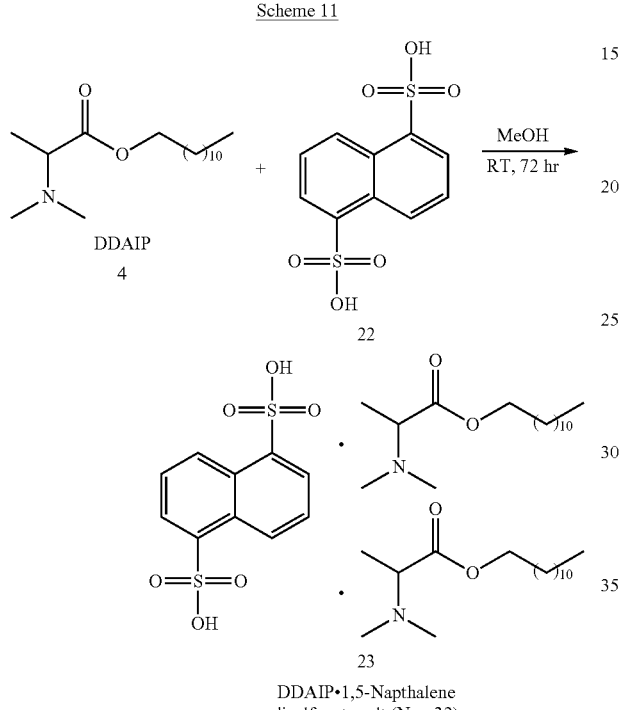

DDAIP•1,5-Napthalene disulfonate salt (Nex-32)

Synthesis of Dodecyl 2-(dimethylamino)propanoate 1,5-napthalene disulfonate salt (23, Nex-32)

A stirred solution of DDAIP base 4 (80 g, 280 mmol) in methanol (500 mL) was cooled to 0° C., then 1,5-napthalene disulfonic acid 22 (50.5 g, 140 mmol) was added in one lot. After addition the temperature of the reaction mixture was slowly raised to RT and stirred at RT for 72 h; the reaction mixture was monitored by TLC. The reaction mixture was concentrated under vacuum and flushed with ethyl acetate (2×30 mL). The obtained residue was taken in n-hexane (200 mL) and stirred at RT for ½ h (sticky solid). The reaction mixture was concentrated under vacuum and flushed with hexane (3×100 mL) to afford dodecyl 2-(dimethylamino)propanoate 1,5-napthalene disulfonate salt (23, Nex-32) (120 g, 92.3%) as a white solid. Mp: 135-140° C. $^1$H-NMR (400 MHz, CDCl$_3$): δ 0.9 (t, 3H), 1.2-1.3 (m, 18H), 1.6 (d, 3H), 1.65 (q, 2H), 2.9 (s, 6H), 4.15 (t, 2H), 4.2 (q, 1H), 7.55 (t, 2H), 8.22 (d, 2H), 9.1 (d, 2H); LCMS: 286 (M$^+$+1); HPLC: 80.48%.

Figure 10A:
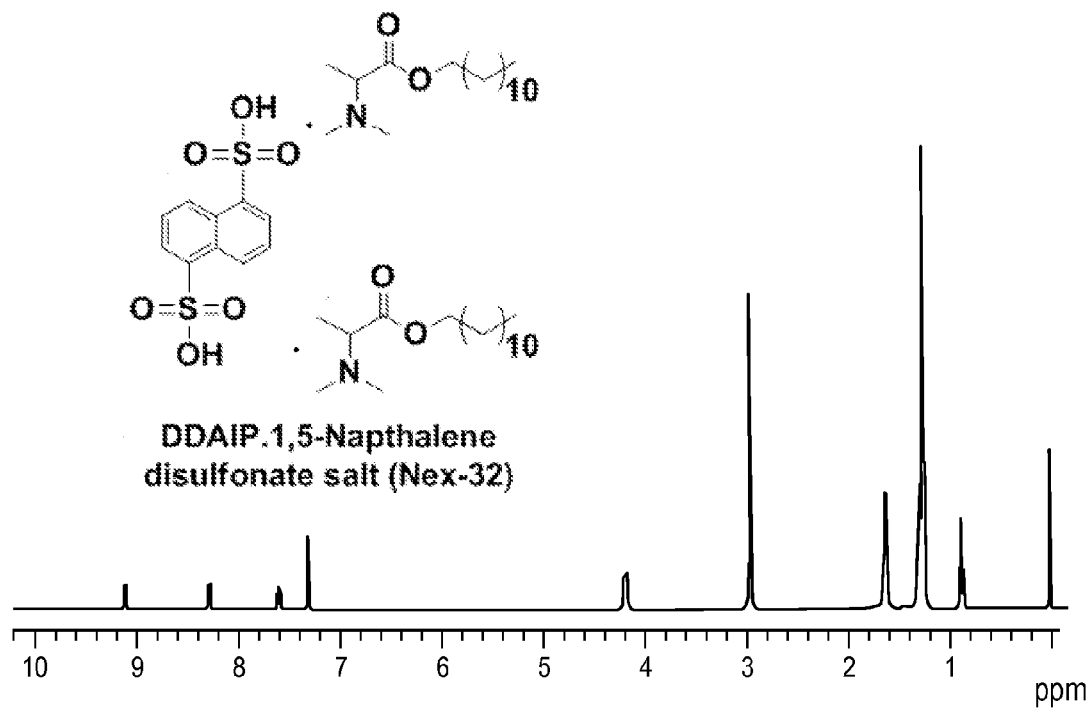
FIG. 10A is a $^1$H-NMR spectrum (400 MHz, CDCl$_3$) dodecyl 2-(dimethylamino)propanoate 1,5-napthalene disulfonate salt (Nex-32).

FIG. 10A is a $^1$H-NMR spectrum (400 MHz, CDCl$_3$) dodecyl 2-(dimethylamino)propanoate 1,5-napthalene disulfonate salt (Nex-32).

Figure 10B:
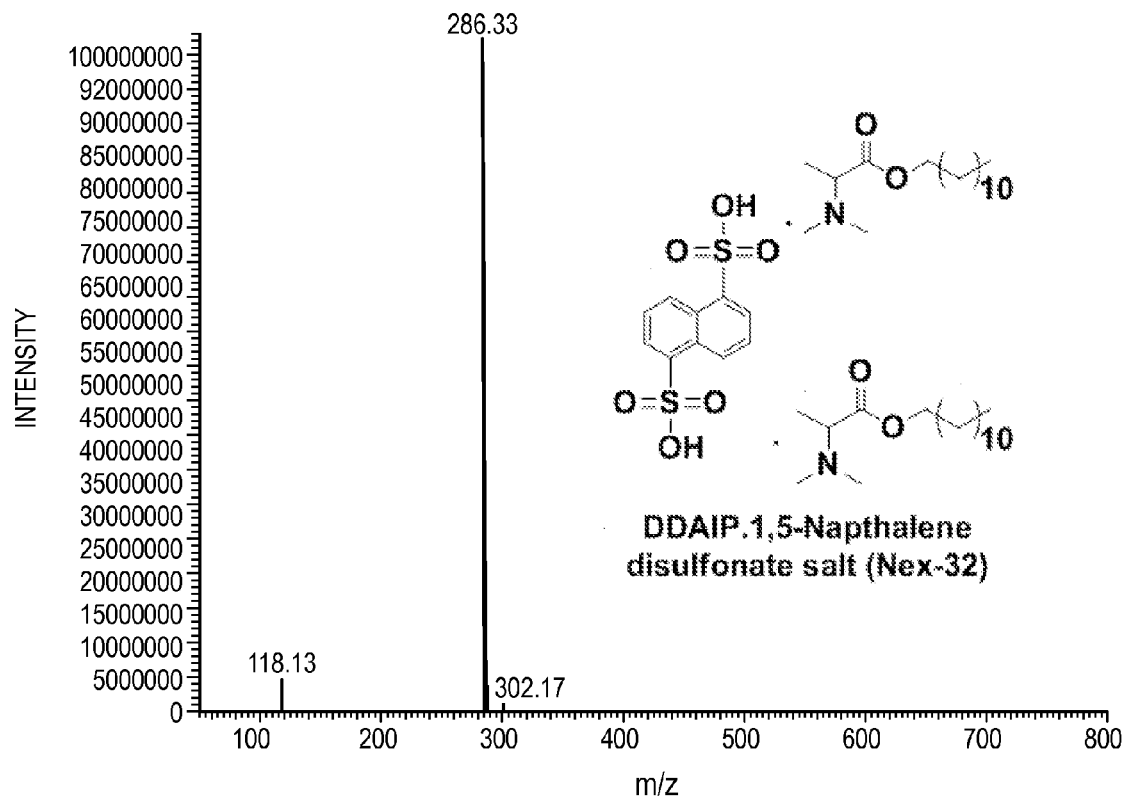
FIG. 10B is a LCMS spectrum: 286 (M$^+$+1) of dodecyl 2-(dimethylamino)propanoate 1,5-napthalene disulfonate salt.

FIG. 10B is a LCMS spectrum: 286 (M$^+$+1) of dodecyl 2-(dimethylamino)propanoate 1,5-napthalene disulfonate salt.

Figure 10C:
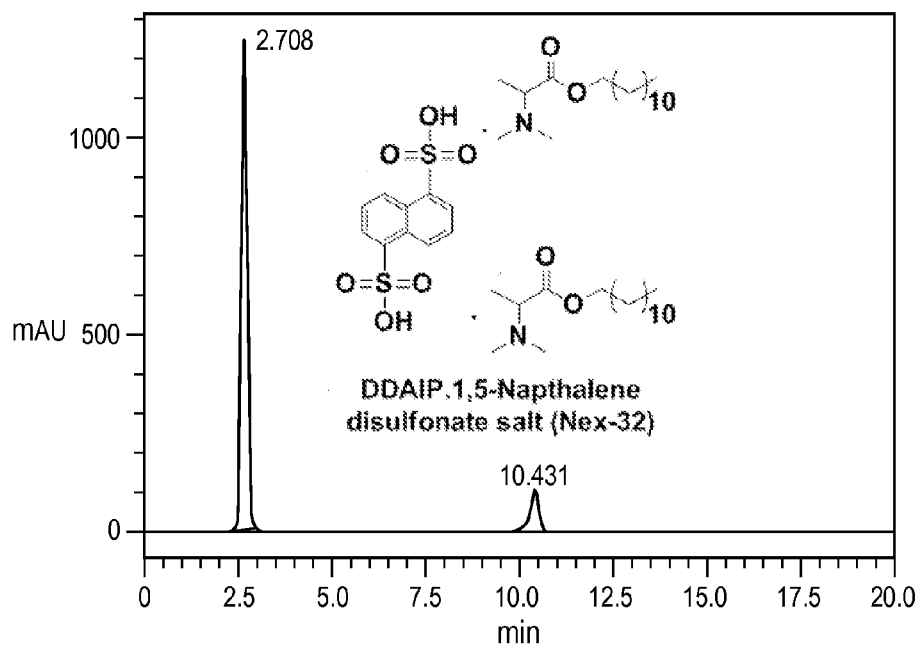
FIG. 10C is a HPLC chromatogram of dodecyl 2-(dimethylamino)propanoate 1,5-napthalene disulfonate salt showing a peak area of 87.2%. Methods as in FIG. 1C.

FIG. 10C is a HPLC chromatogram of dodecyl 2-(dimethylamino)propanoate 1,5-napthalene disulfonate salt showing a peak area of 87.2%. Methods as in FIG. 1C.

Example 12

Synthesis of Dodecyl 2-(dimethylamino)propanoate 2-hydroxyethanesulfonate Salt (Nex-46)

Scheme 12

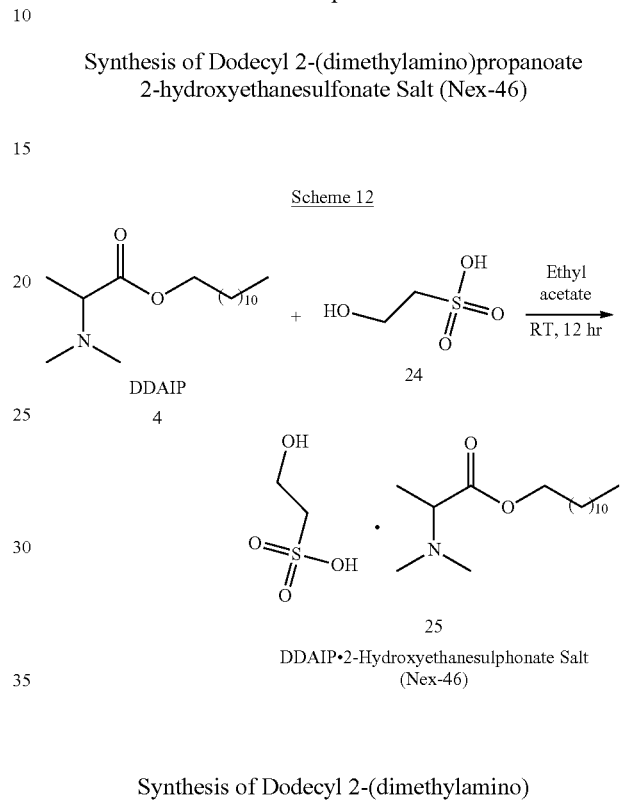

DDAIP•2-Hydroxyethanesulphonate Salt (Nex-46)

Synthesis of Dodecyl 2-(dimethylamino) 2-hydroxyethanesulfonate salt (25, Nex-46)

To a stirred solution of DDAIP base 4 (85 g, 298 mmol) in ethyl acetate (500 mL) cooled to 0° C. was added 2-hydroxyethanesulfonic acid 24 (80% pure only) (45 g, 357 mmol) in one lot. After addition, the temperature of the reaction mixture was slowly raised to room temperature and stirred at RT for 12 h; the reaction mixture was monitored by TLC. The reaction mixture was concentrated under vacuum. The obtained residue was taken in n-hexane (20 mL) and stirred at RT for ½ h (No solid). The obtained sticky solid was kept in deep freezer for 48 h to afford dodecyl 2-(dimethylamino)propanoate 2-hydroxyethanesulfonate salt (25, Nex-46) (125 g, yield: 96.15%) as a waxy hygroscopic solid, Mp: 58-63° C. $^1$H-NMR (400 MHz, CDCl$_3$): δ 0.8 (t, 31H), 1.2-1.3 (m, 181H), 1.6 (d, 3H), 2.9 (s, 6H), 3.05 (t, 2H), 3.9 (t, 2H), 4.1 (q, 2H), 4.2 (t, 2H); LCMS: 286 (M$^+$+1); HPLC: 100%.

Figure 11A:
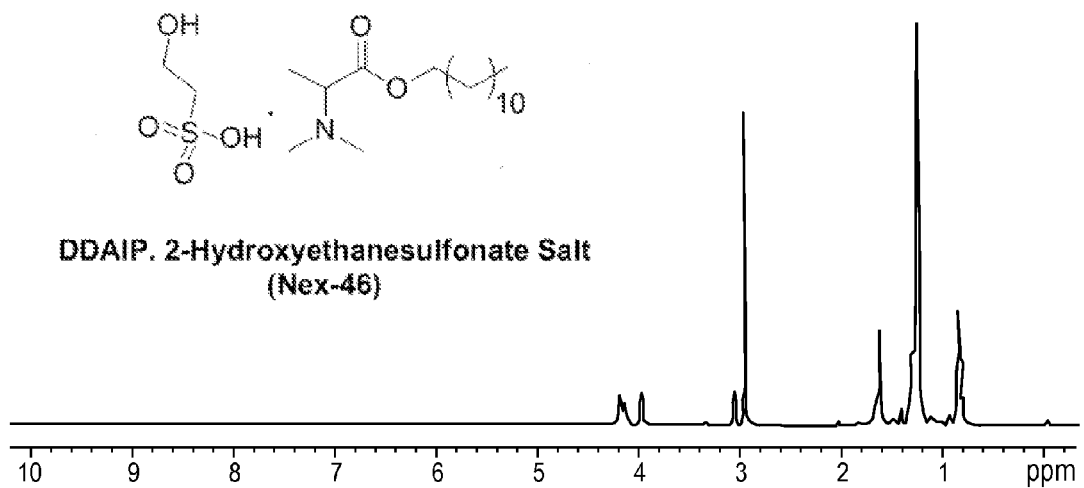
FIG. 11A is a $^1$H-NMR spectrum (400 MHz, CDCl$_3$) of dodecyl 2-(dimethylamino)propanoate 2-hydroxyethanesulfonate salt (Nex-46).

FIG. 11A is a $^1$H-NMR spectrum (400 MHz, CDCl$_3$) of dodecyl 2-(dimethylamino)propanoate 2-hydroxyethanesulfonate salt (Nex-46).

Figure 11B:
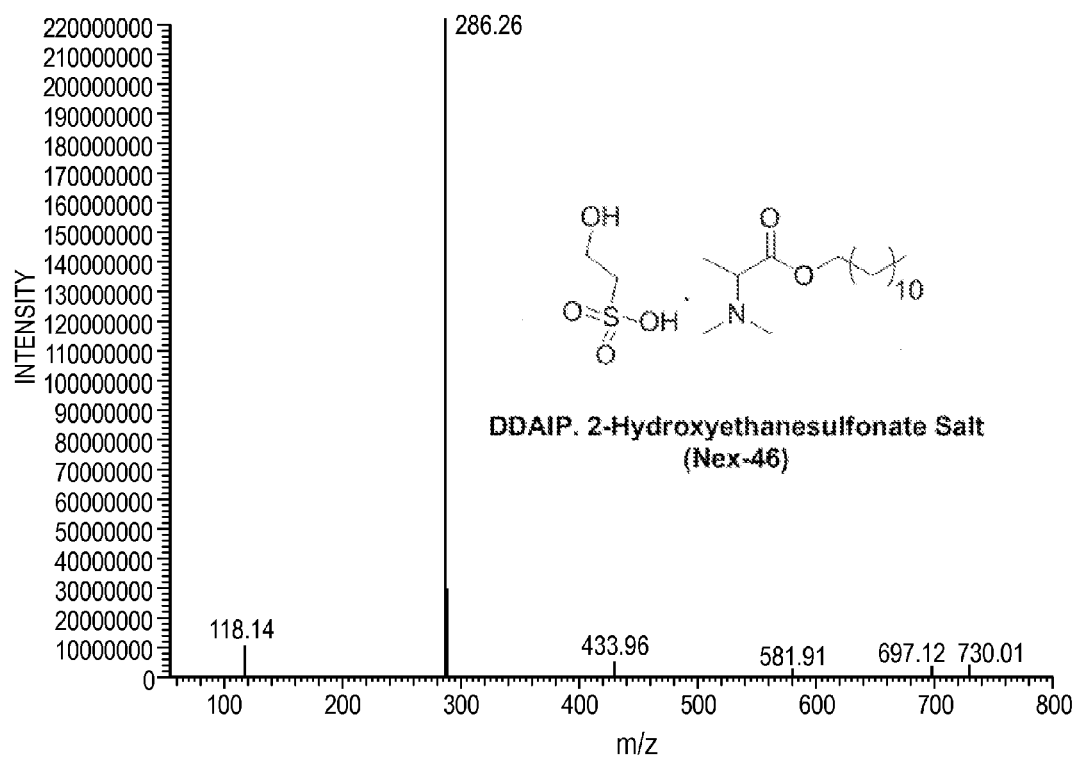
FIG. 11B is a LCMS spectrum: 286 (M$^+$+1) of dodecyl 2-(dimethylamino)propanoate 2-hydroxyethanesulfonate salt.

FIG. 11B is a LCMS spectrum: 286 (M$^+$+1) of dodecyl 2-(dimethylamino)propanoate 2-hydroxyethanesulfonate salt.

Figure 11C:
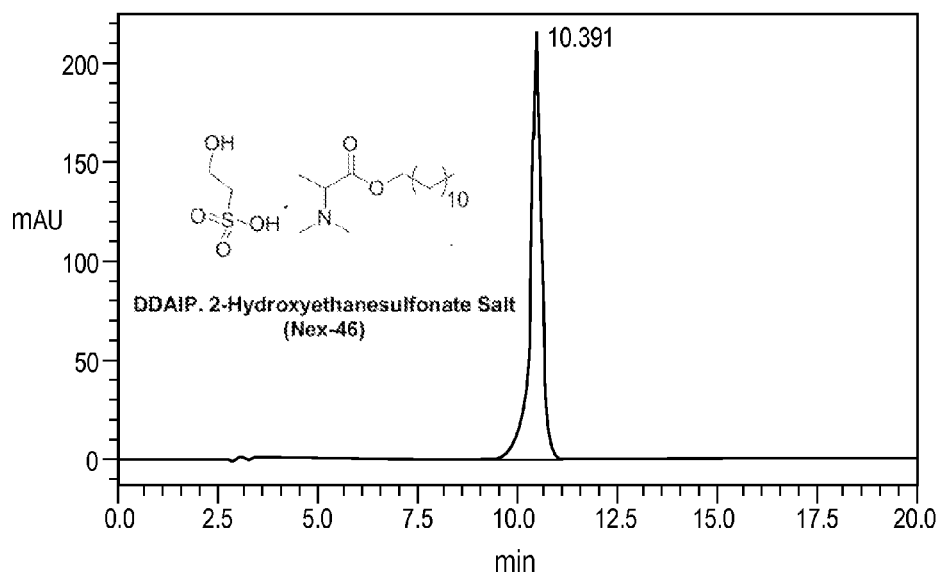
FIG. 11C is a HPLC chromatogram of dodecyl 2-(dimethylamino)propanoate 2-hydroxyethanesulfonate salt showing a peak area of 100%. Methods as in FIG. 1C.

FIG. 11C is a HPLC chromatogram of dodecyl 2-(dimethylamino)propanoate 2-hydroxyethanesulfonate salt showing a peak area of 100%. Methods as in FIG. 1C.

Example 13

Synthesis of Dodecyl 2-(dimethylamino)-3-hydroxybutanoate.HCl (Nex-51)

Scheme 13

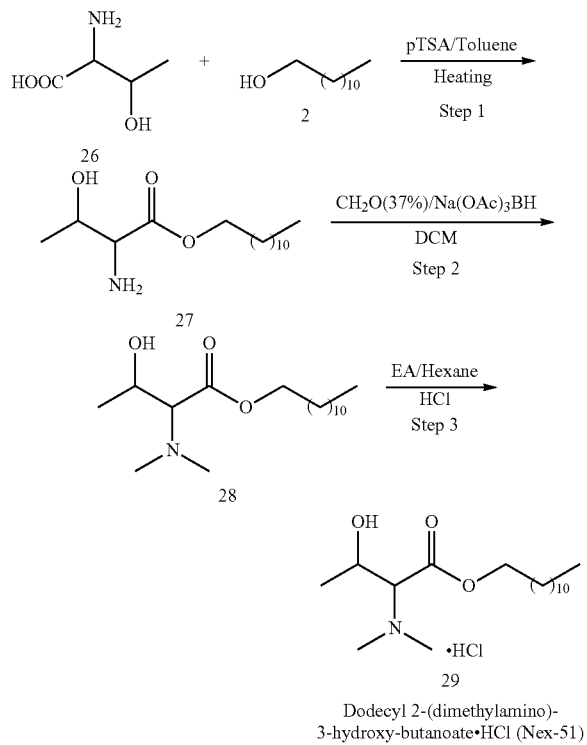

Dodecyl 2-(dimethylamino)-3-hydroxy-butanoate•HCl (Nex-51)

Synthesis of Dodecyl 2-amino-3-hydroxybutanoate (27)

To a stirred solution of DL-threonine 26 (5 g, 41.9 mmol) in toluene (100 mL) was added 1-dodecanol 2 (7 g, 37.7 mmol) in one lot, followed by pTSA (8.77 g, 46.16 mmol). After addition, the temperature of the reaction mixture was slowly raised to reflux temperature and the water was separated azeotropically. The reaction mixture was monitored by TLC. The reaction mixture was concentrated under vacuum. The obtained residue was taken in ethyl acetate (200 mL) and washed with aqueous 5% $Na_2CO_3$ (3×50 mL) followed by brine solution. The organic layer was dried over $Na_2SO_4$ and concentrated under vacuum to afford crude 27 (11 g, yield: 91%) as a liquid.

Synthesis of Dodecyl 2-(dimethylamino)-3-hydroxybutanoate (28)

To a stirred solution of 27 (11 g, 38.3 mmol) in DCM (100 mL) was added aqueous formaldehyde solution (37% w/v) (4.02 g, 134 mmol) in one lot at 0° C., and $Na(OAc)_3BH$ (20.3 g, 95.8 mmol) was added slowly over a period of 1 h. After addition, the temperature of the reaction mixture was slowly raised to RT and stirred at RT for 12 h, and the reaction mixture was monitored by TLC. The reaction mixture was quenched with ice-cold water, the organic layer was separated and the aqueous layer was extracted with DCM (2×40 mL). The combined organic layers were washed with brine solution. The organic layer was dried over $Na_2SO_4$, and concentrated under vacuum. The obtained crude product was purified by column chromatography to afford 28 (8 g, yield: 66.6%) as a liquid.

Synthesis of Dodecyl 2-(dimethylamino)-3-hydroxybutanoate.HCl (29, Nex-51)

A stirred solution of 28 (8 g, 25.3 mmol) in hexane (50 mL) was cooled to 0° C. The reaction mixture was purged with dry HCl gas for 30 minutes, and the reaction mixture was monitored by TLC. The reaction mixture was concentrated under vacuum, and the obtained residue was flushed with ethyl acetate (3×50 mL) followed by hexane (5×50 mL) to afford wet dodecyl 2-(dimethylamino)-3-hydroxybutanoate.HCl (29, Nex-51) (8 g) as a semi solid. This semi solid was taken in hexane (50 mL) and heated to reflux, stirred at reflux for 30 minutes. The reaction mixture was slowly cooled to RT and kept for 12 h, then to 0° C. The obtained semi solid was filtered under nitrogen & dried under vacuum to afford dodecyl 2-(dimethylamino)-3-hydroxybutanoate.HCl salt (29, Nex-51) (8 g, yield: 89.8%) as a white hygroscopic semi solid. $^1$H-NMR (400 MHz, CDCl$_3$): δ 4.3-4.1 (m, 4H), 3.1 (s, 3H), 2.9 (s, 3H), 1.7 (m, 2H), 1.4-1.1 (m, 21H), 0.9 (t, 3H) LCMS: 316 (M$^+$+1); HPLC: 99.55%.

Figure 12A:
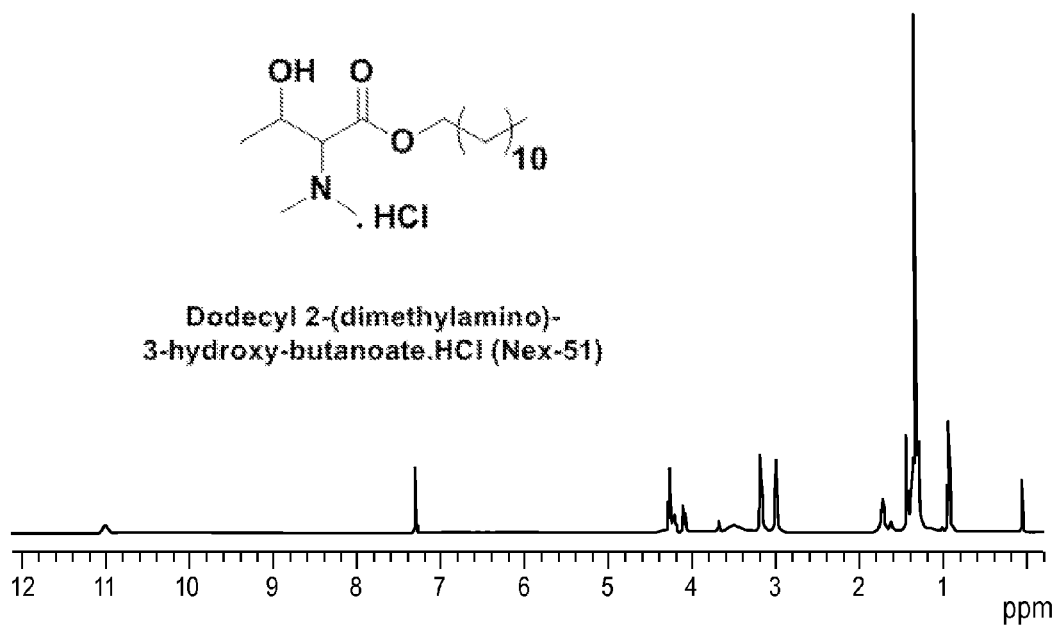
FIG. 12A is a $^1$H-NMR spectrum (400 MHz, CDCl$_3$) of dodecyl 2-(dimethylamino)-3-hydroxybutanoate HCl salt (Nex-51).

FIG. 12A is a $^1$H-NMR spectrum (400 MHz, CDCl$_3$) of dodecyl 2-(dimethylamino)-3-hydroxybutanoate.HCl salt (Nex-51).

Figure 12B:
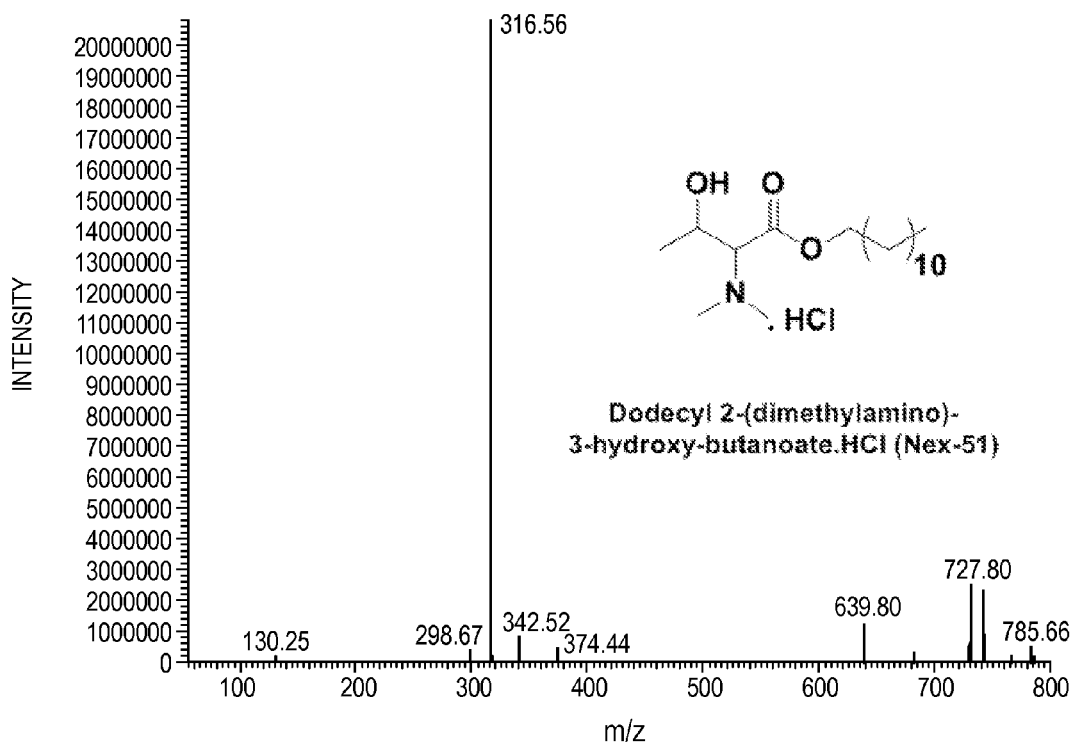
FIG. 12B is a LCMS spectrum: 316 (M$^+$+1) of dodecyl 2-(dimethylamino)-3-hydroxybutanoate.HCl salt.

FIG. 12B is a LCMS spectrum: 316 (M$^+$+1) of dodecyl 2-(dimethylamino)-3-hydroxybutanoate.HCl salt.

Figure 12C:
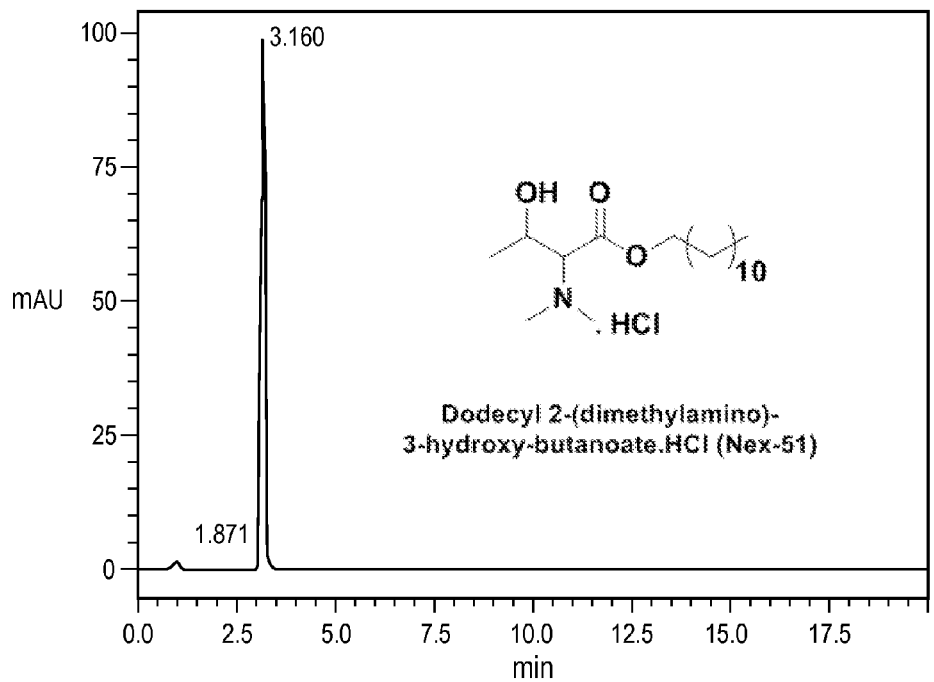
FIG. 12C is a HPLC chromatogram of dodecyl 2-(dimethylamino)-3-hydroxy-butanoate.HCl salt showing a peak area of 100%. Methods as in FIG. 4D.

FIG. 12C is a HPLC chromatogram of dodecyl 2-(dimethylamino)-3-hydroxy-butanoate-HCl salt showing a peak area of 100%. Methods as in FIG. 4D.

Example 14

Synthesis of Dodecyl 2-(dimethylamino)acetate-HCl (Nex-52)

Scheme 14

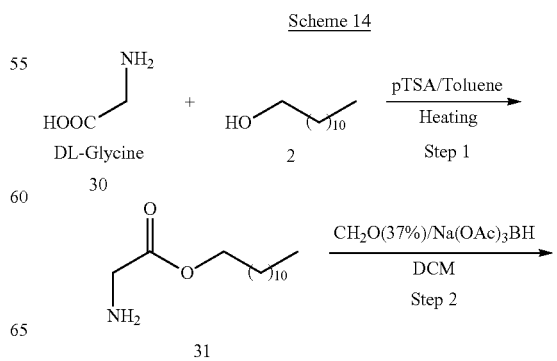

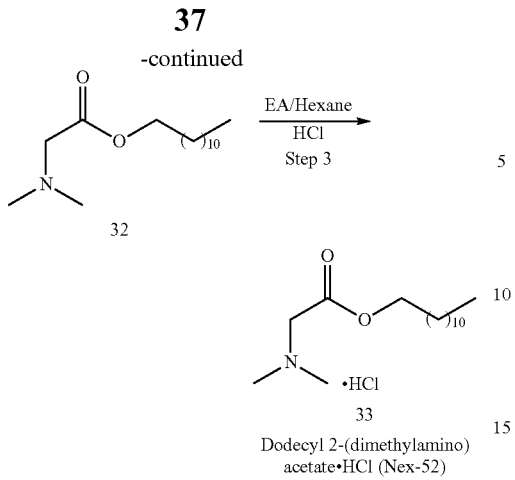

Dodecyl 2-(dimethylamino) acetate•HCl (Nex-52)

Synthesis of Dodecyl 2-aminoacetate (31)

To a stirred solution of DL-glycine 30 (20 g, 266 mmol) in toluene (200 mL) was added 1-dodecanol 2 (44.7 g, 239.9 mmol) in one lot, followed by pTSA (55.78 g, 293 mmol). After addition, the temperature of the reaction mixture was slowly raised to reflux temperature, the water was separated azeotropically, and the reaction mixture was monitored by TLC. The reaction mixture was concentrated under vacuum, the obtained residue was taken in ethyl acetate (200 mL) and washed with aqueous 5% $Na_2CO_3$ (3×50 mL) followed by brine solution. The organic layer was dried over $Na_2SO_4$ and concentrated under vacuum to afford crude dodecyl 2-aminoacetate 31 (40 g, yield: 61.7%) as a liquid.

Synthesis of Dodecyl 2-(dimethylamino)acetate (32)

To a stirred solution of 31 (40 g, 164 mmol) in DCM (500 mL) was added aqueous formaldehyde solution (37% w/v) (17.2 g, 576 mmol) in one lot at 0° C. $Na(OAc)_3BH$ (87 g, 415 mmol) was added slowly over a period of 1 h. After addition the temperature of the reaction mixture was slowly raised to RT and stirred at RT for 24 h; and the reaction mixture was monitored by TLC. The reaction mixture was quenched with ice-cold water. The organic layer was separated, and the aqueous layer was extracted with DCM (2×40 mL). The combined organic layers were washed with brine solution. The organic layer was dried over $Na_2SO_4$, and concentrated under vacuum to afford 32 (44.5 g, yield: 99.7%) as a liquid.

Synthesis of Dodecyl 2-(dimethylamino)acetate.HCl (33, Nex-52)

A stirred solution of 32 (44.5 g, 164 mmol) in ethyl acetate/hexane (50:400 mL) was cooled to 0° C. The reaction mixture was purged with dry HCl gas for 30 minutes. The reaction mixture was monitored by TLC. The reaction mixture was concentrated under vacuum, and the obtained residue was flushed with ethyl acetate (3×50 mL) followed by hexane (5×50 mL) to afford wet dodecyl 2-(dimethylamino)acetate-.HCl 33 (45 g) as a semi solid. This semi solid was taken in ethyl acetate/hexane (10:90 mL), heated to reflux, stirred at reflux for 30 minutes. The reaction mixture was slowly cooled to RT and then to 0° C. The obtained solid was filtered under nitrogen and dried under vacuum to afford dodecyl 2-(dimethylamino)acetate.HCl salt (33, Nex-52) (28 g, yield: 54.9%) as a white hygroscopic solid, mp: 65-70° C. $^1$H-NMR (400 MHz, $CDCl_3$): δ 4.2 (t, 2H), 3.9 (s, 2H), 3.0 (s, 6H), 1.6-1.7 (m, 2H), 1.2-1.4 (m, 18H), 0.9 (t, 3H) LCMS: 272 ($M^++1$); HPLC: 99.28%.

Figure 13A:
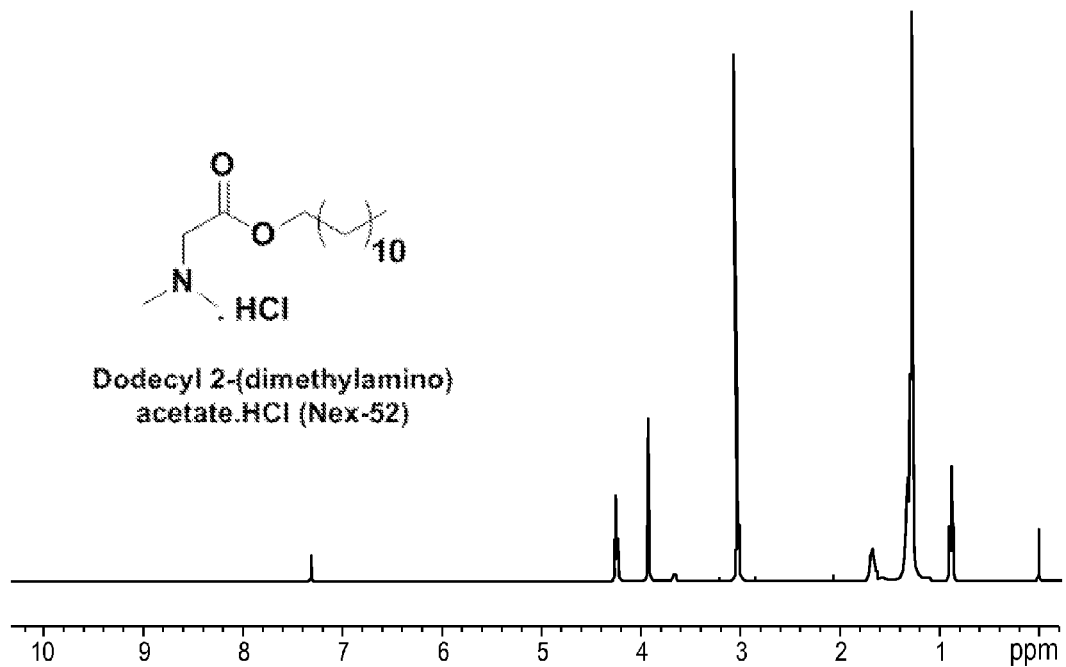
FIG. 13A is a $^1$H-NMR spectrum (400 MHz, CDCl$_3$) of dodecyl 2-(dimethylamino)acetate.HCl salt (Nex-52).

FIG. 13A is a $^1$H-NMR spectrum (400 MHz, $CDCl_3$) of dodecyl 2-(dimethylamino)acetate.HCl salt (Nex-52).

Figure 13B:
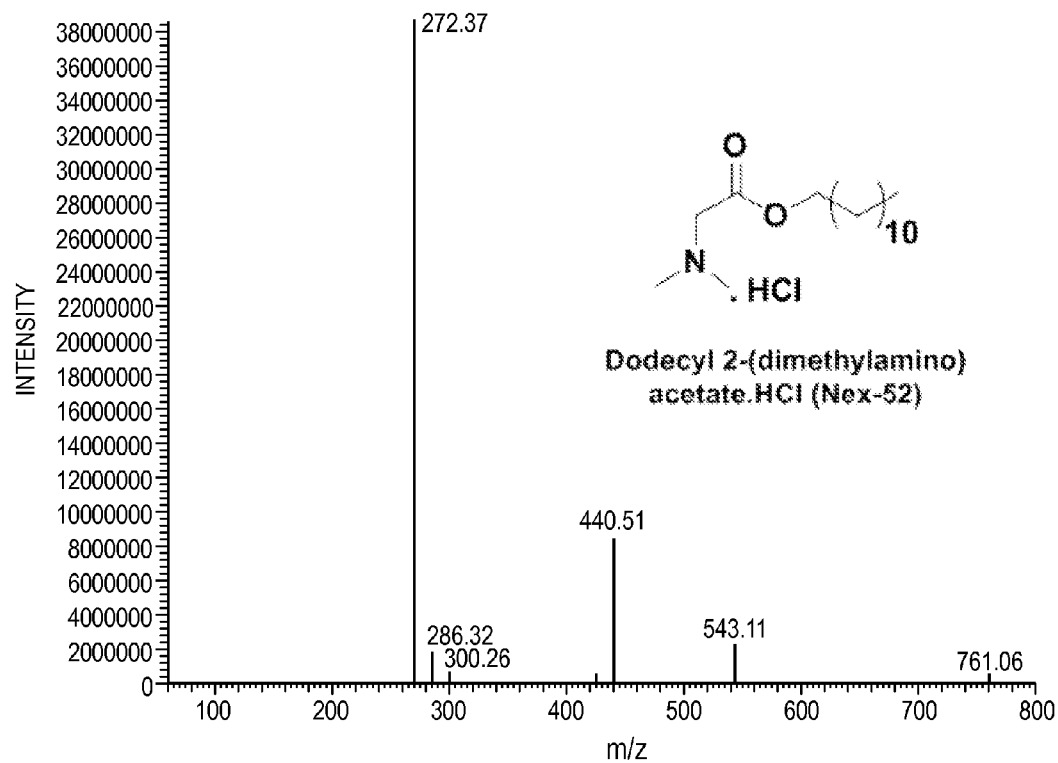
FIG. 13B is a LCMS spectrum: 272 (M$^+$+1) of dodecyl 2-(dimethylamino)acetate.HCl salt.

FIG. 13B is a LCMS spectrum: 272 ($M^++1$) of dodecyl 2-(dimethylamino)acetate.HCl salt.

Figure 13C:
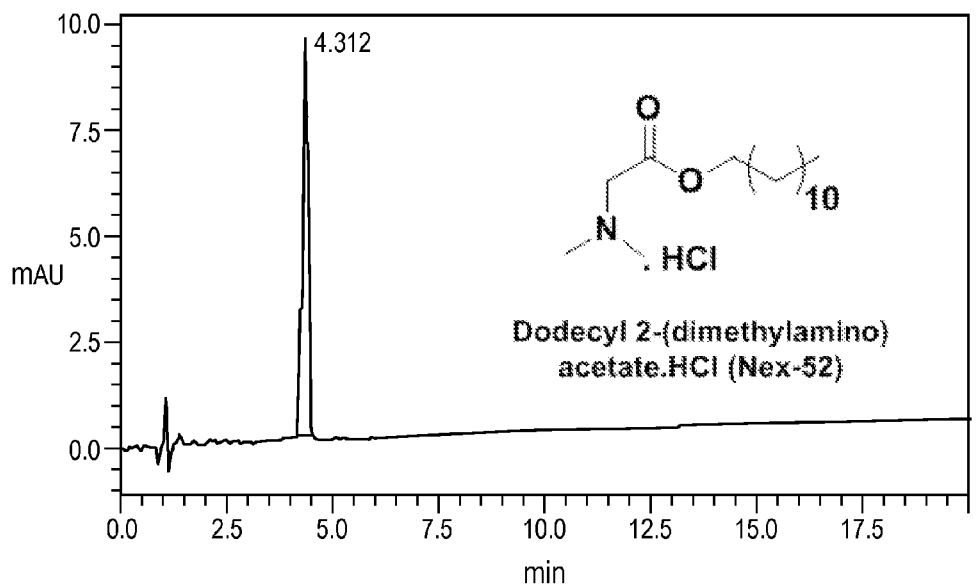
FIG. 13C is a HPLC chromatogram of dodecyl 2-(dimethylamino)acetate.HCl salt showing a peak area of 99.28%. Methods as in FIG. 4D.

FIG. 13C is a HPLC chromatogram of dodecyl 2-(dimethylamino)acetate.HCl salt showing a peak area of 99.28%. Methods as in FIG. 4D.

Example 15

Synthesis of Dodecyl 2-(dimethylamino)-3-methylbutanoate.HCl (Nex-53)

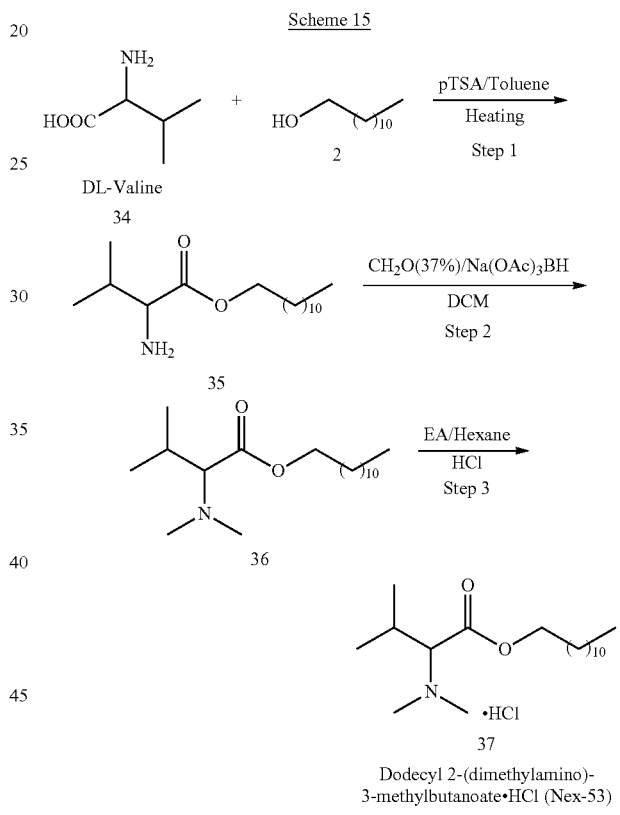

Dodecyl 2-(dimethylamino)-3-methylbutanoate•HCl (Nex-53)

Synthesis of Dodecyl 2-amino-3-methylbutanoate (35)

To a stirred solution of DL-valine 34 (20 g, 170.7 mmol) in toluene (200 mL) was added 1-dodecanol 2 (28.6 g, 153 mmol) in one lot, followed by pTSA (35.7 g, 187.7 mmol). After addition, the temperature of the reaction mixture was slowly raised to reflux temperature and the water was separated azeotropically. The reaction mixture was monitored by TLC. The reaction mixture was concentrated under vacuum. The obtained residue was taken in ethyl acetate (200 mL) and washed with aqueous 5% $Na_2CO_3$ (3×50 mL) followed by brine solution. The organic layer was dried over $Na_2SO_4$ and concentrated under vacuum to afford crude 35 (40 g, yield, 82%) as a liquid.

Synthesis of Dodecyl 2-(dimethylamino)-3-methylbutanoate (36)

To a stirred solution of 35 (40 g, 140 mmol) in DCM (500 mL) was added aqueous formaldehyde solution (37% w/v) (14.7 g, 490 mmol) in one lot at 0° C. and slowly added Na(OAc)₃BH (74.2 g, 350 mmol) over a period of 1 h. After addition, the temperature of the reaction mixture was slowly raised to RT and stirred at RT for 24 h. The reaction mixture was monitored by TLC. The reaction mixture was quenched with ice-cold water, the organic layer was separated and the aqueous layer was extracted with DCM (2×40 mL). The combined organic layers were washed with brine solution. The organic layer was dried over Na₂SO₄, and concentrated under vacuum to afford 36 (42 g, yield: 96%) as a liquid.

Synthesis of dodecyl 2-(dimethylamino)-3-metbylbutanoate.HCl (37, Nex-53)

A stirred solution of 36 (42 g, 133 mmol) in ethyl acetate/hexane (50:150 mL) and was cooled to 0° C. The reaction mixture was purged with dry HCl gas for 30 minutes, and the reaction mixture was monitored by TLC. The reaction mixture was concentrated under vacuum. The obtained residue was flushed with ethyl acetate (3×50 mL) followed by hexane (5×50 mL) to afford wet dodecyl 2-(dimethylamino)3-methylbutanoate.HCl 37 (40 g) as a semi solid. The semi solid was taken in ethyl acetate/hexane (10:90 mL), heated to reflux, stirred at reflux for 30 minutes. The reaction mixture was slowly cooled to RT and then to 0° C. The obtained solid was filtered under nitrogen and dried under vacuum to afford dodecyl 2-(dimethylamino)3-methylbutanoate.HCl salt (37, Nex-53) (27 g, yield: 57.6%) as a white hygroscopic solid, mp: 106-110° C. $^1$H-NMR (400 MHz, CDCl₃): δ 4.3 (t, 2H), 3.6 (m, 1H), 3.0-2.8 (dd, 6H), 2.4 (q, 1H), 1.7 (m, 2H), 1.2-1.4 (m, 21H) 1.1 (d, 3H), 0.9 (t, 3H) LCMS: 314 (M⁺+1); HPLC: 99.98%.

Figure 14A:
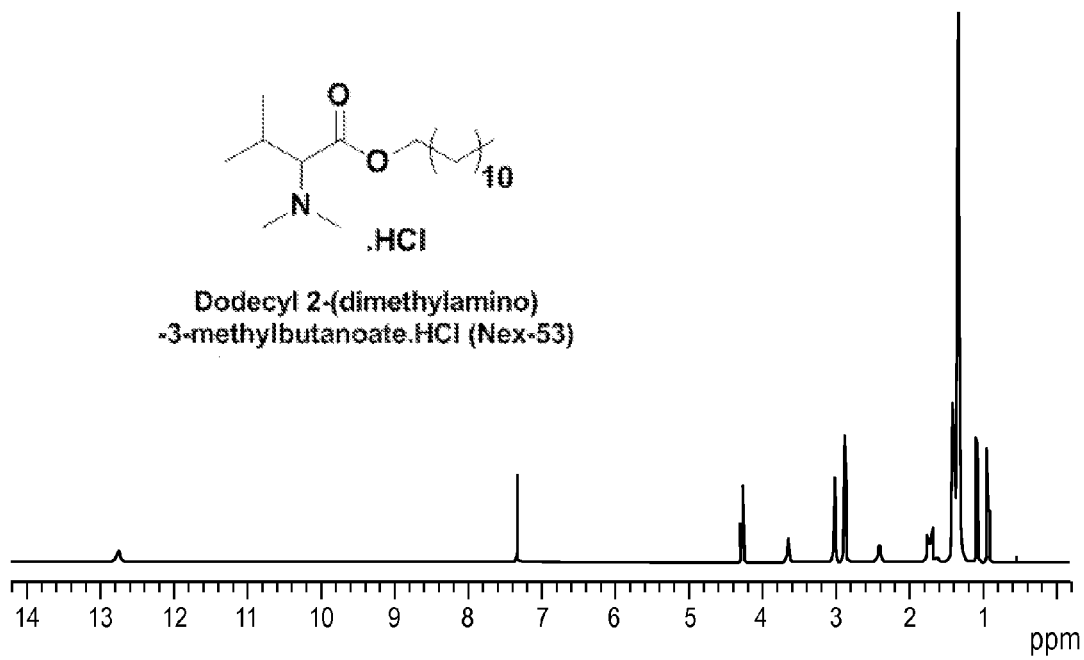
FIG. 14A is a $^1$H-NMR spectrum (400 MHz, CDCl$_3$) of dodecyl 2-(dimethylamino)3-methylbutanoate.HCl salt (Nex-53).

FIG. 14A is a $^1$H-NMR spectrum (400 MHz, CDCl₃) of dodecyl 2-(dimethylamino)3-methylbutanoate.HCl salt (Nex-53).

Figure 14B:
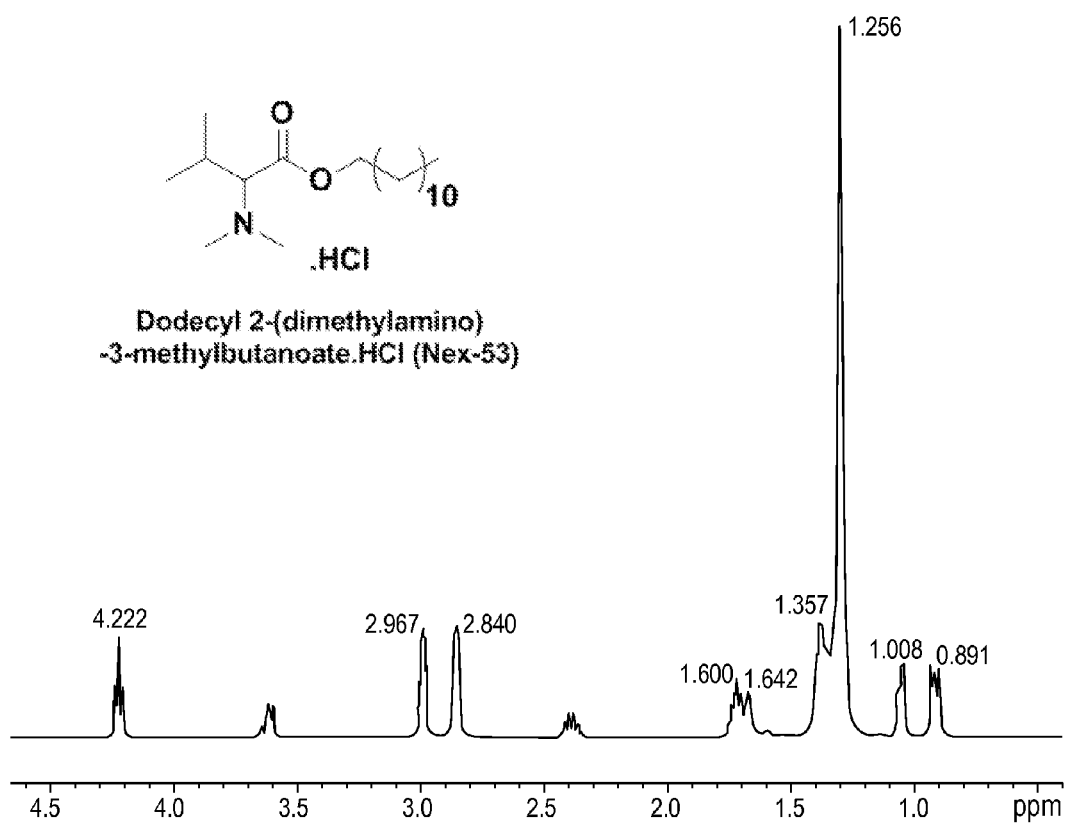
FIG. 14B is a $^1$H-NMR spectrum at a higher resolution to resolve the peaks of FIG. 14A.

FIG. 14B is a $^1$H-NMR spectrum at a higher resolution to resolve the peaks of FIG. 14A.

Figure 14C:
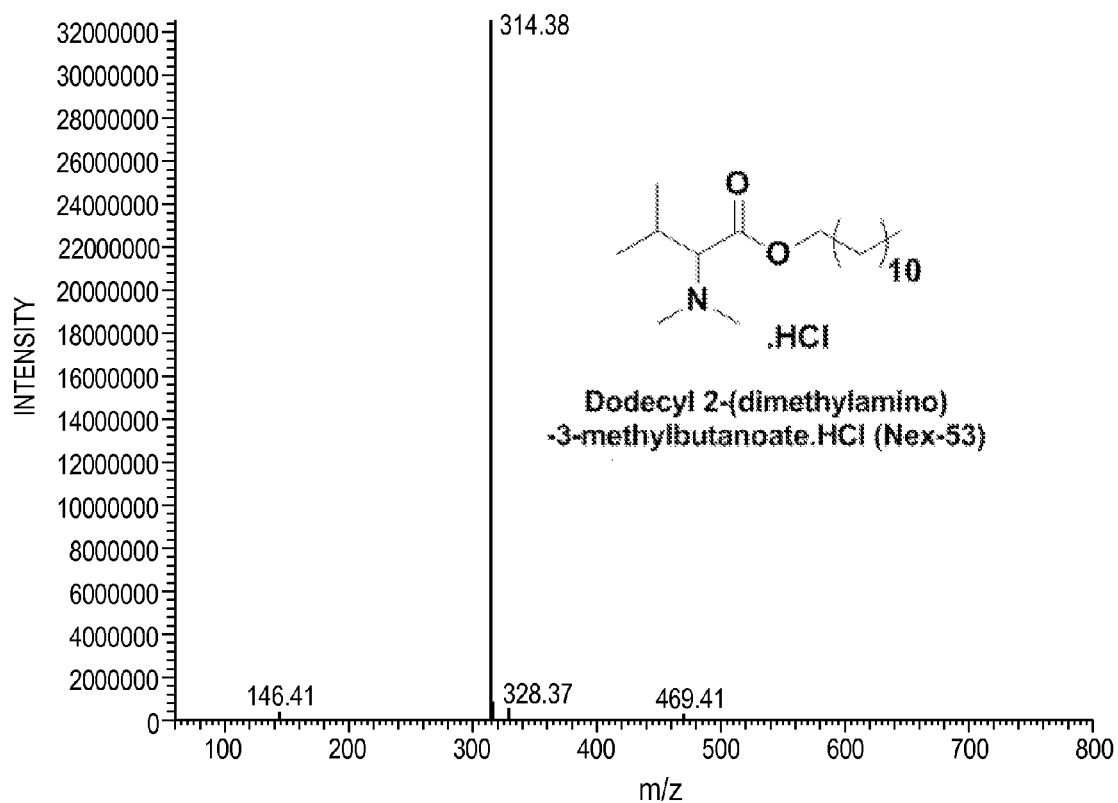
FIG. 14C is a LCMS spectrum: 314 (M$^+$+1) of dodecyl 2-(dimethylamino)3-methylbutanoate.HCl salt.

FIG. 14C is a LCMS spectrum: 314 (M⁺+1) of dodecyl 2-(dimethylamino)3-methylbutanoate.HCl salt.

Figure 14D:
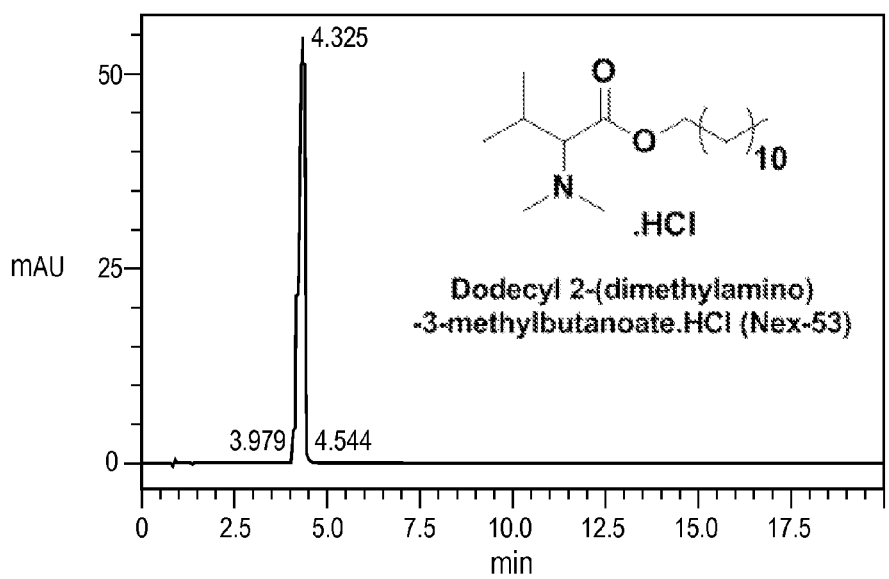
FIG. 14D is a HPLC chromatogram of dodecyl 2-(dimethylamino)3-methylbutanoate.HCl salt showing a peak area of 99.98%. Methods as in FIG. 4D.

FIG. 14D is a HPLC chromatogram of dodecyl 2-(dimethylamino)3-methylbutanoate.HCl salt showing a peak area of 99.98%. Methods as in FIG. 4D.

Example 16

Synthesis of Dodecyl 2-(dimethylamino)3-phenyl propanoate HCl (Nex-54)

Scheme 16

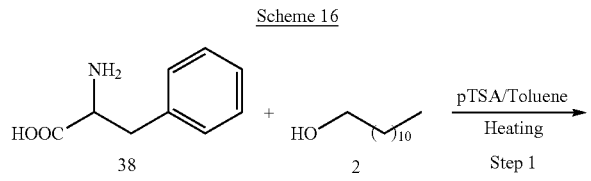

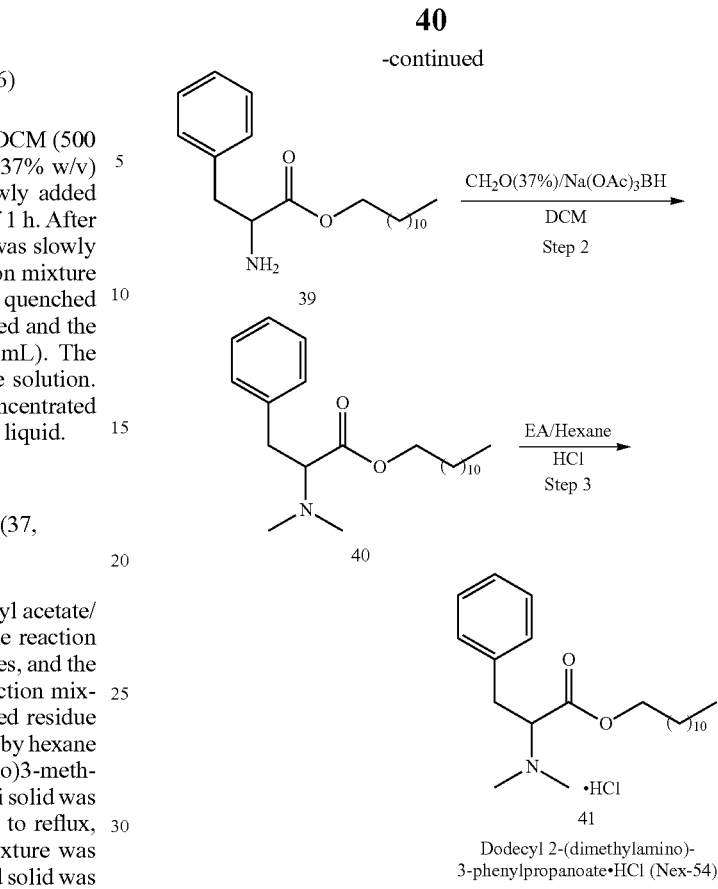

Dodecyl 2-(dimethylamino)-3-phenylpropanoate•HCl (Nex-54)

Synthesis of Dodecyl 2-amino-3-phenylpropanoate (39)

To a stirred solution of DL-phenylalanine 38 (5 g, 30.26 mmol) in toluene (100 mL) was added dodecanol 2 (5.08 g, 27.24 mmol) in one lot, followed by pTSA (6.33 g, 33.29 mmol). The temperature of the reaction mixture was slowly raised to reflux temperature, and the water was separated azeotropically The reaction mixture was monitored by TLC. The reaction mixture was concentrated under vacuum. The obtained residue was taken in ethyl acetate (200 mL) and washed with aqueous 5% Na₂CO₃ (3×50 mL) followed by brine solution. The organic layer was dried over Na₂SO₄ and concentrated under vacuum to afford crude 39 (9 g, yield: 89.1%) as a liquid.

Synthesis of dodecyl 2-(dimethylamino)3-phenylpropanoate (40)

To a stirred solution of 39 (9 g, 26.97 mmol) in DCM (45 mL) was added aqueous formaldehyde solution (37% w/v) (2.83 g, 94.3 mmol) in one lot at 0° C. and Na(OAC)₃BH (14.29 g, 67.4 mmol) was slowly added over a period of ½ h. After the addition, the temperature of the reaction mixture was slowly raised to RT and stirred at RT for 24 h. The reaction mixture was monitored by TLC. The reaction mixture was quenched with ice-cold water, the organic layer was separated and the aqueous layer was extracted with DCM (2×40 mL). The combined organic layers were washed with brine solution. The organic layer was dried over Na2SO4, and concentrated under vacuum to afford 40 (9 g, yield: 92.7%) as a liquid.

Synthesis of dodecyl 2-(dimethylamino)3-phenyl propanoate.HCl (41, Nex-54)

To a stirred solution of 40 (9 g, 24.8 mmol) in ethyl acetate/hexane (10:90 mL) and then cooled to 0° C. The reaction mixture was purged with dry HCl gas for 15 minutes, and the reaction mixture was monitored by TLC. The reaction mixture was concentrated under vacuum. The obtained residue was flushed with ethyl acetate (3×50 mL) followed by hexane (5×50 mL) to afford wet dodecyl 2-(dimethylamino)3-phenyl propanoate. HCl 41 (9 g) as a semi solid. Above semi solid was taken in ethyl acetate/hexane (10:90 mL) and heated to reflux, stirred at reflux for 30 minutes. The reaction mixture was slowly cooled to RT and then to 0° C. The reaction mixture was filtered under nitrogen and dried under vacuum to afford dodecyl 2-(dimethylamino)3-phenyl propanoate-.HCl salt (7 g, yield: 70.07%) as a white hygroscopic solid, mp: 71-76° C. $^1$H-NMR (400 MHz, CDCl$_3$): δ 7.4-7.2 (m, 5H), 4.1-4.0 (m, 3H), 3.8 (d, 1H), 3.1 (m, 1H), 3.0 (s, 3H), 2.8 (s, 3H) 1.4 (m, 2H), 1.35-1.0 (m, 18H), 0.9 (t, 3H) LCMS: 362 (M$^+$+1); HPLC: 99.8%.

Figure 15A:
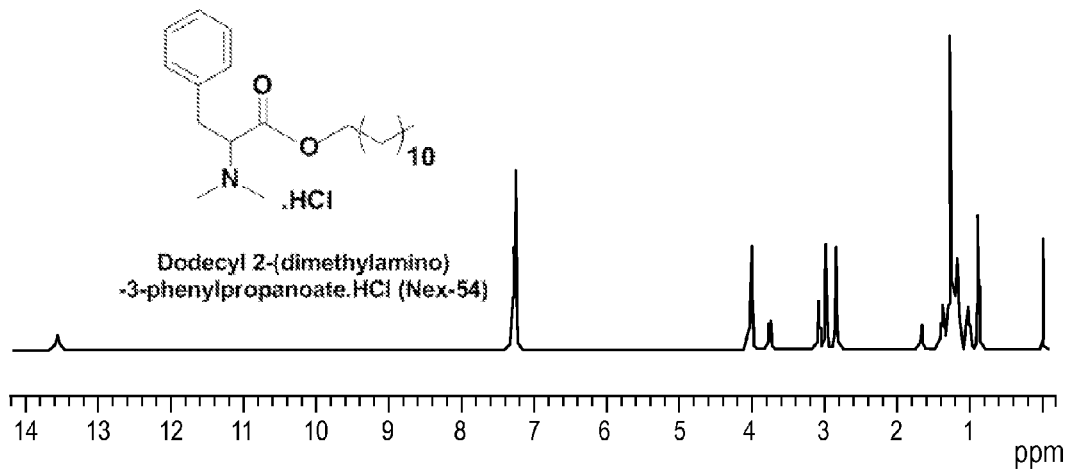
FIG. 15A is a $^1$H-NMR spectrum (400 MHz, CDCl$_3$) of dodecyl 2-(dimethylamino)3-phenyl propanoate.HCl salt (Nex-54).

FIG. 15A is a $^1$H-NMR spectrum (400 MHz, CDCl$_3$) of dodecyl 2-(dimethylamino)3-phenyl propanoate.HCl salt (Nex-54).

Figure 15B:
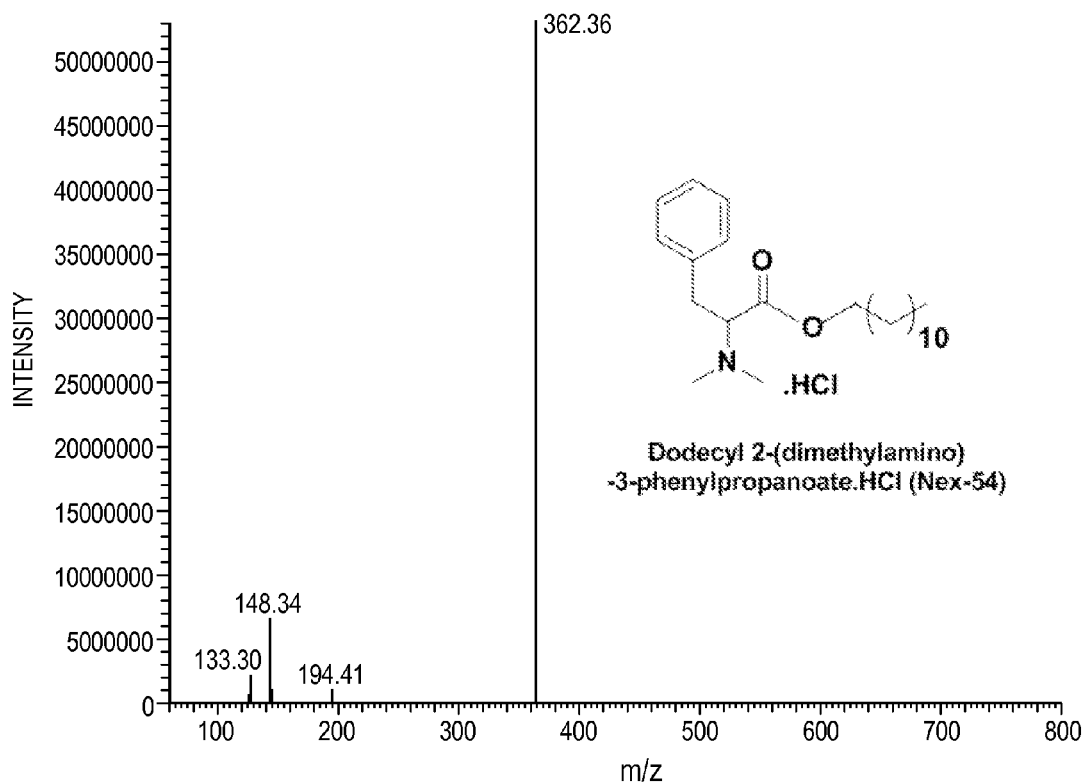
FIG. 15B is a LCMS spectrum: 314 (M$^+$+1) of dodecyl 2-(dimethylamino)3-phenyl propanoate.HCl salt.

FIG. 15B is a LCMS spectrum: 314 (M$^+$+1) of dodecyl 2-(dimethylamino)3-phenyl propanoate.HCl salt.

Figure 15C:
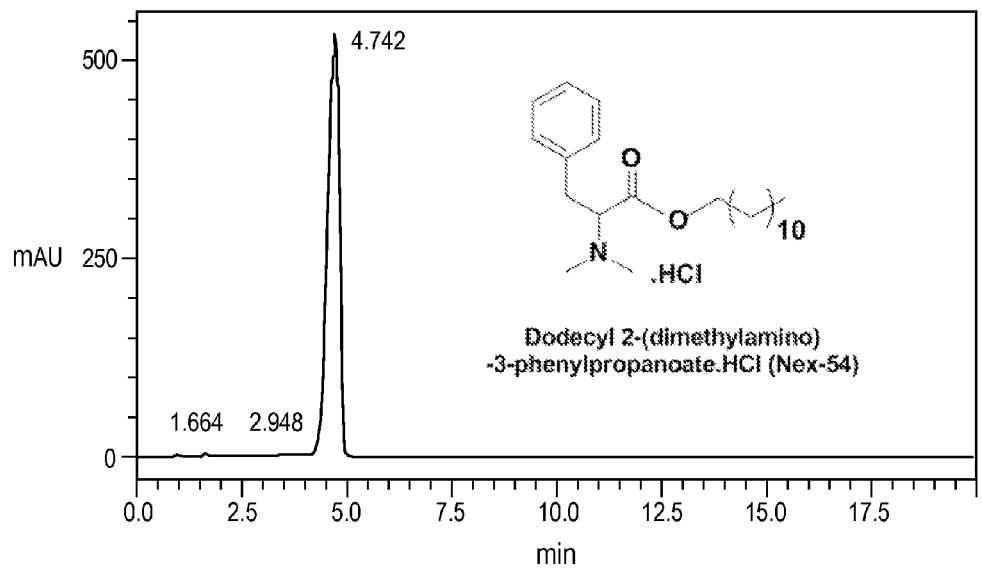
FIG. 15C is a HPLC chromatogram of dodecyl 2-(dimethylamino)3-phenyl propanoate.HCl salt showing a peak area of 99.98%. Methods as in FIG. 4D

FIG. 15C is a HPLC chromatogram of dodecyl 2-(dimethylamino)3-phenyl propanoate.HCl salt showing a peak area of 99.98%. Methods as in FIG. 4D Example 17

Dodecyl 2-(dimethylamino)-4-methylpentanoate.HCl (Nex-55)

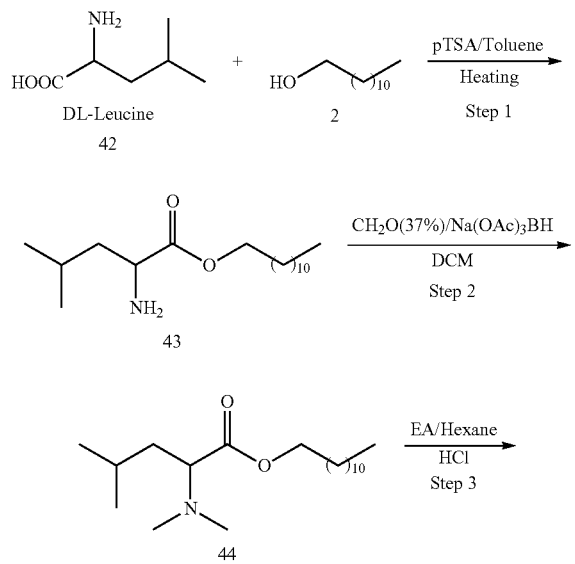

Scheme 17

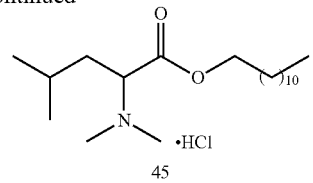

Dodecyl 2-(dimethylamino)-4-methylpropanoate•HCl (Nex-55)

Synthesis of dodecyl 2-amino-4-methylpentanoate (43)

To a stirred solution of DL-leucine 42 (20 g, 152 mmol) in toluene (400 mL) was added 1-dodecanol 2 (25.56 g, 137.2 mmol) in one lot, followed by pTSA (31.9 g, 167.7 mmol). After addition, the temperature of the reaction mixture was slowly raised to reflux temperature, the water was separated azeotropically, and the reaction mixture was monitored by TLC. The reaction mixture was concentrated under vacuum, the obtained residue was taken in ethyl acetate (200 mL) and washed with aqueous 5% Na$_2$CO$_3$ (3×50 mL) followed by brine solution. The organic layer was dried over Na$_2$SO$_4$ and concentrated under vacuum to afford crude 43 (42 g, yield: 91.9%) as a liquid.

Synthesis of dodecyl 2-(dimethylamino)-4-methylpentanoate (44)

To a stirred solution of 43 (40 g, 133 mmol) in DCM (500 mL) was added aqueous formaldehyde solution (37% w/v) (14 g, 467 mmol) in one lot at 0° C. Na(OAc)$_3$BH (70.7 g, 333.8 mmol) was slowly added over a period of 1 h. After the addition, the temperature of the reaction mixture was slowly raised to RT and stirred at RT for 24 h. The reaction mixture was monitored by TLC. The reaction mixture was quenched with ice-cold water, the organic layer was separated, and the aqueous layer was extracted with DCM (2×40 mL). The combined organic layers were washed with brine solution. The organic layer was dried over Na$_2$SO$_4$, and concentrated under vacuum to afford 44 (42 g, yield: 91%) as a liquid.

Synthesis of dodecyl 2-(dimethylamino)-4-methylpentanoate.HCl (45, Nex-55)

A stirred solution of 44 (40 g, 121 mmol) in ethyl acetate/hexane (50:150 mL) was cooled to 0° C. The reaction mixture was purged with dry HCl gas for 30 minutes, and the reaction mixture was monitored by TLC. The reaction mixture was concentrated under vacuum. The obtained residue was flushed with ethyl acetate (3×50 mL) followed by hexane (5×50 mL) to afford wet dodecyl 2-(dimethylamino)-4-methylpentanoate.HCl 45 (40 g) as a semi solid. The semi solid was taken in ethyl acetate/hexane (10:90 mL), heated to reflux, and stirred at reflux for 30 minutes. The reaction mixture was slowly cooled to RT and then to 0° C. The reaction mixture was filtered under nitrogen and dried under vacuum to afford dodecyl 2-(dimethylamino)-4-methylpentanoate.HCl salt (25 g, yield: 56.2%) as a white hygroscopic solid, mp: 104-109° C. $^1$H-NMR (400 MHz, CDCl$_3$): δ 4.2 (t, 2H), 3.9 (d, 1H), 2.8-2.6 (dd, 6H), 2.0-1.8 (m, 2H), 1.7 (m, 31H), 1.4-1.2 (m, 18H), 1.35-1.0 (m, 18H), 1.0 (dd, 6H), 0.7 (t, 3H) LCMS: 328 (M$^+$+1); HPLC: 99.92%.

Figure 16A:
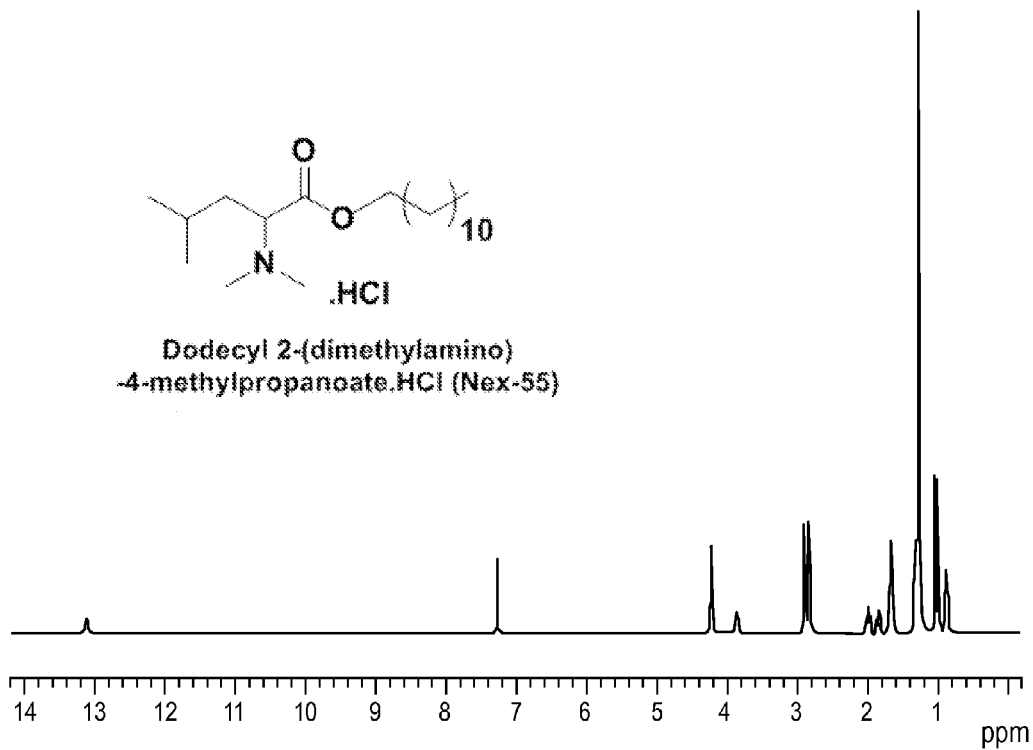
FIG. 16A is a $^1$H-NMR spectrum of dodecyl 2-(dimethylamino)-4-methylpentanoate.HCl salt (Nex-55).

FIG. 16A is a ¹H-NMR spectrum of dodecyl 2-(dimethylamino)-4-methylpentanoate.HCl salt (Nex-55).

Figure 16B:
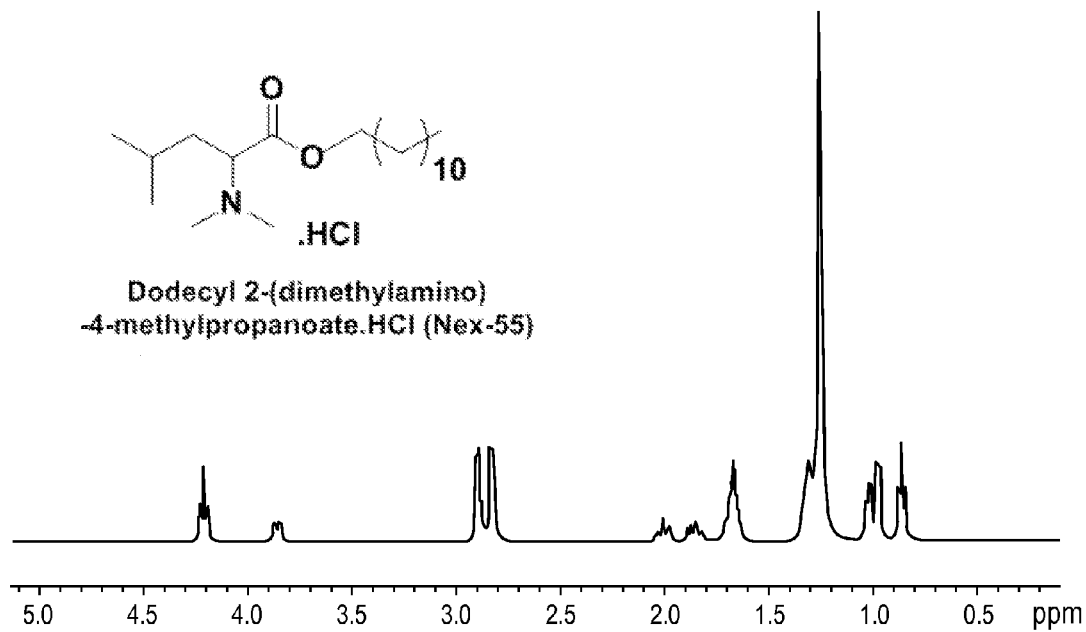
FIG. 16B is a ¹H-NMR spectrum at a higher resolution to resolve the peaks of FIG. 16A.

FIG. 16B is a ¹H-NMR spectrum at a higher resolution to resolve the peaks of FIG. 16A.

Figure 16C:
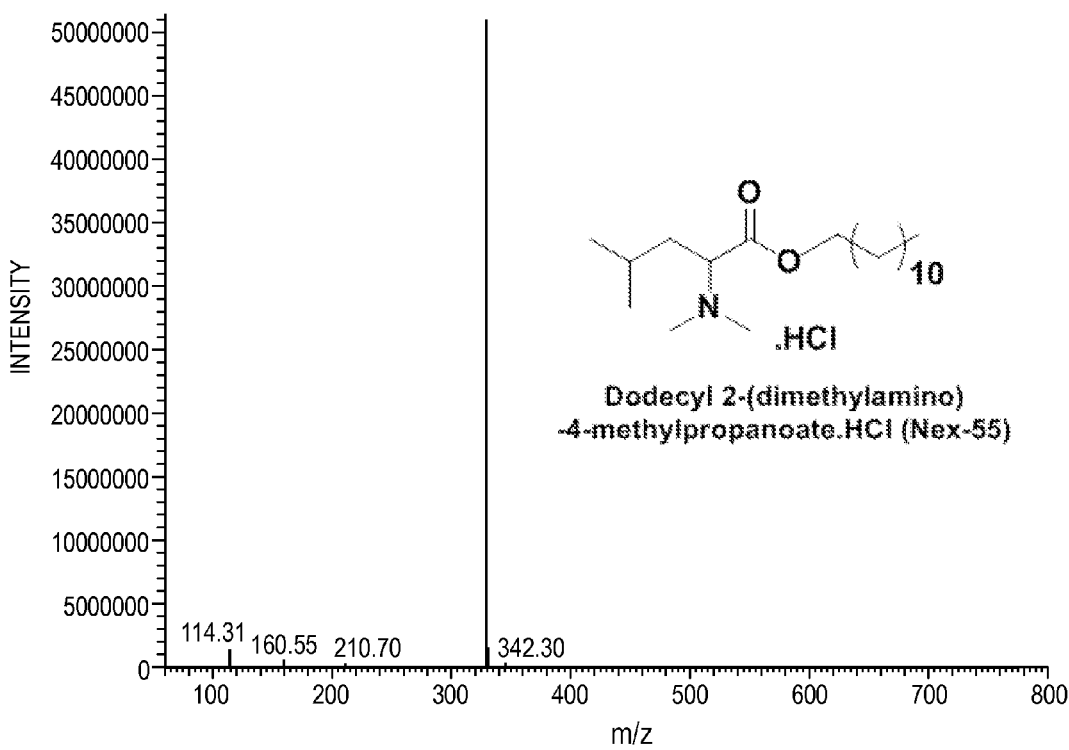
FIG. 16C is a LCMS spectrum: 328 (M⁺+1) of dodecyl 2-(dimethylamino)-4-methylpentanoate.HCl salt.

FIG. 16C is a LCMS spectrum: 328 (M⁺+1) of dodecyl 2-(dimethylamino)-4-methylpentanoate.HCl salt.

Figure 16D:
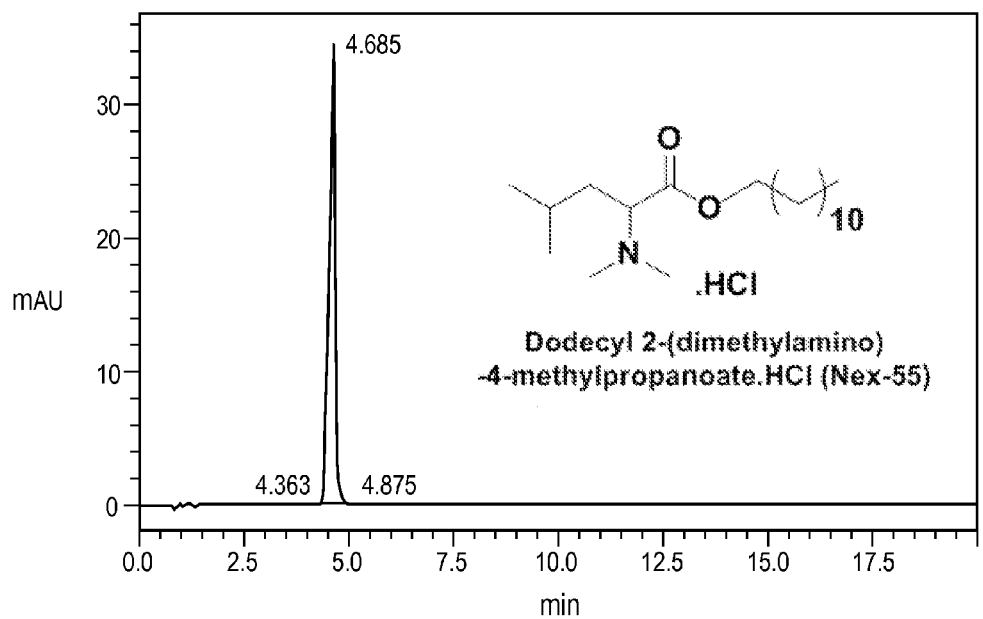
FIG. 16D is a HPLC chromatogram of dodecyl 2-(dimethylamino)-4-methylpentanoate.HCl salt showing a peak area of 99.92%. Methods as in FIG. 4D.

FIG. 16D is a HPLC chromatogram of dodecyl 2-(dimethylamino)-4-methylpentanoate.HCl salt showing a peak area of 99.92%. Methods as in FIG. 4D.

Example 18

D-Dodecyl 2-(dimethylamino)propanoate hydrochloride (Nex-56)

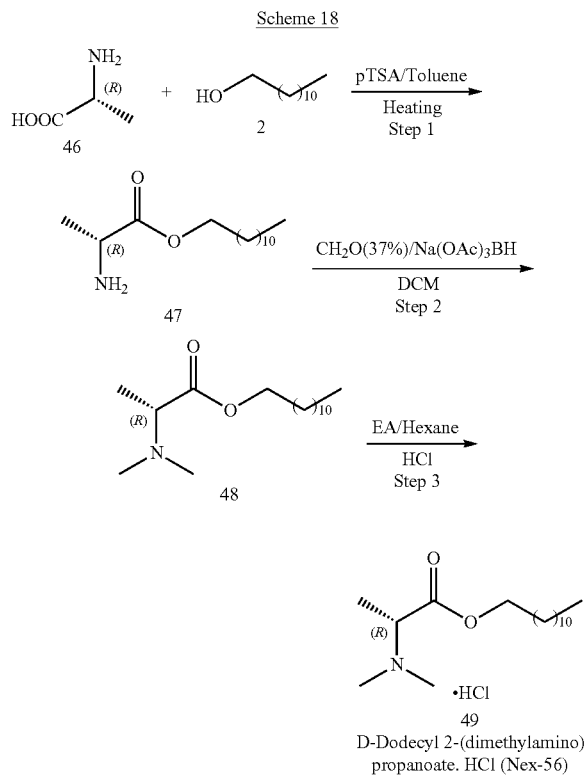

Scheme 18

D-Dodecyl 2-(dimethylamino) propanoate. HCl (Nex-56)

Synthesis of D-Dodecyl 2-amino propanoate (47)

To a stirred solution of D-alanine 46 (15 g, 168.5 mmol) in toluene (200 mL) was added 1-dodecanol 2 (28.26 g, 151.6 mmol) in one lot, followed by pTSA (35.25 g, 185.3 mmol). After the addition, the temperature of the reaction mixture was slowly raised to reflux temperature, the water was separated azeotropically, and the reaction mixture was monitored by TLC. The reaction mixture was concentrated under vacuum. The obtained residue was taken in ethyl acetate (200 mL) and washed with aqueous 5% $Na_2CO_3$ (3×50 mL) followed by brine solution. The organic layer was dried over $Na_2SO_4$ and concentrated under vacuum to afford 47 (42 g, yield: 97.6%) as a liquid.

Synthesis of D-Dodecyl 2-(dimethylamino)propanoate (48)

To a stirred solution of 47 (42 g, 163 mmol) in DCM (500 mL) was added aqueous formaldehyde solution (37% w/v) (17.13 g, 571 mmol) in one lot at 0° C. $Na(OAC)_3BH$ (86.47 g, 408 mmol) was slowly added over a period of 1 h. After the addition, the temperature of the reaction mixture was slowly raised to RT and stirred at RT for 12 h; the reaction mixture was monitored by TIC. The reaction mixture was quenched with ice-cold water, the organic layer was separated and the aqueous layer was extracted with DCM (2×250 mL). The combined organic layers were washed with brine solution. The organic layer was dried over $Na_2SO_4$, and concentrated under vacuum to afford D-Dodecyl 2-(dimethylamino)propanoate 48 (42 g, yield: 96.9%) as a liquid.

Synthesis of D-Dodecyl 2-(dimethylamino)propanoate hydrochloride (49, Nex-56)

A stirred solution of D-Dodecyl 2-(dimethylamino)propanoate 48 (42 g, 147 mmol) in ethyl acetate/hexane/MeOH (100:100:10 mL) was cooled to 0° C. The reaction mixture was purged with dry HCl gas for 30 minutes, and the reaction mixture was monitored by TLC. The reaction mixture was concentrated under vacuum, and the obtained residue was flushed with ethyl acetate (3×52 mL) followed by hexane (3×25 mL) to afford D-Dodecyl 2-(dimethylamino)propanoate hydrochloride salt 49 (42 g) as a semi solid. The semi solid was taken in hexane (100 mL), heated to reflux, and stirred at reflux for 30 minutes. The reaction mixture was slowly cooled to RT and then to 0° C. The reaction mixture was filtered under nitrogen and dried under vacuum to afford (R)-Dodecyl 2-(dimethylamino)propanoate hydrochloride salt 49 (27 g, yield: 57.4%) as a white hygroscopic solid, mp: 86-89° C. ¹H-NMR (400 MHz, $CDCl_3$): δ 4.25 (m, 2H), 4.0 (m, 1H), 3.9 (s, 6H), 1.8-1.6 (m, 5H), 1.4-1.2 (m, 18H), 0.9 (t, 3H); LCMS: 286 (M⁺+1); HPLC: 99.8%.

Figure 17A:
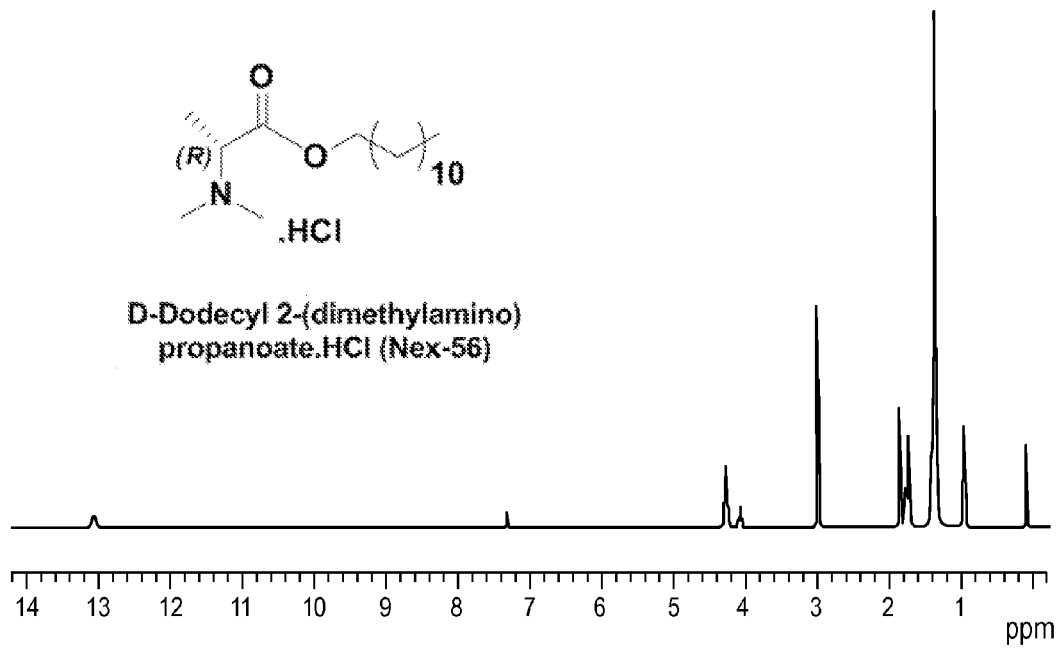
FIG. 17A is a ¹H-NMR spectrum (400 MHz, CDCl₃) of D-dodecyl 2-(dimethylamino)propanoate hydrochloride salt (Nex-56).

FIG. 17A is a ¹H-NMR spectrum (400 MHz, $CDCl_3$) of (R)-dodecyl 2-(dimethylamino)propanoate hydrochloride salt (Nex-56).

Figure 17B:
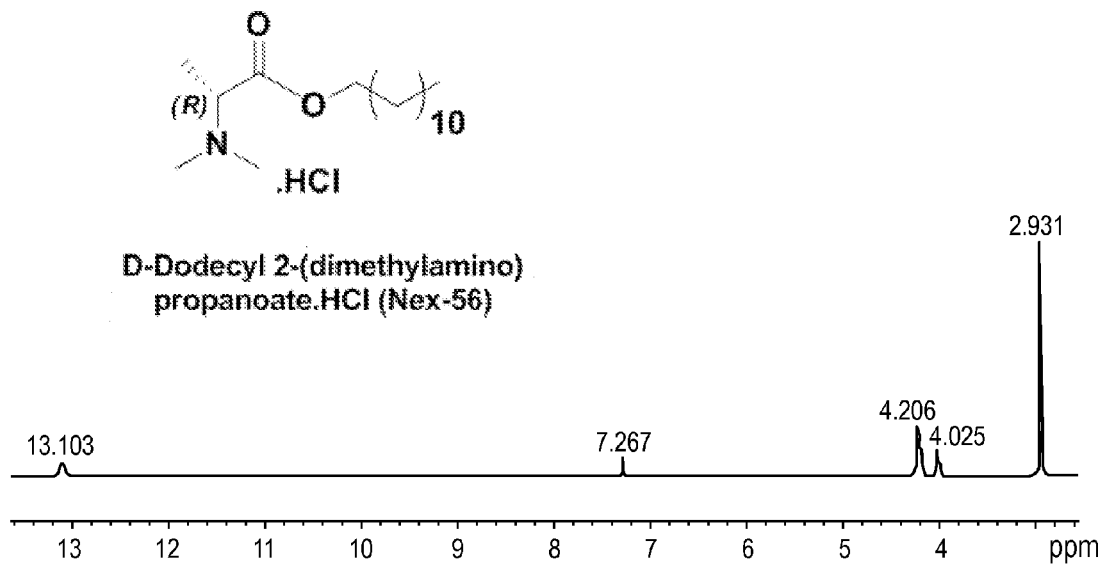
FIG. 17B is a ¹H-NMR spectrum at a higher resolution to resolve the peaks of FIG. 17A.

FIG. 17B is a ¹H-NMR spectrum at a higher resolution to resolve the peaks of FIG. 17A.

Figure 17C:
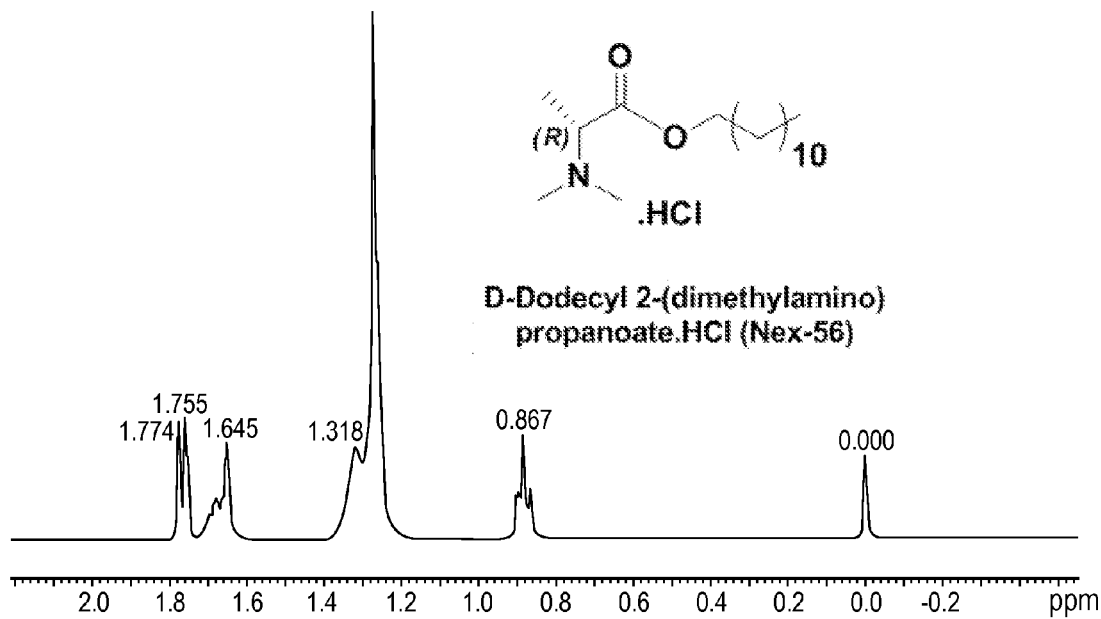
FIG. 17C is a ¹H-NMR spectrum at a higher resolution to resolve the peaks of FIG. 17A.

FIG. 17C is a ¹H-NMR spectrum at a higher resolution to resolve the peaks of FIG. 17A.

Figure 17D:
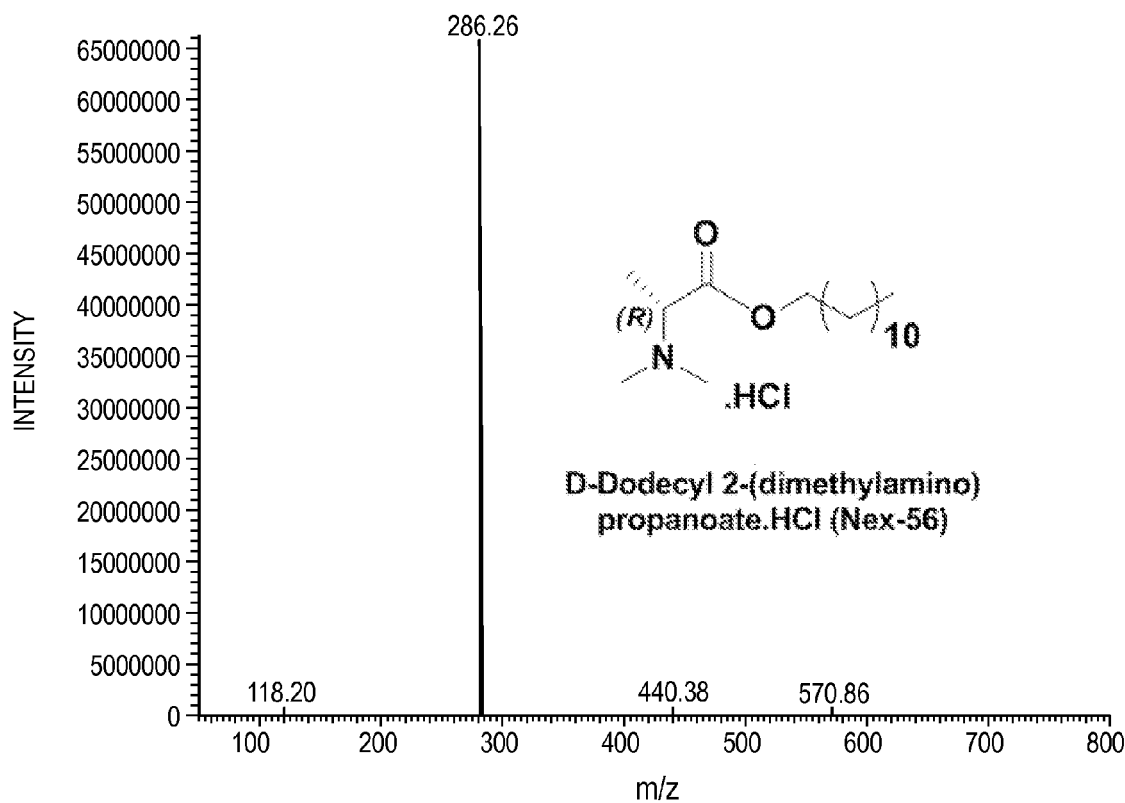
FIG. 17D is a LCMS spectrum: 286.26 (M⁺+1) of D-dodecyl 2-(dimethylamino)propanoate hydrochloride salt.

FIG. 17D is a LCMS spectrum: 286.26 (M⁺+1) of (R)-dodecyl 2-(dimethylamino)propanoate hydrochloride salt.

Figure 17E:
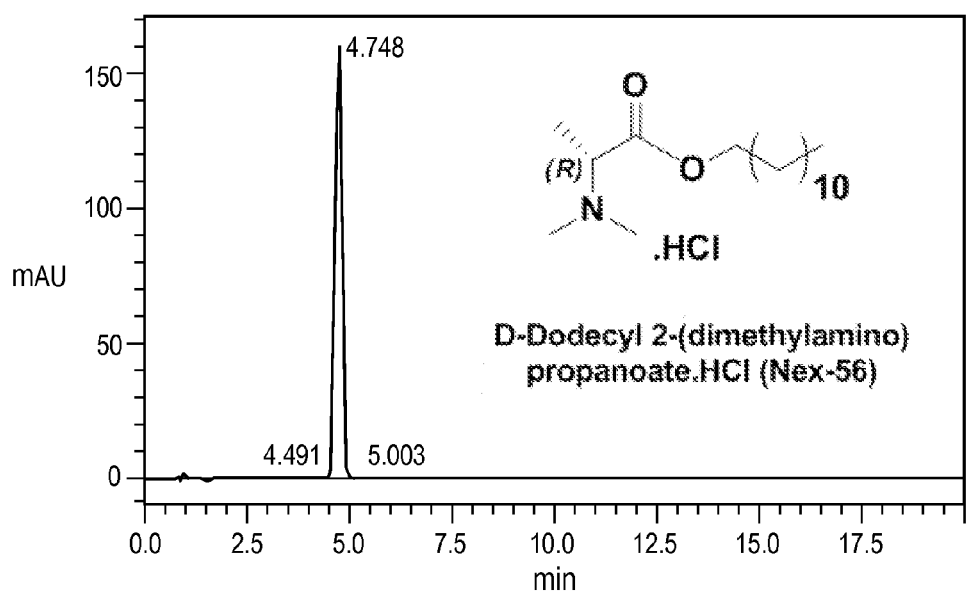
FIG. 17E is a HPLC chromatogram of D-dodecyl 2-(dimethylamino)propanoate hydrochloride salt showing a peak area of 99.92%. Methods as in FIG. 4D.
Figure 17F:
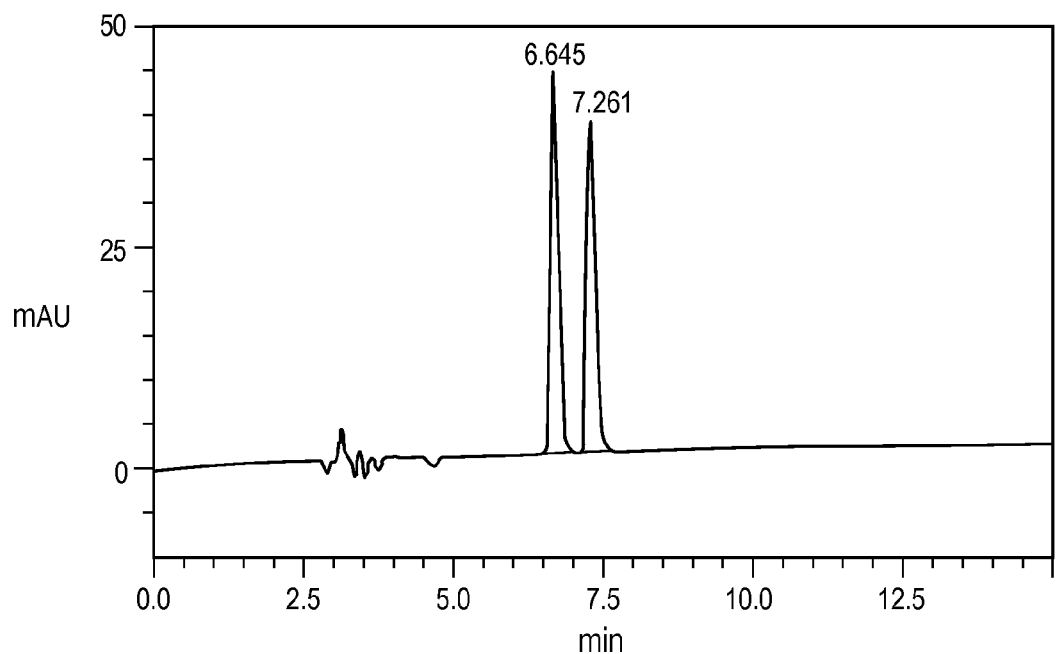
FIG. 17F is a HPLC chromatogram of the DL-dodecyl 2-(dimethylamino)propanoate hydrochloride salt racemate showing the separate peaks of the two stereoisomers. Methods: column: Chiralpak AD-3 (250×4.6 mm, 3 μm); mobile phase: 0.1% diethyl amine in Methanol (100:0.1); injection volume 10 μL, column temperature, 15° C., flow rate 1.0 mL/min; detection 235 nm 4 nm.

FIG. 17E is a HPLC chromatogram of (R)-dodecyl 2-(dimethylamino)propanoate hydrochloride salt showing a peak area of 99.92%. Methods as in FIG. 4D FIG. 17F is a HPLC chromatogram of the DL-dodecyl 2-(dimethylamino)propanoate hydrochloride salt racemate showing the separate peaks of the two stereoisomers. Methods: column: Chiralpak AD-3 (250×4.6 mm, 3 Mm); mobile phase: 0.1% diethyl amine in Methanol (100:0.1); injection volume 10 μL, column temperature, 15° C., flow rate 1.0 mL/min; detection 235 nm 4 nm.

Figure 17G:
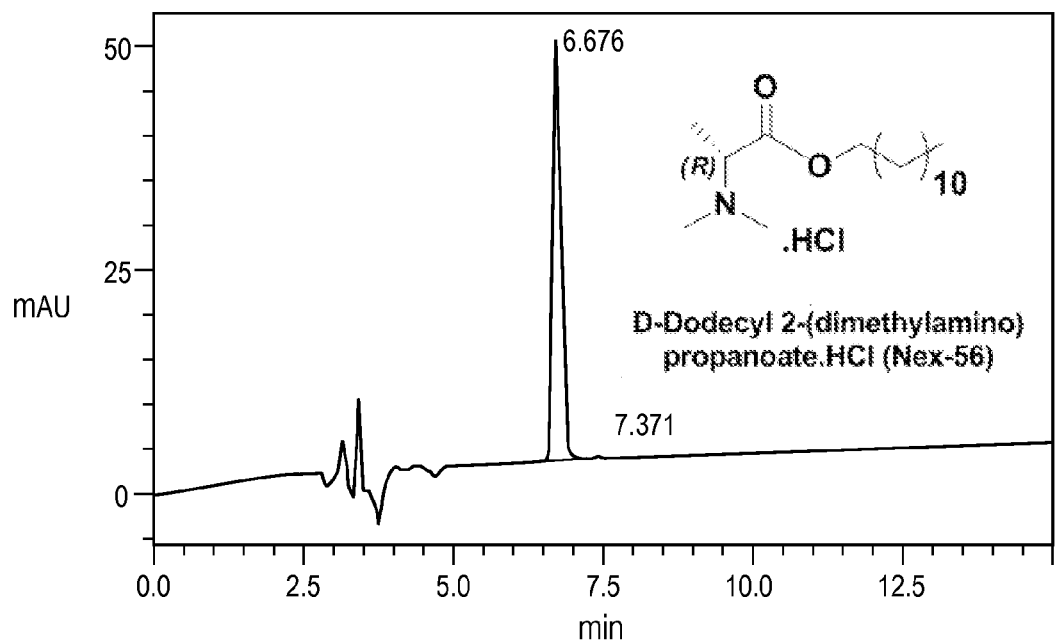
FIG. 17G is a HPLC chromatogram of D-dodecyl 2-(dimethylamino)propanoate hydrochloride salt showing a peak area of 99.92%. Methods as in FIG. 17F, except that the detection was 235 nm 8 nm.

FIG. 17G is a HPLC chromatogram of D-dodecyl 2-(dimethylamino)propanoate hydrochloride salt showing a peak area of 99.92%. Methods as in FIG. 17F, except that the detection was 235 nm 8 nm.

Example 19

L-Dodecyl 2-(dimethylamino)propanoate hydrochloride (Nex-57)

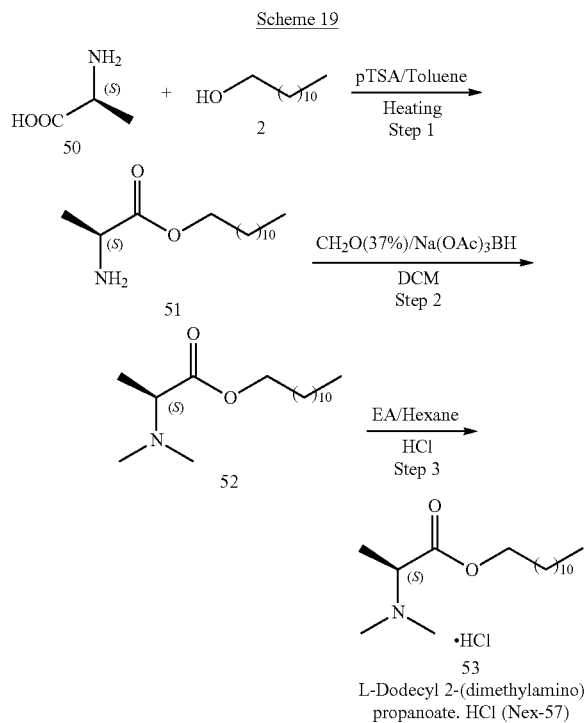

Scheme 19

Synthesis of L-dodecyl 2-amino propanoate (51)

To a stirred solution of (S) L-alanine 50 (15 g, 168.5 mmol) in toluene (200 mL) was added 1-dodecanol 2 (28.26 g, 151.6 mmol) in one lot, followed by pTSA (35.25 g, 185.3 mmol). After the addition, the temperature of the reaction mixture was slowly raised to reflux temperature, the water was separated azeotropically, and the reaction mixture was monitored by TLC. The reaction mixture was concentrated under vacuum. The obtained residue was taken in ethyl acetate (200 mL) and washed with aqueous 5% $Na_2CO_3$ (3×50 mL) followed by brine solution. The organic layer was dried over $Na_2SO_4$ and concentrated under vacuum to afford 51 (42 g, yield: 97.6%) as a liquid.

Synthesis of L-Dodecyl 2-(dimethylamino)propanoate (52)

To a stirred solution of 51 (42 g, 163 mmol) in DCM (500 mL) was added aqueous formaldehyde solution (37% w/v) (17.13 g, 571 mmol) in one lot at 0° C. and $Na(OAC)_3BH$ (86.47 g, 408 mmol) was slowly added over a period of 1 h. After the addition, the temperature of the reaction mixture was slowly raised to RT and stirred at RT for 12 h. The reaction mixture was monitored by TLC. The reaction mixture was quenched with ice-cold water, the organic layer was separated, and the aqueous layer was extracted with DCM (2×250 mL). The combined organic layers were washed with brine solution. The organic layer was dried over $Na_2SO_4$, and concentrated under vacuum to afford L-DDAIP 52 (42 g, yield: 96.9%) as a liquid.

Synthesis of L-Dodecyl 2-(dimethylamino)propanoate hydrochloride

A stirred solution of L-DDAIP 52 (42 g, 147 mmol) in ethyl acetate/hexane/MeOH (100:100:10 mL) was cooled to 0° C. The reaction mixture was purged with dry HC gas for 30 minutes; the reaction mixture was monitored by TLC. The reaction mixture was concentrated under vacuum, and the obtained residue was flushed with ethyl acetate (3×52 mL) followed by hexane (3×25 ml) to afford L-dodecyl 2-(dimethylamino)propanoate hydrochloride (53, Nex-57) salt (42 g) as a semi solid. The semi solid was taken in hexane (100 mL), heated to reflux, and stirred at reflux for 30 minutes. The reaction mixture was slowly cooled to RT and then to 0° C. The reaction mixture was filtered under nitrogen and dried under vacuum to afford L-dodecyl 2-(dimethylamino)propanoate hydrochloride salt (27 g, yield; 57.4%) as a white hygroscopic solid, mp: 86-90° C. $^1$H-NMR (400 MHz, $CDCl_3$): δ 4.25 (m, 2H), 4.0 (m, 1H), 3.9 (s, 6H), 1.8-1.6 (m, 5H), 1.4-1.2 (m, 18H), 0.9 (t, 3H); LCMS: 286 ($M^++1$); HPLC: 99.8%.

Figure 18A:
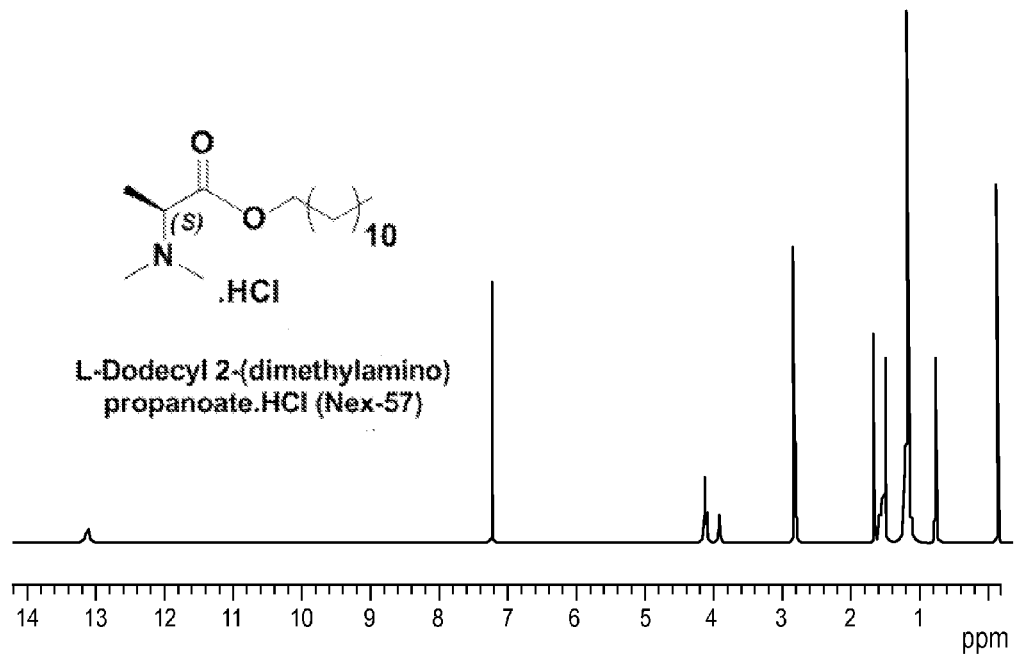
FIG. 18A is a ¹H-NMR spectrum (400 MHz, CDCl₃) of L-dodecyl 2-(dimethylamino)propanoate hydrochloride salt (Nex-57).

FIG. 18A is a $^1$H-NMR spectrum (400 MHz, $CDCl_3$) of L-dodecyl 2-(dimethylamino)propanoate hydrochloride salt (Nex-57).

Figure 18B:
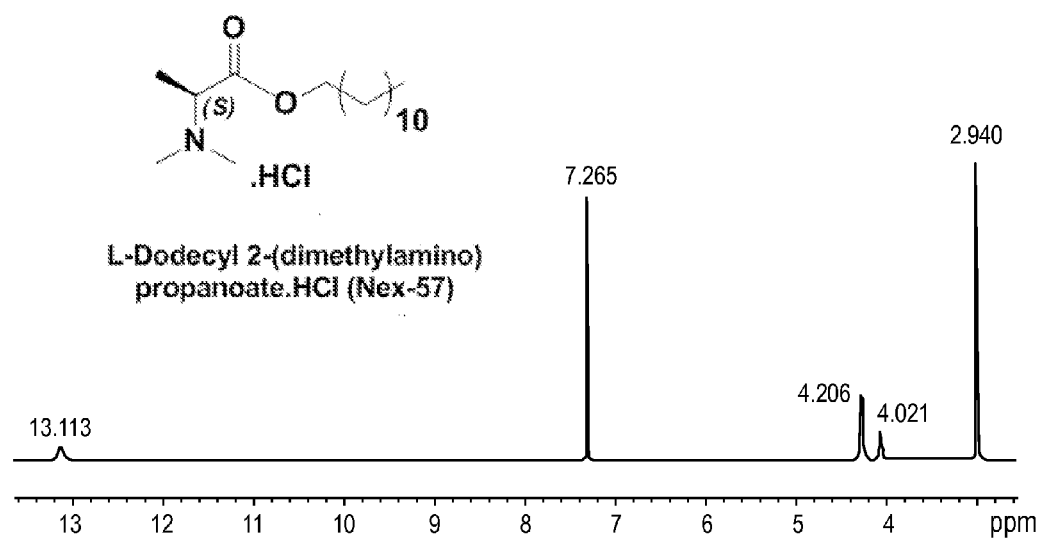
FIG. 18B is a ¹H-NMR spectrum at a higher resolution to resolve the peaks of FIG. 18A.

FIG. 18B is a $^1$H-NMR spectrum at a higher resolution to resolve the peaks of FIG. 18A.

Figure 18C:
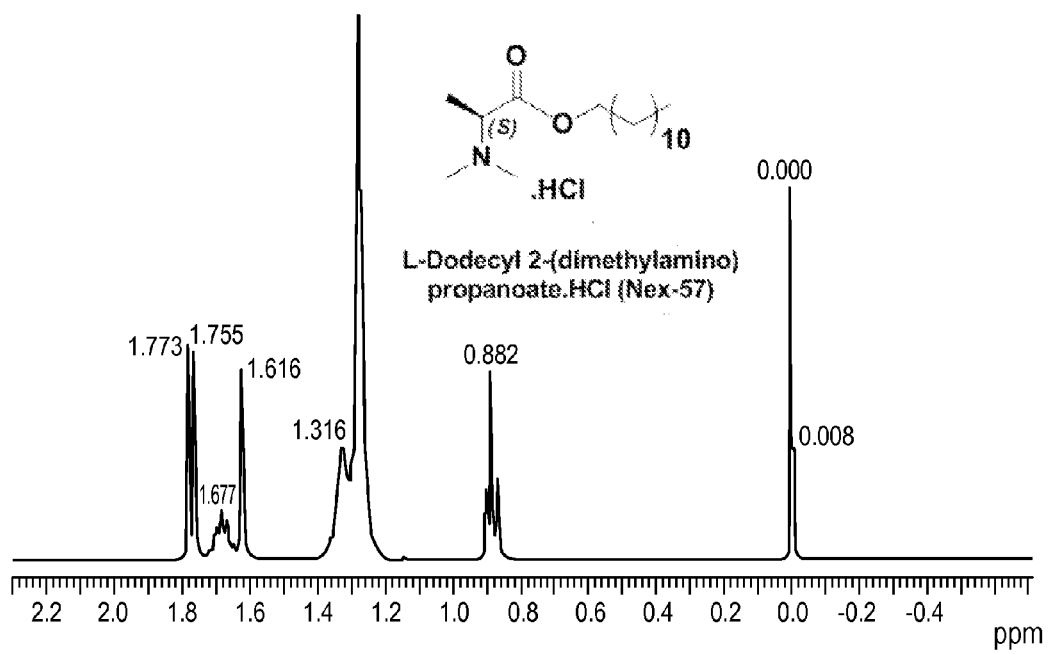
FIG. 18C is a ¹H-NMR spectrum at a higher resolution to resolve the peaks of FIG. 18A.

FIG. 18C is a $^1$H-NMR spectrum at a higher resolution to resolve the peaks of FIG. 18A.

Figure 18D:
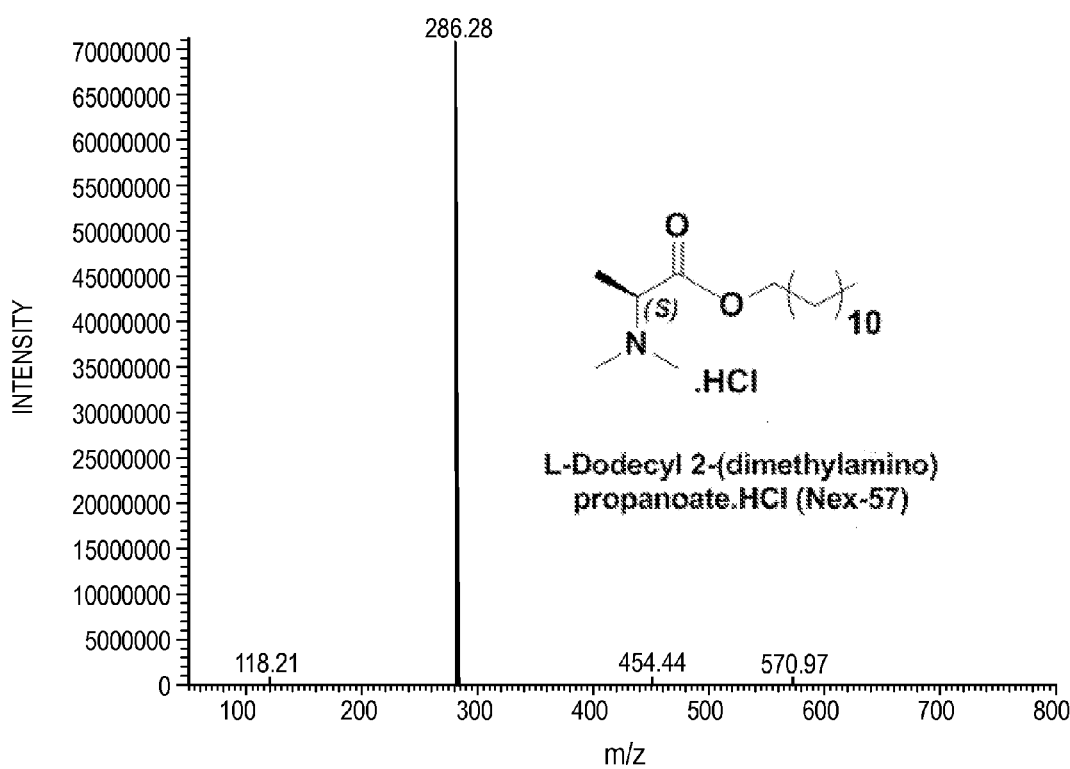
FIG. 18D is a LCMS spectrum: 286.28 (M⁺+1) of L-dodecyl 2-(dimethylamino)propanoate hydrochloride salt.

FIG. 18D is a LCMS spectrum: 286.28 ($M^++1$) of L-dodecyl 2-(dimethylamino)propanoate hydrochloride salt.

Figure 18E:
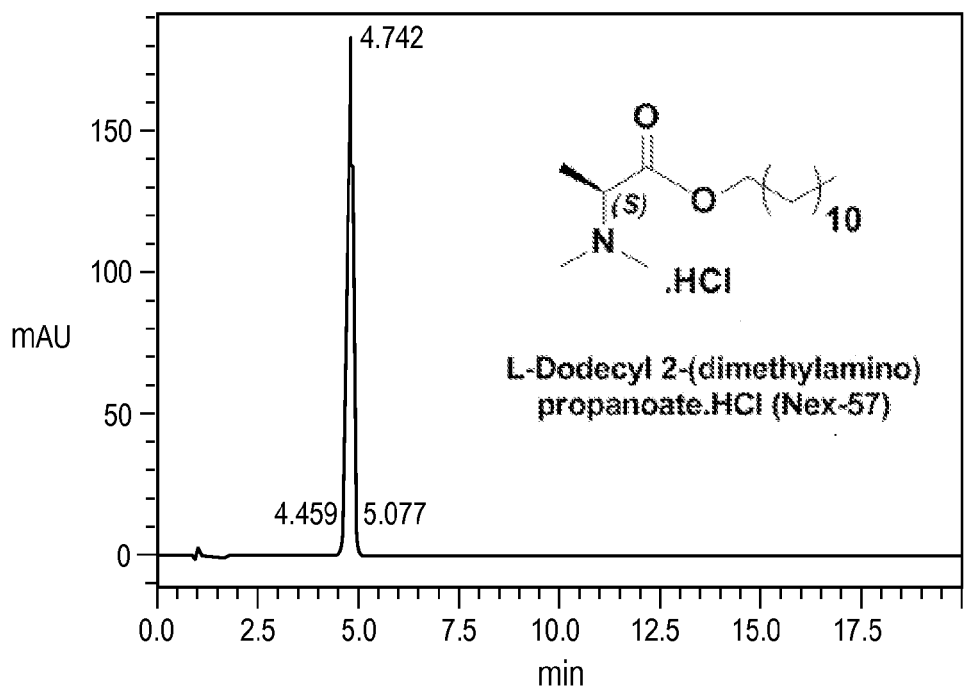
FIG. 18E is a HPLC chromatogram of L-dodecyl 2-(dimethylamino)propanoate hydrochloride salt showing a peak area of 99.85%. Methods as in FIG. 4D.

FIG. 18E is a HPLC chromatogram of L-dodecyl 2-(dimethylamino)propanoate hydrochloride salt showing a peak area of 99.85%. Methods as in FIG. 4D

Figure 18F:
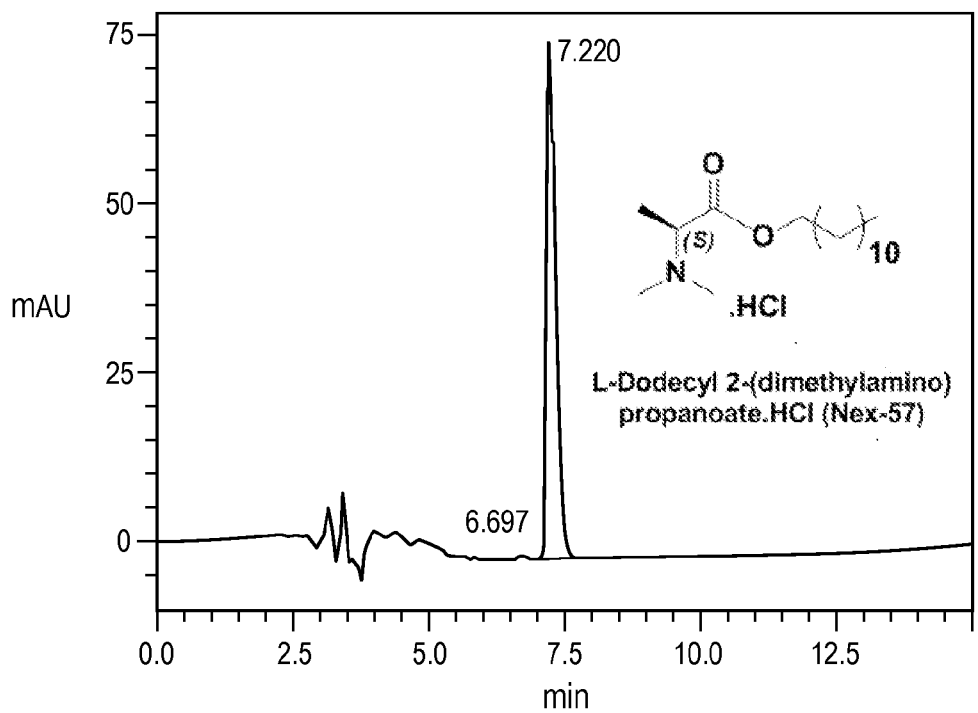
FIG. 18F is a HPLC chromatogram of L-dodecyl 2-(dimethylamino)propanoate hydrochloride salt showing a peak area of 99.5%. Methods as in FIG. 17F.

FIG. 18F is a HPLC chromatogram of L-dodecyl 2-(dimethylamino)propanoate hydrochloride salt showing a peak area of 99.5%. Methods as in FIG. 17F.

Example 20

Dodecyl 2-(dimethylamino)-2-methylpropanoate hydrochloride (Nex-58)

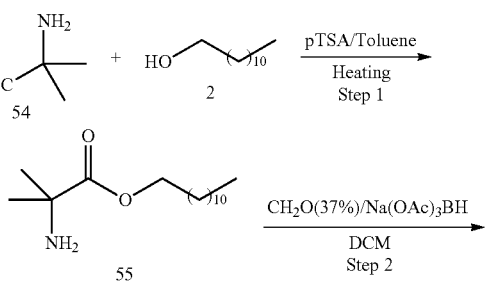

Scheme 20

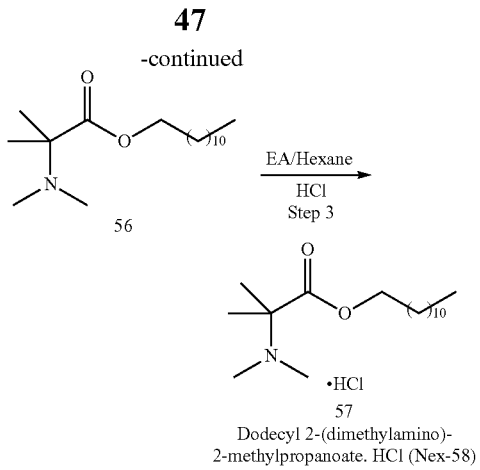

56

Dodecyl 2-(dimethylamino)-
2-methylpropanoate. HCl (Nex-58)

57

Synthesis of dodecyl 2-amino-2-methylpropanoate (55)

To a stirred solution of 2-aminoisobutyric acid 54 (10 g, 96.9 mmol) in toluene (200 mL) was added 1-dodecanol 2 (16.26 g, 87.27 mmol) in one lot, followed by pTSA (20.27 g, 106.6 mmol). After the addition, the temperature of the reaction mixture was slowly raised to reflux temperature, the water was separated azeotropically, and the reaction mixture was monitored by TLC. The reaction mixture was concentrated under vacuum, the obtained residue was taken in ethyl acetate (200 mL) and washed with aqueous 5% $Na_2CO_3$ (3×50 mL) followed by brine solution. The organic layer was dried over $Na_2SO_4$ and concentrated under vacuum to afford 56 (22 g, yield: 83.65%) as a liquid.

Synthesis of dodecyl 2-(dimethylamino)-2-methylpropanoate (56)

To a stirred solution of 55 (5 g, 18.45 mmol) in DCM (200 mL) was added aqueous formaldehyde solution (37% w/v) (1.93 g, 64.5 mmol) in one lot at 0° C., and $Na(OAC)_3BH$ (9.77 g, 46.12 mmol) was added over a period of 1 h. After the addition, the temperature of the reaction mixture was slowly raised to RT and stirred at RT for 24 h; the reaction mixture was monitored by TLC. The reaction mixture was quenched with ice-cold water, the organic layer was separated, and the aqueous layer was extracted with DCM (2×40 mL). The combined organic layers were washed with brine solution. The organic layer was dried over $Na_2SO_4$, and concentrated under vacuum to afford dodecyl 2-(dimethylamino)-2-methylpropanoate 56 (5.0 g, yield: 90.9%) as a liquid.

Synthesis of Dodecyl 2-(dimethylamino)-2-methylpropanoate hydrochloride (57, Nex-58)

A stirred solution of DDAIP Derivative (5 g, 16.7 mmol) in ethyl acetate/hexane/MeOH (25:25:5 mL) was cooled to 0° C. The reaction mixture was purged with dry HCl gas for 30 minutes, and the reaction mixture was monitored by TLC. The reaction mixture was concentrated under vacuum, the obtained residue was flushed with ethyl acetate (3×52 mL) followed by hexane (3×25 mL) to afford Dodecyl 2-(dimethylamino)-2-methylpropanoate hydrochloride (57, Nex-58) (5 g) as a semi solid. The semi solid was taken in ethyl acetate/ hexane (10:10 mL), heated to reflux, and stirred at reflux for 30 minutes. The reaction mixture was slowly cooled to RT and then to 0° C. The reaction mixture was filtered under nitrogen and dried under vacuum to afford Dodecyl 2-(dimethylamino)-2-methylpropanoate hydrochloride (57, Nex-58) salt (3.2 g, yield: 57.1%) as a white hygroscopic solid, mp: 68-74° C. $^1$H-NMR (400 MHz, $CDCl_3$): δ 0.82 (t, 3H), 1.3 (m, 18H), 1.7 (q, 2H), 1.8 (s, 6H), 4.2 (t, 2H); LCMS: 300 ($M^+$+1); HPLC: 98.07%.

Figure 19A:
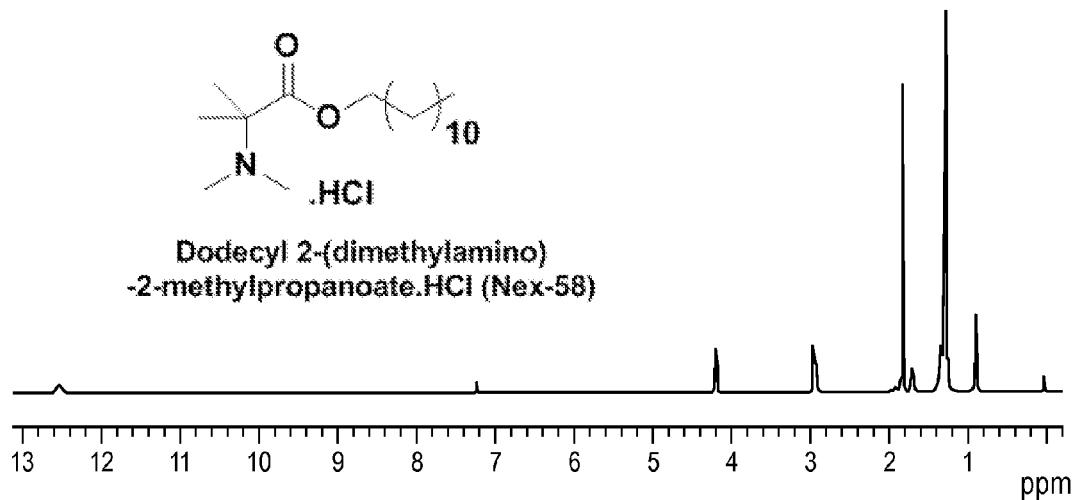
FIG. 19A is a 1H-NMR spectrum (400 MHz, CDCl₃) of dodecyl 2-(dimethylamino)-2-methylpropanoate hydrochloride salt (Nex-58).

FIG. 19A is a $^1$H-NMR spectrum (400 MHz, $CDCl_3$) of dodecyl 2-(dimethylamino)-2-methylpropanoate hydrochloride salt (Nex-58).

Figure 19B:
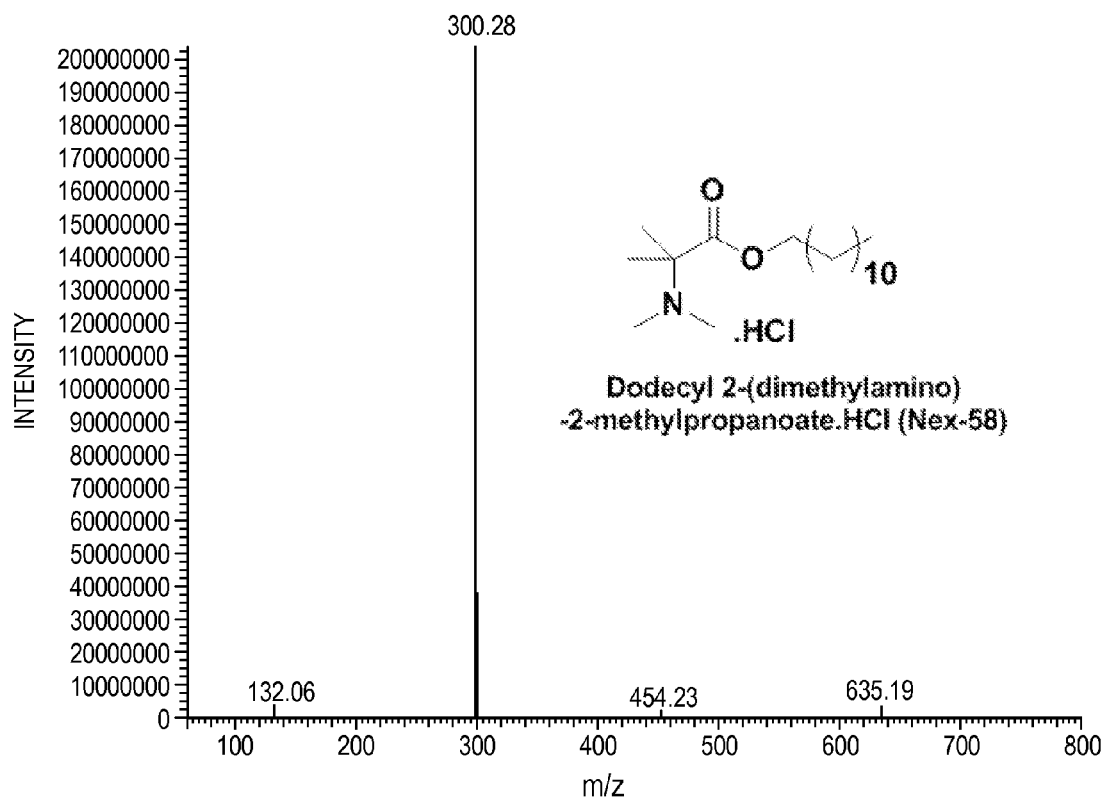
FIG. 19B is a LCMS spectrum: 300 (M⁺+1) of dodecyl 2-(dimethylamino)-2-methylpropanoate hydrochloride salt.

FIG. 19B is a LCMS spectrum: 300 ($M^+$+1) of dodecyl 2-(dimethylamino)-2-methylpropanoate hydrochloride salt.

Figure 19C:
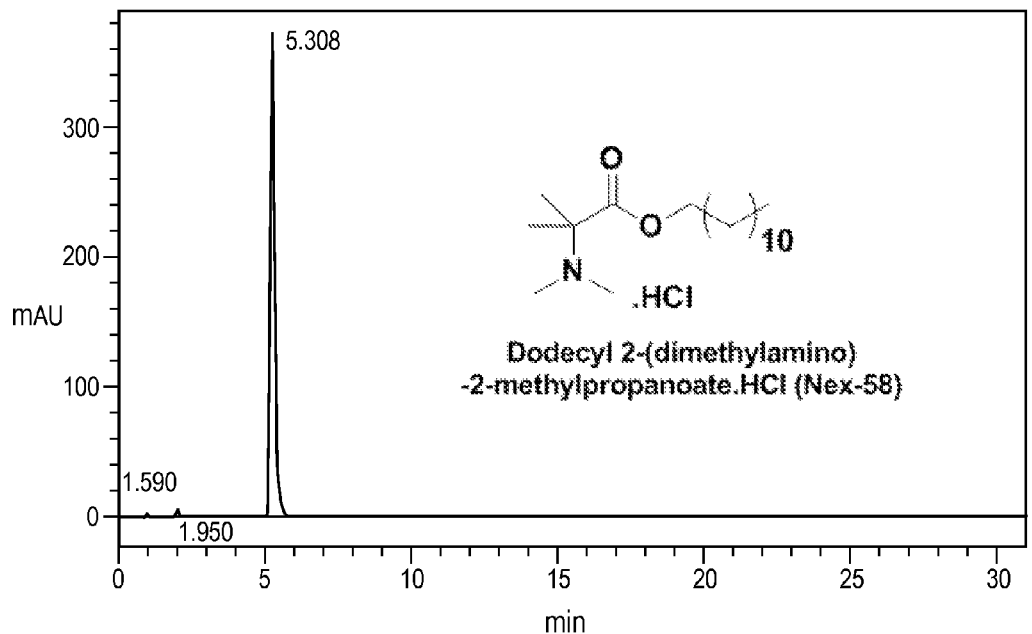
FIG. 19C is a HPLC chromatogram of dodecyl 2-(dimethylamino)-2-methylpropanoate hydrochloride salt showing a peak area of 98.07%. Methods as in FIG. 4D.

FIG. 19C is a HPLC chromatogram of dodecyl 2-(dimethylamino)-2-methylpropanoate hydrochloride salt showing a peak area of 98.07%. Methods as in FIG. 4D Example 21

Dodecyl 2-(methylamino)propanoate hydrochloride (Nex-59)

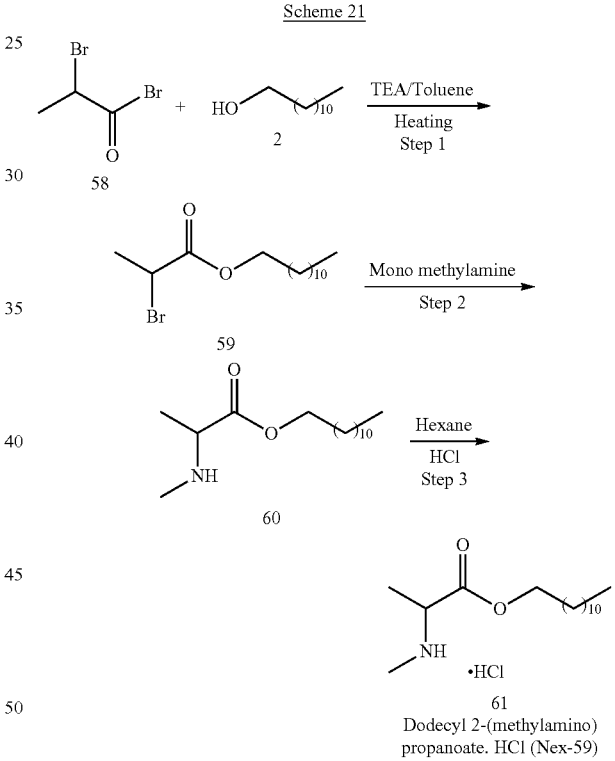

Scheme 21

61

Dodecyl 2-(methylamino) propanoate. HCl (Nex-59)

Synthesis of dodecyl 2-bromopropanoate (59)

To a stirred solution of 1-decanol 2 (10 g, 53.7 mmol) in toluene (100 mL) was added triethylamine (7.5 mL, 53.7 mmol)) and followed by 2-bromo propionyl bromide 58 (12.7 g, 59.1 mmol) at 5-10° C. The reaction mixture was stirred for 3 hour at 55-60° C., and the reaction was monitored by TLC. The reaction mixture was quenched with saturated sodium bicarbonate solution and stirred for 15 minutes at 25-35° C. The aqueous and organic layers were separated, the combined organic layers were washed with brine solution. The organic layer was dried over $Na_2SO_4$ and concentrated under vacuum to afford crude 59 (16.19 g, yield: 94%) as a liquid.

Synthesis of dodecyl 2-(methylamino)propanoate (60)

To a stirred solution of 59 (10 g, 31.2 mmol) in acetonitrile (20 mL) was added sodium bicarbonate (2.62 g, 31.2 mmol) and followed by mono methyl amine (40% in water) (30 mL, 3 vol) at 25-30° C. The reaction mixture was stirred for 3 hour at 25-30° C.; the reaction was monitored by TLC. The solid obtained in the reaction mixture was filtered under vacuum. The solvent was concentrated, diluted with ethyl acetate/water and stirred for 15 minutes at 25-30° C. The aqueous and organic layers were separated, and the aqueous layer was extracted with ethyl acetate (2×10 mL). The combined organic layers were washed with brine solution, dried over $Na_2SO_4$ and concentrated under vacuum to afford crude 60 (7 g, yield: 82.3%) as a liquid

Synthesis of dodecyl 2-(methylamino)propanoate hydrochloride (61, Nex-59)

A stirred solution of 60 (7 g, 25.8 mmol) in hexane (30 mL) was cooled to 0° C. The reaction mixture was purged with dry HCl gas for 10 minutes, and the reaction mixture was monitored by TLC. The reaction mixture was concentrated under vacuum, and the obtained residue was flushed with ethyl acetate (3×25 mL) followed by hexane (5×20 mL) to afford wet dodecyl 2-(methylamino)propanoate hydrochloride salt (61, Nex-59) (7 g) as a waxy solid. The waxy solid was taken in ethyl hexane (50 mL), heated to reflux, and stirred at reflux for 30 minutes. The reaction mixture was slowly cooled to RT and then to 0° C. The reaction mixture was filtered under nitrogen and dried under vacuum to afford dodecyl 2-(methylamino)propanoate hydrochloride salt (3 g, yield: 37.9%) as a white hygroscopic solid, mp: 78-83° C. $^1$H-NMR (400 MHz, $CDCl_3$): δ 4.3-4.2 (m, 2H), 3.9 (d, 1H), 2.8 (s, 3H), 1.8-1.6 (m, 5H), 1.4-1.2 (m, 18H), 0.9 (t, 3H) LCMS: 272.31 ($M^+$+1); HPLC: 98.45%.

Figure 20A:
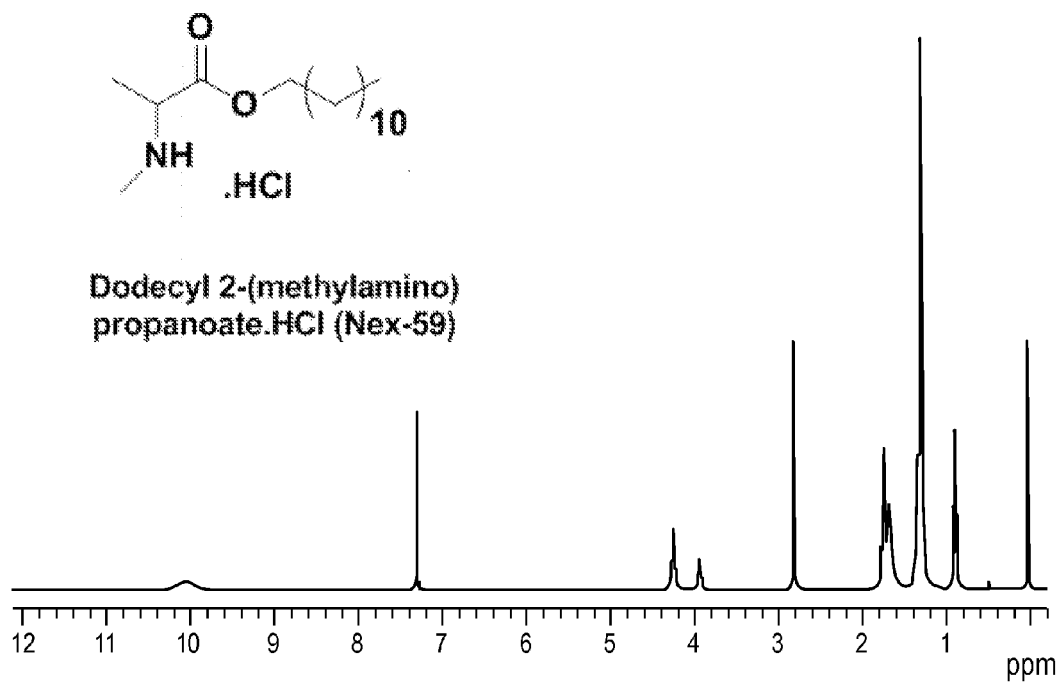
FIG. 20A is a ¹H-NMR spectrum (400 MHz, CDCl₃) of dodecyl 2-(methylamino)propanoate hydrochloride salt (Nex-59).

FIG. 20A is a $^1$H-NMR spectrum (400 MHz, $CDCl_3$) of dodecyl 2-(methylamino)propanoate hydrochloride salt (Nex-59)

Figure 20B:
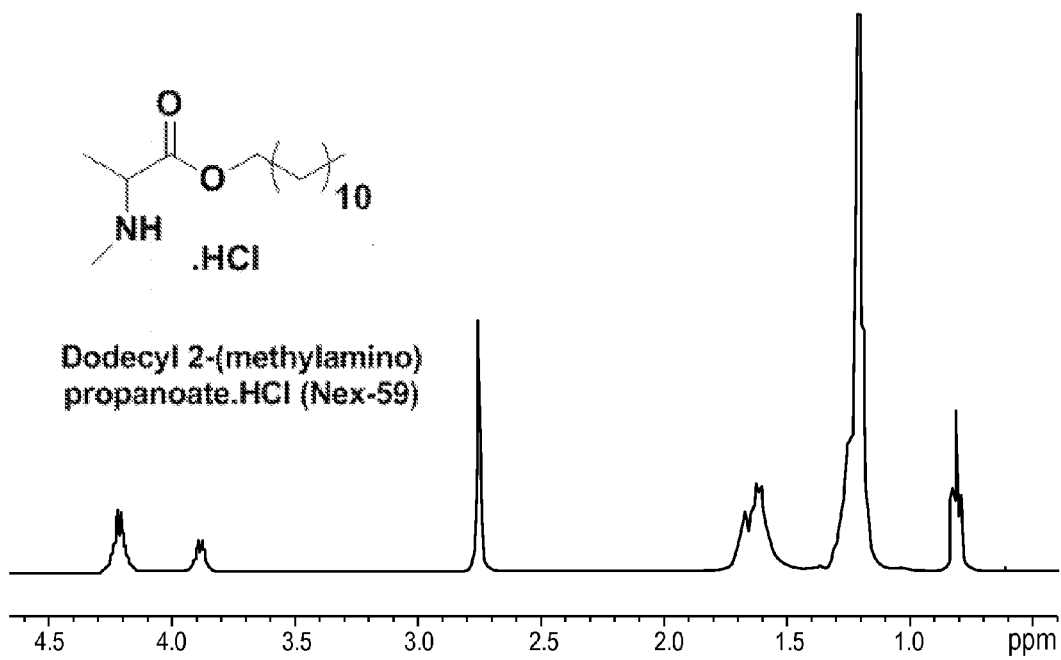
FIG. 20B is a ¹H-NMR spectrum at a higher resolution to resolve the peaks of FIG. 20A.

FIG. 20B is a $^1$H-NMR spectrum at a higher resolution to resolve the peaks of FIG. 20A.

Figure 20C:
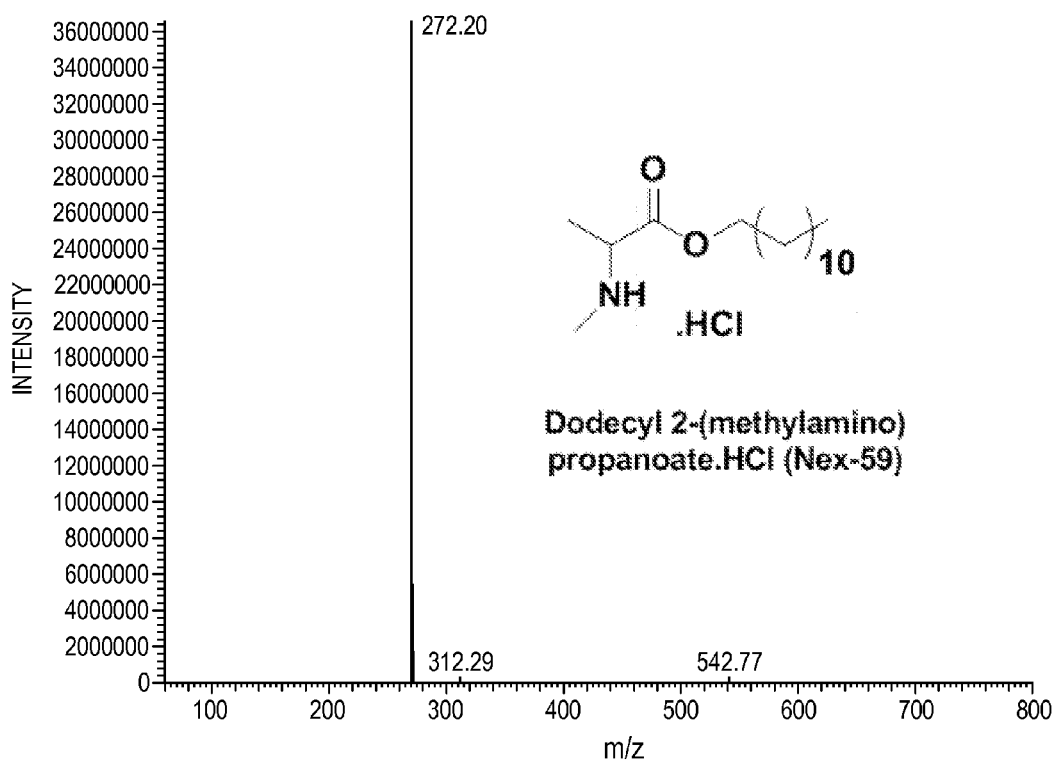
FIG. 20C is a LCMS spectrum: 272.3 (M⁺+1) of dodecyl 2-(methylamino)-2-methylpropanoate hydrochloride salt.

FIG. 20C is a LCMS spectrum: 272.3 ($M^+$+1) of dodecyl 2-(methylamino)-2-methylpropanoate hydrochloride salt.

Figure 20D:
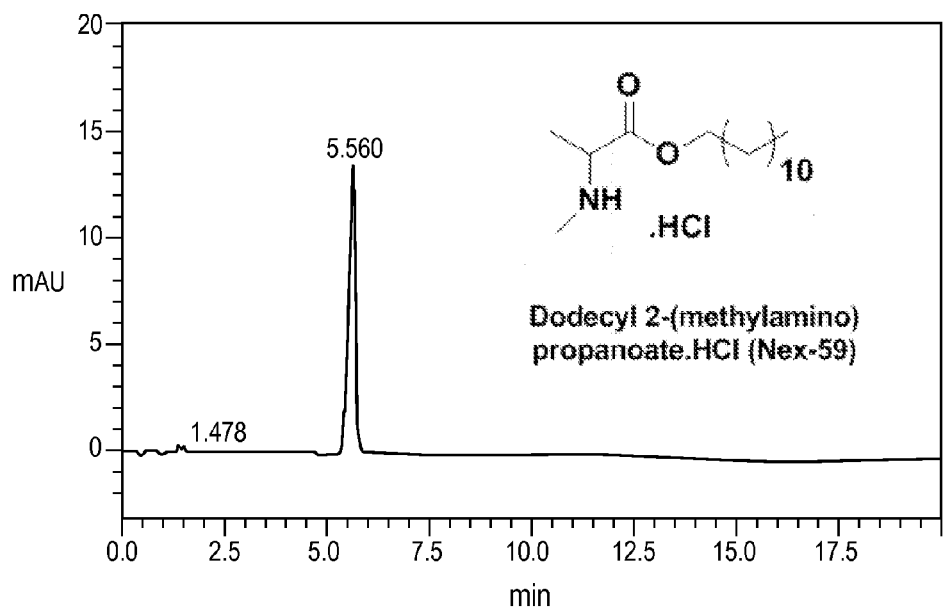
FIG. 20D is a HPLC chromatogram of dodecyl 2-(methylamino)propanoate hydrochloride salt showing a peak area of 98.45%. Methods as in FIG. 4D.
Figure 21A:
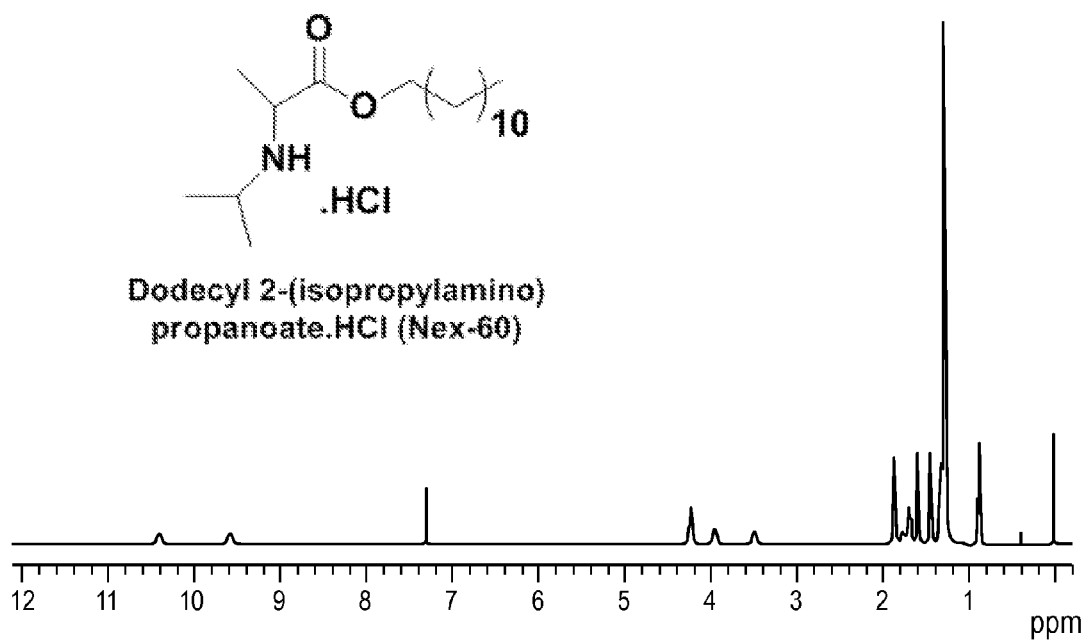
FIG. 21A is a ¹H-NMR spectrum (400 MHz, CDCl₃) of dodecyl 2-(isopropyl amino)propanoate hydrochloride salt (Nex-60)
Figure 21B:
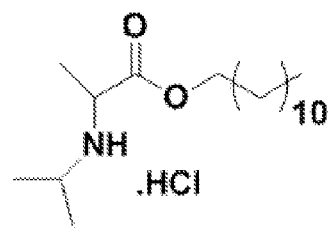
FIG. 21B is a ¹H-NMR spectrum at a higher resolution to resolve the peaks of FIG. 21A.
Figure 21B:
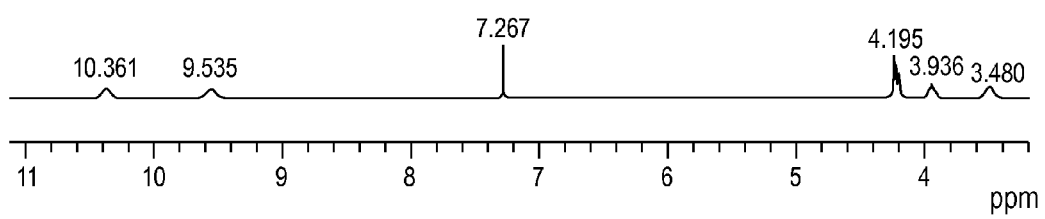
Figure 21C:
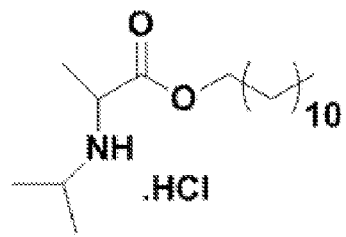
FIG. 21C is a ¹H-NMR spectrum at a higher resolution to resolve the peaks of FIG. 21A
Figure 21C:
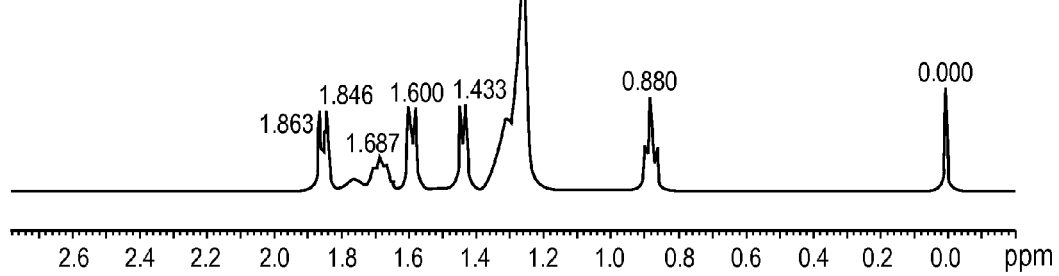
Figure 21D:
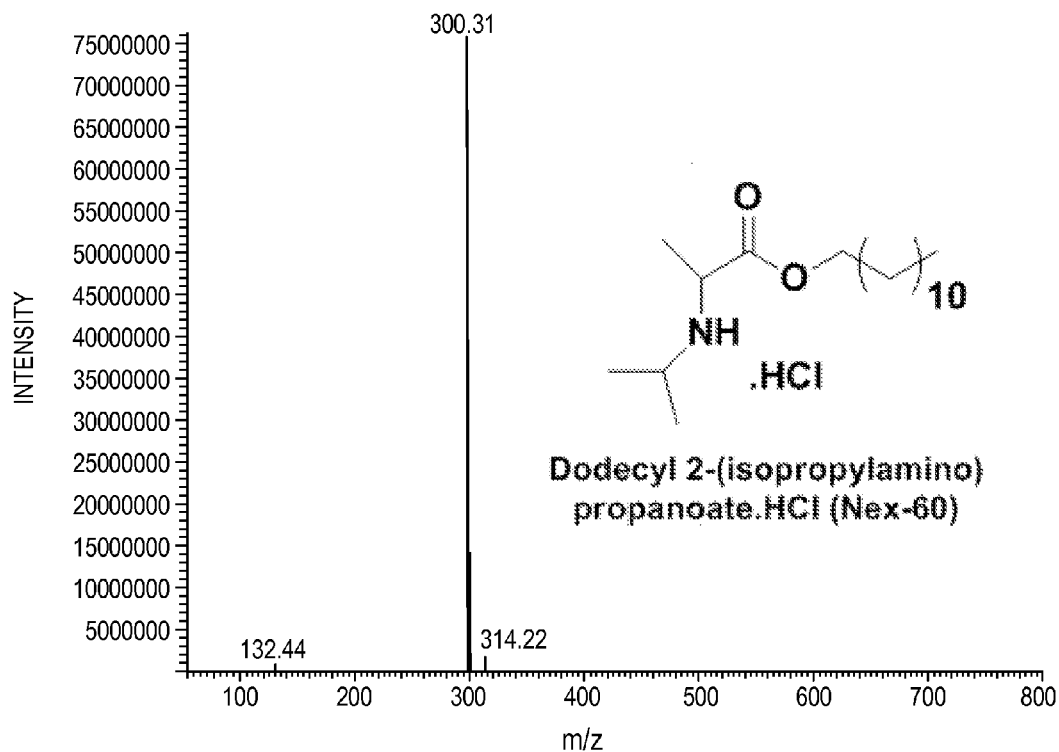
FIG. 21D is a LCMS spectrum: 300.31 (M⁺+1) of dodecyl 2-(isopropyl amino)propanoate hydrochloride salt.
Figure 21E:
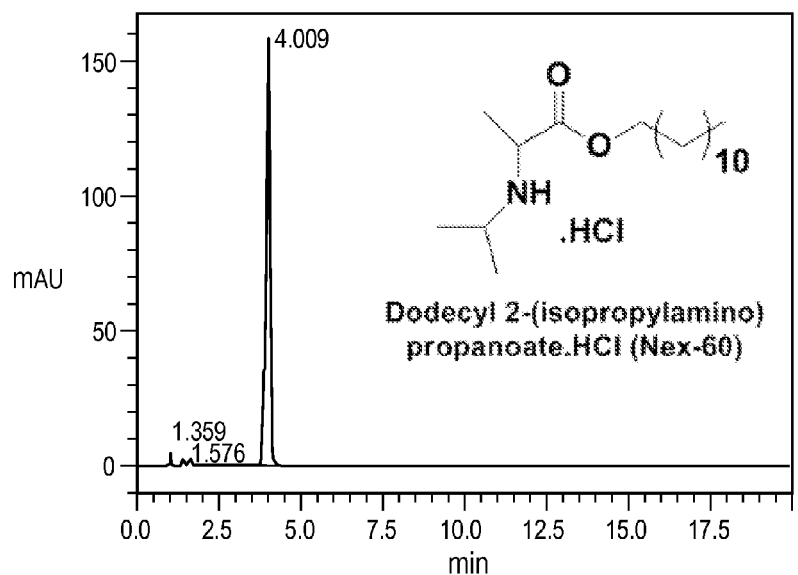
FIG. 21E is a HPLC chromatogram of dodecyl 2-(methylamino)propanoate hydrochloride salt showing a peak area of 98.6%. Methods as in FIG. 4D.
Figure 22A:
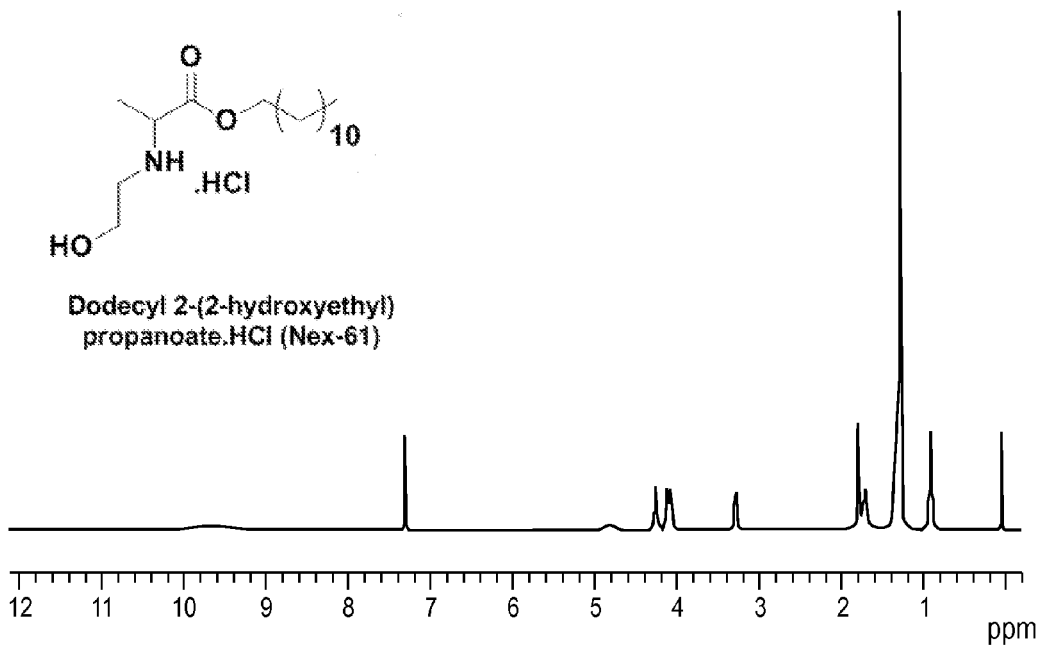
FIG. 22A is a ¹H-NMR spectrum (400 MHz, CDCl₃) of dodecyl 2-((2-hydroxyethyl)amino)propanoate hydrochloride salt (Nex-61).
Figure 22B:
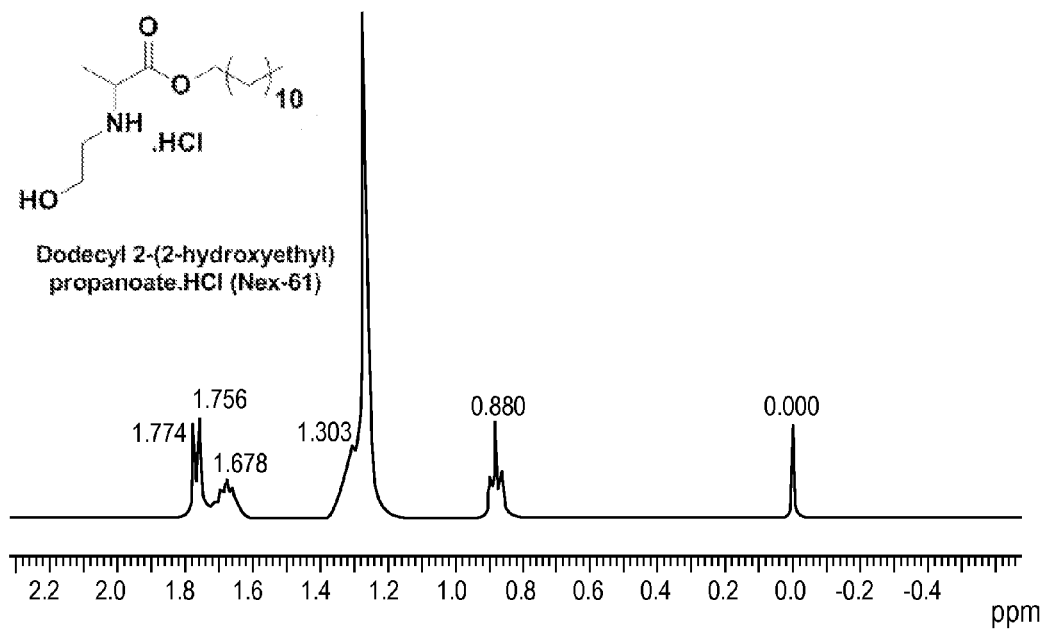
FIG. 22B is a ¹H-NMR spectrum at a higher resolution to resolve the peaks of FIG. 22A.
Figure 22C:
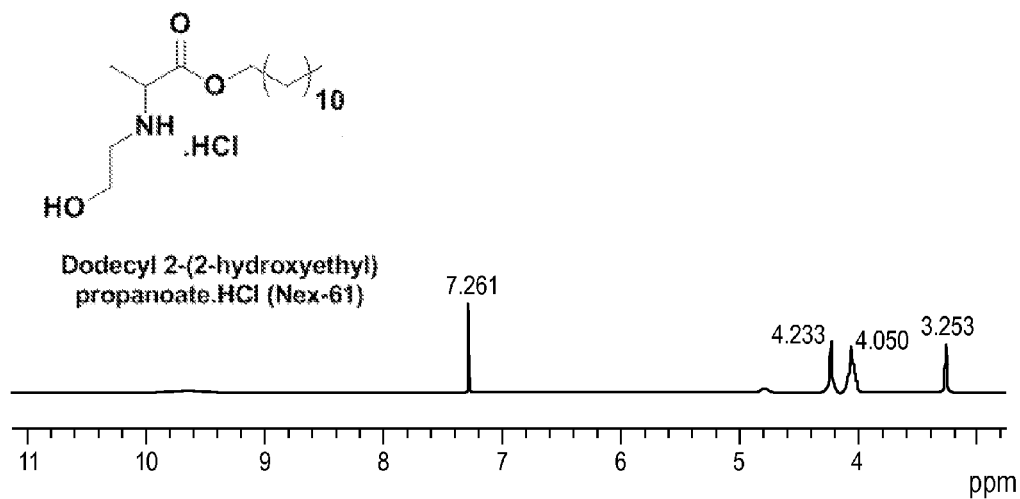
FIG. 22C is a ¹H-NMR spectrum at a higher resolution to resolve the peaks of FIG. 22A.
Figure 22D:
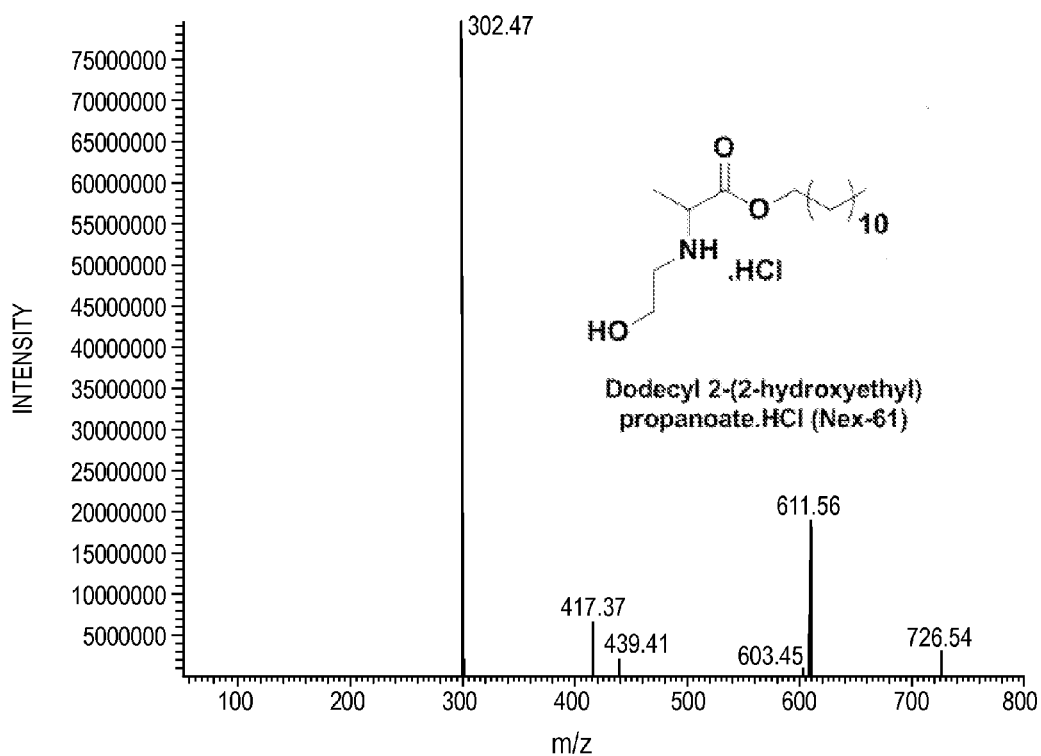
FIG. 22D is a LCMS spectrum: 302.47 (M⁺+1) of dodecyl 2-(isopropyl amino)propanoate hydrochloride salt.
Figure 22E:
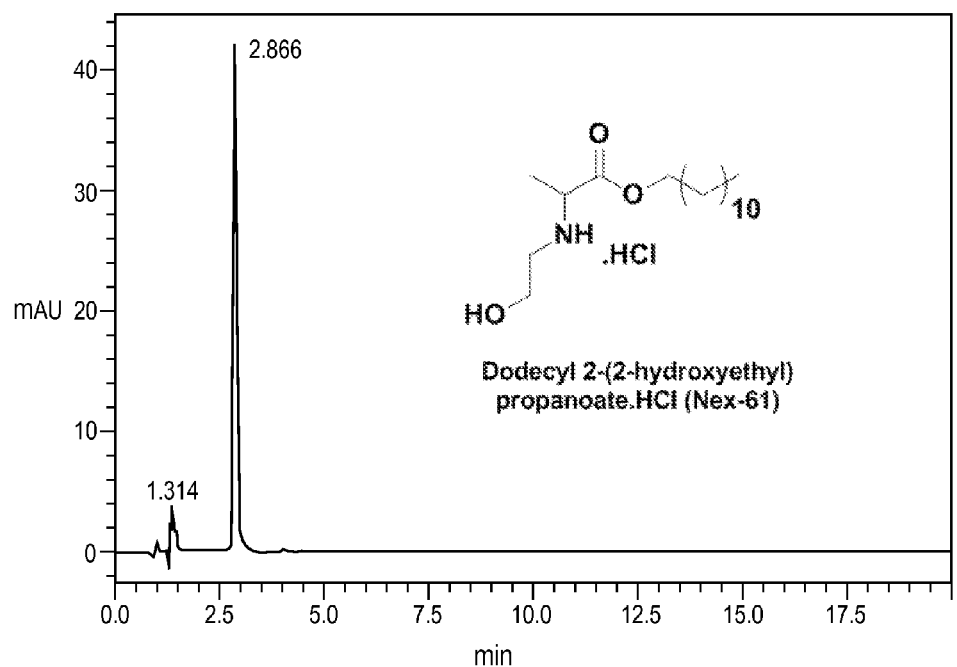
FIG. 22E is a HPLC chromatogram of dodecyl 2-(methylamino)propanoate hydrochloride salt showing a peak area of 93.9%. Methods as in FIG. 4D.
Figure 23A:
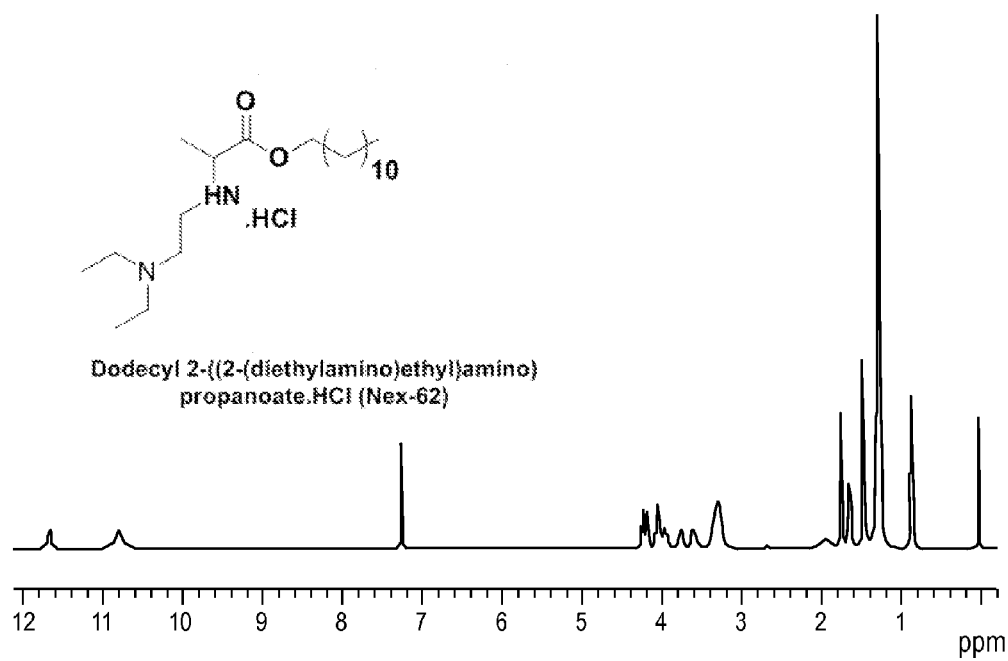
FIG. 23A is a ¹H-NMR spectrum (400 MHz, CDCl₃) of dodecyl 2-((2-(diethyl amino)ethyl)amino)propanoate hydrochloride salt (Nex-62).
Figure 23B:
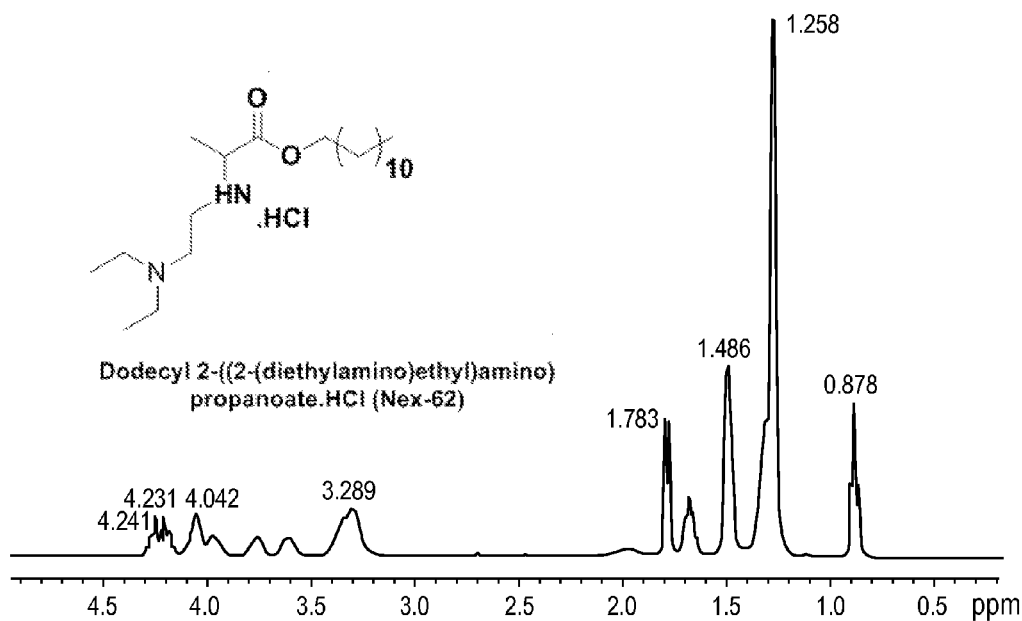
FIG. 23B is a ¹H-NMR spectrum at a higher resolution to resolve the peaks of FIG. 23A.
Figure 23C:
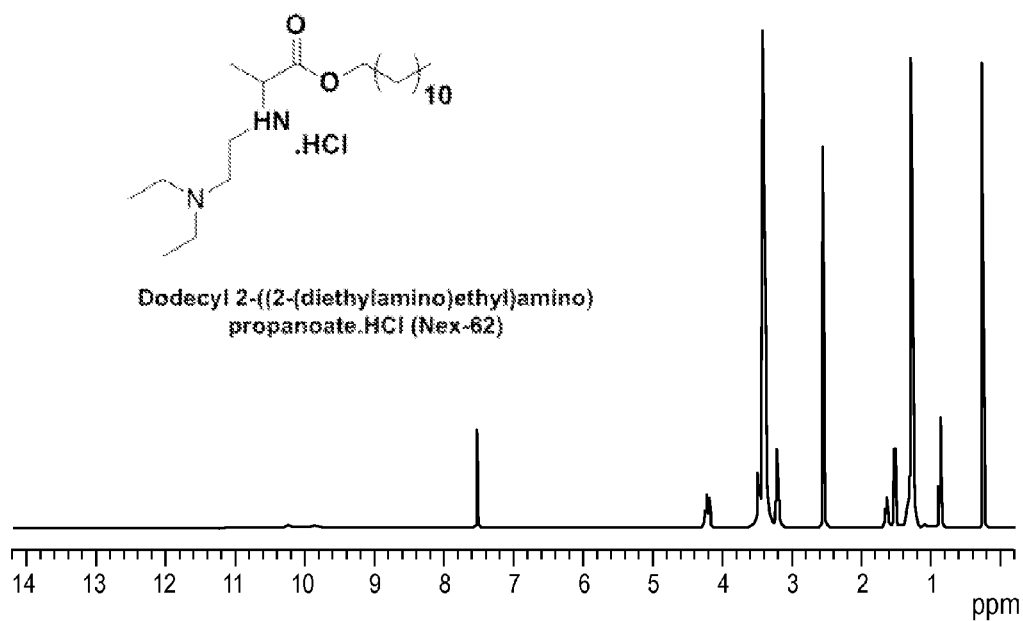
FIG. 23C is a ¹H-NMR spectrum (400 MHz, DMSO-d₆); compare to FIG. 23A
Figure 23D:
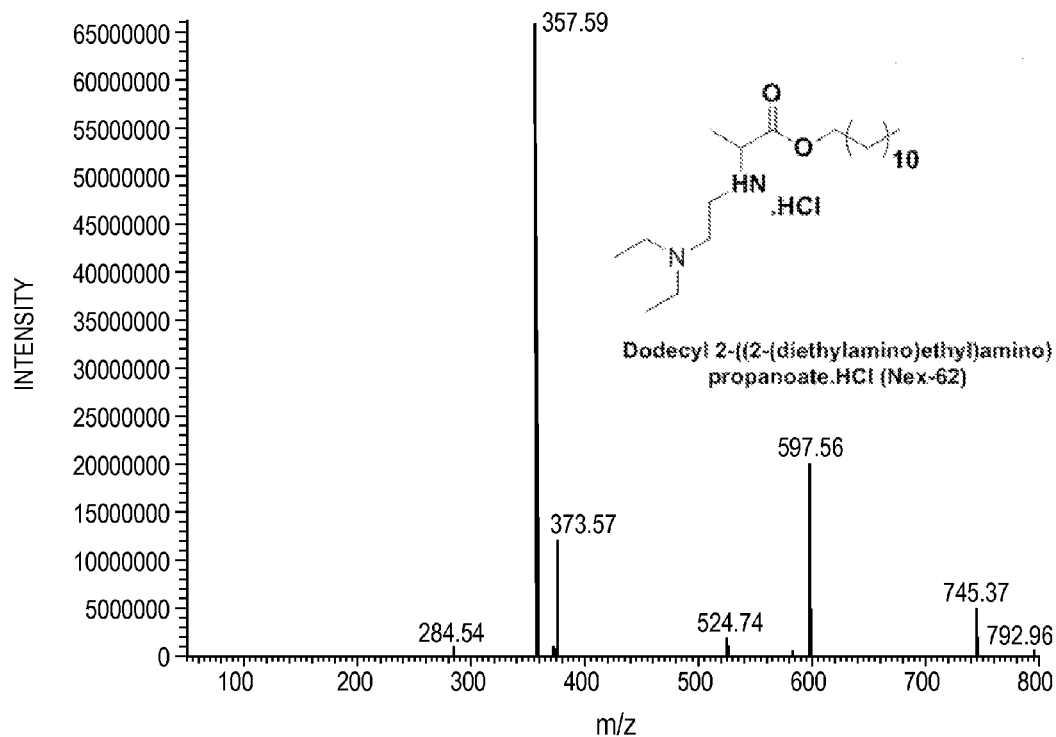
FIG. 23D is a LCMS spectrum: 357.59 (M⁺+1) of dodecyl 2-((2-(diethyl amino)ethyl)amino)propanoate hydrochloride salt.
Figure 24A:
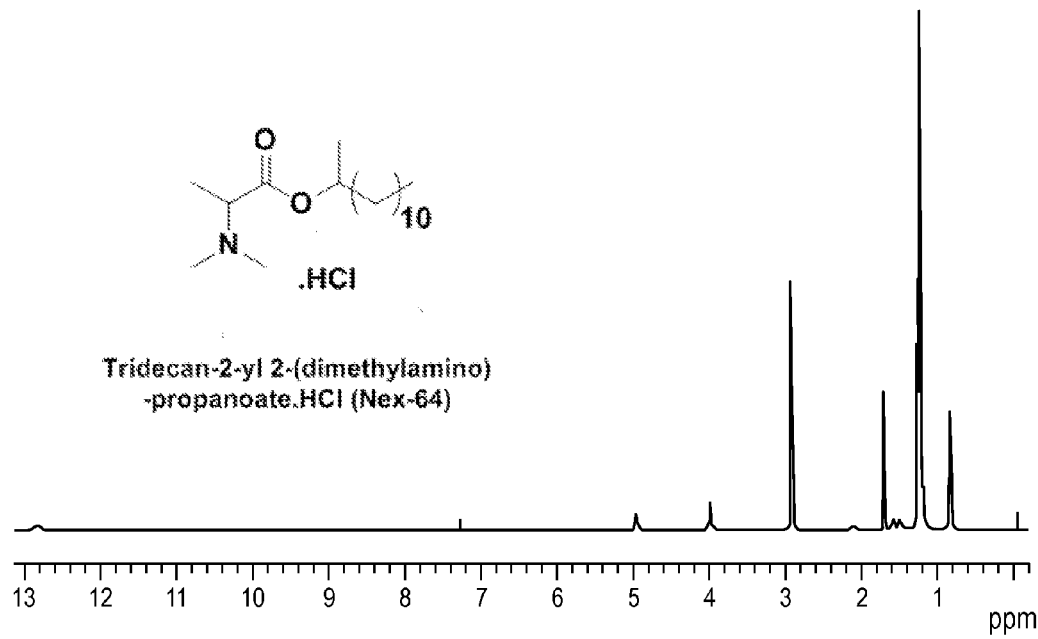
FIG. 24A is a ¹H-NMR spectrum (400 MHz, CDCl₃) of tridecan-2-yl 2-(dimethylamino)propanoate hydrochloride salt (Nex-64).
Figure 24B:
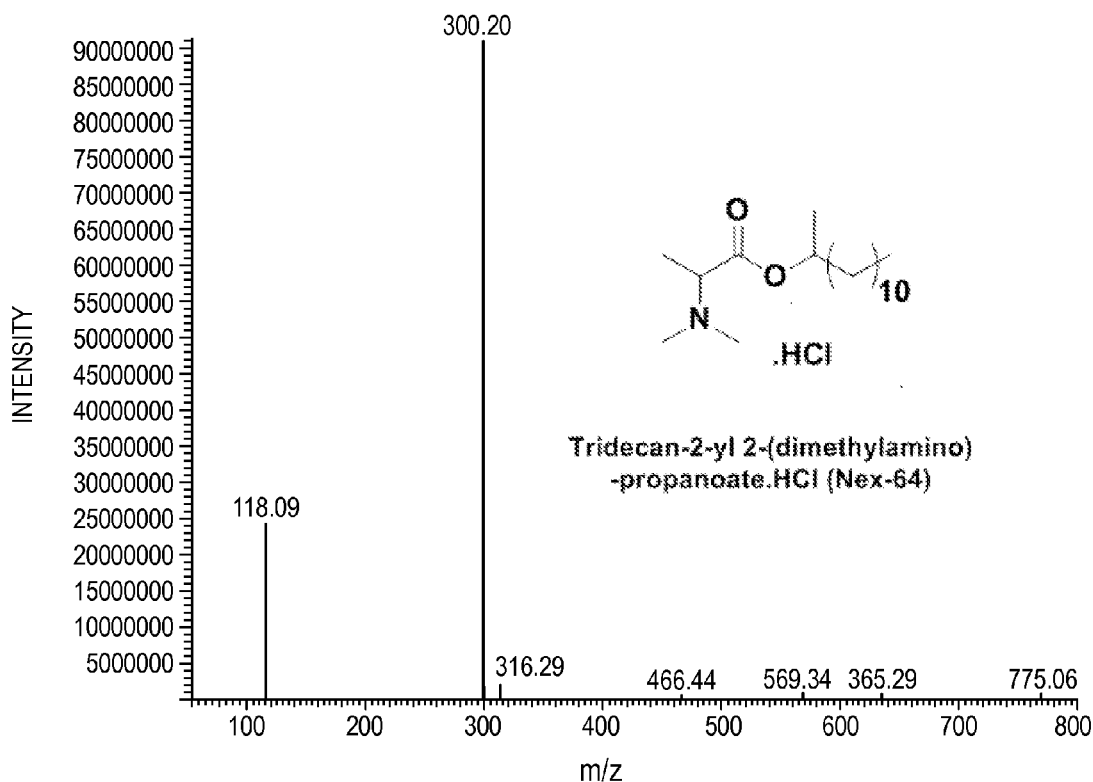
FIG. 24B is a LCMS spectrum: 357.59 (M⁺+1) of tridecan-2-yl 2-(dimethylamino)propanoate hydrochloride salt.
Figure 24C:
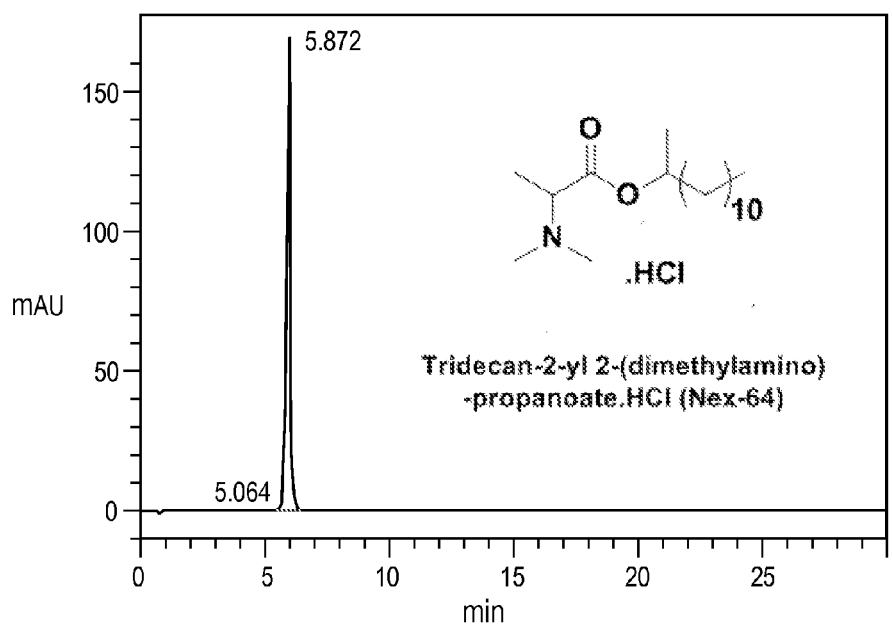
FIG. 24C is a HPLC chromatogram of tridecan-2-yl 2-(dimethylamino)propanoate hydrochloride salt showing a peak area of 99.62%. Methods as in FIG. 4D.
Figure 25A:
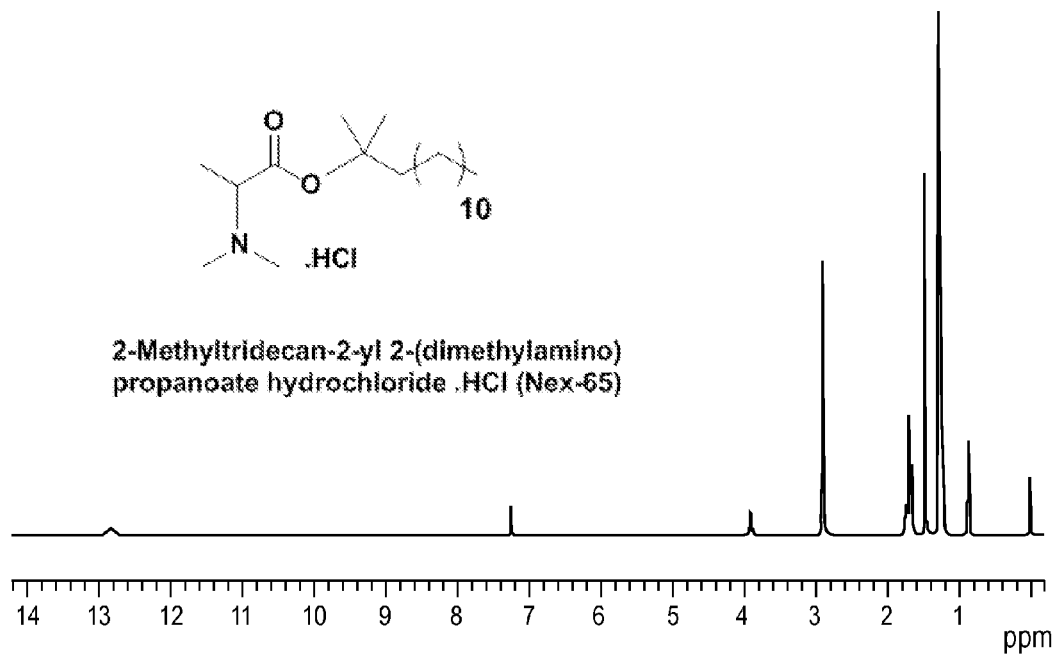
FIG. 25A is a ¹H-NMR spectrum (400 MHz, CDCl₃) of 2-methyltridecan-2-yl 2-(dimethylamino)propanoate hydrochloride salt (Nex-65).
Figure 25B:
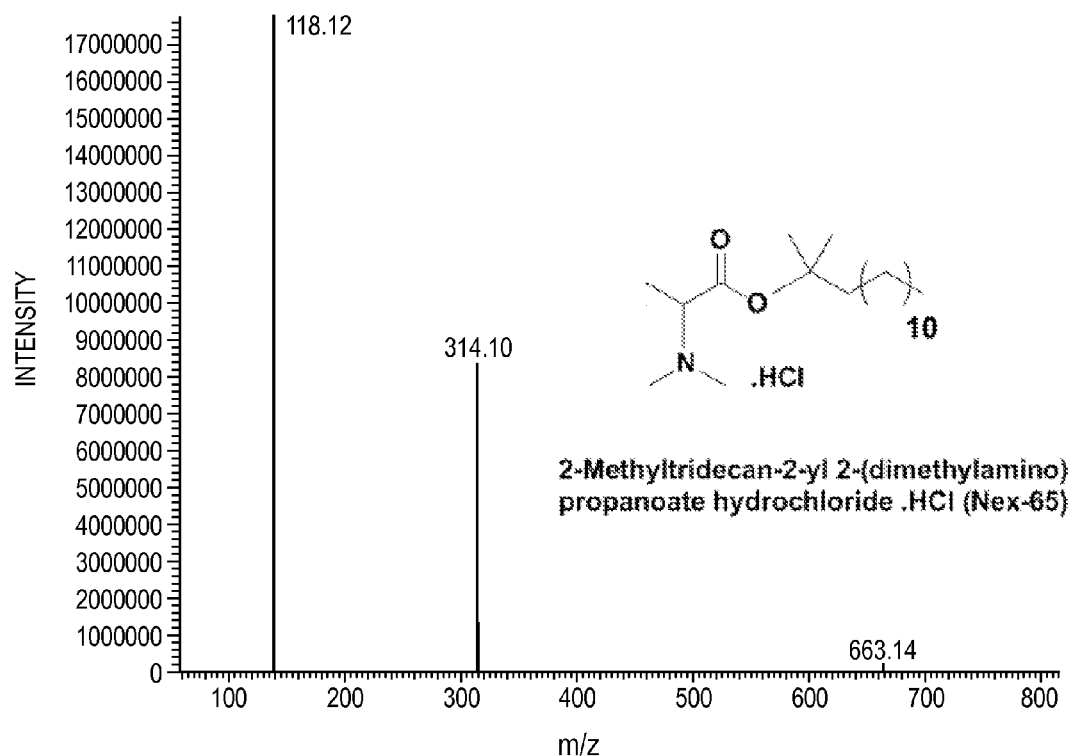
FIG. 25B is a LCMS spectrum: 314 (M++) of 2-methyltridecan-2-yl 2-(dimethylamino)propanoate hydrochloride salt.
Figure 25C:
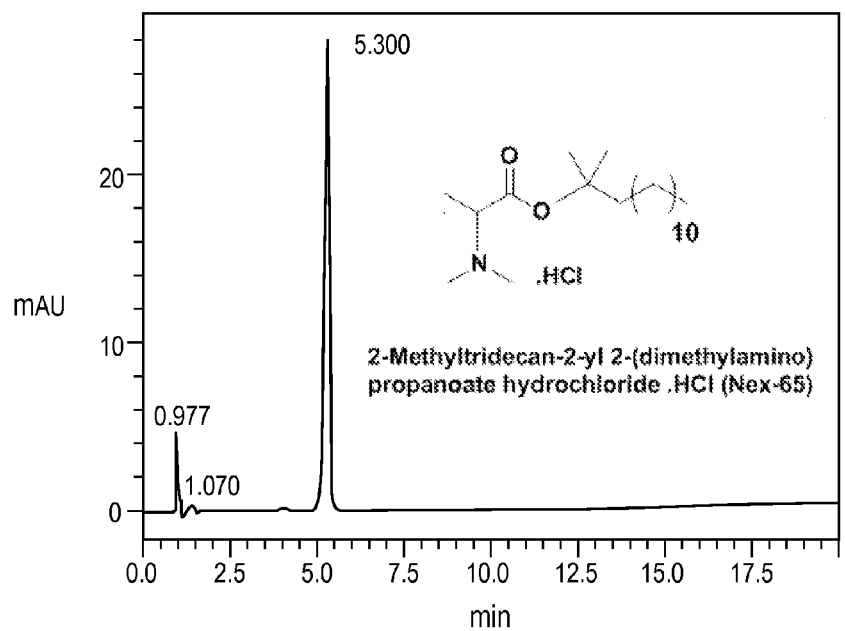
FIG. 25C is a HPLC chromatogram of 2-methyltridecan-2-yl 2-(dimethylamino)propanoate hydrochloride salt showing a peak area of 95.7%. Methods as in FIG. 4D.
Figure 26A:
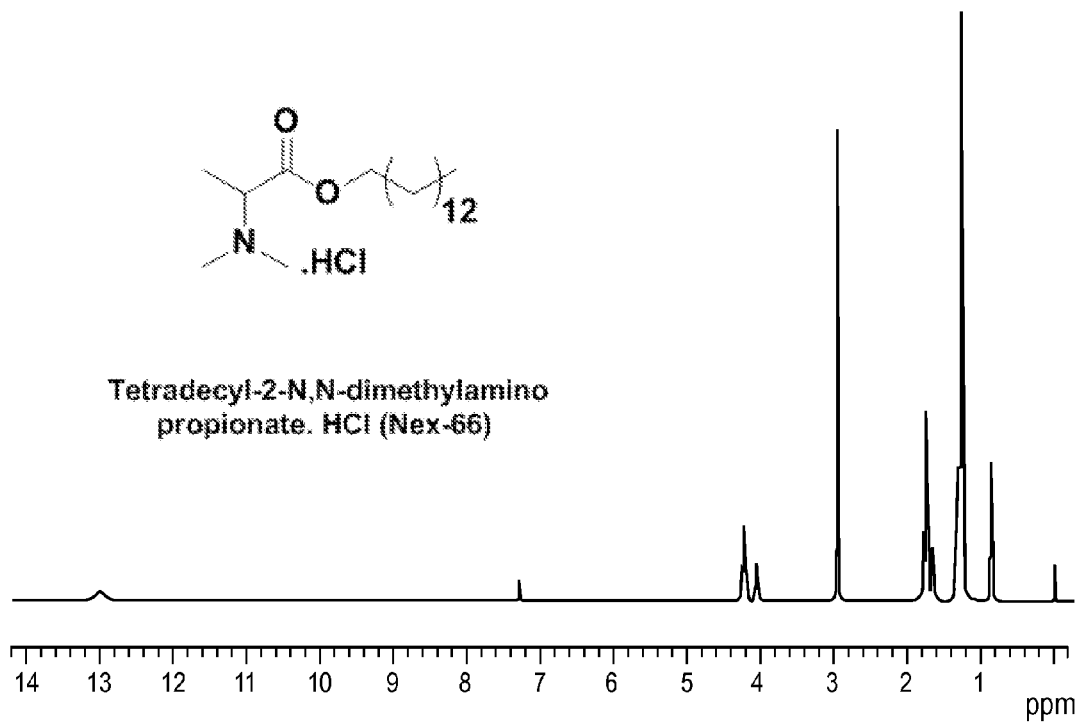
FIG. 26A is a ¹H-NMR spectrum (400 MHz, CDCl₃) of tetradecyl-2-N,N-dimethylaminopropionate hydrochloride (Nex-66).
Figure 26B:
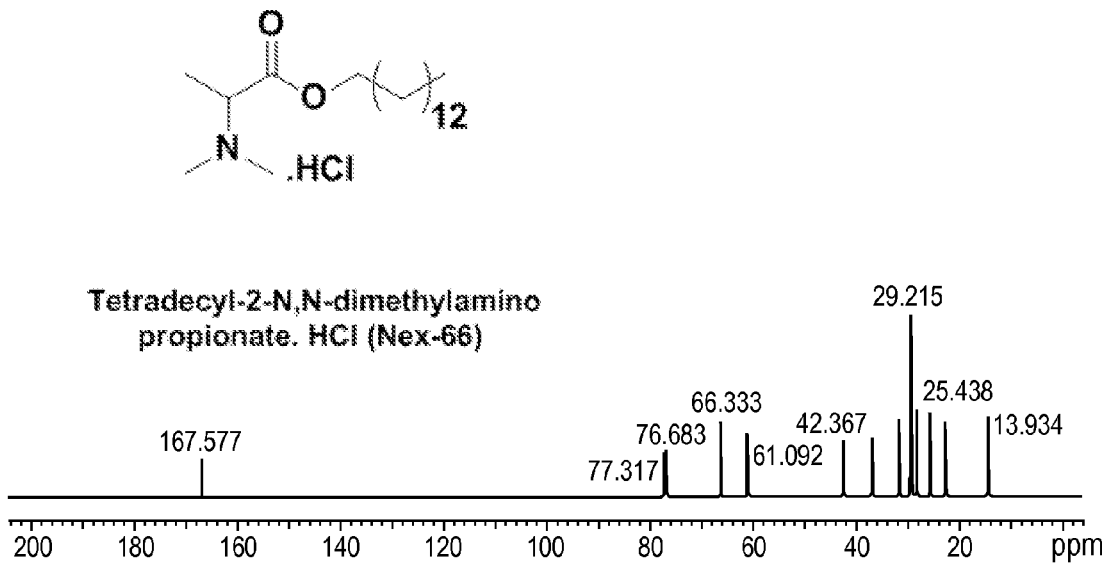
FIG. 26B is a ¹³C NMR spectrum (400 MHz, CDCl₃); compare to FIG. 26A.
Figure 26C:
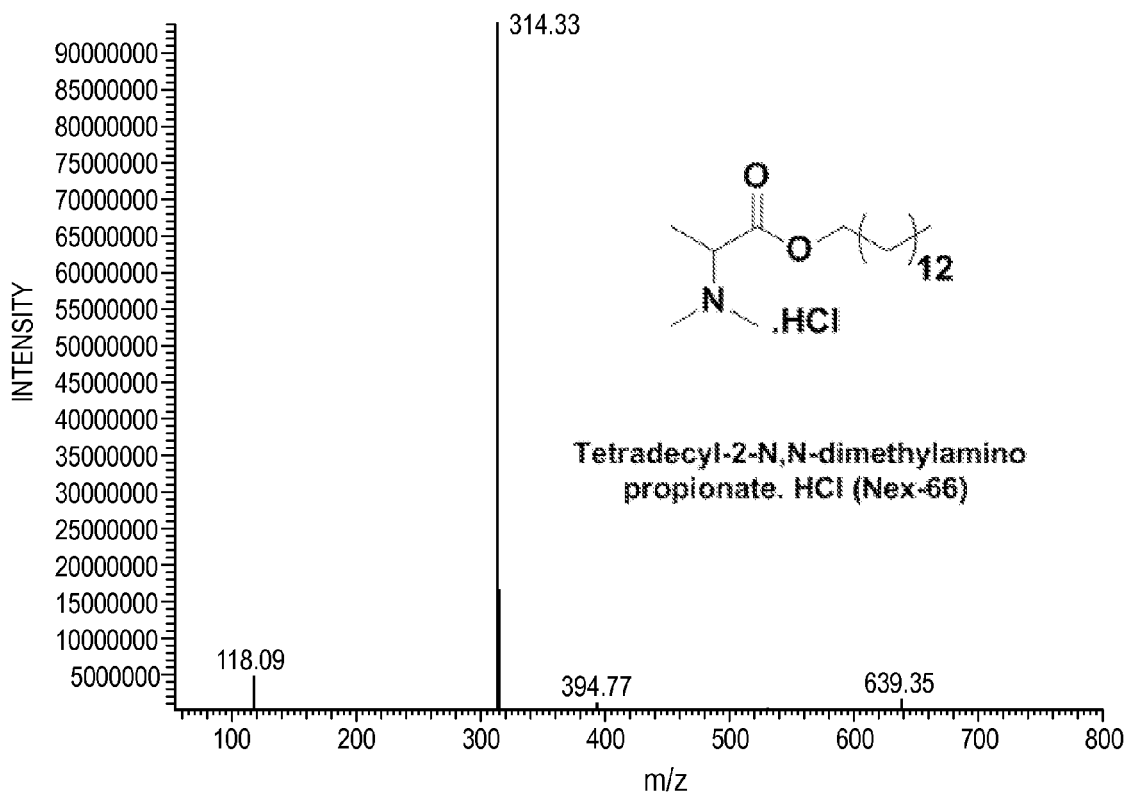
FIG. 26C is a LCMS spectrum: 314 (M⁺+1) of tetradecyl-2-N,N-dimethylaminopropionate hydrochloride salt.
Figure 26D:
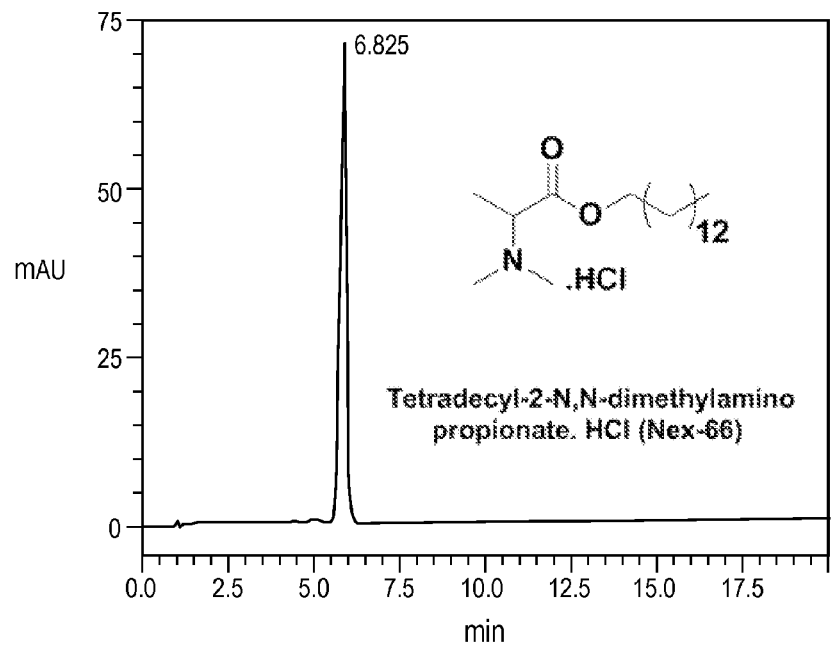
FIG. 26D is a HPLC chromatogram of tetradecyl-2-N,N-dimethyl amino-propionate hydrochloride salt showing a peak area of 99.7%. Methods as in FIG. 4D.
Figure 27A:
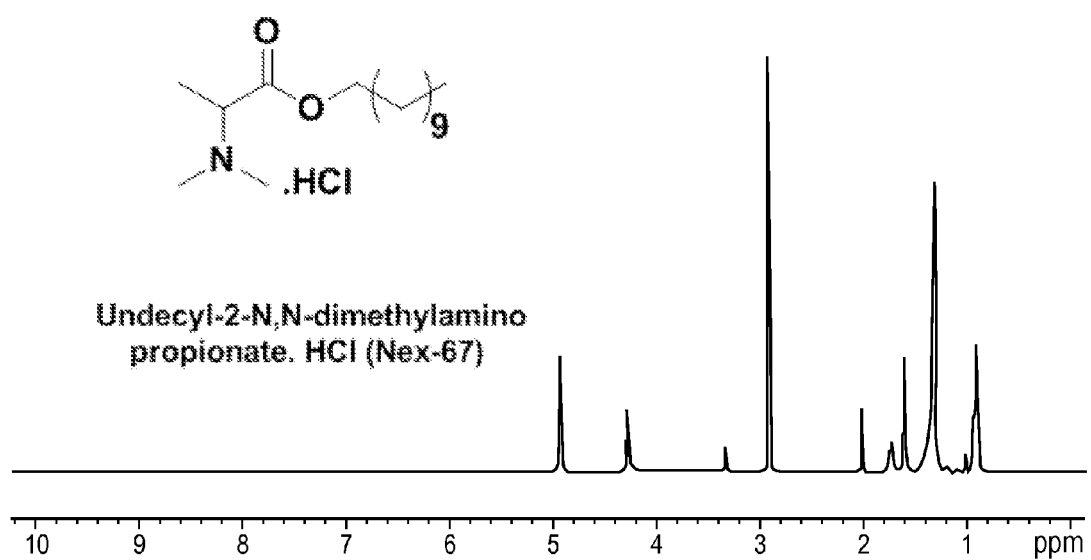
FIG. 27A is a ¹H-NMR spectrum (400 MHz, DMSO-d6) of undecyl-2-N,N-dimethylaminopropionate hydrochloride (Nex-67).
Figure 27B:
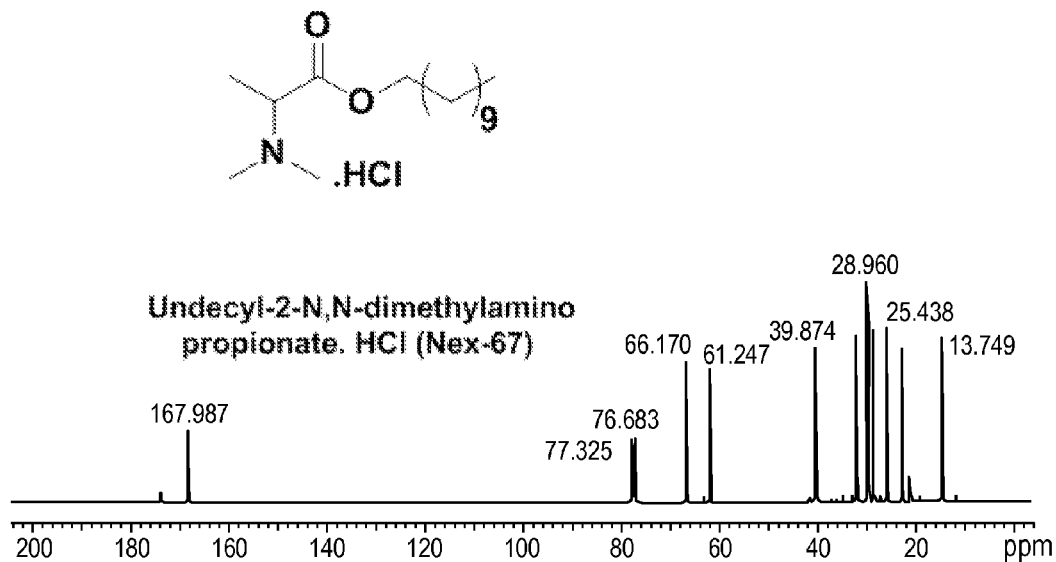
FIG. 27B is a ¹³C NMR spectrum (400 MHz, CDCl₃); compare to FIG. 27A.
Figure 27C:
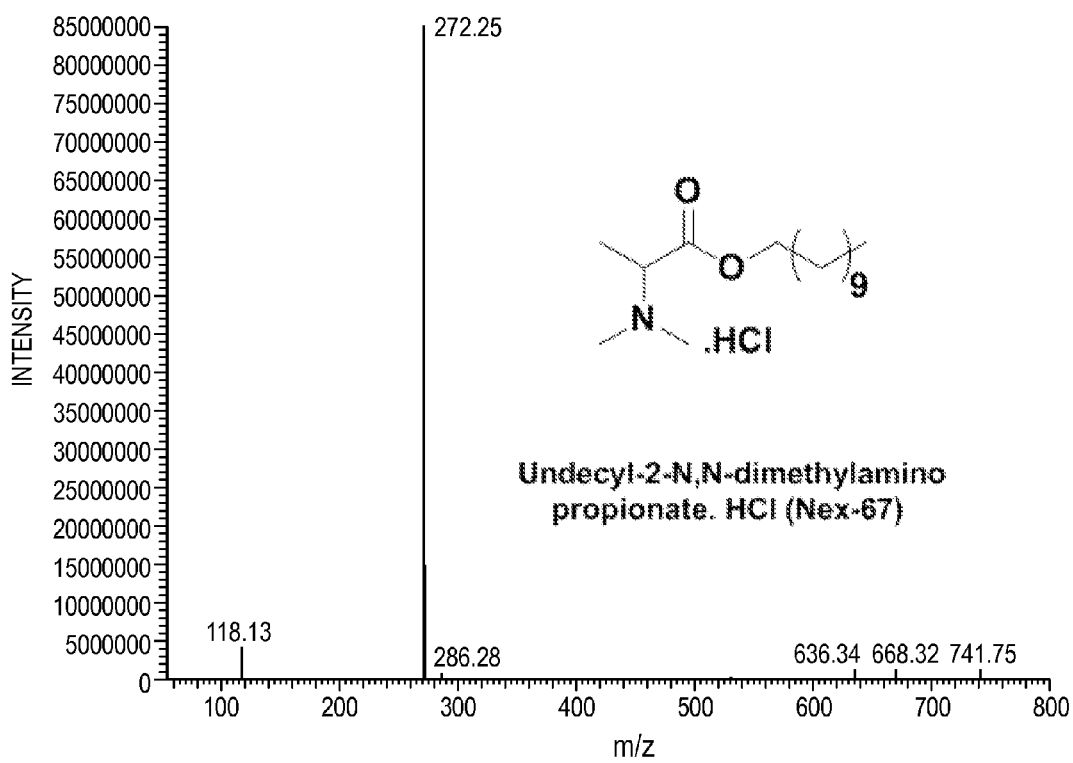
FIG. 27C is a LCMS spectrum: 272 (M⁺+1) of undecyl-2-N,N-dimethylamino-propionate hydrochloride salt.
Figure 27D:
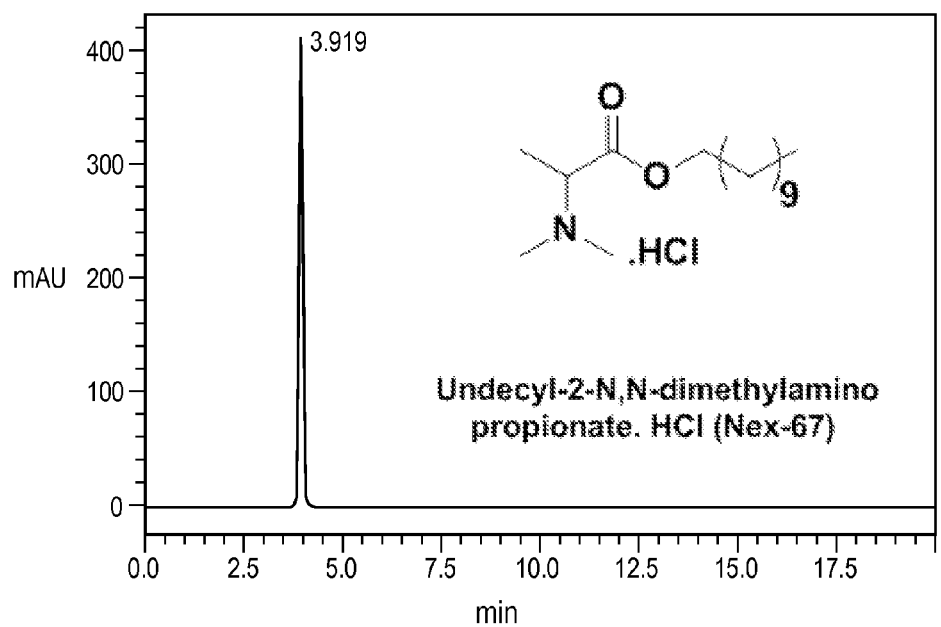
FIG. 27D is a HPLC chromatogram of undecyl-2-N,N-dimethylaminopropionate hydrochloride salt showing a peak area of 99.6%. Methods as in FIG. 4D.
Figure 28A:
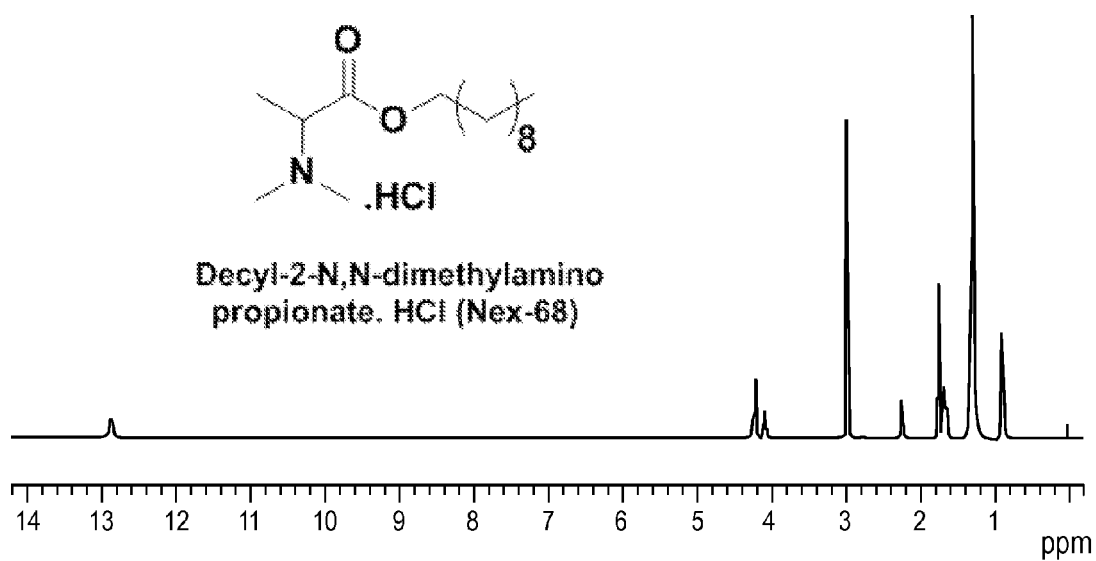
FIG. 28A is a $^1$H-NMR spectrum (400 MHz, CDCl$_3$) of decyl-2-N,N-dimethyl-aminopropionate hydrochloride (Nex-68).
Figure 28B:
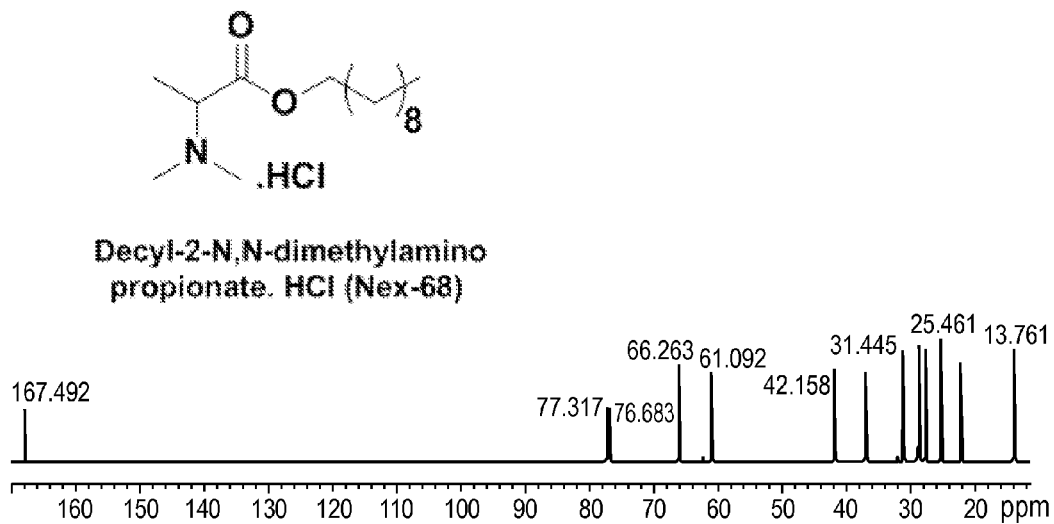
FIG. 28B is a $^{13}$C NMR spectrum (400 MHz, CDCl$_3$); compare to FIG. 28A.
Figure 28C:
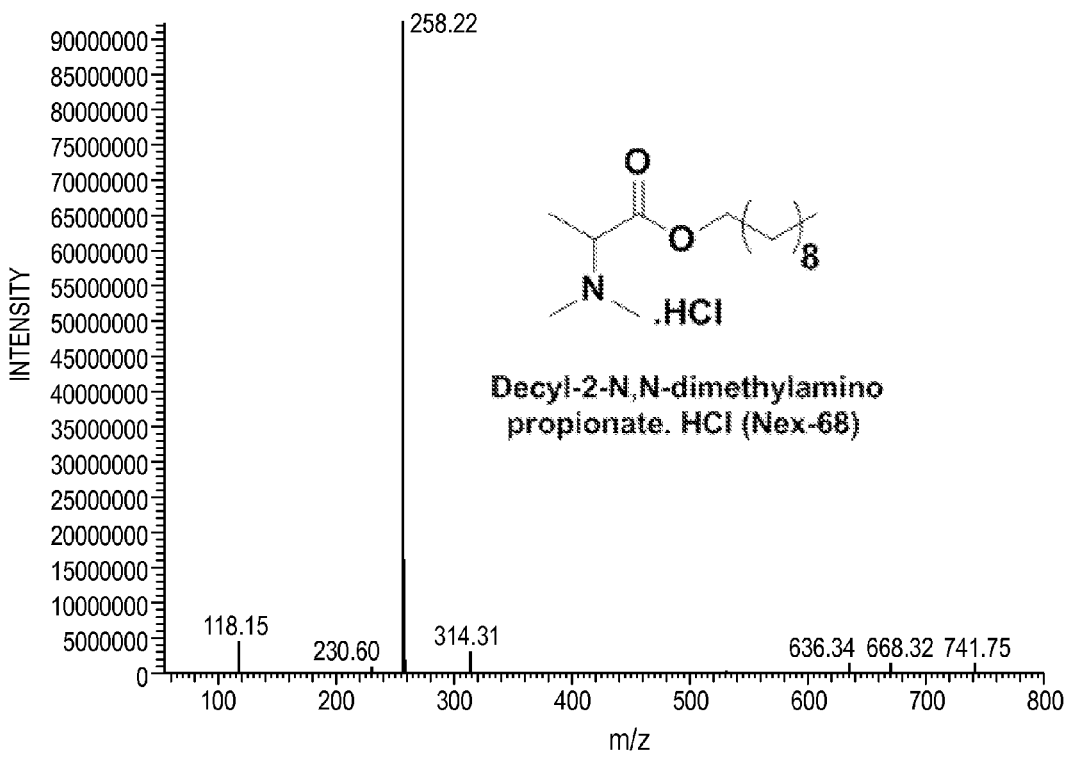
FIG. 28C is a LCMS spectrum: 258 (M$^+$+1) of decyl-2-N,N-dimethylamino-propionate hydrochloride salt.
Figure 28D:
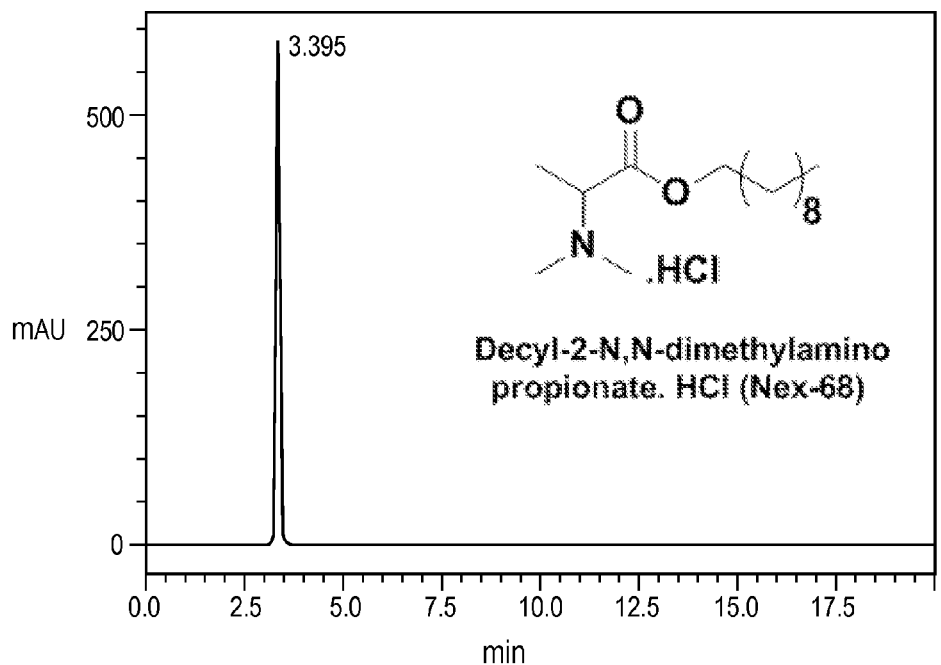
FIG. 28D is a HPLC chromatogram of decyl-2-N,N-dimethylaminopropionate hydrochloride salt showing a peak area of 99.18%. Methods as in FIG. 4D.
Figure 29A:
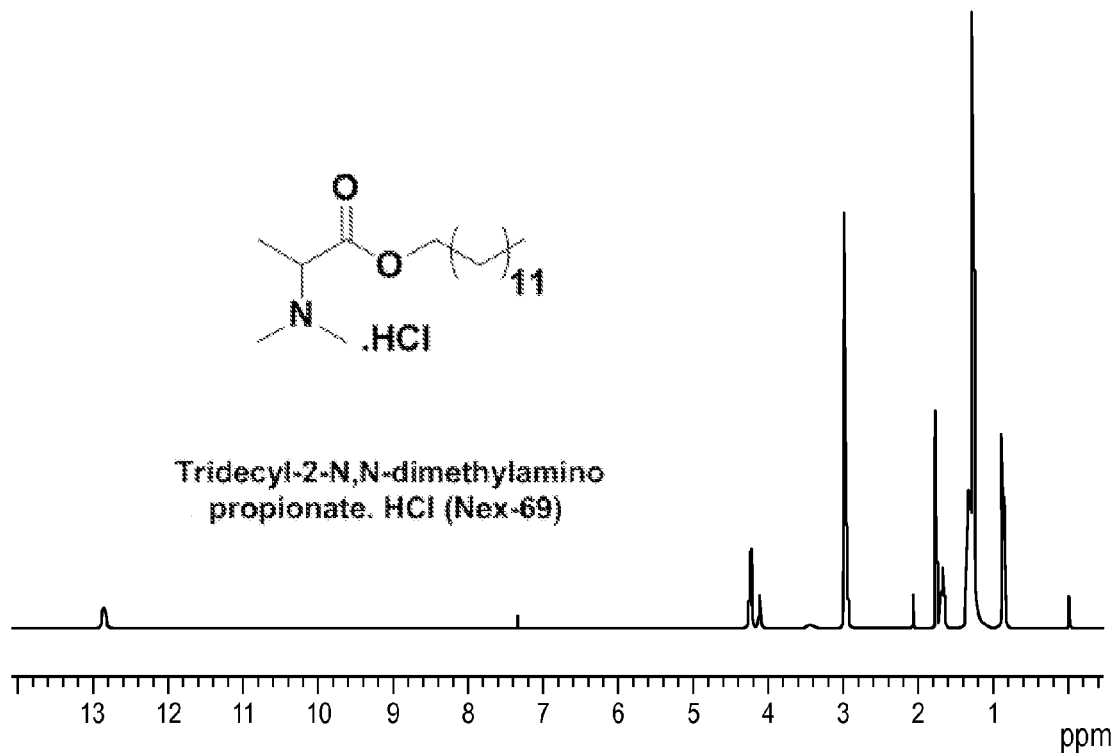
FIG. 29A is a $^1$H-NMR spectrum (400 MHz, CDCl$_3$) of tridecyl-2-N,N-dimethyl-aminopropionate hydrochloride (Nex-69).
Figure 29B:
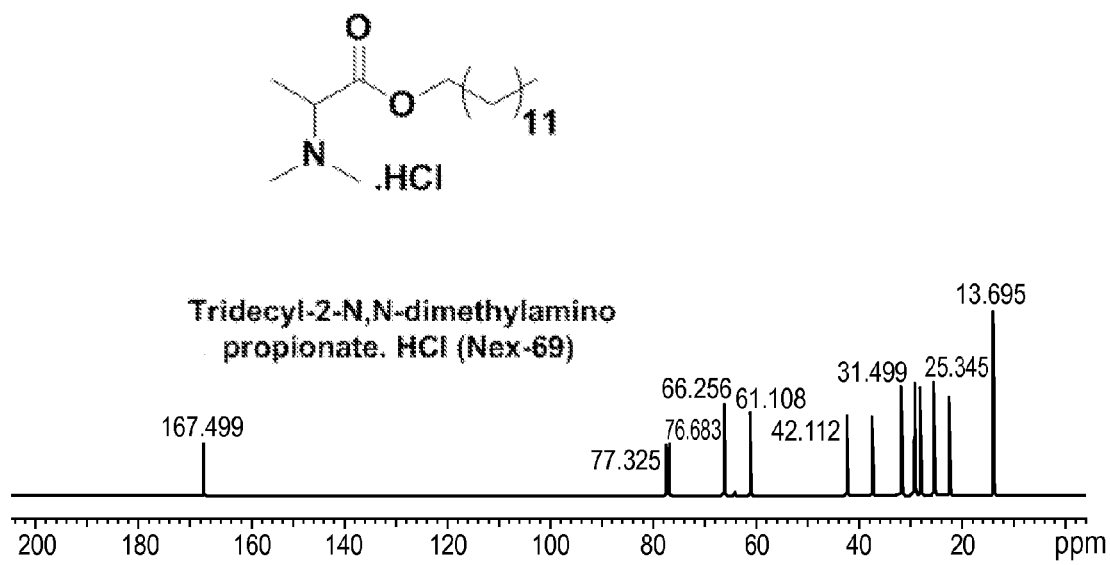
FIG. 29B is a $^{13}$C NMR spectrum (400 MHz, CDCl$_3$); compare to FIG. 29A.
Figure 29C:
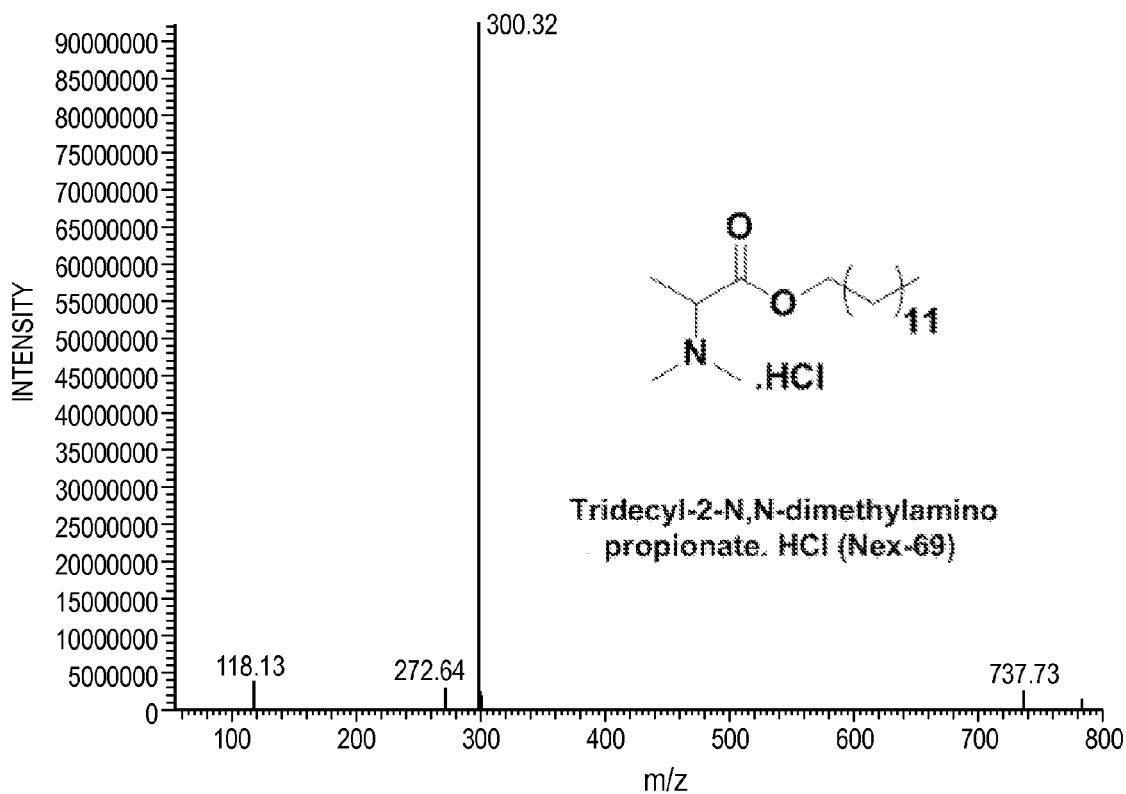
FIG. 29C is a LCMS spectrum: 258 (M$^+$+1) of tridecyl-2-N,N-dimethylamino-propionate hydrochloride salt.
Figure 29D:
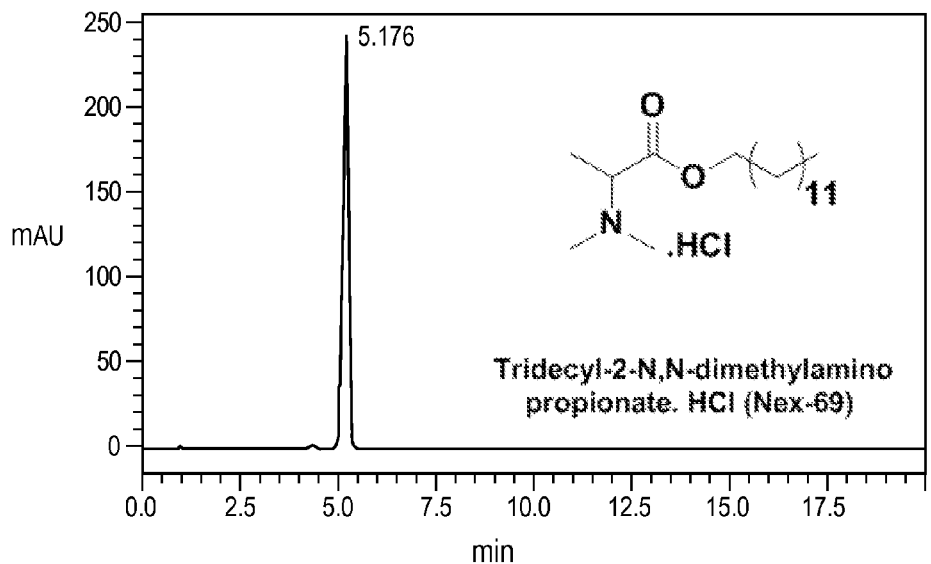
FIG. 29D is a HPLC chromatogram of tridecyl-2-N,N-dimethylaminopropionate hydrochloride salt showing a peak area of 99.18%. Methods as in FIG. 4I).
Figure 30A:
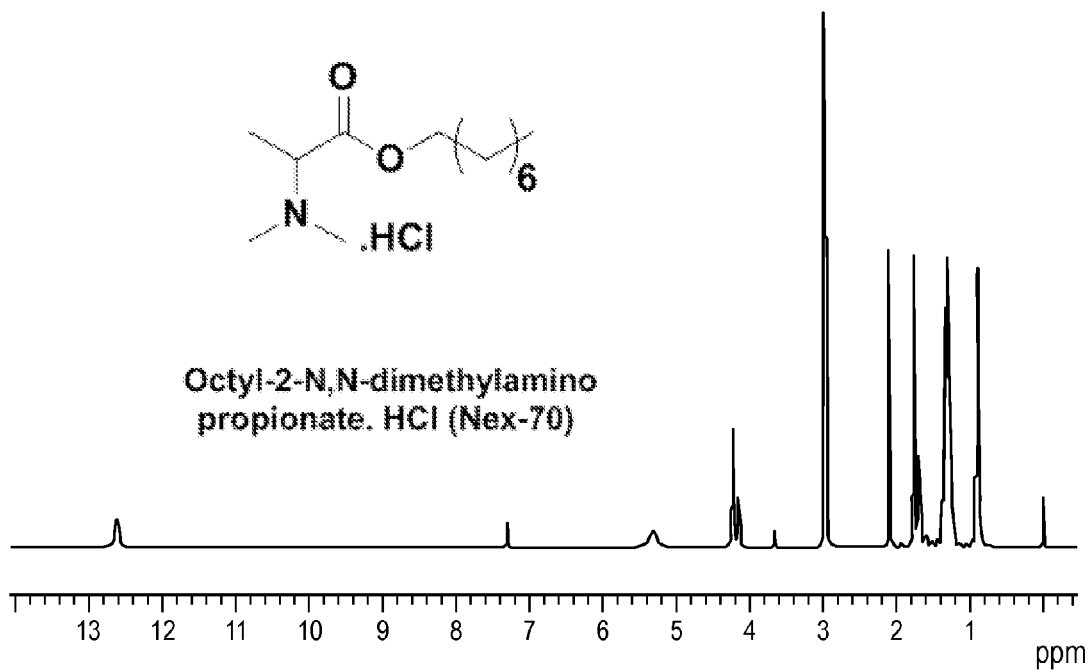
FIG. 30A is a $^1$H-NMR spectrum (400 MHz, CDCl$_3$) of octyl-2-N,N-dimethyl-aminopropionate hydrochloride (Nex-70).
Figure 30B:
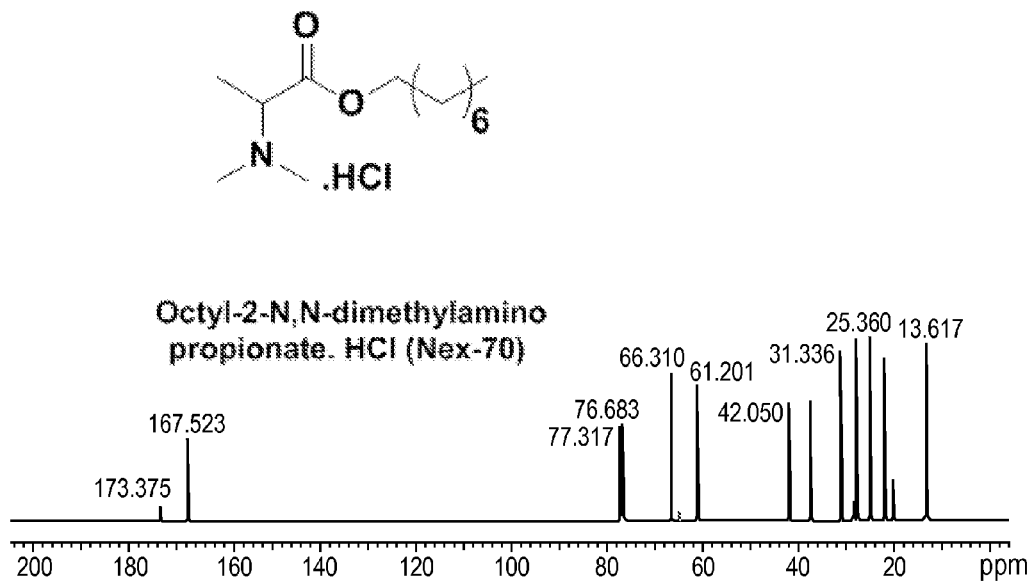
FIG. 30B is a $^{13}$C NMR spectrum (400 MHz, CDCl$_3$); compare to FIG. 30A.
Figure 30C:
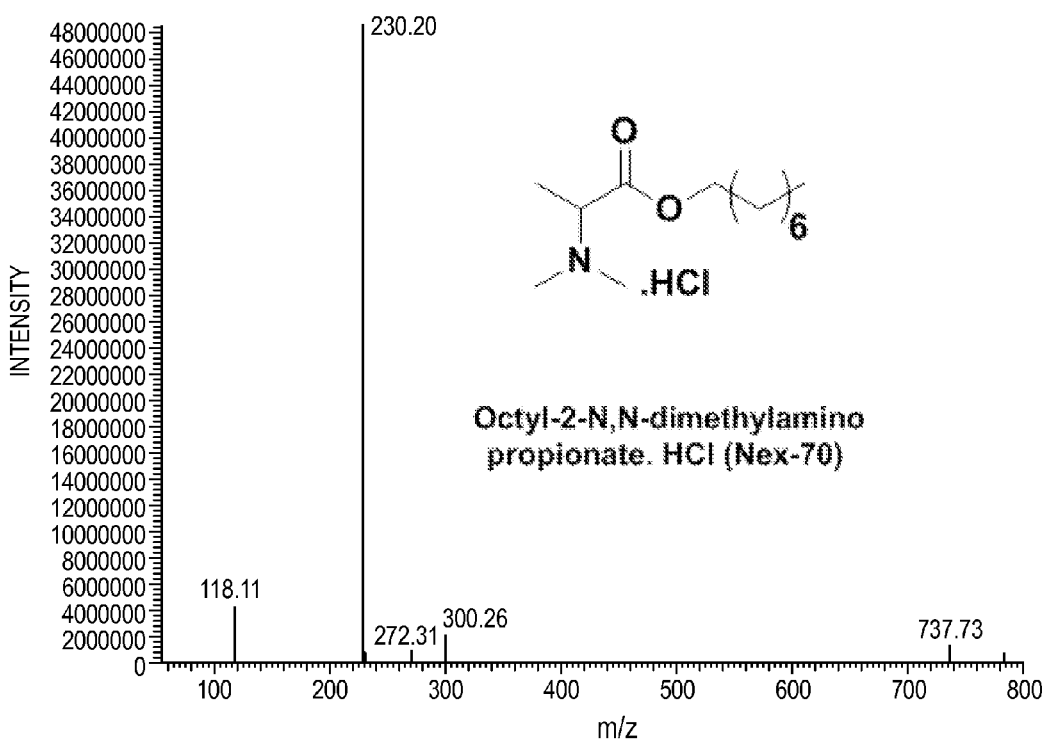
FIG. 30C is a LCMS spectrum: 258 (M$^+$+1) of octyl-2-N,N-dimethylamino-propionate hydrochloride salt.
Figure 30D:
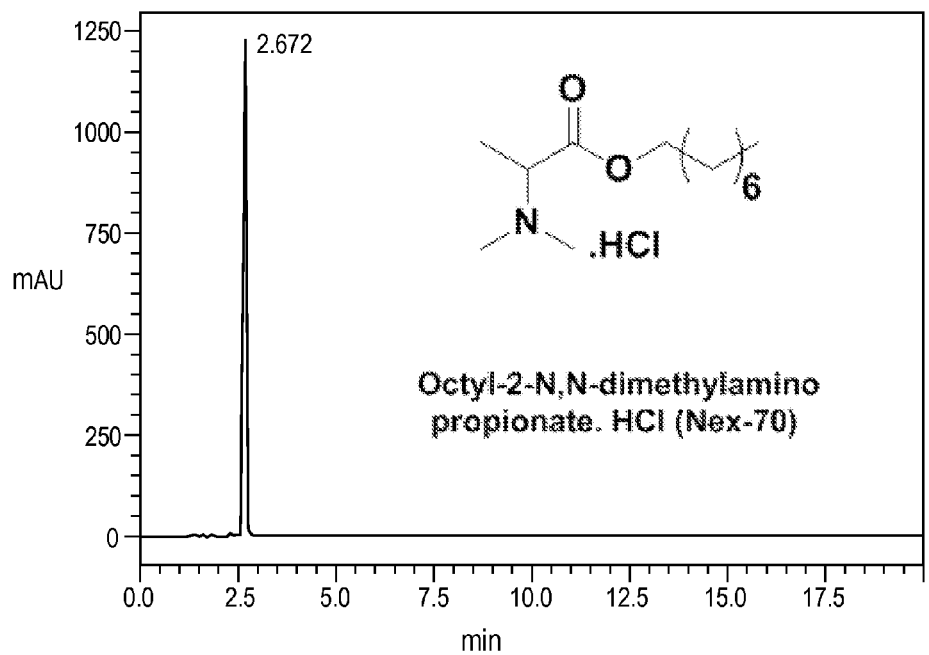
FIG. 30D is a HPLC chromatogram of octyl-2-N,N-dimethylaminopropionate hydrochloride salt showing a peak area of 99.18%. Methods as in FIG. 4D.
Figure 31A:
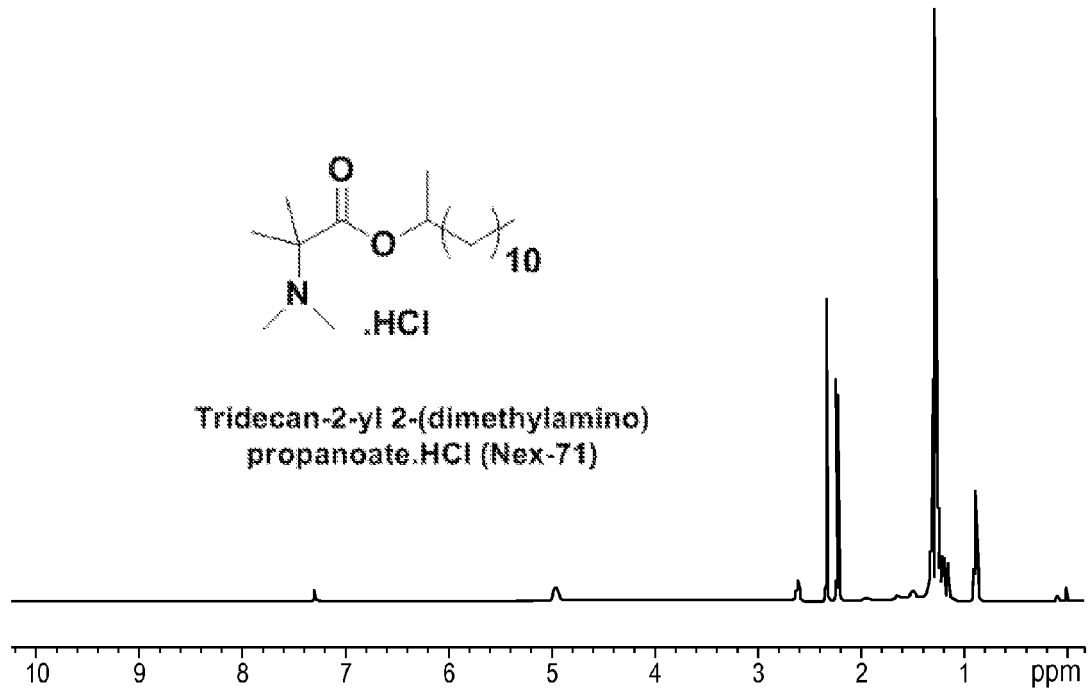
FIG. 31A is a $^1$H-NMR spectrum (400 MHz, CDCl$_3$) of tridecan-2-yl 2-(dimethyl-amino)2-methyl propanoate hydrochloride (Nex-71).
Figure 31B:
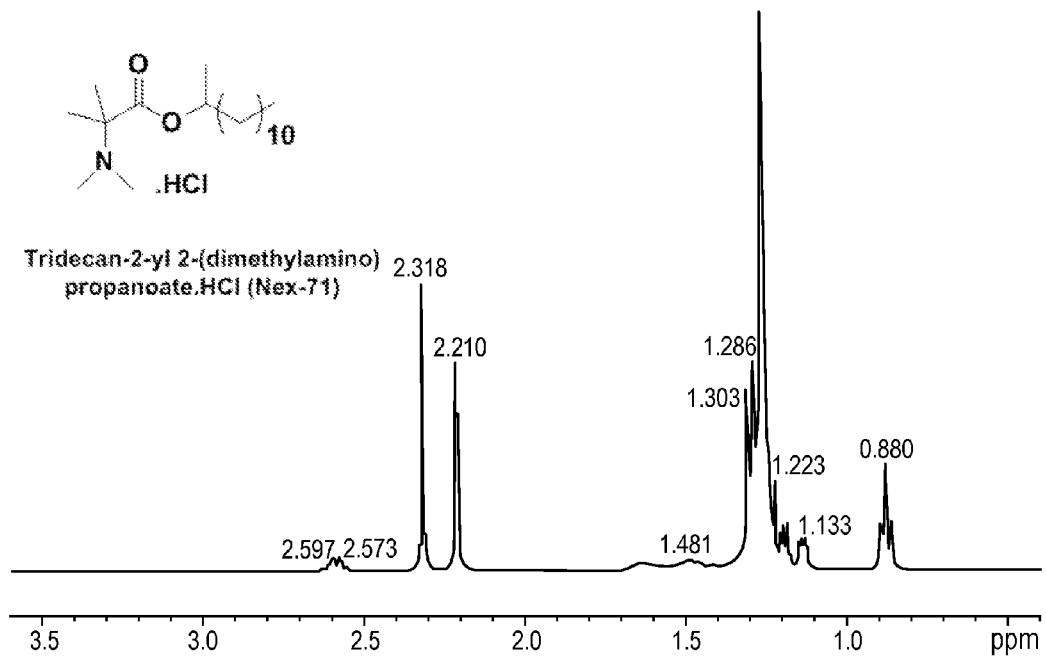
FIG. 31B is a $^1$H-NMR spectrum (400 MHz, CDCl$_3$); compare to FIG. 31A.
Figure 31C:
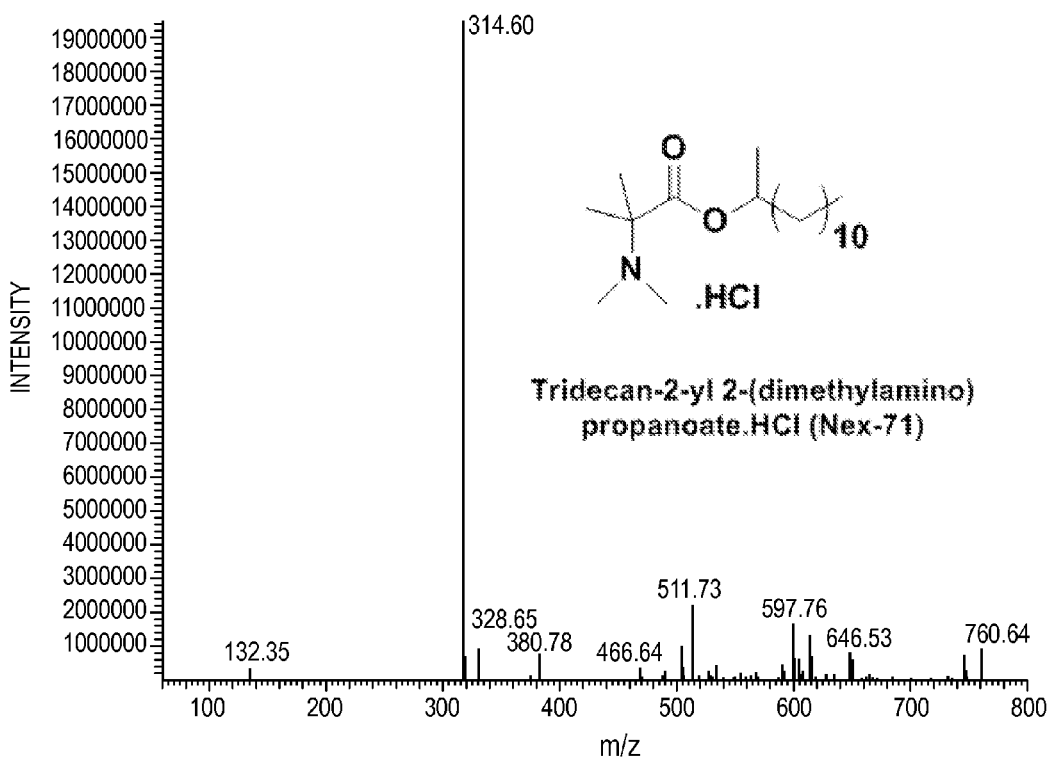
FIG. 31C is a LCMS spectrum: 314 (M$^+$+1) of tridecan-2-yl 2-(dimethylamino) 2-methyl propanoate hydrochloride salt.
Figure 31D:
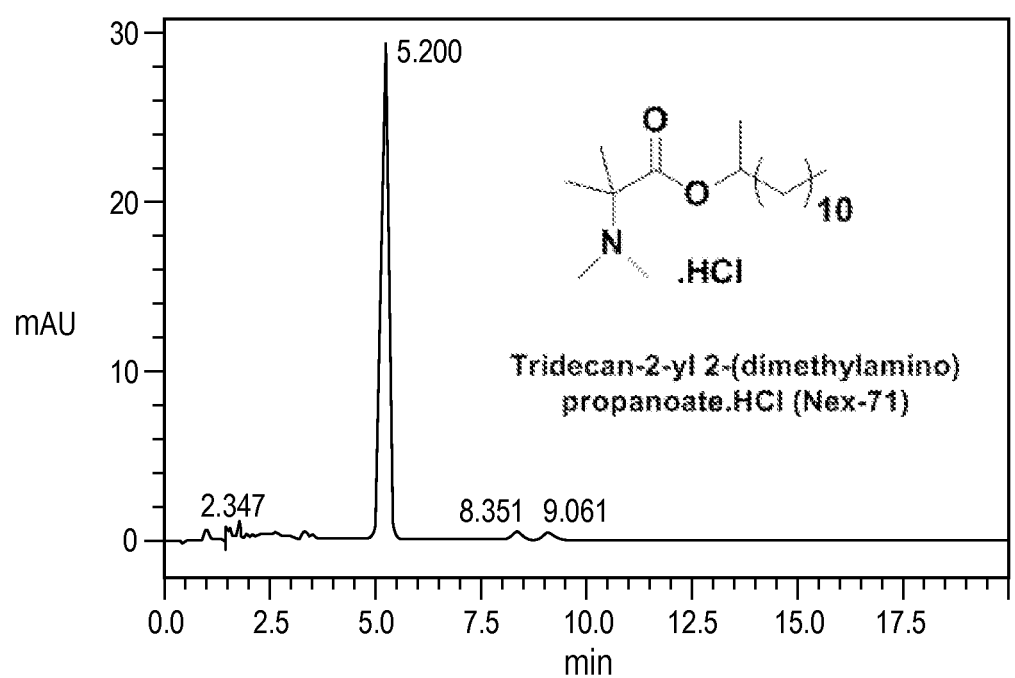
FIG. 31D is a HPLC chromatogram of tridecan-2-yl 2-(dimethylamino) 2-methyl propanoate hydrochloride salt showing a peak area of 94.48%. Methods as in FIG. 4D.

FIG. 20D is a HPLC chromatogram of dodecyl 2-(methylamino)propanoate hydrochloride salt showing a peak area of 98.45%. Methods as in FIG. 4D.

Example 22

Dodecyl 2-(isopropyl amino)propanoate hydrochloride (Nex-60)

Scheme 22

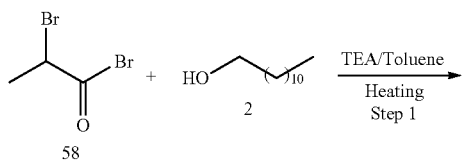

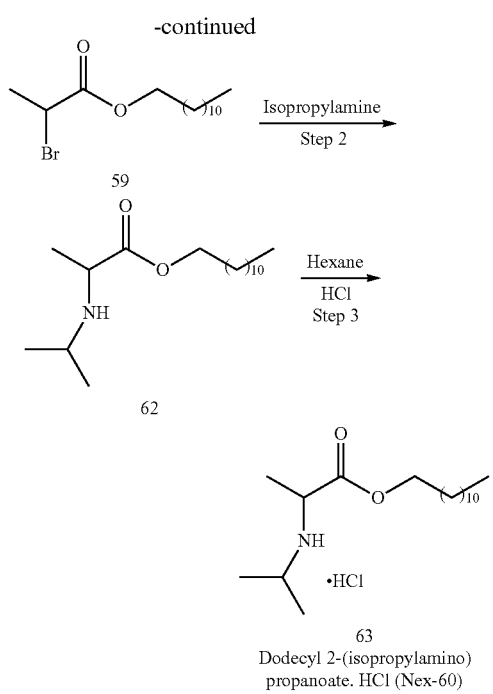

63
Dodecyl 2-(isopropylamino) propanoate. HCl (Nex-60)

Synthesis of dodecyl 2-bromopropanoate (59)

To a stirred solution of 1-decanol 2 (10 g, 53.7 mmol) in toluene (100 mL) was added triethylamine (7.5 mL, 53.7 mmol)), followed by 2-bromo propionyl bromide 58 (12.7 g, 59.1 mmol) at 5-10° C. The reaction mixture was stirred for 3 hour at 55-60° C. and the reaction was monitored by TLC. The reaction mixture was quenched with saturated sodium bicarbonate solution and stirred for 15 minutes at 25-35° C. The aqueous and organic layers were separated, the organic layer was washed with brine, and the combined organic layers were washed with brine solution. The organic layer was dried over $Na_2SO_4$ and concentrated under vacuum to afford crude 59 (16.2 g, yield: 94%) as a liquid.

Synthesis of dodecyl 2-(isopropyl amino)propanoate (62)

To a stirred solution of 59 (10 g, 31.2 mmol) in acetonitrile (30 mL) was added sodium bicarbonate (2.62 g, 31.2 mmol) and followed by isopropyl amine (50% in water) (30 mL, 3 vol) at 25-30° C. The reaction mixture was stirred for 12 h at 55-60° C. and the reaction was monitored by TLC. The solid obtained in the reaction mixture was filtered under vacuum. The solvent was concentrated, diluted with ethyl acetate/water and stirred for 15 minutes at 25-30° C. The aqueous and organic layers were separated, and the aqueous layer was extracted with ethyl acetate (2×10 mL). The combined organic layers were washed with brine solution. The organic layer was dried over $Na_2SO_4$ and concentrated under vacuum to afford crude 62 (7 g, yield: 75.2%) as a liquid.

Synthesis of dodecyl 2-(isopropyl amino)propanoate hydrochloride

A stirred solution of 62 (7 g, 23.4 mmol) in hexane (50 mL) was cooled to 0° C. The reaction mixture was purged with dry HCl gas for 10 minutes, and the reaction mixture was monitored by TLC. The reaction mixture was concentrated under vacuum, the obtained residue was flushed with ethyl acetate (3×25 mL) followed by hexane (5×20 mL) to afford wet dodecyl 2-(isopropyl amino)propanoate hydrochloride 63 ((7 g) as a solid. The solid was taken in hexane (30 mL) and heated to reflux, and stirred at reflux for 30 minutes. The reaction mixture was slowly cooled to RT and then to 0° C. The reaction mixture was filtered under nitrogen and dried under vacuum to afford Dodecyl 2-(isopropyl amino)propanoate hydrochloride salt (63, Nex-60) (5 g, yield: 64%) as a white hygroscopic solid, mp: 86-91° C. $^1$H-NMR (400 MHz, CDCl$_3$) δ 4.3-4.2 (m, 2H), 3.9 (m, 1H), 3.5 (m, 1H), 1.9 (d, 3H), 1.7 (m, 2H), 1.6 (d, 3H), 1.45 (d, 3H), 1.4-1.2 (m, 18H), 0.9 (t, 3H). LCMS: 300.31 (M$^+$+1); HPLC: 98.6%.

Example 23

2-(2-hydroxyethyl) propanoate hydrochloride (Nex-61)

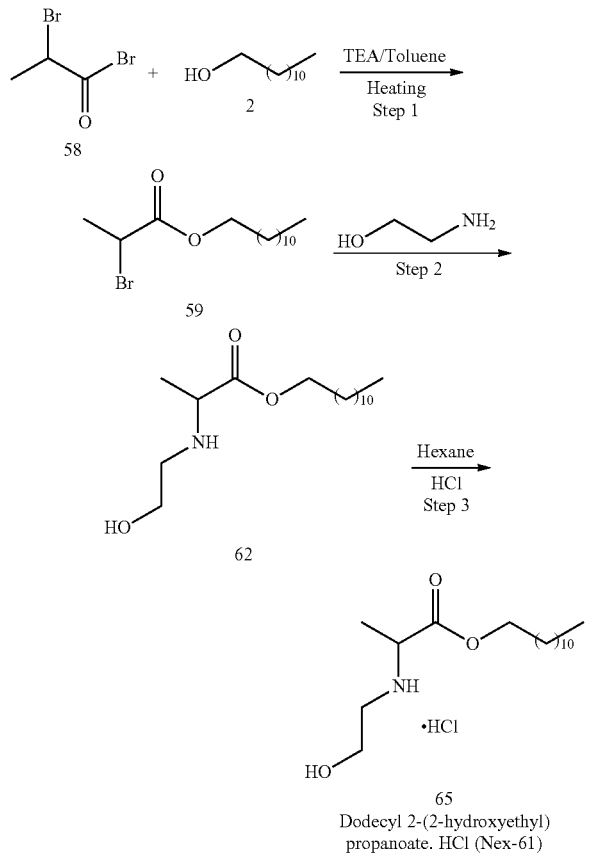

65
Dodecyl 2-(2-hydroxyethyl) propanoate. HCl (Nex-61)

Synthesis of dodecyl 2-bromopropanoate (59)

To a stirred solution of 1-decanol 2 (10 g, 53.7 mmol) in toluene (100 mL) was added triethylamine (7.5 mL, 53.7 mmol)) and followed by 2-bromo propionyl bromide 58 (12.7 g, 59.1 mmol) at 5-10° C. The reaction mixture was stirred for 3 hour at 55-60° C., and the reaction was monitored by TLC. The reaction mixture was quenched with saturated sodium bicarbonate solution and stirred for 15 minutes at 25-35° C. The aqueous and organic layers were separated, the organic layer was washed with brine, and the combined organic layers were washed with brine solution. The organic layer was dried over Na$_2$SO$_4$ and concentrated under vacuum to afford crude 59 (16.2 g, yield: 94%) as a liquid.

Synthesis of dodecyl 2-((2-hydroxyethyl)amino)propanoate (64)

To a stirred solution of 3 (1 g, 3.2 mmol) in acetonitrile/water (5:5 mL) was added sodium bicarbonate (0.262 g 3.2 mmol) and followed by ethanol amine (0.5 mL, 0.5 vol) at 25-30° C. The reaction mixture was stirred for 12 h at RT; the reaction was monitored by TLC. The solid obtained in the reaction mixture was filtered under vacuum, the solvent concentrated, diluted with ethyl acetate/water and stirred for 15 minutes at 25-30° C. The aqueous and organic layers were separated, and the aqueous layer was extracted with ethyl acetate (2×10 mL). The combined organic layers were washed with brine solution. The organic layer was dried over Na$_2$SO$_4$ and concentrated under vacuum to afford crude 64 (0.9 g, yield: 95%) as a liquid Synthesis of dodecyl 2-((2-hydroxyethyl)amino)propanoate hydrochloride (65, Nex-61)

A stirred solution of 64 (0.9 g, 2.99 mmol) in hexane (10 mL) was cooled to 0° C. The reaction mixture was purged with dry HCl gas for 10 minutes; the reaction mixture was monitored by TLC. The reaction mixture was concentrated under vacuum, and the obtained residue was flushed with ethyl acetate (3×25 mL) followed by hexane (5×20 mL) to afford wet dodecyl 2-((2-hydroxyethyl)amino)propanoate hydrochloride 65 (1 g) as a solid. The solid was taken in hexane (10 mL), heated to reflux, and stirred at reflux for 30 minutes. The reaction mixture was slowly cooled to RT and then to 0° C. The reaction mixture was filtered under nitrogen and dried under vacuum to afford dodecyl 2-((2-hydroxyethyl)amino)propanoate hydrochloride salt 65 (0.52 g, yield: 52%) as a white hygroscopic solid, mp: 134-139° C. $^1$H-NMR (400 MHz, CDCl$_3$): δ 4.3-4.2 (m, 2H), 4.1-4.0 (m, 3H), 3.3 (m, 2H), 1.8-1.6 (m, 5H), 1.4-1.2 (m, 18H), 0.9 (t, 3H), LCMS: 302.47 (M$^+$+1); HPLC: 93.9%.

Example 24

Dodecyl 2-((2-(diethylamino)ethyl)amino)propanoate hydrochloride (Nex-62)

Scheme 24

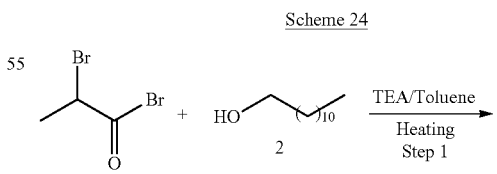

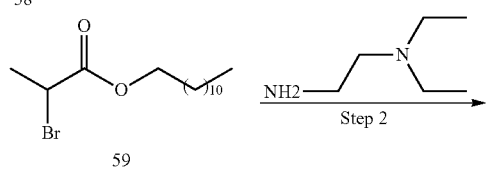

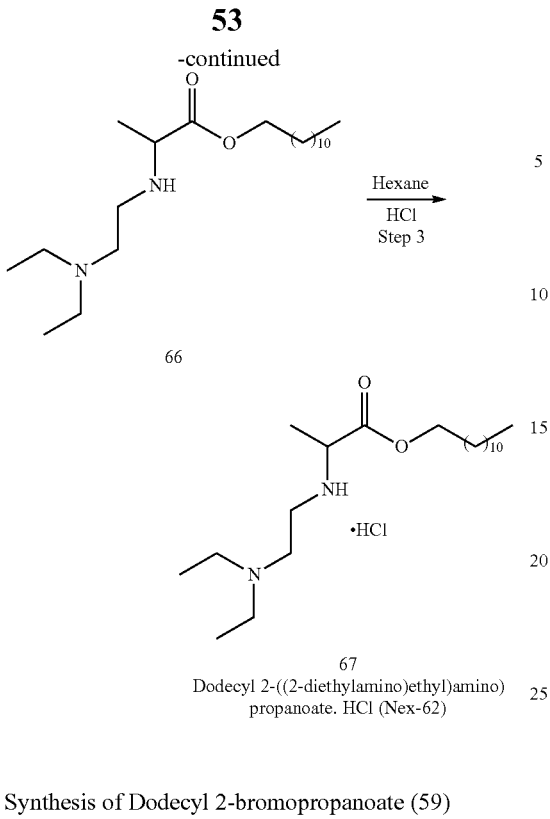

66

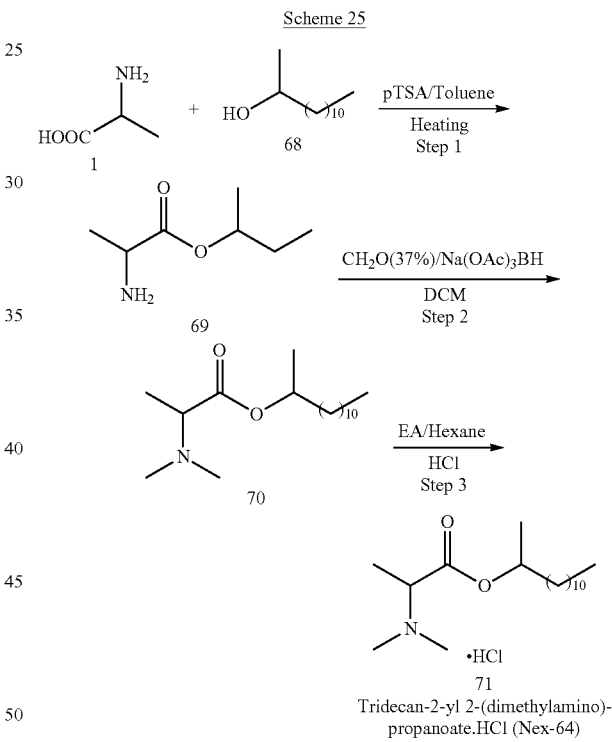

67
Dodecyl 2-((2-diethylamino)ethyl)amino) propanoate. HCl (Nex-62)

Synthesis of Dodecyl 2-bromopropanoate (59)

To a stirred solution of 1-decanol 2 (10 g, 53.7 mmol) in toluene (100 mL) was added triethylamine (7.5 mL, 53.7 mmol)) followed by 2-bromo propionyl bromide 58 (12.7 g, 59.1 mmol) at 5-10° C. The reaction mixture was stirred for 3 hours at 55-60° C.; the reaction was monitored by TLC. The reaction mixture was quenched with saturated sodium bicarbonate solution and stirred for 15 minutes at 25-35° C. The aqueous and organic layers were separated, the organic layer was washed with brine, and the combined organic layers were washed with brine solution. The organic layer was dried over $Na_2SO_4$ and concentrated under vacuum to afford crude 59 (16.2 g, yield: 94%) as a liquid.

Synthesis of dodecyl 2-((2-(diethyl amino)ethyl)amino)propanoate (66)

To a stirred solution of 59 (1 g, 3.2 mmol) in acetonitrile/water (5:5 mL) was added sodium bicarbonate (0.262 g 3.2 mmol) and followed by N, N-diethyl-1,2-diamine (0.5 mL, 0.5 vol) at 25-30° C. The reaction mixture was stirred for 12 h at RT; the reaction was monitored by TLC. The solid obtained in the reaction mixture was filtered under vacuum. The solvent was concentrated, diluted with ethyl acetate/water and stirred for 15 minutes at 25-30° C. The aqueous and organic layers were separated, and the aqueous layer was extracted with ethyl acetate (2×10 mL). The combined organic layers were washed with brine solution. The organic layer was dried over $Na_2SO_4$ and concentrated under vacuum to afford crude 66 (0.9 g, yield: 95%) as a liquid

Synthesis of dodecyl 2-((2-(diethyl amino)ethyl)amino)propanoate hydrochloride A stirred solution of 66 (0.9 g, 2.99 mmol) in hexane (10 mL) was cooled to 0° C. The reaction mixture was purged with dry HCl gas for 10 minutes; the reaction mixture was monitored by TLC. The reaction mixture was concentrated under vacuum, and the obtained residue was flushed with ethyl acetate (3×25 mL) followed by hexane (5×20 mL) to afford wet dodecyl 2-((2-(diethyl amino)ethyl)amino)propanoate hydrochloride (67, Nex-62) (1 g) as a solid. The solid was taken in hexane (10 mL), heated to reflux, stirred at reflux for 30 minutes. The reaction mixture was slowly cooled to RT and then to 0° C. The reaction mixture was filtered under nitrogen and dried under vacuum to afford dodecyl 2-((2-(diethyl amino)ethyl)amino)propanoate hydrochloride salt 67 (0.25 g, yield: 52%) as a white hygroscopic solid. $^1$H-NMR (400 MHz, $CDCl_3$) δ 4.3-4.2 (m, 2H), 4.1-3.9 (m, 3H), 3.8-3.6 (d, 2H), 3.4-3.2 (m, 4H), 1.8-1.6 (m, 5H), 1.5 (d, 6H), 1.4-1.2 (m, 18H), 0.9 (t, 3H). LCMS: 357.59 (M*+1); q-$^1$HNMR: 96.94%.

Example 25

Synthesis of Tridecan-2-yl 2-(dimethylamino)propanoate hydrochloride (Nex-64)

Scheme 25

Synthesis of Tridecan-2-yl 2-aminopropanoate (69)

To a stirred solution of DL-alanine 1 (15 g, 168.5 mmol) in toluene (300 mL) was added 2-tridecanol 68 (30.3 g, 151.68 mmol) in one lot, followed by pTSA (35.26 g, 185.38 mmol). After the addition, the temperature of the reaction mixture was slowly raised to reflux temperature, the water was separated azeotropically and the reaction mixture was monitored by TLC. The reaction mixture was concentrated under vacuum, the obtained residue was taken in ethyl acetate (200 mL) and washed with aqueous 5% $Na_2CO_3$ (3×50 mL) followed by brine solution. The organic layer was dried over $Na_2SO_4$ and concentrated under vacuum to afford 69 (36 g, yield: 78.9%) as a liquid.

Synthesis of tridecan-2-yl 2-(dimethylamino)propanoate (70)

To a stirred solution of 69 (5 g, 18.4 mmol) in DCM (200 mL) was added aqueous formaldehyde solution (37% w/v) (1.93 g, 64.4 mmol) in one lot at 0° C. and Na(OAC)$_3$BH (9.76 g, 46.06 mmol) was slowly added over a period of 1 h. After the addition, the temperature of the reaction mixture was slowly raised to RT and stirred at RT for 24 h. The reaction mixture was monitored by TLC. The reaction mixture was quenched with ice-cold water, the organic layer was separated, and the aqueous layer was extracted with DCM (2×30 mL). The combined organic layers were washed with brine solution. The organic layer was dried over Na$_2$SO$_4$, and concentrated under vacuum to afford tridecan-2-yl 2-(dimethylamino)propanoate (70) (5 g, yield: 90.9%) as a liquid.

Synthesis of tridecan-2-yl 2-(dimethylamino)propanoate hydrochloride (71, Nex-64)

A stirred solution of 70 (5 g, 16.7 mmol) in ethyl acetate/hexane/MeOH (25:25:5 mL) was cooled to 0° C. The reaction mixture was purged with dry HCl gas for 30 minutes, and the reaction mixture was monitored by TLC. The reaction mixture was concentrated under vacuum, the obtained residue was flushed with ethyl acetate (3×25 mL) followed by hexane (3×25 mL) to afford tridecan-2-yl 2-(dimethylamino)propanoate hydrochloride salt 71 (5 g) as a liquid. The liquid taken in ethyl acetate/hexane (10:10 mL), heated to reflux, stirred at reflux for 30 minutes. The reaction mixture was slowly cooled to RT and then to 0° C. The obtained semi solid was filtered under nitrogen. The obtained wet solid was taken in hexane (25 mL) and heated to reflux, stirred at reflux for 30 minutes. The reaction mixture was slowly cooled to RT over a period of 12 h and then to 0° C. The obtained solid was filtered under nitrogen, and dried under vacuum to afford tridecan-2-yl 2-(dimethylamino)propanoate hydrochloride (71, Nex-64) (2.5 g, yield: 44.6%) as a white hygroscopic solid, mp: 88-94° C. $^1$H-NMR (400 MHz, DMSO-d$_6$): δ 1.8 (t, 3H), 1.3 (m, 18H), 1.3 (d, 3H), 1.45 (m, 1H), 1.6 (m, 1H), 1.7 (d, 3H), 2.9 (s, 6H); LCMS: 300 (M$^+$+1); HPLC: 99.62%.

Example 26

Synthesis of 2-Methyltridecan-2-yl 2-(dimethylamino)propanoate hydrochloride (Nex-65)

Scheme 26

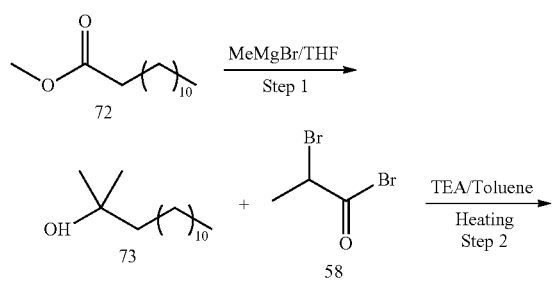

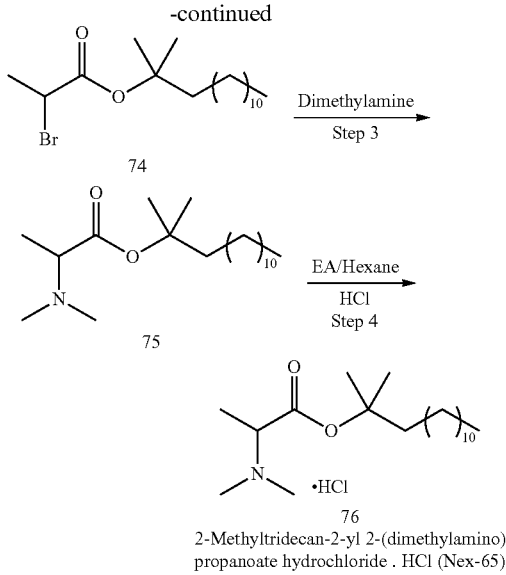

2-Methyltridecan-2-yl 2-(dimethylamino) propanoate hydrochloride . HCl (Nex-65)

Synthesis of 2-methyltridecan-2-ol (72)

To a cooled solution of methyl laurate 72 (31 g, 144 mmol) in THF (600 mL) in an ice-water bath was added a solution of 3M methyl magnesium bromide in ether (100 mL, 303 mmol) drop wise via cannula and the stirred reaction mixture was allowed to warm ambient temperature and stirred for 12 hours, and the reaction mixture was monitored by TLC. The reaction mixture was poured into 500 mL of 2M sulfuric acid solution and was extracted with ethyl acetate. The combined organic layers were washed with brine solution. The organic layer was dried over Na$_2$SO$_4$ and concentrated under vacuum to obtained crude. The obtained crude was purified by column chromatography (5%-10% Ethyl acetate in hexane) to afford 73 (20 g yield: 64.9%) as a liquid.

Synthesis of 2-methyltridecan-2-yl 2-bromopropanoate (74)

To a stirred solution of 2-methyltridecan-2-ol 73 (5 g, 23.4 mmol) in Toluene (50 mL) was added triethylamine (3.29 mL, 23.4 mmol)) and followed by 2-bromopropionyl bromide 58 (5.11 g, 23.7 mmol) at 5-10° C. The reaction mixture was stirred for 3 hours at 55-60° C.; the reaction was monitored by TLC. The reaction mixture was quenched with saturated sodium bicarbonate solution and stirred for 15 minutes at 25-35° C. The aqueous and organic layers were separated, the organic layer was washed with brine, and the combined organic layers were washed with brine solution. The organic layer was dried over Na$_2$SO$_4$ and concentrated under vacuum to afford crude 74 (5 g, yield: 61.27%) as a liquid.

Synthesis of 2-methyltridecan-2-yl 2-(dimethylamino)propanoate (75)

To a stirred solution of 74 (2 g, 5.7 mmol) in acetonitrile (10 mL) was added sodium bicarbonate (0.48 g, 5.74 mmol) and followed by dimethyl amine (40% in water) (10 mL, 88.8 mmol) at 25-30° C. The reaction mixture was stirred for 3 hours at 25-30° C.; the reaction was monitored by TLC. The solid obtained in the reaction mixture was filtered under vacuum. The solvent was concentrated, diluted with ethyl acetate/water and stirred for 15 minutes at 25-30° C. The aqueous and organic layers were separated, and the aqueous layer was extracted with ethyl acetate (2×10 mL). The combined organic layers were washed with brine solution. The organic layer was dried over Na$_2$SO$_4$ and concentrated under vacuum to afford crude 75 (1.49 g, yield: 83%) as a liquid.

Synthesis of 2-methyltridecan-2-yl 2-(dimethylamino)propanoate hydrochloride (76, Nex-65)

A stirred solution of 75 (1.49 g, 4.74 mmol) in ethyl acetate/hexane (1:9 mL) was cooled to 0° C. The reaction mixture was purged with dry HCl gas for 10 minutes, and the reaction mixture was monitored by TLC. The reaction mixture was concentrated under vacuum, the obtained residue was flushed with ethyl acetate (3×25 mL) followed by hexane (5×20 mL) to afford wet 2-methyltridecan-2-yl 2-(dimethylamino)propanoate hydrochloride (76, Nex-65) (1.4 g) as a semi solid. Above semi solid was taken in ethyl acetate/hexane (1:9 mL) and heated to reflux, stirred at reflux for 30 minutes. The reaction mixture was slowly cooled to RT and then to 0° C. The reaction mixture was filtered under nitrogen and dried under vacuum to afford 2-methyltridecan-2-yl 2-(dimethylamino)propanoate hydrochloride salt (0.49 g, yield: 29.5%) as a white hygroscopic solid, mp: 100-106° C. $^1$H-NMR (400 MHz, CDCl$_3$): δ 3.9 (m, 1H), 2.9 (s, 6H), 1.8-1.6 (m, 5H), 1.5 (s, 6H), 1.3-1.2 (m, 18H), 0.9 (t, 3H). LCMS: 314 (M$^+$+1); HPLC: 95.7%.

Example 27

Synthesis of Tetradecyl-2-N,N-dimethylaminopropionate hydrochloride (Nex-66)

Scheme 27

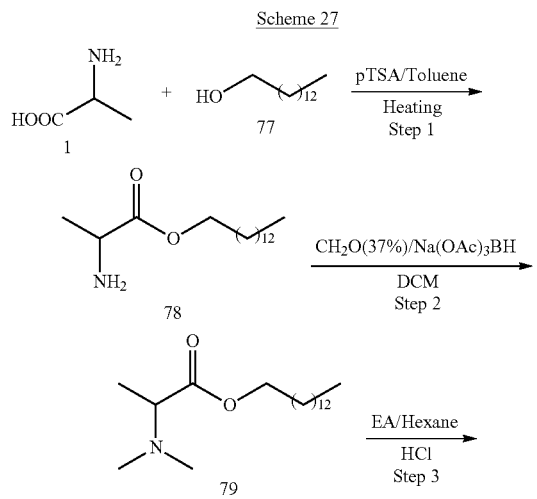

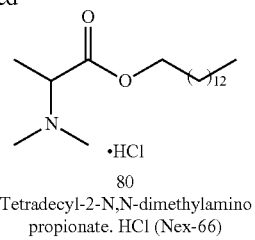

80
Tetradecyl-2-N,N-dimethylamino propionate. HCl (Nex-66)

Synthesis of tetradecyl 2-aminopropanoate (78)

To a stirred solution of DL-alanine 1 (10 g, 112.35 mmol) in toluene (200 mL) was added 1-Tetradecanol (21.6 g, 101.12 mmol) in one lot, followed by pTSA (23.5 g, 123.58 mmol). After addition the temperature of the reaction mixture was slowly raised to reflux temperature, the water was separated azeotropically, and the reaction mixture was monitored by TLC. The reaction mixture was concentrated under vacuum, the obtained residue was taken in ethyl acetate (200 mL) and washed with aqueous 5% Na$_2$CO$_3$ (3×50 mL) followed by brine solution. The organic layer was dried over Na$_2$SO$_4$ and concentrated under vacuum to afford 78 (30 g, yield: 93.75%) as a liquid.

Synthesis of tetradecyl 2-(dimethylamino)propanoate (79)

To a stirred solution of 78 (30 g, 105.26 mmol) in DCM (200 mL) was added aqueous formaldehyde solution (37% w/v) (11.05 g, 368.4 mmol) in one lot at 0° C. and slowly added Na(OAc)$_3$BH (55.77 g, 263.15 mmol) over a period of 1 h. After the addition, the temperature of the reaction mixture was slowly raised to RT, stirred at RT for 24 h, and the reaction mixture was monitored by TLC. The reaction mixture was quenched with ice-cold water, the organic layer was separated and the aqueous layer was extracted with DCM (2×40 mL). The combined organic layers were washed with brine solution. The organic layer was dried over Na$_2$SO$_4$, and concentrated under vacuum to afford 79 (30 g, yield: 90.9%) as a liquid.

Synthesis of Tetradecyl-2-N,N-dimethylaminopropionate hydrochloride (80, Nex-66)

A stirred solution of 79 (30 g, 95.84 mmol) in ethyl acetate/hexane/MeOH (100:100:10 mL) was cooled to 0° C. The reaction mixture was purged with dry HCl gas for 30 minutes, and the reaction mixture was monitored by TLC. The reaction mixture was concentrated under vacuum, the obtained residue was flushed with ethyl acetate (3×50 mL) followed by hexane (5×50 mL) to afford tetradecyl-2-N,N-dimethylaminopropionate HCl salt 80 (35 g) as a semi solid. Above semi solid was taken in ethyl acetate/hexane (100:100 mL) and heated to reflux, stirred at reflux for 30 minutes. The reaction mixture was slowly cooled to RT and then to 0° C. The reaction mixture was filtered under nitrogen and dried under vacuum to afford Tetradecyl-2-N,N-dimethylaminopropionate. HCl salt (23 g, yield: 68.6%) as a white hygroscopic solid, mp: 93-96.5° C. $^1$H-NMR (400 MHz, CDCl$_3$): δ 4.3 (m, 2H), 4.0 (q, 1H), 2.9 (s, 6H), 1.8-1.6 (m, 5H), 1.4-1.2 (m, 22H), 0.9 (t, 3H); LCMS: 314 (M⁺+1); HPLC: 99.70/0.

Example 28

Synthesis of Undecyl-2-N,N-dimethylaminopropionate hydrochloride (Nex-67)

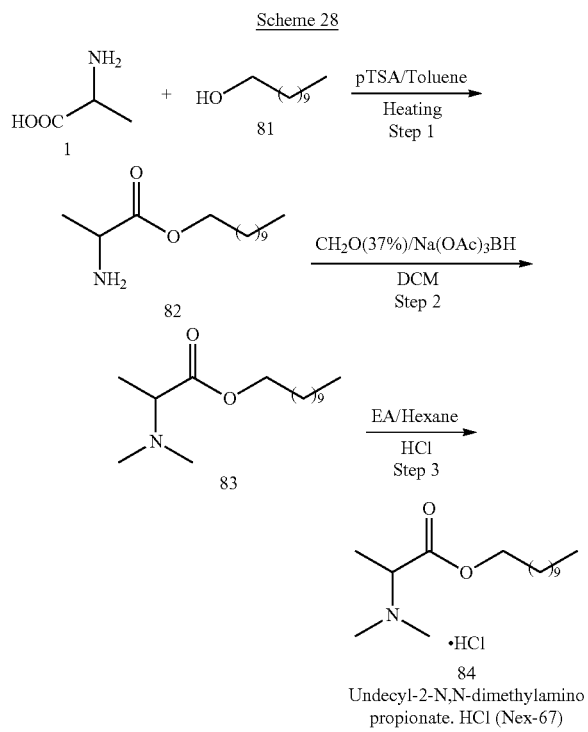

Synthesis of undecyl 2-aminopropanoate (82)

To a stirred solution of DL-alanine 1 (15 g, 168.5 mmol) in toluene (300 mL) was added 1-undecanol 81 (26.22 g, 151.68 mmol) in one lot, followed by pTSA (35.38 g, 185.35 mmol). After the addition, the temperature of the reaction mixture was slowly raised to reflux temperature, the water was separated azeotropically and the reaction mixture was monitored by TLC. The reaction mixture was concentrated under vacuum, the obtained residue was taken in ethyl acetate (200 mL) and washed with aqueous 5% $Na_2CO_3$ (3×50 mL) followed by brine solution. The organic layer was dried over $Na_2SO_4$ and concentrated under vacuum to afford 82 (40 g, yield: 97.56%) as a liquid.

Synthesis of undecyl 2-(dimethylamino)propanoate (83)

To a stirred solution of 82 (40 g, 164.39 mmol) in DCM (200 mL) was added aqueous formaldehyde solution (37% w/v) (17.26 g, 575.39 mmol) in one lot at 0° C. and slowly added $Na(OAC)_3BH$ (9.76 g, 410.99 mmol) over a period of 1 h. After the addition, the temperature of the reaction mixture was slowly raised to rt, stirred at RT for 24 h; the reaction mixture was monitored by TLC. The reaction mixture was quenched with ice-cold water, the organic layer was separated and the aqueous layer was extracted with DCM (2×30 mL). The combined organic layers were washed with brine solution. The organic layer was dried over $Na_2SO_4$, and concentrated under vacuum to afford 83 (42 g, yield: 95.45%) as a liquid.

Synthesis of undecyl-2-N,N-dimethylaminopropionate hydrochloride (84, Nex-67)

To a stirred solution of 83 (42 g, 154.8 mmol) in ethyl acetate/hexane/MeOH (25:25:5 mL) and then cooled to 0° C. The reaction mixture was purged with dry HCl gas for 30 minutes; the reaction mixture was monitored by TLC. The reaction mixture was concentrated under vacuum, the obtained residue was flushed with ethyl acetate (3×25 mL) followed by hexane (3×25 mL) to afford undecyl-2-N,N-dimethylaminopropionate.HCl salt 84 (40 g) as a liquid. The liquid taken in ethyl acetate/hexane (100:100 mL) and heated to reflux, stirred at reflux for 30 minutes. The reaction mixture was slowly cooled to RT and then to 0° C. The obtained semi solid was filtered under nitrogen. The obtained wet solid was taken in hexane (50 mL) and heated to reflux, stirred at reflux for 30 minutes. The reaction mixture was slowly cooled to RT over a period of 12 h and then to 0° C. The obtained waxy solid was filtered under nitrogen, dried under vacuum to afford undecyl-2-N,N-dimethylaminopropionate.HCl salt 84 (27 g, yield: 59.94%) as a waxy hygroscopic solid. ¹H-NMR (400 MHz, DMSO-$d_6$): δ 4.3-4.15 (m, 3H), 2.9 (s, 6H), 1.7 (t, 3H), 1.55 (d, 3H), 1.4-1.2 (m, 16H), 1.9 (m, 3H); LCMS: 272 (M+1); HPLC: 99.6%.

Example 29

Synthesis of Decyl-2-N,N-dimethylaminopropionate hydrochloride (Nex-68)

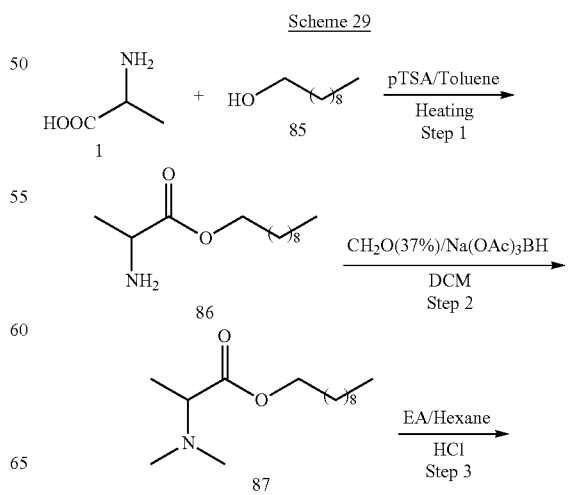

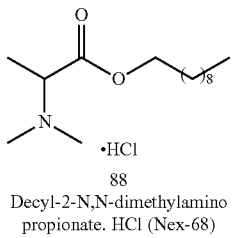

88
Decyl-2-N,N-dimethylamino
propionate. HCl (Nex-68)

Synthesis of decyl 2-aminopropanoate (86)

To a stirred solution of DL-alanine 1 (15 g, 168.5 mmol) in toluene (300 mL) was added 1-decanol 85 (23.9 g, 151.68 mmol) in one lot, followed by pTSA (35.26 g, 185.38 mmol), After the addition, the temperature of the reaction mixture was slowly raised to reflux temperature, the water was separated azeotropically and the reaction mixture was monitored by TLC. The reaction mixture was concentrated under vacuum. The obtained residue was taken in ethyl acetate (200 mL) and washed with aqueous 5% $Na_2CO_3$ (3×50 mL) followed by brine solution. The organic layer was dried over $Na_2SO_4$ and concentrated under vacuum to afford 86 (35 g, yield: 90.6%) as a liquid.

Synthesis of decyl 2-(dimethylamino)propanoate (87)

To a stirred solution of 86 (35 g, 152.8 mmol) in DCM (200 mL) was added aqueous formaldehyde solution (37% w/v) (16.04 g, 534.9 mmol) in one lot at 0° C. $Na(OAc)_3BH$ (80.98 g, 382.09 mmol) was slowly added over a period of 1 h. After addition, the temperature of the reaction mixture was slowly raised to RT and stirred at RT for 24 h. The reaction mixture was monitored by TLC. The reaction mixture was quenched with ice-cold water, the organic layer was separated and the aqueous layer was extracted with DCM (2×30 mL). The combined organic layers were washed with brine solution. The organic layer was dried over $Na_2SO_4$, and concentrated under vacuum to afford 87 (38.4 g, yield: 97.95%) as a liquid.

Synthesis of decyl-2-N,N-dimethylaminopropionate hydrochloride (88, Nex-68)

A stirred solution of 87 (38.4 g, 149.4 mmol) in ethyl acetate/hexane/MeOH (100:100:10 mL) was cooled to 0° C. The reaction mixture was purged with dry HCl gas for 30 minutes, and the reaction mixture was monitored by TLC. The reaction mixture was concentrated under vacuum. The obtained residue was flushed with ethyl acetate (3×50 mL) followed by hexane (3×50 mL) to afford decyl-2-N,N-dimethylaminopropionate.HCl salt 88 (35 g) as a wet solid. The wet solid was taken in ethyl acetate/hexane (100:100 mL), heated to reflux, and stirred at reflux for 30 minutes. The reaction mixture was slowly cooled to RT and then to 0° C. The obtained semi solid was filtered under nitrogen. The obtained wet solid was taken in hexane (50 mL) and heated to reflux, and stirred at reflux for 30 minutes. The reaction mixture was slowly cooled to RT over a period of 12 h and then to 0° C. The obtained solid was filtered under nitrogen, dried under vacuum to afford Decyl-2-N,N-dimethylaminopropionate. HCl salt 88 (26 g, yield: 59.3%) as a white hygroscopic solid, mp: 77-82° C. $^1$H-NMR (400 MHz, DMSO-$d_6$): δ 4.3 (m, 2H), 4.1 (q, 1H), 3 (s, 6H), 1.8-1.6 (m, 5H), 1.4-1.2 (m, 14H), 0.9 (t, 3H); LCMS: 258 (M$^+$+1); HPLC: 99.18%

Example 30

Synthesis of Tridecyl-2-N,N-dimethylaminopropionate (Nex-69)

Scheme 30

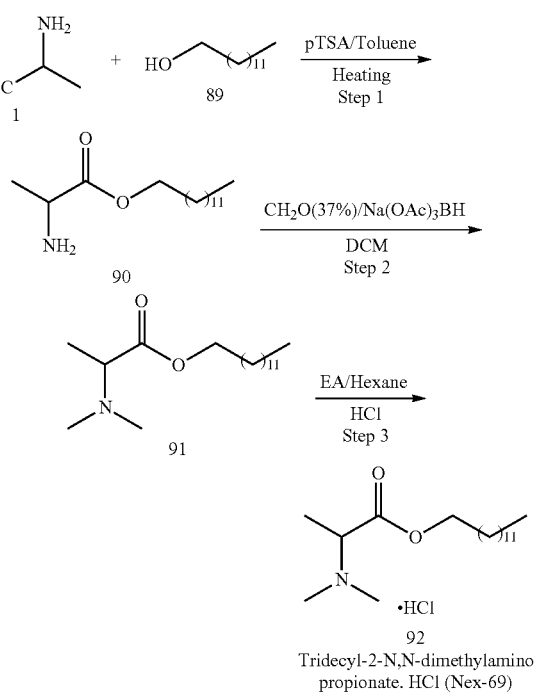

92
Tridecyl-2-N,N-dimethylamino
propionate. HCl (Nex-69)

Synthesis of Tridecyl 2-aminopropanoate (90)

To a stirred solution of DL-alanine 1 (15 g, 168.5 mmol) in toluene (300 mL) was added 1-tridecanol 89 (30.39 g, 151.68 mmol) in one lot, followed by pTSA (35.26 g, 185.38 mmol). After the addition, the temperature of the reaction mixture was slowly raised to reflux temperature, the water was separated azeotropically and the reaction mixture was monitored by TLC. The reaction mixture was concentrated under vacuum, the obtained residue was taken in ethyl acetate (200 mL) and washed with aqueous 5% $Na_2CO_3$ (3×50 mL) followed by brine solution. The organic layer was dried over $Na_2SO_4$ and concentrated under vacuum to afford 90 (38 g, yield: 83.15%) as a liquid.

Synthesis of tridecyl 2-(dimethylamino)propanoate (91)

To a stirred solution of 90 (38 g, 140 mmol) in DCM (200 mL) was added aqueous formaldehyde solution (37% w/v) (14.7 g, 490.1 mmol) in one lot at 0° C. $Na(OAc)_3BH$ (74 g, 350 mmol) was slowly added over a period of 1 h. After addition, the temperature of the reaction mixture was slowly raised to room temperature and stirred at RT for 24 h. The reaction mixture was monitored by TLC. The reaction mixture was quenched with ice-cold water, the organic layer was separated, and the aqueous layer was extracted with DCM

Synthesis of tridecyl-2-N,N-dimethylaminopropionate hydrochloride (92, Nex-69)

(2×30 mL). The combined organic layers were washed with brine solution. The organic layer was dried over Na$_2$SO$_4$, and concentrated under vacuum to afford 91 (40 g, yield: 95.4%) as a liquid.

A stirred solution of 91 (40 g, 133.6 mmol) in ethyl acetate/hexane/MeOH (100:100:10 mL) was cooled to 0° C. The reaction mixture was purged with dry HC gas for 30 minutes, and the reaction mixture was monitored by TLC. The reaction mixture was concentrated under vacuum. The obtained residue was flushed with ethyl acetate (3×50 mL) followed by hexane (3×50 mL) to afford tridecyl-2-N,N-dimethylaminopropionate.HCl salt 92 (38 g) as a liquid. The liquid was taken in ethyl acetate/hexane (100:100 mL), heated to reflux, and stirred at reflux for 30 minutes. The reaction mixture was slowly cooled to RT and then to 0° C. The obtained semi solid was filtered under nitrogen. The obtained wet solid was taken in hexane (50 mL), heated to reflux, stirred at reflux for 30 minutes. The reaction mixture was slowly cooled to RT over a period of 12 h and then to 0° C. The obtained solid was filtered under nitrogen, dried under vacuum to afford tridecyl-2-N,N-dimethylaminopropionate.HCl salt 92 (22 g, yield: 49%) as a white hygroscopic solid. $^1$H-NMR (400 MHz, DMSO-d$_6$): δ 4.3-4.2 (m, 2H), 4.1 (q, 1H), 3 (s, 6H), 1.8-1.6 (m, 5H), 1.4-1.2 (m, 20H), 0.9 (t, 3H); LCMS: 300 (M$^+$+1); HPLC: 99.89%.

Example 31

Synthesis of Octyl-2-N,N-dimethylaminopropionate hydrochloride (Nex-70)

Synthesis of octyl 2-aminopropanoate (94)

To a stirred solution of DL-alanine 1 (20 g, 224.7 mmol) in toluene (300 mL) was added 1-octanol 94 (26.08 g, 202.24 mmol) in one lot, followed by pTSA (47.02 g, 247.19 mmol). After the addition, the temperature of the reaction mixture was slowly raised to reflux temperature, the water was separated azeotropically, and the reaction mixture was monitored by TLC. The reaction mixture was concentrated under vacuum. The obtained residue was taken in ethyl acetate (200 mL) and washed with aqueous 5% Na$_2$CO$_3$ (3×50 mL) followed by brine solution. The organic layer was dried over Na$_2$SO$_4$ and concentrated under vacuum to afford 94 (40 g, yield: 89.08) as a liquid.

Synthesis of octyl 2-(dimethylamino)propanoate (95)

To a stirred solution of 94 (40 g, 200 mmol) in DCM (200 mL) was added aqueous formaldehyde solution (37% w/v) (21 g, 700 mmol) in one lot at 0° C. Na(OAc)$_3$BH (106 g, 500 mmol) was slowly added over a period of 1 h. After addition, the temperature of the reaction mixture was slowly raised to room temperature and stirred at RT for 24 h. The reaction mixture was monitored by TLC. The reaction mixture was quenched with ice-cold water, the organic layer was separated and the aqueous layer was extracted with DCM (2×30 mL). The combined organic layers were washed with brine solution. The organic layer was dried over Na$_2$SO$_4$, and concentrated under vacuum to afford 95 (42 g, yield: 92.1%) as a liquid.

Synthesis of octyl-2-N,N-dimethylaminopropionate hydrochloride (96, Nex-70)

A stirred solution of 95 (42 g, 184.2 mmol) in ethyl acetate/hexane/MeOH (100:100:10 mL) was cooled to 0° C. The reaction mixture was purged with dry HCl gas for 30 minutes, and the reaction mixture was monitored by TLC. The reaction mixture was concentrated under vacuum, and the obtained residue was flushed with ethyl acetate (3×50 mL) followed by hexane (3×50 mL) to afford octyl-2-N,N-dimethylaminopropionate. HCl salt 96 (40 g) as a liquid. The liquid was taken in ethyl acetate/hexane (100:100 mL), heated to reflux, and stirred at reflux for 30 minutes. The reaction mixture was slowly cooled to RT and then to 0° C. The obtained semi solid was filtered under nitrogen. The obtained wet solid was taken in hexane (100 mL, heated to reflux, and stirred at reflux for 30 minutes. The reaction mixture was slowly cooled to RT over a period of 12 h and then to 0° C. The obtained solid was filtered under nitrogen, dried under vacuum to afford octyl-2-N,N-dimethylaminopropionate.HCl salt (96, Nex-70) (30 g, yield: 62.5%) as a hygroscopic waxy solid. $^1$H-NMR (400 MHz, DMSO-d$_6$): δ 4.3-4.1 (m, 3H), 3 (s, 6H), 1.8-1.6 (m, 5H), 1.4-1.2 (m, 10H), 0.9 (t, 3H); LCMS: 230 (M$^+$+1); HPLC: 99.56%.

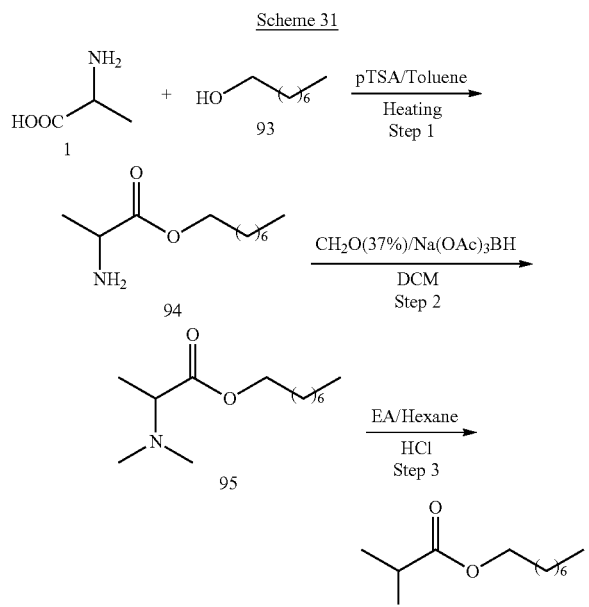

Scheme 31

Example 32

Synthesis of Tridecan-2-yl 2-(dimethylamino) 2-methyl propanoate hydrochloride (Nex-71)

Scheme 32

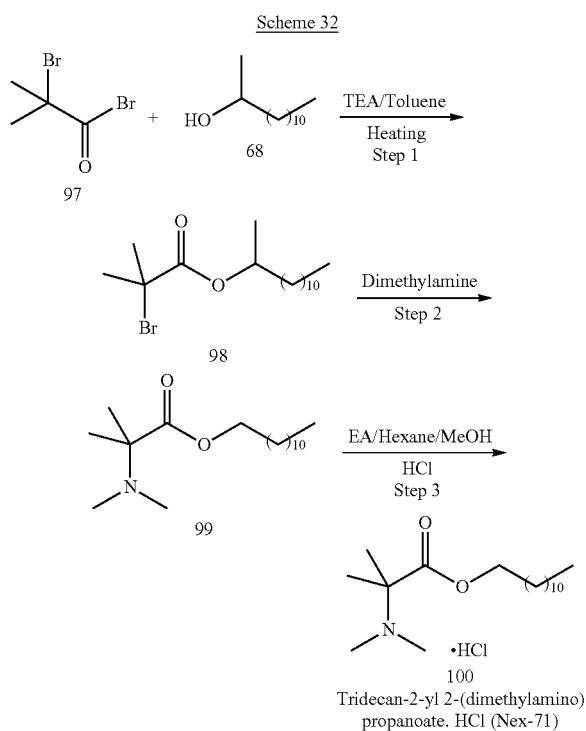

Tridecan-2-yl 2-(dimethylamino) propanoate. HCl (Nex-71)

Synthesis of tridecen-2-yl 2-bromopropanoate (98)

To a stirred solution of tridecan-2-ol 68 (5 g, 24.9 mmol) in toluene (50 mL) was added triethylamine (3.5 mL, 27.45 mmol)) and followed by 2-bromo-2-methylpropionyl bromide 97 (6.31 g, 27.45 mmol) at 5-10° C. The reaction mixture was stirred for 3 hour at 55-60° C., and the reaction was monitored by TLC. The reaction mixture was quenched with saturated sodium bicarbonate solution and stirred for 15 minutes at 25-35° C. The aqueous and organic layers were separated. The organic layer was washed with brine, and the combined organic layers were washed with brine solution. The organic layer was dried over $Na_2SO_4$ and concentrated under vacuum to afford crude 98 (8.1 g, yield: 96%) as a liquid.

Synthesis of tridecan-2-yl 2-(dimethylamino) 2-methyl propanoate (99)

To a stirred solution of 98 (8.1 g, 23.1 mmol) in acetonitrile (50 mL) was added sodium bicarbonate (1.94 g, 23.1 mmol) and followed by dimethyl amine (40% in water) (50 mL, 444 mmol) at 25-30° C. The reaction mixture was stirred for 3 hour at 25-30° C. and the reaction was monitored by TLC. The reaction mixture was filtered under vacuum, the solvent was concentrated, diluted with ethyl acetate/water and stirred for 15 minutes at 25-30° C. The aqueous and organic layers were separated and the aqueous layer was extracted with ethyl acetate (2×10 mL). The combined organic layers were washed with brine solution. The organic layer was dried over $Na_2SO_4$ and concentrated under vacuum to afford a crude product, which was purified by column chromatography to afford 99 (7 g, yield: 95.8%) as a liquid. $^1$H-NMR (400 MHz, CDCl$_3$) δ 4.9 (m, 1H), 2.3 (s, 3H), 2.2 (s, 3H), 1.7-1.5 (m, 2H), 1.4-1.1 (in, 27H), 0.9 (t, 3H). LCMS: 314 (M$^+$+1); HPLC: 92.4%.

Synthesis of tridecan-2-yl 2-(dimethylamino) 2-methyl propanoate hydrochloride (100, Nex-71)

A stirred solution of 99 (7 g, 22.3 mmol) in ethyl acetate/hexane (1:9 mL) was cooled to 0° C. The reaction mixture was purged with dry HCl gas for 10 minutes, and the reaction mixture was monitored by TLC. The reaction mixture was concentrated under vacuum, and the obtained residue was flushed with ethyl acetate (3×25 mL) followed by hexane (5×20 mL) to afford wet tridecan-2-yl 2-(dimethylamino) 2-methyl propanoate hydrochloride 100 (7 g) as a waxy solid. The waxy solid was taken in ethyl acetate/hexane (1:9 mL), heated to reflux, and stirred at reflux for 30 minutes. The reaction mixture was slowly cooled to RT and then to 0° C. The obtained waxy solid was not filterable, and was dried under vacuum to afford tridecan-2-yl 2-(dimethylamino) 2-methyl propanoate hydrochloride salt 100 (5.6 g, yield: 72%) as a white waxy hygroscopic semi solid. $^1$H-NMR (400 MHz, CDCl$_3$): δ 5.0 (m, 1H), 2.9-2.7 (m, 6H), 1.8 (m, 6H), 1.6-1.4 (m, 2H), 1.4-1.2 (m, 21H), 0.9 (t, 3H). LCMS: 314 (M$^+$+1); HPLC: 94.36%.

Example 33

Minimum Inhibitory Concentration Assays and Time Kill Studies

Thirty compounds were tested for antimicrobial activity using standard procedures and standard strains for both the minimum inhibitory concentration (MIC) assay and a time kill study. Both the MIC assay and the time kill study were performed according to Clinical and Laboratory Standards Institute (CLSI) guidelines. Three bacteria strains, *Escherichia coli* (ATCC 25922), *Pseudomonas aeruginosa* (ATCC 27853), *Staphulococcus aureus* (ATCC 29213), and two fungus strains, *Candida albicans* (ATCC 90029) and *Aspergillus niger* (CMCC 98003), were used in the experiments. The strains used in the standard tests of Examples 33, 34 and 35 are listed in Table 2, below.

TABLE 2

Standard Strains of Pathogens Used For Testing

| Pathogen (Strain) | Comments from ATCC Catalog Description |
|---|---|
| *Acinetobacter baumannii* (ATCC 19606) | Quality control strain |
| *Acinetobacter iwoffi* (ATCC 15309) | Type strain |
| *Aspergillus niger* (CMCC 98803) | |

TABLE 2-continued

Standard Strains of Pathogens Used For Testing

| Pathogen (Strain) | Comments from ATCC Catalog Description |
| --- | --- |
| *Bacillus subtilis* (ATCC 6633) | Quality control strain, testing antibacterial activity |
| *Burkholderia cepacia* (ATCC 25416) | Quality control strain, assay of antimicrobial preservatives |
| *Candida albicans* (ATCC 10231) | Quality control strain, testing fungicides |
| *Candida albicans* (ATCC 90029) | Susceptibility testing of antifungal agents |
| *Corynebacterium jeikeium* (ATCC 43734) | Type strain |
| *Enterobacter aerogenes* (ATCC 13048) | Quality control strain, assay of antimicrobial preservatives |
| *Enterobacter cloacae* (ATCC 13047) | Quality control strain |
| *Enterococcus faecalis* (ATCC 51299) | Quality control strain, low-level vancomycin-resistant, VanB |
| *Enterococcus faecalis* (ATCC 19433) | Quality control strain |
| *Enterococcus faecium* (ATCC 19434) | Testing antimicrobial hand washing formulations |
| *Escherichia coli* (ATCC 11229) | Testing antimicrobial hand washing formulations |
| *Escherichia coli* (ATCC 25922) | Quality control strain |
| *Haemophilus influenza* (ATCC 19418) | Biovar III reference strain, media testing |
| *Klebsiella oxytoca* (ATCC 43165) | Quality control strain |
| *Klebsiella pneumonia* (ATCC 11296) | Type strain |
| *Micrococcus luteus* (ATCC 4698) | Type strain, quality control strain |
| *Proteus mirabilis* (ATCC 7002) | Quality control strain |
| *Pseudomonas aeruginosa* (ATCC 9027) | Quality control strain, assay of antimicrobial preservatives |
| *Pseudomonas aeruginosa* (ATCC 27853) | Quality control strain, susceptability testing |
| *Serratia marcescens* (ATCC 14756) | Sterility assurance, testing antimicrobial agent, testing antimicrobial hand washing formulations |
| *Staphylococcus aureus* (ATCC 6538) | Quality control strain, testing antimicrobial agents, hand washing formulations, disinfectants, testing sanitizers, bactericides |
| *Staphylococcus aureus* (MRSA) (ATCC 33592) | Gentamicin- and methicillin-resistant |
| *Staphylococcus aureus* (ATCC 29213) | Quality control strain, susceptibility testing |
| *Staphylococcus epidermidis* (ATCC 12238) | Quality control strain, inhibition testing, susceptibility testing |
| *Staphylococcus haemolyticus* (ATCC 29970) | Type strain, quality control strain |
| *Staphylococcus hominis* (ATCC 27844) | Type strain. |
| *Streptococcus pneumonia* (ATCC 6303) | Media testing |
| *Staphylococcus saprophyticus* (ATCC 15305) | Type strain, quality control |
| *Streptococcus pyogenes* (ATCC 19615) | Quality control strain, control strain for *Streptococcus* Group A |

Reagents included MH agar (HKM, 028050), MHB base (OXOID, CM0405), RPMI 1640 (Invitrogen, 31800-022), PDA (KAYON, P0185), YM agar (KAYVON, P0271), MOPS (3-(N-morpholino)propanesulfonic acid, Sigma M3183), Amikacin USP (1019508), Ceftazidime Pentahydrate USP (1098130), Amphotericin B (amresco 0414), and Fluconazole (TCI YY10840).

MIC values were tested using six two-fold compound dilutions in duplicate with the dilution range of 12.5 mg/mL to 0.39 mg/mL. For compounds with MIC value lower than 0.39 mg/mL, MIC test was repeated using further diluted compound ranges.

Time kill studies for all compounds with an MIC value lower than 12.5 mg/mL were performed at IX MIC concentration for four time points (0, 30 sec, 1 minute, and 5 minutes). The viable counts in $Log_{10}$ CFU/mL at each time point were recorded.

Preparation of cultures. Before the experiment, two days for the bacteria strains and five days for fungus strains, an aliquot was removed from the cultures frozen at −80° C. Medium was added to the surface of an appropriate agar plate and streaked with the aliquot. The plate was incubated for 20 to 24 hrs at 35±2° C. for bacteria or for 5 days at 26-30° C. in incubator for fungus. From the resulting growth on each plate, one isolated colony of similar morphology was selected and re-streaked onto a fresh agar plate using a sterile disposable loop. The plate was incubated 20 to 24 hrs at 35-2° C. or for 5 days at 26-30° C. in an incubator.

Preparation of Assay Plates with Medium and Drugs. On the day of the assay, CAMHB medium or RPMI 1640 medium was removed from 4° C. storage and allowed to reach room temperature. Ninety microliters (µL) of room temperature CAMHB or RPMI 1640 (supplemented with the appropriate concentration of DMSO, if required) were added to rows B-G of each 96-well microtiter plate. Using a pipette, duplicate 180 µL aliquots of each drug stock solution were added to column 1 (e.g. A1 and B1 or C1 and D1 or E1 and F1 or G1 and H1). Using a multichannel pipette or the Provision 2000 liquid handler, serial 2-fold dilutions (90 µL) were performed in each row across the plate to row G. Eighty µL of compounds dilutions were transferred to a 96-deep well plate. Medium, 1,520 µL of CAMHB or RPMI 1640, was added to each well. The contents of the wells were mixed thoroughly. A 50 µL aliquot of each of the resulting mixtures was transferred to a 96-well assay plate.

For bacteria, a sterile inoculating loop was used to transfer growth from an agar plate culture into about 5 mL of test medium. Using a turbidity meter, this inoculum was adjusted so that its density (600 nm) was equivalent to a 0.5 McFarland barium sulfate standard (0.08-0.13). The resulting suspension was diluted 1:100 into medium to obtain two times test inoculums.

For *Candida albicans*, a sterile inoculating loop was used to transfer growth from an agar plate culture into a tube with RPMI1640 medium. This inoculum was adjusted so that its density at 530 nm was in the ranges from 0.08 to 0.13. The resulting suspension was diluted 1:50 and further diluted 1:20 with the medium to obtain two times test inoculums.

For *Aspergillus niger*, sporulating colonies were covered with RPMI 1640, and a suspension was prepared by gently probing the colonies with the tip of a transfer pipette. The suspension was transferred to a sterile tube and mixed with a vortex mixer for 15 seconds. The densities at 530 nm were adjusted to 0.09-0.13 for each sample. The resulting suspension was diluted 1:50 with the medium to obtain two times test inoculums. Fifty μL/well of this inoculum suspension was added to wells of drug-containing plates (1:2 dilution). Plates were incubated at 35° C. for the appropriate times. The MIC was read and recorded according to CLSI guidelines.

Time kill studies. Strain suspensions were prepared as described above for the MIC test, and strain suspensions and compound solutions were mixed in the same volume. Samples were removed at specified times including 0 min, 30 sec, 1 min and 5 mins, were diluted in the test medium and streaked on agar. Colonies were counted after 24 to 48 hrs of incubation.

The MIC assay was performed using six 2-fold decremental compound dilutions in duplicate with the dilution range of 12.5 mg/mL to 0.39 mg/mL. For compounds with MIC value lower than 0.39 mg/mL, the MIC test was repeated using further diluted compound ranges. The MIC values for thirty compounds against *Escherichia coli*, *Pseudomonas aeruginosa*, *Staphulococcus aureus*, *Candida albicans*, and *Aspergillus niger* were recorded and are presented in Table 3 and Table 4. The time kill study was performed at 1×MIC concentration for compounds with MIC values lower than 12.5 mg/mL. The viable counts in $Log_{10}$ CFU/mL for above five microorganisms were recorded, and are presented in Table 5 to Table 9 below.

TABLE 3

MIC (mg/ml) values for two reference compounds and thirty test compounds against *Escherichia coli*, *Staphylococcus aureus*, and *Pseudomonas aeruginosa*

| | n = 1 | | | n = 2 | | |
|---|---|---|---|---|---|---|
| compound | E. coli | S. aureus | P. aeruginosa | E. coli | S. aureus | P. aeruginosa |
| Amikacin | 0.002 | 0.002 | 0.002 | 0.002 | 0.002 | 0.002 |
| Ceftazidime | 0.0005 | 0.008 | 0.002 | 0.0005 | 0.016 | 0.002 |
| Nex-01 | 3.13 | 3.13 | >12.5 | 3.13 | 3.13 | >12.5 |
| Nex-03 | 1.56 | 1.56 | 3.13 | 1.56 | 1.56 | 3.13 |
| Nex-05 | 3.13 | 3.13 | 6.25 | 3.13 | 1.56 | 6.25 |
| Nex-07 | 0.78 | 1.56 | 3.13 | 1.56 | 0.78 | 3.13 |
| Nex-15 | >12.5 | 0.39 | >12.5 | >12.5 | 0.2 | >12.5 |
| Nex-16 | 3.13 | 3.13 | 12.5 | 3.13 | 3.13 | 12.5 |
| Nex-20 | 1.56 | 3.13 | 6.25 | 1.56 | 1.56 | 6.25 |
| Nex-22 | 3.13 | 3.13 | 6.25 | 3.13 | 3.13 | 6.25 |
| Nex-30 | 3.13 | 3.13 | 6.25 | 3.13 | 3.13 | 6.25 |
| Nex-32 | 3.13 | 1.56 | 6.25 | 3.13 | 1.56 | 6.25 |
| Nex-46 | 3.13 | 3.13 | 6.25 | 3.13 | 3.13 | 6.25 |
| Nex-52 | 1.56 | 0.2 | 6.25 | 1.56 | 0.1 | 6.25 |
| Nex-53 | 6.25 | 6.25 | 6.25 | 6.25 | 6.25 | 6.25 |
| Nex-54 | >12.5 | >12.5 | >12.5 | 12.5 | 12.5 | 12.5 |
| Nex-55 | 6.25 | 6.25 | 6.25 | 6.25 | 6.25 | 6.25 |
| Nex-56 | 3.13 | 3.13 | 6.25 | 3.13 | 3.13 | 6.25 |
| Nex-57 | 3.13 | 3.13 | 6.25 | 3.13 | 3.13 | 6.25 |
| Nex-58 | 3.13 | 3.13 | 6.25 | 3.13 | 1.56 | 6.25 |
| Nex-59 | 0.05 | 0.05 | 3.13 | 0.05 | 0.05 | 3.13 |
| Nex-60 | 3.13 | 1.56 | 6.25 | 3.13 | 1.56 | 6.25 |
| Nex-61 | 0.78 | 0.05 | 6.25 | 1.56 | 0.05 | 6.25 |
| Nex-62 | 0.1 | 0.025 | 6.25 | 0.1 | 0.025 | 6.25 |
| Nex-64 | 3.13 | 3.13 | 6.25 | 3.13 | 3.13 | 6.25 |
| Nex-65 | 3.13 | 3.13 | 6.25 | 3.13 | 3.13 | 6.25 |
| Nex-66 | 3.13 | 3.13 | 6.25 | 3.13 | 3.13 | 6.25 |
| Nex-67 | 1.56 | 3.13 | 6.25 | 1.56 | 1.56 | 6.25 |
| Nex-68 | 0.78 | 3.13 | 3.13 | 1.56 | 3.13 | 3.13 |
| Nex-69 | 3.13 | 3.13 | 6.25 | 3.13 | 3.13 | 6.25 |
| Nex-70 | 0.78 | 3.13 | 3.13 | 0.78 | 3.13 | 3.13 |
| Nex-88 | 3.13 | 3.13 | 6.25 | 3.13 | 3.13 | 6.25 |

TABLE 4

MIC (mg/mL) values for two reference compounds and thirty test compounds against *Candida albicans* and *Aspergillus niger*

| | Candida albicans | | Aspergillus niger | |
|---|---|---|---|---|
| Compound | n = 1 | n = 2 | n = 1 | n = 2 |
| Amphotericin B | 0.0005 | 0.0005 | 2 | 2 |
| Fluconazole | 0.00025 | 0.00025 | >4 | >4 |
| Nex-01 | >12.5 | >12.5 | >12.5 | >12.5 |
| Nex-03 | 12.5 | 6.25 | >12.5 | >12.5 |
| Nex-05 | >12.5 | >12.5 | >12.5 | >12.5 |
| Nex-07 | 12.5 | 6.25 | 12.5 | 12.5 |
| Nex-15 | 0.05 | 0.05 | 12.5 | >12.5 |
| Nex-16 | >12.5 | 12.5 | >12.5 | >12.5 |
| Nex-20 | 12.5 | 12.5 | >12.5 | >12.5 |
| Nex-22 | >12.5 | >12.5 | >12.5 | >12.5 |
| Nex-30 | >12.5 | >12.5 | >12.5 | >12.5 |
| Nex-32 | >12.5 | >12.5 | >12.5 | >12.5 |
| Nex-46 | >12.5 | >12.5 | >12.5 | >12.5 |
| Nex-52 | 0.05 | 0.05 | 3.13 | 3.13 |
| Nex-53 | >12.5 | >12.5 | >12.5 | >12.5 |
| Nex-54 | 6.25 | 6.25 | 12.5 | 12.5 |
| Nex-55 | >12.5 | >12.5 | >12.5 | >12.5 |
| Nex-56 | >12.5 | >12.5 | >12.5 | >12.5 |
| Nex-57 | >12.5 | >12.5 | >12.5 | >12.5 |

TABLE 4-continued

MIC (mg/mL) values for two reference compounds and thirty test compounds against Candida albicans and Aspergillus niger

| | Candida albicans | | Aspergillus niger | |
|---|---|---|---|---|
| Compound | n = 1 | n = 2 | n = 1 | n = 2 |
| Nex-58 | >12.5 | >12.5 | >12.5 | >12.5 |
| Nex-59 | 0.025 | 0.025 | 0.05 | 0.05 |
| Nex-60 | 12.5 | 12.5 | >12.5 | >12.5 |
| Nex-61 | 0.0125 | 0.0125 | 0.05 | 0.025 |
| Nex-62 | 0.00625 | 0.00625 | 0.0125 | 0.0125 |
| Nex-64 | >12.5 | >12.5 | >12.5 | >12.5 |
| Nex-65 | >12.5 | >12.5 | >12.5 | >12.5 |
| Nex-66 | >12.5 | >12.5 | >12.5 | >12.5 |
| Nex-67 | 6.25 | 6.25 | 12.5 | 12.5 |
| Nex-68 | 0.39 | 0.2 | 3.13 | 3.13 |
| Nex-69 | 12.5 | 12.5 | >12.5 | >12.5 |
| Nex-70 | 0.78 | 0.78 | 12.5 | 12.5 |
| Nex-88 | >12.5 | >12.5 | >12.5 | >12.5 |

TABLE 5

Viable counts in $Log_{10}$ CFU/mL for Escherichia coli time kill study

| compound | 0 | 0.5 min | 1 min | 5 min |
|---|---|---|---|---|
| Nex-01 | 5.62 | 5.73 | 5.39 | <3.52 |
| Nex-03 | 4.92 | 4.90 | 4.18 | 3.82 |
| Nex-05 | 5.77 | <4.0 | <3.70 | <3.52 |
| Nex-07 | 5.88 | 6.02 | 6.02 | 5.68 |
| Nex-16 | 5.94 | 5.97 | 5.81 | 5.16 |
| Nex-20 | 5.86 | 5.84 | 5.92 | 4.37 |
| Nex-22 | 5.78 | 4.6 | <3.70 | <3.52 |
| Nex-30 | 5.83 | 5.46 | 3.7 | <3.52 |
| Nex-32 | 6.05 | 5.77 | 4.7 | <3.52 |
| Nex-46 | 5.87 | 5.74 | 5.91 | 3.97 |
| Nex-52 | 5.95 | 6.12 | 5.86 | 5.24 |
| Nex-53 | 5.64 | 5.72 | 5.71 | <3.52 |
| Nex-55 | 5.68 | 5.71 | 5.51 | 4.6 |
| Nex-56 | 5.92 | <4.0 | <3.70 | <3.52 |
| Nex-57 | 5.78 | <4.0 | <3.70 | <3.52 |
| Nex-58 | 5.91 | <4.0 | <3.70 | <3.52 |
| Nex-59 | 5.34 | 5.04 | 5.11 | 4.56 |
| Nex-60 | 5.88 | <4.0 | 3.7 | <3.52 |
| Nex-61 | 5.78 | 5.54 | 5.61 | 4.9 |
| Nex-62 | 4.82 | 4.78 | 5.02 | 3.82 |
| Nex-64 | 5.71 | 5.73 | 5.7 | <3.52 |
| Nex-65 | 5.68 | 5.72 | 5.97 | 4.22 |
| Nex-66 | 5.7 | 5.91 | 6.03 | 5.81 |
| Nex-67 | 5.64 | 5.81 | 5.28 | 3.82 |
| Nex-68 | 5.88 | 5.53 | 4.3 | <3.52 |
| Nex-69 | 6.25 | 5.72 | 5.54 | <3.52 |
| Nex-70 | 5.0 | <4.0 | <3.70 | <3.52 |
| Nex-88 | 5.71 | <4.0 | <3.70 | <3.52 |

TABLE 6

Viable counts in $Log_{10}$ CFU/mL for Staphylococcus aureus time kill study

| compound | 0 | 0.5 mm | 1 mm | 5 min |
|---|---|---|---|---|
| Nex-01 | 6.1 | 6.22 | 6.17 | 6.14 |
| Nex-03 | 6.11 | 6.1 | 6.12 | 6.11 |
| Nex-05 | 6.07 | 6.1 | 6.18 | 6.1 |
| Nex-07 | 6.21 | 6.11 | 6.26 | 6.16 |
| Nex-15 | 6.23 | 6.16 | 6.14 | 6.14 |
| Nex-16 | 6.05 | 6.24 | 6.22 | 6.16 |
| Nex-20 | 6.15 | 6.18 | 6.15 | 5.61 |
| Nex-22 | 6.08 | 6.2 | 6.18 | 6.21 |
| Nex-30 | 6.24 | 6.23 | 6.22 | 6.21 |
| Nex-32 | 6.25 | 6.31 | 6.23 | 6.2 |
| Nex-46 | 6.26 | 6.25 | 6.21 | 6.21 |

TABLE 6-continued

Viable counts in $Log_{10}$ CFU/mL for Staphylococcus aureus time kill study

| compound | 0 | 0.5 mm | 1 mm | 5 min |
|---|---|---|---|---|
| Nex-52 | 6.26 | 6.27 | 6.12 | 6.13 |
| Nex-53 | 6.35 | 6.2 | 6.24 | 6.21 |
| Nex-55 | 6.23 | 6.22 | 6.21 | 6.18 |
| Nex-56 | 6.33 | 6.27 | 6.16 | 5.9 |
| Nex-57 | 6.29 | 6.17 | 6.19 | 5.92 |
| Nex-58 | 6.26 | 6.15 | 6.11 | 5.81 |
| Nex-59 | 6.33 | 6.33 | 6.22 | 6.15 |
| Nex-60 | 6.28 | 6.23 | 6.25 | 6.21 |
| Nex-61 | 6.38 | 6.15 | 6.07 | 5.54 |
| Nex-62 | 6.34 | 6.32 | 6.35 | 6.31 |
| Nex-64 | 6.34 | 6.41 | 6.38 | 6.36 |
| Nex-65 | 6.34 | 6.39 | 6.35 | 6.17 |
| Nex-66 | 6.27 | 6.5 | 6.41 | 6.39 |
| Nex-67 | 6.27 | 6.1 | 6.13 | 5.88 |
| Nex-68 | 6.39 | 5.82 | 5.88 | 5.57 |
| Nex-69 | 6.41 | 6.39 | 6.31 | 6.38 |
| Nex-70 | 6.37 | 6.42 | 6.37 | 6.22 |
| Nex-88 | 6.44 | 6.54 | 6.39 | 6.4 |

TABLE 7

Viable counts in $Log_{10}$ CFU/mL for Pseudomonas aeruginosa time kill study

| compound | 0 | 0.5 min | 1 min | 5 min |
|---|---|---|---|---|
| Nex-03 | 5.6 | <4.0 | <3.70 | <3.52 |
| Nex-05 | 5.64 | <4.0 | <3.70 | <3.52 |
| Nex-07 | 5.48 | <4.0 | <3.70 | <3.52 |
| Nex-16 | 5.64 | 4 | 3.7 | <3.52 |
| Nex-20 | 5.56 | <4.0 | 3.7 | <3.52 |
| Nex-22 | 5.64 | <4.0 | <3.70 | <3.52 |
| Nex-30 | 5.67 | <4.0 | <3.70 | <3.52 |
| Nex-32 | 5.73 | 5.62 | 4.48 | 4.12 |
| Nex-46 | 5.67 | 4.48 | 3.7 | <3.52 |
| Nex-52 | 5.56 | 4.7 | 4 | <3.52 |
| Nex-53 | 5.54 | 5.54 | 5.47 | 5.49 |
| Nex-55 | 5.37 | 5.61 | 5.58 | 5.45 |
| Nex-56 | 5.56 | <4.0 | <3.70 | <3.52 |
| Nex-57 | 5.45 | <4.0 | <3.70 | <3.52 |
| Nex-58 | 5.54 | <4.0 | <3.70 | <3.52 |
| Nex-59 | 5.65 | 5.26 | 4.78 | <3.52 |
| Nex-60 | 5.58 | 4.6 | 3.7 | <3.52 |
| Nex-61 | 5.71 | 4 | <3.70 | <3.52 |
| Nex-62 | 5.52 | 4 | <3.70 | <3.52 |
| Nex-64 | 5.45 | 4 | <3.70 | <3.52 |
| Nex-65 | 5.52 | 5.36 | 5.52 | <3.52 |
| Nex-66 | 5.64 | 5.91 | 5.68 | 5.56 |
| Nex-67 | 5.71 | <4.0 | <3.70 | <3.52 |
| Nex-68 | 5.78 | 5.18 | 4.88 | 4.87 |
| Nex-69 | 5.65 | 5.75 | 5.74 | 5.21 |
| Nex-70 | 5.62 | <4.0 | <3.70 | <3.52 |
| Nex-88 | 5.74 | <4.0 | <3.70 | 3.52 |

TABLE 8

Viable counts in $Log_{10}$ CFU/mL for Candida albicans time kill study

| compound | 0 | 0.5 min | 1 min | 5 min |
|---|---|---|---|---|
| Nex-03 | 5.6 | 5.53 | 5.54 | 5.52 |
| Nex-07 | 5.57 | 5.54 | 5.5 | 5.45 |
| Nex-15 | 5.12 | 5.23 | 5.25 | 5.28 |
| Nex-52 | 5.24 | 5.19 | 5.17 | 5.23 |
| Nex-54 | 5.56 | 5.56 | 5.52 | 5.48 |
| Nex-59 | 5.3 | 5.18 | 5.32 | 5.23 |
| Nex-61 | 5.23 | 5.19 | 5.36 | 5.3 |
| Nex-62 | 5.12 | 5.37 | 5.18 | 5.18 |
| Nex-67 | 5.58 | 5.53 | 5.49 | 5.41 |

TABLE 8-continued

Viable counts in Log$_{10}$ CFU/mL for *Candida albicans* time kill study

| compound | 0 | 0.5 min | 1 min | 5 min |
|---|---|---|---|---|
| Nex-68 | 5.47 | 5.35 | 5.15 | 5.13 |
| Nex-70 | 5.55 | 5.53 | 5.51 | 5.49 |

TABLE 9

Viable counts in Log$_{10}$ CFU/mL for *Aspergillus niger* time kill study

| compound | 0 | 0.5 min | 1 min | 5 mm |
|---|---|---|---|---|
| Nex-52 | 5.30 | 5.28 | 5.28 | 4.95 |
| Nex-59 | 5.27 | 5.30 | 5.33 | 5.18 |
| Nex-61 | 5.36 | 5.30 | 5.16 | 5.11 |
| Nex-62 | 5.27 | 5.32 | 5.21 | 5.02 |
| Nex-68 | 5.25 | 5.25 | 5.25 | 5.25 |

Example 34

Extended Time Kill Studies

The time kill studies of Example 33 were extended for five compounds (Nex-59, Nex-60, Nex-61, Nex-62, and Nex-88) using the same methods at longer time periods and at higher multiples of MIC. Nex-88 is a code number for DDAIP.HCl from a different supplier. Time kill studies for five compounds were performed at 1×MIC, 2×MIC and 4×MIC concentration at six time points (0, 1 hour, 2 hours, 4 hours, 6 hours and 24 hours). The viable counts in Log$_{10}$ CFU/mL for the five microorganisms were recorded, and are presented in Table 10 to Table 14 below.

Nex-59  Dodecyl 2-(methylamino) propanoate hydrochloride

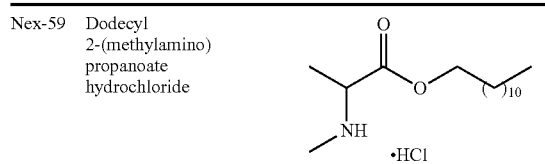

Nex-60  Dodecyl 2-(isopropylamino) propanoate hydrochloride

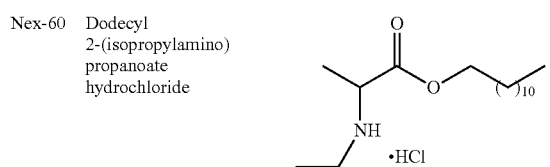

Nex-61  Dodecyl 2-((2-hydroxyethyl)amino) propanoate hydrochloride

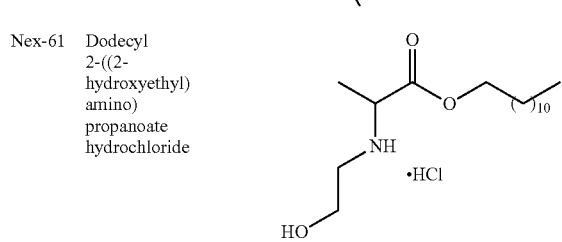

Nex-62  Dodecyl 2-((2-(diethylamino)-ethyl)amino) propanoate dihydrochloride

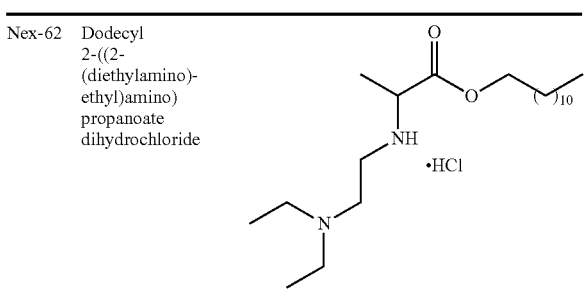

Nex-05, Nex-88 DDAIP •HCl  Dodecyl 2-(dimethylamino) propanoate hydrochloride

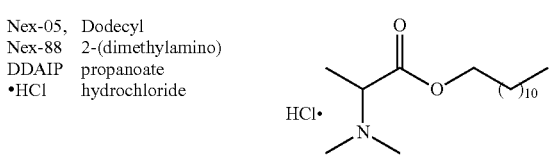

TABLE 10

Viable counts in Log$_{10}$ CFU/mL for *Escherichia coli* time kill study

| Compound | | 0 | 1 h | 2 h | 4 h | 6 h | 24 h |
|---|---|---|---|---|---|---|---|
| NEX-59 | 1 × MIC (0.05 mg/mL) | 5 | 1 | <1 | 1.85 | 2.81 | 7.91 |
| | 2 × MIC (0.1 mg/mL) | 5.12 | <1 | <1 | <1 | <1 | <1 |
| | 4 × MIC (0.2 mg/mL) | 5.04 | <1 | <1 | <1 | <1 | <1 |
| NEX-60 | 1 × MIC (3.13 mg/mL) | 5.02 | <1 | <1 | <1 | <1 | <1 |
| | 2 × MIC (6.25 mg/mL) | 5.14 | <1 | <1 | <1 | <1 | <1 |
| | 4 × MIC (12.5 mg/mL) | 5.07 | <1 | <1 | <1 | <1 | <1 |
| NEX-61 | 1 × MIC (0.78 mg/mL) | 5.08 | 1.70 | 1.60 | 3.16 | 4.38 | 7.75 |
| | 2 × MIC (1.56 mg/mL) | 5.03 | <1 | <1 | <1 | <1 | <1 |
| | 4 × MIC (3.13 mg/mL) | 5.05 | <1 | <1 | <1 | <1 | <1 |
| NEX-62 | 1 × MIC (0.1 mg/mL) | 5.06 | 1 | 1 | <1 | 2.18 | 7.99 |
| | 2 × MIC (0.2 mg/mL) | 5.18 | <1 | <1 | <1 | <1 | <1 |
| | 4 × MIC (0.4 mg/mL) | 5.12 | <1 | <1 | <1 | <1 | <1 |
| NEX-88 | 1 × MIC (3.13 mg/mL) | 5.10 | <1 | <1 | <1 | <1 | <1 |
| | 2 × MIC (6.25 mg/mL) | 5.16 | <1 | <1 | <1 | <1 | <1 |
| | 4 × MIC (12.5 mg/mL) | 5.21 | <1 | <1 | <1 | <1 | <1 |

TABLE 11

Viable counts in Log$_{10}$ CFU/mL for *Staphylococcus aureus* time kill study

| Compound | | 0 | 1 h | 2 h | 4 h | 6 h | 24 h |
|---|---|---|---|---|---|---|---|
| Nex-59 | 1 × MIC (0.05 mg/mL) | 6.20 | <3 | <3 | <3 | <3 | <1 |
| | 2 × MIC (0.1 mg/mL) | 6.19 | <3 | <3 | <3 | <3 | <1 |
| | 4 × MIC (0.2 mg/mL) | 6.18 | <3 | <3 | <3 | <3 | <1 |
| Nex-60 | 1 × MIC (1.56 mg/mL) | 6.22 | 6.23 | 6.24 | 6.16 | 5.97 | 6.57 |
| | 2 × MIC | 6.20 | <3 | <3 | <3 | <3 | <1 |

TABLE 11-continued

Viable counts in Log$_{10}$ CFU/mL for *Staphylococcus aureus* time kill study

| Compound | | 0 | 1 h | 2 h | 4 h | 6 h | 24 h |
|---|---|---|---|---|---|---|---|
| | (3.13 mg/mL) | | | | | | |
| | 4 × MIC | 6.21 | <3 | <3 | <3 | <3 | <1 |
| | (6.25 mg/mL) | | | | | | |
| Nex-61 | 1 × MIC | 6.14 | 5 | <3 | <3 | <3 | <1 |
| | (0.05 mg/mL) | | | | | | |
| | 2 × MIC | 6.20 | <3 | <3 | <3 | <3 | <1 |
| | (0.1 mg/mL) | | | | | | |
| | 4 × MIC | 6.18 | <3 | <3 | <3 | <3 | <1 |
| | (0.2 mg/mL) | | | | | | |
| Nex-62 | 1 × MIC | 6.23 | 6.00 | 5.66 | 4.70 | 4.48 | <1 |
| | (0.025 mg/mL) | | | | | | |
| | 2 × MIC | 6.25 | 5.30 | <3 | <3 | <3 | <1 |
| | (0.05 mg/mL) | | | | | | |
| | 4 × MIC | 6.20 | 5.30 | <3 | <3 | <3 | <1 |
| | (0.1 mg/mL) | | | | | | |
| Nex-88 | 1 × MIC | 6.24 | <3 | <3 | <3 | <3 | <1 |
| | (3.13 mg/mL) | | | | | | |
| | 2 × MIC | 6.25 | <3 | <3 | <3 | <3 | <1 |
| | (6.25 mg/mL) | | | | | | |
| | 4 × MIC | 6.23 | <3 | <3 | <3 | <3 | <1 |
| | (12.5 mg/mL) | | | | | | |

TABLE 12

Viable counts in Log$_{10}$ CFU/mL for *Pseudomonas aeruginosa* time kill study

| Compound | | 0 | 1 h | 2 h | 4 h | 6 h | 24 h |
|---|---|---|---|---|---|---|---|
| NEX-59 | 1 × MIC | 5.18 | <1 | <1 | <1 | <1 | <1 |
| | (3.13 mg/mL) | | | | | | |
| | 2 × MIC | 5.16 | <1 | <1 | <1 | <1 | <1 |
| | (6.25 mg/mL) | | | | | | |
| | 4 × MIC | 5.21 | <1 | <1 | <1 | <1 | <1 |
| | (12.5 mg/mL) | | | | | | |
| NEX-60 | 1 × MIC | 5.30 | <1 | <1 | <1 | <1 | <1 |
| | (6.25 mg/mL) | | | | | | |
| | 2 × MIC | 5.28 | <1 | <1 | <1 | <1 | <1 |
| | (12.5 mg/mL) | | | | | | |
| | 4 × MIC | 5.31 | <1 | <1 | <1 | <1 | <1 |
| | (25.0 mg/mL) | | | | | | |
| NEX-61 | 1 × MIC | 5.28 | <1 | <1 | <1 | <1 | <1 |
| | (6.25 mg/mL) | | | | | | |
| | 2 × MIC | 5.29 | <1 | <1 | <1 | <1 | <1 |
| | (12.5 mg/mL) | | | | | | |
| | 4 × MIC | 5.26 | <1 | <1 | <1 | <1 | <1 |
| | (25.0 mg/mL) | | | | | | |
| NEX-62 | 1 × MIC | 5.20 | <1 | <1 | <1 | <1 | <1 |
| | (6.25 mg/mL) | | | | | | |
| | 2 × MIC | 5.25 | <1 | <1 | <1 | <1 | <1 |
| | (12.5 mg/mL) | | | | | | |
| | 4 × MIC | 5.23 | <1 | <1 | <1 | <1 | <1 |
| | (25.0 mg/mL) | | | | | | |
| NEX-88 | 1 × MIC | 5.30 | <1 | <1 | <1 | <1 | <1 |
| | (6.25 mg/mL) | | | | | | |
| | 2 × MIC | 5.22 | <1 | <1 | <1 | <1 | <1 |
| | (12.5 mg/mL) | | | | | | |
| | 4 × MIC | 5.26 | <1 | <1 | <1 | <1 | <1 |
| | (25.0 mg/mL) | | | | | | |

TABLE 13

Viable counts in Log$_{10}$ CFU/mL for *Candida albicans* time kill study

| Compound | | 0 | 1 h | 2 h | 4 h | 6 h | 24 h |
|---|---|---|---|---|---|---|---|
| Nex-59 | 1 × MIC | 5.68 | 5.41 | 5.24 | 4.96 | 4.40 | >6 |
| | (0.025 mg/mL) | | | | | | |
| | 2 × MIC | 5.75 | 3.48 | 3.00 | 3.00 | <2.70 | <1 |
| | (0.05 mg/mL) | | | | | | |
| | 4 × MIC | 5.63 | <3 | <3 | <2.70 | <2.70 | <1 |
| | (0.1 mg/mL) | | | | | | |
| Nex-60 | 1 × MIC | 5.56 | 5.51 | 5.50 | 5.18 | 5.09 | >6 |
| | (12.5 mg/mL) | | | | | | |
| | 2 × MIC | 5.51 | 3.30 | 3.00 | 3.00 | <2.70 | <1 |
| | (25.0 mg/mL) | | | | | | |
| | 4 × MIC | 5.62 | 3.78 | 3.30 | 3.00 | <2.70 | <1 |
| | (50.0 mg/mL) | | | | | | |
| Nex-61 | 1 × MIC | 5.43 | 5.37 | 5.37 | 5.32 | 5.54 | >6 |
| | (0.0125 mg/mL) | | | | | | |
| | 2 × MIC | 5.48 | <3 | <3 | <2.70 | <2.70 | >6 |
| | (0.025 mg/mL) | | | | | | |
| | 4 × MIC | 5.39 | <3 | <3 | <2.70 | <2.70 | <1 |
| | (0.05 mg/mL) | | | | | | |
| Nex-62 | 1 × MIC | 5.74 | 5.75 | 5.78 | 6.04 | 6.21 | >6 |
| | (0.00625 mg/mL) | | | | | | |
| | 2 × MIC | 5.76 | 5.68 | 5.67 | 5.68 | 5.58 | >6 |
| | (0.0125 mg/mL) | | | | | | |
| | 4 × MIC | 5.69 | 5.32 | 5.33 | 5.00 | 4.53 | <1 |
| | (0.025 mg/mL) | | | | | | |
| Nex-88 | 1 × MIC | 5.82 | 5.62 | 5.60 | 5.60 | 6.02 | >6 |
| | (>12.5 mg/mL) | | | | | | |
| | 2 × MIC | 5.81 | 4.99 | 4.88 | 4.62 | 4.58 | 2.57 |
| | (25.0 mg/mL) | | | | | | |
| | 4 × MIC | 5.79 | 3.95 | 3.90 | <2.70 | <2.70 | <1 |
| | (50 mg/mL) | | | | | | |

TABLE 14

Viable counts in Log$_{10}$ CFU/mL for *Aspergillus niger* time kill study

| Compound | | 0 | 1 h | 2 h | 4 h | 6 h | 24 h |
|---|---|---|---|---|---|---|---|
| NEX-59 | 1 × MIC | 5.41 | 5.34 | 5.48 | 5.08 | 5.30 | 3.78 |
| | (0.05 mg/mL) | | | | | | |
| | 2 × MIC | 5.36 | 5.11 | 4.70 | 4.48 | 3.95 | <2 |
| | (0.1 mg/mL) | | | | | | |
| | 4 × MIC | 5.29 | 5.08 | 4.48 | 3.85 | 4.04 | <2 |
| | (0.2 mg/mL) | | | | | | |
| NEX-60 | 1 × MIC | 5.52 | 4.60 | 4.78 | 4.60 | 4.30 | 3.81 |
| | (12.5 mg/mL) | | | | | | |
| | 2 × MIC | 5.47 | 4.30 | 4.78 | 3.85 | 3.78 | 4.30 |
| | (25.0 mg/mL) | | | | | | |
| | 4 × MIC | 5.60 | 4.00 | 4.48 | 3.60 | 3 | <2 |
| | (50.0 mg/mL) | | | | | | |
| NEX-61 | 1 × MIC | 5.28 | 5.48 | 5.36 | 5.18 | 4.95 | 4.48 |
| | (0.025 mg/mL) | | | | | | |
| | 2 × MIC | 5.33 | 5.52 | 5.57 | 4.48 | 4.90 | 3 |
| | (0.05 mg/mL) | | | | | | |
| | 4 × MIC | 5.26 | 5.34 | 5.41 | 5.28 | 4.95 | <2 |
| | (0.1 mg/mL) | | | | | | |
| NEX-62 | 1 × MIC | 5.51 | 5.53 | 5.51 | 5.15 | 4.78 | 4 |
| | (0.0125 mg/mL) | | | | | | |
| | 2 × MIC | 5.49 | 5.48 | 5.57 | 5.08 | 5.38 | 5.58 |
| | (0.025 mg/mL) | | | | | | |
| | 4 × MIC | 5.56 | 5.49 | 5.49 | 5.00 | 5.20 | 3.85 |
| | (0.05 mg/mL) | | | | | | |
| NEX-88 | 1 × MIC | 5.41 | 5.28 | 4.78 | 4.60 | 4.30 | 3.30 |
| | (12.5 mg/mL) | | | | | | |
| | 2 × MIC | 5.38 | 4.30 | 4.70 | 3 | 4 | <2 |
| | (25.0 mg/mL) | | | | | | |
| | 4 × MIC | 5.50 | 4.48 | 4 | 3 | 4 | <2 |
| | (50.0 mg/mL) | | | | | | |

Example 35

Minimum Inhibitory Concentration Assays with Different Strains of Microorganisms The minimum inhibitory concentration (MIC) is used to determine the lowest concentration of a test product claiming antimicrobial effects that will inhibit growth of a microorganism. Each microbial suspension was adjusted approximately $10^7$ to $10^8$ colony forming units (CFU) per mL and labeled as the stock suspension. The stock suspension was further diluted to 1:200 in Mueller Hinton broth to obtain a test sample having a concentration of $10^1$ to $10^6$ CFU/mL. The test sample was then tested for MIC as described in M202.R02. After incubation, each tube was examined for turbidity, which indicated growth or no growth. For the tubes where the product rendered the media turbid, an aliquot of the media was streaked onto agar plates to confirm growth or lack of growth. The results are presented in Tables 15-18, below.

TABLE 15

DDAIP•HCl MIC

| | Sample Concentration | | | | | | | | | | |
|---|---|---|---|---|---|---|---|---|---|---|---|
| | 10% | 5% | 2.5% | 1.25% | 0.625% | 0.313% | 0.156% | 0.078% | 0.039% | Control | MIC |
| Escherichia coli ATCC 11229 | NG | NG | NG | NG | NG | Growth | Growth | Growth | Growth | Growth | 0.625% |
| Pseudomonas aeruginosa ATCC 9027 | NG | NG | NG | NG | NG | Growth | Growth | Growth | Growth | Growth | 1.25% |
| Staphylococcus aureus ATCC 6538 | NG | NG | NG | Growth | Growth | Growth | Growth | Growth | Growth | Growth | 2.5% |
| Bacillus subtilis ATCC# 6633 | NG | NG | NG | NG | NG | NG | Growth | Growth | Growth | Growth | 0.313% |
| Candida albicans ATCC 10231 | NG | NG | NG | NG | NG | NG | Growth | Growth | Growth | Growth | 0.313% |
| Acinetobacter baumannii ATCC 19606 | NG | NG | NG | NG | NG | NG | Growth | Growth | Growth | Growth | 0.313% |
| Burkholderia cepacia ATCC 25416 | NG | NG | NG | Growth | Growth | Growth | Growth | Growth | Growth | Growth | 2.5% |
| Enterococcus faecalis ATCC 51299 | NG | NG | NG | NG | NG | NG | Growth | Growth | Growth | Growth | 0.313% |
| Klebsiella pneumoniae ATCC# 11296 | NG | NG | NG | NG | NG | NG | Growth | Growth | Growth | Growth | 0.625% |
| Staphylococcus aureus (MRSA) ATCC 33592 | NG | NG | NG | NG | NG | Growth | Growth | Growth | Growth | Growth | 0.625% |
| Staphylococcus haemolyticus ATCC 29970 | NG | NG | NG | NG | NG | NG | Growth | Growth | Growth | Growth | 0.313% |

TABLE 16

DDAIP•HCl MIC

| | Sample Concentration | | | | | | | | | | |
|---|---|---|---|---|---|---|---|---|---|---|---|
| | 10% | 5% | 2.5% | 1.25% | 0.625% | 0.313% | 0.156% | 0.078% | 0.039% | Control | MIC |
| Enterobacter cloacae ATCC 13047 | NG | NG | NG | NG | NG | Growth | Growth | Growth | Growth | Growth | 0.625% |
| Proteus mirabilis ATCC 7002 | NG | NG | NG | NG | Growth | Growth | Growth | Growth | Growth | Growth | 1.25% |
| Micrococcus luteus ATCC 4698 | NG | NG | NG | NG | NG | NG | Growth | Growth | Growth | Growth | 0.313% |
| Enterobacter aerogenes ATCC 13048 | NG | NG | NG | NG | Growth | Growth | Growth | Growth | Growth | Growth | 1.25% |
| Streptococcus pyogenes ATCC 19615 | NG | NG | NG | NG | NG | NG | Growth | Growth | Growth | Growth | 0.313% |
| Escherichia coli ATCC 25922 | NG | NG | NG | NG | Growth | Growth | Growth | Growth | Growth | Growth | 1.25% |
| Klebsiella oxytoca ATCC 43165 | NG | NG | NG | NG | Growth | Growth | Growth | Growth | Growth | Growth | 1.25% |

TABLE 16-continued

DDAIP•HCl MIC

| | Sample Concentration | | | | | | | | | | |
|---|---|---|---|---|---|---|---|---|---|---|---|
| | 10% | 5% | 2.5% | 1.25% | 0.625% | 0.313% | 0.156% | 0.078% | 0.039% | Control | MIC |
| Serratia marcescens ATCC 14756 | NG | NG | NG | Growth | Growth | Growth | Growth | Growth | Growth | Growth | 2.5% |
| Staphylococcus saprophyticus ATCC 15305 | NG | NG | NG | NG | NG | Growth | Growth | Growth | Growth | Growth | 0.625% |
| Corynbacterium jeikeium ATCC 43734 | NG | NG | NG | NG | NG | Growth | Growth | Growth | Growth | Growth | 0.625% |
| Enterococcus faecalis ATCC 19433 | NG | NG | NG | NG | Growth | Growth | Growth | Growth | Growth | Growth | 1.25% |
| Staphylococcus epidermidis ATCC 12228 | NG | NG | NG | NG | NG | NG | Growth | Growth | Growth | Growth | 0.313% |
| Staphylococcus hominis ATCC 27844 | NG | NG | NG | NG | NG | Growth | Growth | Growth | Growth | Growth | 0.625% |
| Streptococcus pneumoniae ATCC 6303 | NG | NG | NG | NG | NG | NG | NG | Growth | Growth | Growth | 0.156% |
| Acinetobacter lwoffi ATCC 15309 | NG | NG | NG | NG | NG | NG | NG | Growth | Growth | Growth | 0.156% |
| Haemophilus influenzae ATCC 19418 | NG | NG | Growth | Growth | Growth | Growth | Growth | Growth | Growth | Growth | 5% |

TABLE 17

Nex-59 MIC

| | Sample Concentration | | | | | | | | | | |
|---|---|---|---|---|---|---|---|---|---|---|---|
| | 2.5% | 1.25% | 0.63% | 0.32% | 0.16% | 0.08% | 0.04% | 0.02% | 0.01% | Control | MIC |
| Burkholderia cepacia ATCC 25416 | NG | Growth | Growth | Growth | Growth | Growth | Growth | Growth | Growth | Growth | 2.5% |
| Enterobacter cloacae ATCC 13047 | NG | NG | NG | NG | NG | Growth | Growth | Growth | Growth | Growth | 0.16% |
| Escherichia coli ATCC 11229 | NG | NG | NG | NG | NG | NG | Growth | Growth | Growth | Growth | 0.08% |
| Proteus mirabilis ATCC 7002 | NG | NG | NG | NG | Growth | Growth | Growth | Growth | Growth | Growth | 0.32% |
| Pseudomonas aeruginosa ATCC 9027 | NG | NG | NG | NG | NG | Growth | Growth | Growth | Growth | Growth | 0.16% |
| Bacillus subtilis ATCC 6633 | NG | NG | NG | NG | NG | NG | NG | Growth | Growth | Growth | 0.04% |
| Staphylococcus aureus ATCC 6538 | NG | NG | NG | NG | NG | NG | NG | Growth | Growth | Growth | 0.04% |
| Candida albicans ATCC 10231 | NG | NG | NG | NG | NG | NG | NG | Growth | Growth | Growth | 0.04% |
| Acinetobacter baumannii ATCC19606 | NG | NG | NG | NG | NG | NG | Growth | Growth | Growth | Growth | 0.08% |
| Enterococcus faecium ATCC 19434 | NG | NG | NG | NG | NG | NG | NG | Growth | Growth | Growth | 0.04% |
| Acinetobacter lwoffi ATCC4 15309 | NG | NG | NG | NG | NG | NG | NG | NG | Growth | Growth | 0.02% |
| Streptococcus pneumoniae ATCC 6303 | NG | NG | NG | NG | Growth | Growth | Growth | Growth | Growth | Growth | 0.32% |

TABLE 18

| | Nex-59 MIC | | | | | | | | | | |
|---|---|---|---|---|---|---|---|---|---|---|---|
| | Sample Concentration | | | | | | | | | | |
| | 2.5% | 1.25% | 0.63% | 0.32% | 0.16% | 0.08% | 0.04% | 0.02% | 0.01% | Control | MIC |
| *Klebsiella pneumoniae* ATCC 11296 | No Growth | No Growth | No Growth | No Growth | No Growth | No Growth | Growth | Growth | Growth | Growth | 0.08% |
| *Enterococcus faecalis* ATCC 51299 | No Growth | No Growth | No Growth | No Growth | No Growth | No Growth | No Growth | Growth | Growth | Growth | 0.04% |
| *Enterobacter aerogenes* ATCC 13048 | No Growth | No Growth | No Growth | No Growth | No Growth | Growth | Growth | Growth | Growth | Growth | 0.16% |
| *Micrococcus luteus* ATCC 4698 | No Growth | No Growth | No Growth | No Growth | No Growth | No Growth | No Growth | No Growth | Growth | Growth | 0.02% |
| *Staphylococcus epidermidis* ATCC 12228 | No Growth | No Growth | No Growth | No Growth | No Growth | No Growth | No Growth | No Growth | Growth | Growth | 0.02% |
| *Staphylococcus haemolyticus* ATCC 29970 | No Growth | No Growth | No Growth | No Growth | No Growth | No Growth | No Growth | No Growth | Growth | Growth | 0.02% |
| *Staphylococcus hominis* ATCC 27844 | No Growth | No Growth | No Growth | No Growth | No Growth | No Growth | No Growth | No Growth | Growth | Growth | 0.02% |
| *Staphylococcus saprophyticus* ATCC 15305 | No Growth | No Growth | No Growth | No Growth | No Growth | No Growth | No Growth | No Growth | Growth | Growth | 0.02% |
| *Staphylococcus aureus* (MRSA) ATCC 33592 | No Growth | No Growth | No Growth | No Growth | No Growth | No Growth | No Growth | No Growth | Growth | Growth | 0.02% |
| *Haemophilus influenzae* ATCC 19418 | No Growth | No Growth | No Growth | No Growth | No Growth | No Growth | No Growth | No Growth | No Growth | Growth | ≤0.01% |
| *Streptococcus pyogenes* ATCC 19615 | No Growth | No Growth | No Growth | No Growth | No Growth | No Growth | No Growth | No Growth | No Growth | Growth | ≤0.01% |
| *Corynebacterium jeikeium* ATCC 43734 | No Growth | No Growth | No Growth | No Growth | No Growth | No Growth | No Growth | No Growth | No Growth | Growth | ≤0.01% |
| *Enterococcus faecalis* ATCC 19433 | No Growth | No Growth | No Growth | No Growth | No Growth | No Growth | No Growth | No Growth | No Growth | Growth | ≤0.01% |
| *Escherichia coli* ATCC 25922 | No Growth | No Growth | No Growth | No Growth | No Growth | Growth | Growth | Growth | Growth | Growth | 0.16% |
| *Klebsiella oxytoca* ATCC 43165 | No Growth | No Growth | No Growth | Growth | Growth | Growth | Growth | Growth | Growth | Growth | 0.63% |
| *Serratia marcescens* ATCC 14756 | No Growth | No Growth | No Growth | Growth | Growth | Growth | Growth | Growth | Growth | Growth | >2.5% |

TABLE 19

| | MIC (mg/ml) | | | | | |
|---|---|---|---|---|---|---|
| | Nex-01 | Nex-03 | Nex-05 | Nex-07 | Nex-15 | Nex-16 |
| *Acinetobacter baumannii* (ATCC 19606) | | | | 3.13 | | |
| *Acinetobacter lwoffi* (ATCC 15309) | | | | 1.56 | | |
| *Aspergillus niger* (CMCC 98003) | >12.5 | >12.5 | >12.5 | 12.5 | 12.5 | >12.5 |
| *Bacillus subtilis* (ATCC 6633) | | | | 3.13 | | |
| *Burkholderia cepacia* (ATCC 25416) | | | | 25 | | |
| *Candida albicans* (ATCC 10231) | | | | 3.13 | | |
| *Candida albicans* (ATCC 90029) | >12.5 | 12.5, 6.25 | >12.5 | 12.5, 6.25 | 0.05 | 12.5 |
| *Corynebacterium jeikeium* (ATCC 43734) | | | | 6.25 | | |
| *Enterobacter aerogenes* (ATCC 13048) | | | | 12.5 | | |
| *Enterobacter cloacae* (ATCC 13047) | | | | 6.25 | | |
| *Enterococcus faecalis* (ATCC 51299) | | | | 3.13 | | |
| *Enterococcus faecalis* (ATCC 19433) | | | | 12.5 | | |
| *Enterococcus faecium* (ATCC 19434) | | | | | | |
| *Escherichia coli* (ATCC 11229) | | | | 6.25 | | |
| *Escherichia coli* (ATCC 25922) | 3.13 | 1.56 | 3.13 | 0.78, 1.56, 12.5 | ≥12.5 | 3.13 |
| *Haemophilus influenza* (ATCC 19418) | | | | 50 | | |
| *Klebsiella oxytoca* (ATCC 43615) | | | | 12.5 | | |

TABLE 19-continued

| MIC (mg/ml) | | | | | | |
|---|---|---|---|---|---|---|
| Klebsiella pneumonia (ATCC 11296) | | | | 6.25 | | |
| Micrococcus luteus (ATCC 4698) | >12.5 | 3.13 | 6.25 | 3.13 | >12.5 | 12.5 |
| Proteus mirobilis (ATCC 7002) | | | | 12.5 | | |
| Pseudomonas aeruginosa (ATCC 9027) | | | | 12.5 | | |
| Pseudomonas aeruginosa (ATCC 27853) | | | | 3.13 | | |
| Serratia marcescens (ATCC 14756) | | | | 25 | | |
| Staphylococcus aureus (ATCC 6538) | | | | 25 | | |
| Staphylococcus aureus (MRSA) (ATCC 33592) | | | | 6.25 | | |
| Staphylococcus aureus (ATCC 29213) | 3.13 | 1.56 | 3.13, 1.56 | 1.56, 0.78 | 0.39, 0.2 | 3.13 |
| Staphylococcus epidermidis (ATCC 12228) | | | | 3.13 | | |
| Staphylococcus haemolyticus (ATCC 29970) | | | | 3.13 | | |
| Staphylococcus hominis (ATCC 27844) | | | | 6.25 | | |
| Streptococcus pneumonia (ATCC 6303) | | | | 1.56 | | |
| Staphylococcus saprophyticus (ATCC 15305) | | | | 6.25 | | |
| Streptococcus pyogenes (ATCC 19615) | | | | 3.13 | | |

| | Nex-20 | Nex-22 | Nex-30 | Nex-32 | Nex-46 | Nex-52 |
|---|---|---|---|---|---|---|
| Acinetobacter baumannii (ATCC 19606) | | | | | | |
| Acinetobacter lwoffi (ATCC 15309) | | | | | | |
| Aspergillus niger (CMCC 98003) | >12.5 | >12.5 | >12.5 | >12.5 | >12.5 | 3.13 |
| Bacillus subtilis (ATCC 6633) | | | | | | |
| Burkholderia cepacia (ATCC 25416) | | | | | | |
| Candida albicans (ATCC 10231) | | | | | | |
| Candida albicans (ATCC 90029) | 12.5 | >12.5 | >12.5 | >12.5 | >12.5 | 0.05 |
| Corynebacterium jeikeium (ATCC 43734) | | | | | | |
| Enterobacter aerogenes (ATCC 13048) | | | | | | |
| Enterobacter cloacae (ATCC 13047) | | | | | | |
| Enterococcus faecalis (ATCC 51299) | | | | | | |
| Enterococcus faecalis (ATCC 19433) | | | | | | |
| Enterococcus faecium (ATCC 19434) | | | | | | |
| Escherichia coli (ATCC 11229) | | | | | | |
| Escherichia coli (ATCC 25922) | 1.56 | 3.13 | 3.13 | 3.13 | 3.13 | 1.56 |
| Haemophilus influenza (ATCC 19418) | | | | | | |
| Klebsiella oxytoca (ATCC 43615) | | | | | | |
| Klebsiella pneumonia (ATCC 11296) | | | | | | |
| Micrococcus luteus (ATCC 4698) | | | | | | |
| Proteus mirobilis (ATCC 7002) | | | | | | |
| Pseudomonas aeruginosa (ATCC 9027) | | | | | | |
| Pseudomonas aeruginosa (ATCC 27853) | 6.25 | 6.25 | 6.25 | 6.25 | 6.25 | 6.25 |
| Serratia marcescens (ATCC 14756) | | | | | | |
| Staphylococcus aureus (ATCC 6538) | | | | | | |
| Staphylococcus aureus (MRSA) (ATCC 33592) | | | | | | |
| Staphylococcus aureus (ATCC 29213) | 3.13, 1.56 | 3.13 | 3.13 | 1.56 | 3.13 | 0.2, 0.1 |
| Staphylococcus epidermidis (ATCC 12228) | | | | | | |
| Staphylococcus haemolyticus (ATCC 29970) | | | | | | |
| Staphylococcus hominis (ATCC 27844) | | | | | | |
| Streptococcus pneumonia (ATCC 6303) | | | | | | |
| Staphylococcus saprophyticus (ATCC 15305) | | | | | | |
| Streptococcus pyogenes (ATCC 19615) | | | | | | |

| | Nex-53 | Nex-54 | Nex-55 | Nex-56 | Nex-57 | Nex-58 |
|---|---|---|---|---|---|---|
| Acinetobacter baumannii (ATCC 19606) | | | | | | |
| Acinetobacter lwoffi (ATCC 15309) | | | | | | |
| Aspergillus niger (CMCC 98003) | >12.5 | 12.5 | >12.5 | >12.5 | >12.5 | >12.5 |
| Bacillus subtilis (ATCC 6633) | | | | | | |
| Burkholderia cepacia (ATCC 25416) | | | | | | |
| Candida albicans (ATCC 10231) | | | | | | |
| Candida albicans (ATCC 90029) | >12.5 | 6.25 | >12.5 | >12.5 | >12.5 | >12.5 |
| Corynebacterium jeikeium (ATCC 43734) | | | | | | |
| Enterobacter aerogenes (ATCC 13048) | | | | | | |
| Enterobacter cloacae (ATCC 13047) | | | | | | |
| Enterococcus faecalis (ATCC 51299) | | | | | | |
| Enterococcus faecalis (ATCC 19433) | | | | | | |
| Enterococcus faecium (ATCC 19434) | | | | | | |
| Escherichia coli (ATCC 11229) | | | | | | |
| Escherichia coli (ATCC 25922) | 6.25 | ≥12.5 | 6.25 | 3.13 | 3.13 | 3.13 |
| Haemophilus influenza (ATCC 19418) | | | | | | |
| Klebsiella oxytoca (ATCC 43615) | | | | | | |
| Klebsiella pneumonia (ATCC 11296) | | | | | | |
| Micrococcus luteus (ATCC 4698) | | | | | | |
| Proteus mirobilis (ATCC 7002) | | | | | | |
| Pseudomonas aeruginosa (ATCC 9027) | | | | | | |

TABLE 19-continued

MIC (mg/ml)

| Organism | | | | | | |
|---|---|---|---|---|---|---|
| Pseudomonas aeruginosa (ATCC 27853) | 6.25 | ≥12.5 | 6.25 | 6.25 | 6.25 | 6.25 |
| Serratia marcescens (ATCC 14756) | | | | | | |
| Staphylococcus aureus (ATCC 6538) | | | | | | |
| Staphylococcus aureus (MRSA) (ATCC 33592) | | | | | | |
| Staphylococcus aureus (ATCC 29213) | 6.25 | ≥12.5 | 6.25 | 3.13 | 3.13 | 3.13, 1.56 |
| Staphylococcus epidermidis (ATCC 12228) | | | | | | |
| Staphylococcus haemolyticus (ATCC 29970) | | | | | | |
| Staphylococcus hominis (ATCC 27844) | | | | | | |
| Streptococcus pneumonia (ATCC 6303) | | | | | | |
| Staphylococcus saprophyticus (ATCC 15305) | | | | | | |
| Streptococcus pyogenes (ATCC 19615) | | | | | | |

| | Nex-59 | Nex-60 | Nex-61 | Nex-62 | Nex-64 | Nex-65 |
|---|---|---|---|---|---|---|
| Acinetobacter baumannii (ATCC 19606) | 0.8 | | | | | |
| Acinetobacter lwoffi (ATCC 15309) | 0.2 | | | | | |
| Aspergillus niger (CMCC 98003) | 0.05 | >12.5 | 0.05, 0.025 | 0.0125 | >12.5 | >12.5 |
| Bacillus subtilis (ATCC 6633) | 0.4 | | | | | |
| Burkholderia cepacia (ATCC 25416) | 25 | | | | | |
| Candida albicans (ATCC 10231) | 0.4 | | | | | |
| Candida albicans (ATCC 90029) | 0.05 | 12.5 | 0.0125 | 0.00625 | >12.5 | >12.5 |
| Corynebacterium jeikeium (ATCC 43734) | ≤0.1 | | | | | |
| Enterobacter aerogenes (ATCC 13048) | 1.6 | | | | | |
| Enterobacter cloacae (ATCC 13047) | 1.6 | | | | | |
| Enterococcus faecalis (ATCC 51299) | 0.4 | | | | | |
| Enterococcus faecalis (ATCC 19433) | ≤0.1 | | | | | |
| Enterococcus faecium (ATCC 19434) | 0.4 | | | | | |
| Escherichia coli (ATCC 11229) | 0.8 | | | | | |
| Escherichia coli (ATCC 25922) | 0.05, 1.6 | 3.13 | 0.78, 1.56 | 0.1 | 3.13 | 3.13 |
| Haemophilus influenza (ATCC 19418) | ≤0.1 | | | | | |
| Klebsiella oxytoca (ATCC 43615) | 6.3 | | | | | |
| Klebsiella pneumonia (ATCC 11296) | 0.8 | | | | | |
| Micrococcus luteus (ATCC 4698) | 0.2 | | | | | |
| Proteus mirobilis (ATCC 7002) | 3.2 | | | | | |
| Pseudomonas aeruginosa (ATCC 9027) | 1.6 | | | | | |
| Pseudomonas aeruginosa (ATCC 27853) | 3.13 | 6.25 | 6.25 | 6.25 | 6.25 | 6.25 |
| Serratia marcescens (ATCC 14756) | >25 | | | | | |
| Staphylococcus aureus (ATCC 6538) | 0.4 | | | | | |
| Staphylococcus aureus (MRSA) (ATCC 33592) | 0.2 | | | | | |
| Staphylococcus aureus (ATCC 29213) | 0.05 | 1.56 | 0.05 | 0.025 | 3.13 | 3.13 |
| Staphylococcus epidermidis (ATCC 12228) | 0.2 | | | | | |
| Staphylococcus haemolyticus (ATCC 29970) | 0.2 | | | | | |
| Staphylococcus hominis (ATCC 27844) | 0.2 | | | | | |
| Streptococcus pneumonia (ATCC 6303) | 3.2 | | | | | |
| Staphylococcus saprophyticus (ATCC 15305) | 0.2 | | | | | |
| Streptococcus pyogenes (ATCC 19615) | ≤0.1 | | | | | |

| | Nex-66 | Nex-67 | Nex-68 | Nex-69 | Nex-70 | Nex-88 |
|---|---|---|---|---|---|---|
| Acinetobacter baumannii (ATCC 19606) | | | | | | |
| Acinetobacter lwoffi (ATCC 15309) | | | | | | |
| Aspergillus niger (CMCC 98003) | >12.5 | 12.5 | 3.13 | >12.5 | 12.5 | >12.5 |
| Bacillus subtilis (ATCC 6633) | | | | | | |
| Burkholderia cepacia (ATCC 25416) | | | | | | |
| Candida albicans (ATCC 10231) | | | | | | |
| Candida albicans (ATCC 90029) | >12.5 | 6.25 | 0.39, 0.2 | 12.5 | 0.78 | >12.5 |
| Corynebacterium jeikeium (ATCC 43734) | | | | | | |
| Enterobacter aerogenes (ATCC 13048) | | | | | | |
| Enterobacter cloacae (ATCC 13047) | | | | | | |
| Enterococcus faecalis (ATCC 51299) | | | | | | |
| Enterococcus faecalis (ATCC 19433) | | | | | | |
| Enterococcus faecium (ATCC 19434) | | | | | | |
| Escherichia coli (ATCC 11229) | | | | | | |
| Escherichia coli (ATCC 25922) | 3.13 | 1.56 | 0.78, 1.56 | 3.13 | 0.78 | 3.13 |
| Haemophilus influenza (ATCC 19418) | | | | | | |
| Klebsiella oxytoca (ATCC 43615) | | | | | | |
| Klebsiella pneumonia (ATCC 11296) | | | | | | |
| Micrococcus luteus (ATCC 4698) | | | | | | |
| Proteus mirobilis (ATCC 7002) | | | | | | |
| Pseudomonas aeruginosa (ATCC 9027) | | | | | | |

TABLE 19-continued

|  | MIC (mg/ml) | | | | | |
| --- | --- | --- | --- | --- | --- | --- |
| *Pseudomonas aeruginosa* (ATCC 27853) | 6.25 | 6.25 | 3.13 | 6.25 | 3.13 | 6.25 |
| *Serratia marcescens* (ATCC 14756) | | | | | | |
| *Staphylococcus aureus* (ATCC 6538) | | | | | | |
| *Staphylococcus aureus* (MRSA) (ATCC 33592) | | | | | | |
| *Staphylococcus aureus* (ATCC 29213) | 3.13 | 3.13, 1.56 | 3.13 | 3.13 | 3.13 | 3.13 |
| *Staphylococcus epidermidis* (ATCC 12228) | | | | | | |
| *Staphylococcus haemolyticus* (ATCC 29970) | | | | | | |
| *Staphylococcus hominis* (ATCC 27844) | | | | | | |
| *Streptococcus pneumonia* (ATCC 6303) | | | | | | |
| *Staphylococcus saprophyticus* (ATCC 15305) | | | | | | |
| *Streptococcus pyogenes* (ATCC 19615) | | | | | | |

Table 19, above, is a summary of the MIC results of Example 33 and Example 35 for all tested antimicrobial compounds and all tested strains.

While the disclosure has been described with reference to an exemplary embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

The invention claimed is:

1. The compound of Formula I:

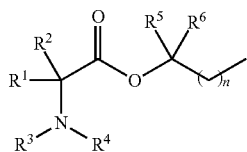

where n is an integer from 6-12 inclusive; $R^1$, and $R^2$, are the same or different and are selected independently from the group consisting of H, substituted or unsubstituted, straight or branched chain $C_1$-$C_{10}$ alkyl, $CH_3$, $CHOHCH_3$, $CH(CH_3)_2$, $CH_2C_6H_6$, and $CH_2CH(CH_3)_2$; $R^3$, and $R^4$, are the same or different and are selected independently from the group consisting of H, substituted or unsubstituted, straight or branched chain $C_1$-$C_{10}$ alkyl, $C_6$-$C_{10}$ aryl or $C_6$-$C_{10}$ heteroaryl, $CH_3$, $CH(CH_3)_2$, $CH_2CH_2OH$, $CH_2CH(CH_3)_2$, and $(CH_2)_2N(CH_2CH_3)_2$, wherein if one of $R^3$ and $R^4$ is selected from H, unsubstituted, straight or branched chain $C_1$-$C_{10}$ alkyl, $CH_3$, $CH(CH_3)_2$, and $CH_2CH(CH_3)_2$, the other is selected from substituted straight or branched chain $C_1$-$C_{10}$ alkyl, $C_6$-$C_{10}$ aryl or $C_6$-$C_{10}$ heteroaryl, $CH_2CH_2OH$, and $(CH_2)_2N(CH_2CH_3)_2$; $R^5$, and $R^6$, are the same or different and are selected independently from the group consisting of H and $CH_3$, and pharmaceutically acceptable salts thereof.

2. The compound of claim 1 wherein $R^1$, and $R^2$, are the same or different and are selected independently from the group consisting of H, $CH_3$, $CHOHCH_3$, $CH(CH_3)_2$, $CH_2C_6H_6$, and $CH_2CH(CH_3)_2$; $R^3$, and $R^4$, are the same or different and are selected independently from the group consisting of H, $CH_3$, $CH(CH_3)_2$, $CH_2CH_2OH$, $CH_2CH(CH_3)_2$, and $(CH_2)_2N(CH_2CH_3)_2$; $R^5$, and $R^6$, are the same or different and are selected independently from the group consisting of H and $CH_3$ and pharmaceutically acceptable salts thereof.

3. The compound of claim 1 wherein $R^1$ is H and $R^2$ is selected from the group consisting of $CHOHCH_3$, $CH(CH_3)_2$, $CH_2C_6H_6$, and $CH_2CH(CH_3)_2$.

4. The compound of claim 1 wherein $R^1$ is $CH_3$ and $R^2$ is $CH_3$.

5. The compound of claim 1 wherein $R^3$ is H and $R^4$ is selected from the group consisting of $CH_2CH_2OH$ and $(CH_2)_2N(CH_2CH_3)_2$.

6. The compound of claim 1 wherein the salt is selected from the group consisting of hydrochloride, phosphate, maleate, 2-hydroxypropane-1,2,3-tricarboxylate, sulfonate, methane sulfonate, ethane sulfonate, 2-hydroxyethane sulfonate, benzene sulfonate, 4-methyl-benzene sulfonate, and heminaphthalene-1,5-disulfonate.

7. A disinfectant composition comprising an effective amount of at least one compound of claim 1 and a suitable carrier.

8. A surface comprising a coating of an antimicrobially effective amount of at least one compound of claim 1.

9. The surface of claim 8 wherein the surface comprises a bandage.

10. The surface of claim 8 wherein the surface comprises a surgical instrument.

11. The surface of claim 8 wherein the surface comprises a medical device.

12. The surface of claim 8 wherein the surface comprises a patch.

13. The surface of claim 8 wherein the coating further comprises an adhesive.

14. The surface of claim 8 further comprising an active pharmaceutical ingredient.

15. The surface of claim 8 further comprising an additive.

16. A method of inhibiting the growth of a microorganism comprising the steps of: providing an effective amount of at least one compound of claim 1; contacting the microorganism with the at least one compound.

17. The method of claim 16 wherein the microorganism is a member of a genus selected from the group consisting of *Acinetobacter, Bacillus, Enterobacter, Enterococcus, Escherichia, Klebsiella, Corynebacterium, Haemophilus, Proteus, Pseudomonas, Serratia, Staphylococcus, Streptococcus, Aspergillus,* and *Candida*.

18. A method of sanitizing a surface comprising the steps of: providing an effective amount of at least one compound of claim 1; contacting the surface with the at least one compound.

19. A method of treating the growth of at least one microorganismcomprising the steps of: providing an amount of at least one compound of claim 1 effective for treating the growth of the at least one microorganism; contacting the microorganism with the at least one compound.

20. The compound of Formula I:

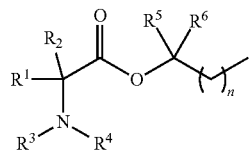

where n is an integer from 6-12 inclusive; $R^1$, and $R^2$, are the same or different and are selected independently from the group consisting of substituted or unsubstituted, straight or branched chain $C_1$-$C_{10}$ alkyl, $CHOHCH_3$, $CH(CH_3)_2$, $CH_2C_6H_6$, and $CH_2CH(CH_3)_2$; $R^3$, and $R^4$, are the same or different and are selected independently from the group consisting of H, substituted or unsubstituted, straight or branched chain $C_1$-$C_{10}$ alkyl, $C_6$-$C_{10}$ aryl or $C_6$-$C_{10}$ heteroaryl, $CH_3$, $CH(CH_3)_2$, $CH_2CH_2OH$, $CH_2CH(CH_3)_2$, and $(CH_2)_2N(CH_2CH_3)_2$; $R^5$, and $R^6$, are the same or different and are selected independently from the group consisting of H and $CH^3$, and pharmaceutically acceptable salts thereof.

21. A disinfectant composition comprising an effective amount of at least one compound of claim 20 and a suitable carrier.

22. A compound selected from the group consisting of:

dodecyl 2-(dimethylamino)-3-hydroxybutanoate hydrochloride, dodecyl 2-(dimethylamino)-3-phenylpropanoate hydrochloride, dodecyl 2-((2-hydroxyethyl)amino)propanoate hydrochloride, and dodecyl 2-((2-(diethylamino)ethyl)amino)propanoate dihydrochloride.

23. A disinfectant composition comprising an effective amount of at least one compound of claim 22 and a suitable carrier.

24. The compound of claim 22 wherein the compound is selected from the group consisting of:

dodecyl 2-((2-hydroxyethyl)amino)propanoate hydrochloride, and dodecyl 2-((2-(diethylamino)ethyl)amino)propanoate dihydrochloride.

25. A disinfectant composition comprising an effective amount of at least one compound of claim 24 and a suitable carrier.

26. A compound selected from the group consisting of:

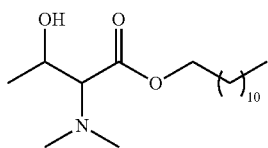

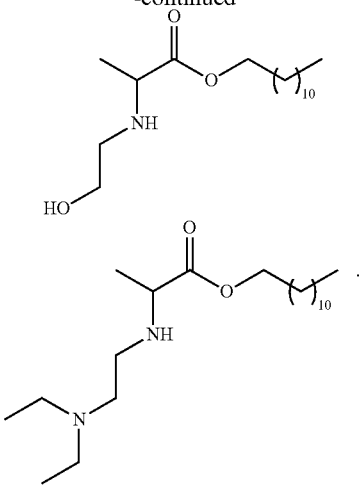

and pharmaceutically acceptable salts thereof.

27. A disinfectant composition comprising an effective amount of at least one compound of claim 26 and a suitable carrier.

28. A composition comprising the compound of Formula I:

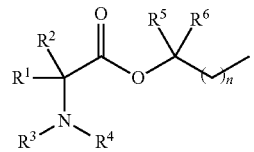

where n is an integer from 6-12 inclusive; $R^1$, and $R^2$, are the same or different and are selected independently from the group consisting of H, substituted or unsubstituted, straight or branched chain $C_1$-$C_{10}$ alkyl, $CH_3$, $CHOHCH_3$, $CH(CH_3)_2$, $CH_2C_6H_6$, and $CH_2CH(CH_3)_2$; $R^3$, and $R^4$, are the same or different and are selected independently from the group consisting of H, substituted or unsubstituted, straight or branched chain $C_1$-$C_{10}$ alkyl, $C_6$-$C_{10}$ aryl or $C_6$-$C_{10}$ heteroaryl, $CH_3$, $CH(CH_3)_2$, $CH_2CH_2OH$, $CH_2CH(CH_3)_2$, and $(CH_2)_2N(CH_2CH_3)_2$, wherein if one of $R^3$ and $R^4$ is selected from H, unsubstituted, straight or branched chain $C_1$-$C_{10}$ alkyl, $CH_3$, $CH(CH_3)_2$, and $CH_2CH(CH_3)_2$, the other is selected from substituted straight or branched chain $C_1$-$C_{10}$ alkyl, $C_6$-$C_{10}$ aryl or $C_6$-$C_{10}$ heteroaryl, $CH_2CH_2OH$, and $(CH_2)_2N(CH_2CH_3)_2$; $R^5$, and $R^6$, are the same or different and are selected independently from the group consisting of H and $CH_3$, and pharmaceutically acceptable salts thereof; and a pharmaceutically acceptable excipient.

29. The composition of claim 28 further comprising an active pharmaceutical ingredient.

30. The composition of claim 28 further comprising an additive.

31. The composition of claim 30 wherein the additive is at least one of a fragrance, an emulsifier, a stabilizer and a preservative.

32. The composition of claim 28 wherein the composition is provided in an unit dosage form.

33. The composition of claim 32 wherein the unit dosage form is a tablet, a pill, a capsule, a powder, a granule, a sterile parenteral solution or a sterile parenteral suspension, a metered aerosol spray, a metered liquid spray, a drop, an ampoule, an auto-injector device, or a suppository.

34. The composition of claim 33 formulated for inhalation, oral, parenteral, intranasal, sublingual or rectal administration.

35. An antibiotic composition according to claim 29 wherein the active pharmaceutical ingredient is an effective amount of an antibiotic.

* * * * *